US009969990B2

(12) United States Patent
Davis et al.

(10) Patent No.: US 9,969,990 B2
(45) Date of Patent: May 15, 2018

(54) KETOACYL ACP SYNTHASE GENES AND USES THEREOF

(71) Applicant: Corbion Biotech, Inc., South San Francisco, CA (US)

(72) Inventors: David Davis, San Bruno, CA (US); George Rudenko, Mountain View, CA (US); Aravind Somanchi, Redwood City, CA (US); Jason Casolari, Palo Alto, CA (US); Scott Franklin, Woodside, CA (US); Aren Ewing, Brisbane, CA (US)

(73) Assignee: Corbion Biotech, Inc., South San Francisco, CA (US)

( * ) Notice: Subject to any disclaimer, the term of this patent is extended or adjusted under 35 U.S.C. 154(b) by 0 days. days.

(21) Appl. No.: 14/796,406

(22) Filed: Jul. 10, 2015

(65) Prior Publication Data

US 2016/0010066 A1 Jan. 14, 2016

Related U.S. Application Data

(60) Provisional application No. 62/023,112, filed on Jul. 10, 2014, provisional application No. 62/081,143, filed on Nov. 18, 2014.

(51) Int. Cl.

| | |
|---|---|
| ***C12N 9/10*** | (2006.01) |
| ***C12N 15/82*** | (2006.01) |
| ***C12P 7/64*** | (2006.01) |
| ***C12P 33/00*** | (2006.01) |

(52) U.S. Cl.

CPC ........... *C12N 9/1029* (2013.01); *C12N 15/82* (2013.01); *C12P 7/64* (2013.01); *C12P 7/6463* (2013.01); *C12P 33/00* (2013.01); *C12Y 203/01041* (2013.01)

(58) Field of Classification Search

CPC .............................. C12N 9/1029; C12N 15/82

See application file for complete search history.

(56) References Cited

U.S. PATENT DOCUMENTS

| | | | |
|---|---|---|---|
| 2,235,056 | A | 3/1941 | Walmesley |
| 2,383,602 | A | 8/1945 | Gerald et al. |
| 2,967,700 | A | 1/1961 | Lee et al. |
| 3,142,135 | A | 7/1964 | Kathrein |
| 3,280,502 | A | 10/1966 | Farrow et al. |
| 3,320,693 | A | 5/1967 | Shirota et al. |
| 3,475,274 | A | 10/1969 | Harned |
| 3,957,578 | A | 5/1976 | Narita et al. |
| 3,962,466 | A | 6/1976 | Nakabayashi |
| 3,983,008 | A | 9/1976 | Shinozaki et al. |
| 4,005,062 | A | 1/1977 | Schnell |
| 4,103,039 | A | 7/1978 | Mandai et al. |
| 4,182,777 | A | 1/1980 | Saunders |
| 4,273,790 | A | 6/1981 | Bosco et al. |
| 4,341,038 | A | 7/1982 | Bloch et al. |
| 4,373,434 | A | 2/1983 | Alexander et al. |
| 4,390,561 | A | 6/1983 | Blair et al. |
| 4,519,845 | A | 5/1985 | Ou |
| 4,627,192 | A | 12/1986 | Fick |
| 4,673,490 | A | 6/1987 | Subramanian et al. |
| 4,755,467 | A | 7/1988 | Scopes et al. |
| 4,901,635 | A | 2/1990 | Williams |
| 4,992,605 | A | 2/1991 | Craig et al. |
| 5,001,059 | A | 3/1991 | Skatrud et al. |
| 5,091,116 | A | 2/1992 | Krishnamurthy et al. |
| 5,130,242 | A | 7/1992 | Barclay |
| 5,212,087 | A | 5/1993 | Fournier et al. |
| 5,252,198 | A | 10/1993 | Harrison et al. |
| 5,270,175 | A | 12/1993 | Moll et al. |
| 5,270,177 | A | 12/1993 | Ramos Lazcano et al. |
| 5,304,481 | A | 4/1994 | Davies et al. |
| 5,330,913 | A | 7/1994 | Nakayama |
| 5,338,673 | A | 8/1994 | Thepenier et al. |
| 5,354,878 | A | 10/1994 | Connemann et al. |
| 5,360,730 | A | 11/1994 | Orndorff et al. |
| 5,391,724 | A | 2/1995 | Kindl et al. |
| 5,395,455 | A | 3/1995 | Scott et al. |
| 5,436,394 | A | 7/1995 | Willmitzer et al. |

(Continued)

FOREIGN PATENT DOCUMENTS

| | | | |
|---|---|---|---|
| CN | 1251108 | A | 4/2000 |
| CN | 1852986 | A | 10/2006 |

(Continued)

OTHER PUBLICATIONS

"Soybean Oil Innovations, 3rd Edition," United Soybean Board, www.soyconnection.com, 8 pages, (2009). [Available from the Internet on Jan. 15, 2009: <URL: http://www.soyconnection.com/sites/defaultifiles/soy-oil-solutions.pdf>].

"Codex Standard for Named Vegetable Oils," CODEX Alimentarius, CODEX STAN 210-1999, pp. 1-16, (1999).

Aggelis et al., "Enhancement of single cell oil production by Yarrowia lipolytica growing in the presence of *Teucrium polium* L. aqueous extract," Biotechnology Letters, 21:747-749, (1999).

Aguirre et al., "Engineering challenges in biodiesel production from microalgae," Critical Reviews in Biotechnology, 33(3): 293-308, (2013).

Altschul et al., "Basic local alignment search tool," J Mol Biol, 215(3):403-410, (1990).

(Continued)

*Primary Examiner* — Yong D Pak

(74) *Attorney, Agent, or Firm* — Weaver Austin Villeneuve & Sampson, LLC.

(57) ABSTRACT

The present invention relates to beta-ketoacyl ACP synthase genes of the KASI/KASIV type and proteins encoded by these genes. The genes can be included in nucleic acid constructs, vectors or host cells. Expression of the gene products can alter the fatty acid profile of host cells. The KAS genes can be combined with a FATA or FATB thioesterase gene to create a cell that produces an increased amount of C8-C16 fatty acids. Suitable host cells include plastidic cells of plants or microalgae. Oleaginous microalga host cells with the new genes are disclosed.

34 Claims, 1 Drawing Sheet

(56) References Cited

U.S. PATENT DOCUMENTS 5,455,167 A 10/1995 Voelker et al.
5,460,870 A 10/1995 Arthurs
5,492,938 A 2/1996 Kyle et al.
5,518,918 A 5/1996 Barclay et al.
5,547,699 A 8/1996 Iizuka et al.
5,563,058 A 10/1996 Davies et al.
5,595,965 A 1/1997 Wiggins
5,597,400 A 1/1997 Nonomura et al.
5,680,812 A 10/1997 Linsgeseder
5,685,218 A 11/1997 Kemper
5,693,507 A 12/1997 Daniell et al.
5,711,983 A 1/1998 Kyle et al.
5,723,761 A 3/1998 Voelker et al.
5,756,135 A 5/1998 Seeley
5,826,500 A 10/1998 Kemper
5,888,947 A 3/1999 Lambert et al.
5,900,370 A 5/1999 Running
5,910,630 A 6/1999 Davies et al.
5,945,585 A 8/1999 Hitz et al.
5,968,791 A 10/1999 Davis et al.
6,139,897 A 10/2000 Goto et al.
6,166,231 A 12/2000 Hoeksema
6,255,505 B1 7/2001 Bijl et al.
6,338,866 B1 1/2002 Criggall et al.
6,344,231 B1 2/2002 Nakajo et al.
6,355,861 B1 3/2002 Thomas
6,372,460 B1 4/2002 Gladue et al.
6,410,281 B1 6/2002 Barclay
6,441,208 B2 8/2002 Bijl et al.
6,534,261 B1 3/2003 Cox, III et al.
6,620,427 B2 9/2003 Lasekan et al.
6,680,426 B2 1/2004 Daniell et al.
6,727,373 B2 4/2004 Bijl et al.
6,750,048 B2 6/2004 Ruecker et al.
6,762,345 B1 7/2004 Cahoon et al.
6,763,345 B1 7/2004 Hempleman et al.
6,867,308 B2 3/2005 Bartok et al.
7,053,267 B2 5/2006 Knauf et al.
7,063,957 B2 6/2006 Chen
7,081,567 B2 7/2006 Xue et al.
7,109,392 B1 9/2006 Broglie et al.
7,135,620 B2 11/2006 Daniell et al.
7,214,297 B2 5/2007 Wang et al.
7,268,276 B2 9/2007 Ruezinsky et al.
7,309,602 B2 12/2007 David
7,351,558 B2 4/2008 Ruecker et al.
7,468,267 B2 12/2008 Monod et al.
7,504,259 B2 3/2009 Yadav et al.
7,588,931 B2 9/2009 Damude et al.
7,622,570 B2 11/2009 Oswald et al.
7,652,156 B2 1/2010 Hillion et al.
7,662,598 B2 2/2010 Ruecker et al.
7,678,931 B2 3/2010 Fichtali et al.
7,781,193 B2 8/2010 Ruecker et al.
7,851,199 B2 12/2010 Bailey et al.
7,879,591 B2 2/2011 Damude et al.
7,883,882 B2 2/2011 Franklin et al.
7,914,832 B2 3/2011 Uchino
7,935,515 B2 5/2011 Franklin et al.
7,939,710 B1 5/2011 Apt et al.
8,003,365 B2 * 8/2011 Yoshikuni ................. C12P 5/02 435/252.1
8,029,579 B2 10/2011 Knuth et al.
8,043,496 B1 10/2011 Schuh et al.
8,088,718 B2 1/2012 Bicerano et al.
8,119,583 B2 2/2012 Day et al.
8,163,675 B2 4/2012 Navarrete et al.
8,187,860 B2 5/2012 Franklin et al.
8,222,010 B2 7/2012 Franklin et al.
8,268,610 B2 9/2012 Franklin et al.
8,278,261 B2 10/2012 Day et al.
8,283,483 B2 10/2012 Williams et al.
8,435,767 B2 5/2013 Franklin et al.
8,450,083 B2 5/2013 Day et al.
8,476,059 B2 7/2013 Trimbur et al.
8,497,116 B2 7/2013 Trimbur et al.
8,512,999 B2 8/2013 Trimbur et al.
8,518,689 B2 8/2013 Trimbur et al.
8,530,207 B2 9/2013 Watts et al.
8,592,188 B2 11/2013 Franklin et al.
8,633,012 B2 1/2014 Franklin et al.
8,647,397 B2 2/2014 Trimbur et al.
8,674,180 B2 3/2014 Franklin et al.
8,697,402 B2 4/2014 Trimbur et al.
8,697,427 B2 4/2014 Franklin et al.
8,765,424 B2 7/2014 Franklin et al.
8,772,575 B2 7/2014 Franklin et al.
8,790,914 B2 7/2014 Trimbur et al.
8,802,422 B2 8/2014 Trimbur et al.
8,822,176 B2 9/2014 Day et al.
8,822,177 B2 9/2014 Day et al.
8,846,352 B2 9/2014 Chua et al.
8,846,375 B2 9/2014 Franklin et al.
8,852,885 B2 * 10/2014 Franklin .............. C12N 9/0071 435/134
8,889,401 B2 11/2014 Trimbur et al.
8,889,402 B2 11/2014 Trimbur et al.
8,945,908 B2 2/2015 Franklin et al.
8,951,777 B2 2/2015 Franklin et al.
9,062,294 B2 6/2015 Franklin et al.
9,066,527 B2 6/2015 Franklin et al.
9,068,213 B2 6/2015 Franklin et al.
9,102,973 B2 8/2015 Franklin et al.
9,109,239 B2 8/2015 Franklin et al.
9,200,307 B2 12/2015 Franklin et al.
9,249,436 B2 2/2016 Franklin et al.
9,249,441 B2 2/2016 Franklin et al.
9,255,282 B2 2/2016 Franklin et al.
9,279,136 B2 3/2016 Franklin et al.
9,353,389 B2 5/2016 Franklin et al.
9,388,435 B2 7/2016 Franklin et al.
9,434,909 B2 9/2016 Trimbur et al.
9,464,304 B2 10/2016 Franklin et al.
9,551,017 B2 1/2017 Franklin et al.
9,593,351 B2 3/2017 Franklin et al.
9,657,299 B2 5/2017 Franklin et al.
9,719,114 B2 8/2017 Franklin et al.
2002/0012979 A1 1/2002 Berry et al.
2002/0059661 A1 5/2002 Dehesh
2002/0122868 A1 9/2002 Floeter et al.
2002/0144455 A1 10/2002 Bertrand et al.
2002/0178467 A1 11/2002 Dehesh
2003/0054524 A1 3/2003 Spener et al.
2003/0079249 A1 4/2003 Shanklin et al.
2003/0082595 A1 5/2003 Jiang et al.
2003/0097686 A1 5/2003 Knauf et al.
2003/0145350 A1 7/2003 Spener et al.
2003/0211594 A1 11/2003 Rosebrook
2003/0229237 A1 12/2003 Haas et al.
2004/0053235 A1 3/2004 Smirnoff et al.
2004/0074760 A1 4/2004 Portnoff et al.
2004/0230085 A1 11/2004 Jakkula et al.
2004/0235123 A1 11/2004 Liao et al.
2004/0033557 A1 12/2004 Scott et al.
2005/0005333 A1 1/2005 Ruezinsky et al.
2005/0102716 A1 5/2005 Venkatramesh et al.
2005/0112735 A1 5/2005 Zappi et al.
2005/0153002 A1 7/2005 Socia Rosales et al.
2005/0170479 A1 8/2005 Weaver et al.
2005/0262588 A1 11/2005 Dehesh et al.
2005/0266537 A1 12/2005 Chen
2005/0272611 A1 12/2005 Lord et al.
2006/0048240 A1 3/2006 Alexandrov et al.
2006/0075522 A1 4/2006 Cleveland et al.
2006/0094088 A1 5/2006 Picataggio et al.
2006/0094089 A1 5/2006 Barclay
2006/0094090 A1 5/2006 Damude et al.
2006/0107346 A1 5/2006 Schneeberger et al.
2006/0122410 A1 6/2006 Fichtali et al.
2006/0130182 A1 6/2006 Heim et al.
2006/0153826 A1 7/2006 Arnould et al.
2006/0156436 A1 7/2006 Nakamura et al.
2006/0162006 A9 7/2006 Sherman et al.
2006/0199984 A1 9/2006 Kuechler et al.

(56) References Cited

U.S. PATENT DOCUMENTS

2006/0225341 A1 10/2006 Rohr et al.
2006/0286205 A1 12/2006 Fichtali et al.
2007/0004016 A1 1/2007 Picataggio et al.
2007/0009988 A1 1/2007 Monod et al.
2007/0048848 A1 3/2007 Sears
2007/0099280 A1 5/2007 Barclay
2007/0118916 A1 5/2007 Puzio et al.
2007/0167396 A1 7/2007 Dillon et al.
2007/0218183 A1 9/2007 Nakhasi et al.
2007/0248531 A1 10/2007 Debryun et al.
2007/0254354 A1 11/2007 Millis et al.
2007/0261138 A1 11/2007 Graham et al.
2007/0275438 A1 11/2007 David
2008/0014620 A1 1/2008 Op Den Camp et al.
2008/0038804 A1 2/2008 Du et al.
2008/0040822 A1 2/2008 Metz et al.
2008/0107776 A1 5/2008 Prakash et al.
2008/0160593 A1 7/2008 Oyler
2008/0194029 A1 8/2008 Hegemann et al.
2008/0206379 A1 8/2008 Fabritius et al.
2008/0229451 A1 9/2008 Cao et al.
2008/0256666 A1 10/2008 Zhu et al.
2008/0283803 A1 11/2008 Rapp et al.
2009/0004715 A1 1/2009 Trimbur et al.
2009/0011480 A1 1/2009 Trimbur et al.
2009/0018300 A1 1/2009 Bloom et al.
2009/0035842 A1 2/2009 Trimbur et al.
2009/0047721 A1 2/2009 Trimbur et al.
2009/0061493 A1 3/2009 Trimbur et al.
2009/0064567 A1 3/2009 Lippmeier et al.
2009/0099260 A1 4/2009 Namal Senanayake et al.
2009/0117253 A1 5/2009 Hong et al.
2009/0142322 A1 6/2009 Ye
2009/0145392 A1 6/2009 Clark et al.
2009/0148918 A1 6/2009 Trimbur et al.
2009/0176272 A1 7/2009 Champagne et al.
2009/0211150 A1 8/2009 Wu et al.
2009/0234146 A1 9/2009 Cooney et al.
2009/0271892 A1 10/2009 Thomasset et al.
2009/0274736 A1 11/2009 Dillon et al.
2009/0298143 A1 12/2009 Roessler et al.
2009/0298159 A1 12/2009 Wu et al.
2009/0305942 A1 12/2009 Day et al.
2009/0317878 A1 12/2009 Champagne et al.
2010/0010088 A1 1/2010 Chilton et al.
2010/0021912 A1 1/2010 Farese et al.
2010/0035320 A1 2/2010 Blanchard et al.
2010/0058651 A1 3/2010 Knuth et al.
2010/0093031 A1 4/2010 Kobayashi et al.
2010/0105955 A1 4/2010 Alibhai et al.
2010/0120643 A1 5/2010 Brown et al.
2010/0137647 A1 6/2010 Bradin
2010/0151112 A1 6/2010 Franklin et al.
2010/0151535 A1 6/2010 Franklin et al.
2010/0151538 A1 6/2010 Franklin et al.
2010/0151539 A1 6/2010 Franklin et al.
2010/0151567 A1 6/2010 Franklin et al.
2010/0154293 A1 6/2010 Hom et al.
2010/0170144 A1 7/2010 Day et al.
2010/0186117 A1 7/2010 Fabijanski et al.
2010/0196575 A1 8/2010 Sanchez et al.
2010/0239712 A1 9/2010 Brooks et al.
2010/0248322 A1 9/2010 Pfeiffer et al.
2010/0249260 A1 9/2010 Casati et al.
2010/0297292 A1 11/2010 Brooks et al.
2010/0297295 A1 11/2010 Brooks et al.
2010/0297296 A1 11/2010 Brooks et al.
2010/0297323 A1 11/2010 Brooks et al.
2010/0297325 A1 11/2010 Brooks et al.
2010/0297331 A1 11/2010 Brooks et al.
2010/0035309 A1 12/2010 Havemen et al.
2010/0303957 A1 12/2010 Brooks et al.
2010/0303961 A1 12/2010 Brooks et al.
2010/0303989 A1 12/2010 Brooks et al.
2010/0303990 A1 12/2010 Brooks et al.
2010/0323413 A1 12/2010 Trimbur et al.
2010/0323414 A1 12/2010 Trimbur et al.
2011/0014665 A1 1/2011 Trimbur et al.
2011/0015417 A1 1/2011 Trimbur et al.
2011/0047863 A1 3/2011 Trimbur et al.
2011/0065821 A1 3/2011 Abraham et al.
2011/0072714 A1 3/2011 Gaertner et al.
2011/0111470 A1 5/2011 Berry et al.
2011/0165634 A1 7/2011 Franklin et al.
2011/0190522 A1 8/2011 Trimbur et al.
2011/0203168 A1 8/2011 Franklin et al.
2011/0250658 A1 10/2011 Franklin et al.
2011/0252696 A1 10/2011 Franklin et al.
2011/0256268 A1 10/2011 Franklin et al.
2011/0256282 A1 10/2011 Piechocki et al.
2011/0284215 A1 11/2011 Pfeiffer et al.
2011/0293785 A1 12/2011 Franklin et al.
2011/0294174 A1 12/2011 Franklin et al.
2012/0009636 A1 1/2012 Berry et al.
2012/0021495 A1 1/2012 Vanzin
2012/0028319 A1 2/2012 Trimbur et al.
2012/0034662 A1 2/2012 Hu et al.
2012/0060242 A1 3/2012 Senger et al.
2012/0119862 A1 5/2012 Franklin et al.
2012/0122192 A1 5/2012 Trimbur et al.
2012/0128851 A1 5/2012 Brooks et al.
2012/0156717 A1 6/2012 Allnutt et al.
2012/0164701 A1 6/2012 Trimbur et al.
2012/0203018 A1 8/2012 Franklin et al.
2012/0277452 A1* 11/2012 Franklin .............. C12N 9/0071
554/219
2012/0277453 A1 11/2012 Franklin et al.
2012/0283460 A1 11/2012 Franklin et al.
2012/0288930 A1 11/2012 Trimbur et al.
2012/0324784 A1 12/2012 Franklin et al.
2012/0329109 A1 12/2012 Chua et al.
2013/0004646 A1 1/2013 Franklin et al.
2013/0006006 A1 1/2013 Day et al.
2013/0031678 A1 1/2013 Zheng et al.
2013/0034887 A1 2/2013 Franklin et al.
2013/0078709 A1 3/2013 Franklin et al.
2013/0089916 A1 4/2013 Franklin et al.
2013/0096211 A1 4/2013 Franklin et al.
2013/0102039 A1 4/2013 Franklin et al.
2013/0116462 A1 5/2013 Durrett et al.
2013/0122180 A1 5/2013 Brooks et al.
2013/0165677 A1 6/2013 Franklin et al.
2013/0197247 A1 8/2013 Franklin et al.
2013/0273621 A1 10/2013 Franklin et al.
2013/0295268 A1 11/2013 Day et al.
2013/0296591 A1 11/2013 Day et al.
2013/0316410 A1 11/2013 Franklin et al.
2013/0323382 A1 12/2013 Franklin et al.
2013/0323823 A1 12/2013 Franklin et al.
2013/0330790 A1 12/2013 Trimbur et al.
2013/0331584 A1 12/2013 Franklin et al.
2013/0338385 A1 12/2013 Franklin et al.
2014/0170716 A1 6/2014 Trimbur et al.
2014/0249342 A1 9/2014 Franklin et al.
2014/0256024 A1 9/2014 Franklin et al.
2014/0256600 A1 9/2014 Dillon et al.
2014/0305031 A1 10/2014 Day et al.
2014/0315267 A1 10/2014 Franklin et al.
2014/0336100 A1 11/2014 Day et al.
2014/0357746 A1 12/2014 Ngantung et al.
2014/0377847 A1 12/2014 Franklin et al.
2015/0073163 A1 3/2015 Chua et al.
2015/0125914 A1 5/2015 Franklin et al.
2015/0218604 A1 8/2015 Franklin et al.
2015/0275149 A1 10/2015 Dummer et al.
2015/0344917 A1 12/2015 Franklin et al.
2016/0024538 A1 1/2016 Franklin et al.
2016/0032332 A1 2/2016 Davis et al.
2016/0186191 A1 6/2016 Franklin et al.
2016/0186219 A1 6/2016 Franklin et al.
2016/0194672 A1 7/2016 Franklin et al.
2016/0348119 A1 12/2016 Franklin et al.
2016/0376617 A1 12/2016 Franklin et al.

(56) References Cited

U.S. PATENT DOCUMENTS

| | | | |
|---|---|---|---|
| 2017/0022436 | A1 | 1/2017 | Trimbur et al. |
| 2017/0145450 | A1 | 5/2017 | Franklin et al. |
| 2017/0314048 | A1 | 11/2017 | Franklin et al. |

FOREIGN PATENT DOCUMENTS

| | | | |
|---|---|---|---|
| CN | 101037639 | A | 9/2007 |
| CN | 101092353 | A | 12/2007 |
| CN | 101108997 | A | 1/2008 |
| CN | 101611125 | A | 12/2009 |
| CN | 101765661 | A | 6/2010 |
| CN | 101824440 | A | 9/2010 |
| DE | 2756977 | A1 | 6/1978 |
| EP | 0 562 504 | B1 | 11/1995 |
| EP | 1 178 118 | A1 | 2/2002 |
| EP | 1 642 959 | A1 | 4/2006 |
| EP | 1 681 337 | A1 | 7/2006 |
| EP | 1 741 767 | A1 | 1/2007 |
| EP | 1 947 189 | A2 | 7/2008 |
| EP | 2 327 776 | A1 | 6/2011 |
| EP | 2 152 849 | B1 | 2/2013 |
| FR | 2924126 | A1 | 5/2009 |
| GB | 824151 | | 11/1959 |
| JP | 57-150379 | | 9/1982 |
| JP | 06-253872 | A | 9/1994 |
| JP | 07-008217 | | 1/1995 |
| JP | 07-075557 | | 3/1995 |
| JP | 09-511650 | | 11/1997 |
| JP | 10-46181 | | 2/1998 |
| JP | 2000-136199 | | 5/2000 |
| JP | 2000-175696 | A | 6/2000 |
| JP | 2002-125601 | | 5/2002 |
| JP | 2002-523864 | A | 7/2002 |
| JP | 2003-102467 | A | 4/2003 |
| JP | 2003-325067 | A | 11/2003 |
| JP | 2007-314549 | A | 12/2007 |
| JP | 2008-081559 | | 4/2008 |
| JP | 2008-514221 | | 5/2008 |
| JP | 2008-148663 | | 7/2008 |
| JP | 2008-178871 | | 8/2008 |
| JP | 2010-528627 | | 8/2010 |
| JP | 2015-500009 | A | 1/2015 |
| JP | 6071904 | | 2/2017 |
| KR | 10-2007-00085649 | A | 8/2007 |
| WO | WO 91/018105 | A1 | 11/1991 |
| WO | WO 92/11373 | A1 | 7/1992 |
| WO | WO 93/006712 | A1 | 4/1993 |
| WO | WO 94/10288 | A2 | 5/1994 |
| WO | WO 95/13390 | A2 | 5/1995 |
| WO | WO 95/27791 | A1 | 10/1995 |
| WO | WO 95/31553 | A1 | 11/1995 |
| WO | WO 97/40698 | A1 | 11/1997 |
| WO | WO 98/032770 | A1 | 7/1998 |
| WO | WO 99/37166 | A1 | 7/1999 |
| WO | WO 99/64618 | | 11/1999 |
| WO | WO 00/011682 | A1 | 3/2000 |
| WO | WO 00/061740 | A1 | 10/2000 |
| WO | WO 00/066750 | A2 | 11/2000 |
| WO | WO 00/74471 | A1 | 12/2000 |
| WO | WO 2011/150410 | A2 | 12/2001 |
| WO | WO 02/008403 | A2 | 1/2002 |
| WO | WO 02/085293 | A2 | 10/2002 |
| WO | WO 2004/016282 | A1 | 2/2004 |
| WO | WO 2004/101753 | A2 | 11/2004 |
| WO | WO 2005/003310 | A2 | 1/2005 |
| WO | WO 2005/035693 | A2 | 4/2005 |
| WO | WO 2006/052807 | A2 | 5/2006 |
| WO | WO 2006/055322 | A2 | 5/2006 |
| WO | WO 2006/122299 | A2 | 11/2006 |
| WO | WO 2007/027669 | A1 | 3/2007 |
| WO | WO 2007/38566 | A2 | 4/2007 |
| WO | WO 2007/106903 | A2 | 9/2007 |
| WO | WO 2007/117511 | A2 | 10/2007 |
| WO | WO 2007/121100 | A2 | 10/2007 |
| WO | WO 2007/134294 | A2 | 11/2007 |
| WO | WO 2007/141257 | A2 | 12/2007 |
| WO | WO 2008/002643 | A2 | 1/2008 |
| WO | WO 2008/011811 | A1 | 1/2008 |
| WO | WO 2008/058664 | A1 | 5/2008 |
| WO | WO 2008/060571 | A2 | 5/2008 |
| WO | WO 2008/083352 | A1 | 7/2008 |
| WO | WO 2008/130372 | A2 | 10/2008 |
| WO | WO 2008/134836 | A2 | 11/2008 |
| WO | WO 2008/151149 | A2 | 12/2008 |
| WO | WO 2009/076559 | A1 | 6/2009 |
| WO | WO 2009/105620 | A1 | 8/2009 |
| WO | WO 2009/124070 | A1 | 10/2009 |
| WO | WO 2009/126843 | A2 | 10/2009 |
| WO | WO 2010/017346 | A2 | 2/2010 |
| WO | WO 2010/019813 | A2 | 2/2010 |
| WO | WO 2010/037209 | A1 | 4/2010 |
| WO | WO 2010/045368 | A2 | 4/2010 |
| WO | WO 2010/063031 | A2 | 6/2010 |
| WO | WO 2010/063032 | A2 | 6/2010 |
| WO | WO 2010/111698 | A2 | 9/2010 |
| WO | WO 2010/120923 | A1 | 10/2010 |
| WO | WO 2010/120939 | A2 | 10/2010 |
| WO | WO 2011/026008 | A1 | 3/2011 |
| WO | WO 2011/075716 | A1 | 6/2011 |
| WO | WO 2011/090730 | A1 | 7/2011 |
| WO | WO 2011/130573 | A1 | 10/2011 |
| WO | WO 2011/130576 | A1 | 10/2011 |
| WO | WO 2011/130578 | A2 | 10/2011 |
| WO | WO 2011/150411 | A1 | 12/2011 |
| WO | WO 2012/061647 | A2 | 5/2012 |
| WO | WO 2012/106560 | A1 | 8/2012 |
| WO | WO 2012/154626 | A1 | 11/2012 |
| WO | WO 2013/082186 | A2 | 6/2013 |
| WO | WO 2013/096891 | A1 | 6/2013 |
| WO | WO 2013/158938 | | 10/2013 |
| WO | WO 2014/176515 | A2 | 10/2014 |
| WO | WO 2015/051319 | A2 | 4/2015 |
| WO | WO 2016/007862 | A2 | 1/2016 |
| WO | WO 2016/164495 | A1 | 10/2016 |
| WO | WO 2017/058802 | A1 | 4/2017 |

OTHER PUBLICATIONS

Amaro et al., "Advances and perspectives in using microalgae to produce biodiesel," Applied Energy, 88:3402-3410, (2011).

Andersen, "Biology and Systematics of Heterokont and Haptophyte Algae," American Journal of Botany, 91(10):1508-1522, (2004).

Appel et al., "A multicopy vector system for genetic studies in Mucor circinelloides and other zygomycetes," Molecular Genetics and Genomics, 271(5):595-602, (2004).

Apt et al., "Stable nuclear transformation of the diatom Phaeodactylum tricornutum," Mol Gen Genet, 252(5):572-579, (1996).

Barnes et al., "Contribution of 5'- and 3'-untranslated regions of plastid mRNAs to the expression of Chlamydomonas reinhardtii chloroplast genes," Mol Genet Genomics, 274(6):625-636, (2005).

Beale et al., "Chlorophyll Synthesis in Chlorella: Regulation by Degree of Light Limitation of Growth," Plant Physiol., 47:230-235, (1971).

Bhunia et al., "Algal Biodiesel Production: Challenges and Opportunities," Bioenergy and Biofuel from Biowastes and Biomass, American Society of Civil Engineers, pp. 313-345, (2010).

Bigogno et al., "Biosynthesis of arachidonic acid in the oleaginous microalga Parietochloris incisa (*Cholorphyceae*): Radiolabeling studies," Lipids 37(2):209-216 (2002); Abstract Only.

Bigogno et al., "Lipid and fatty acid composition of the green oleaginous alga *Parietochloris incisa*, the richest plant source of arachidonic acid," Pytochemistry, 60:497-503, (2002).

Blowers et al., "Studies on Chlamydomonas chloroplast transformation: foreign DNA can be stably maintained in the chromosome," Plant Cell, 1(1):123-132, (1989).

Bohacenko et al., "Detection of Olive Oils Authenticity by Determination of their Sterol Content using LC/GC," Czech J. Food Sci., 19(3):97-103, (2001).

Bonaventure et al., "Disruption of the FATB Gene in Arabidopsis Dethonstrates an Essential Role of Saturated Fatty Acids in Plant Growth," The Plant Cell 15:1020-1033, (2003).

(56) References Cited

OTHER PUBLICATIONS

Sordes et al., "A new recombinant protein expression system for high-throughput screening in the yeast *Yarrowia lipolytica*," Journal of Microbiological Methods, 70(3):493-502, (2007).
Bornscheuer et al. (ed), "Enzymes in Lipid Modification," Wiley-VCH Verlag Gmbh & Co. KGaA, 1st Edition, ISBN: 3-527-30176-3, Sections 1-11, 231 pages, (2000). (part 1 of 2 of book).
Bornscheuer et al. (ed), "Enzymes in Lipid Modification," Wiley-VCH Verlag Gmbh & Co. KGaA, 1st Edition, ISBN: 3-527-30176-3, Sections 12-18, 133 pages, (2000). (part 2 of 2 of book)
Borza et al., "Multiple Metabolic Roles for the Nonphotosynthetic Plastid of the Green Alga *Protothecaal wickerhamii*," Eukaryotic Cell, 4(2):253-261, (2005).
Boutry et al., "Targeting of bacterial chloramphenicol acetyltransferase to mitochondria in transgenic plants," Nature, 328(6128):340-2, (1987).
Boynton et al., "Chloroplast Transformation in Chlamydomonas with High Velocity Microprojectiles," Science, 240(4858):1534-1538, (1988).
Broun et al., "Accumulation of Ricinoleic, Lesquerolic, and Densipolic Acids in Seeds of Transgenic Arabidopsis Plants That Express a Fatty Acyl Hydroxylase cDNA from Castor Bean," Plant Physiol., 113:933-942, (1997).
Broun et al., "Catalytic Plasticity of Fatty Acid Modification Enzymes Underlying Chemical Diversity of Plant Lipids," Science, 282:1315-1317, (1998). [Retrieved from the Internet Feb. 27, 2007: <URL: http://www.sciencemag.org>].
Brown et al., "The amino-acid and sugar composition of 16 species of micralgae used in mariculture," J. Exp. Mar. Biol. Ecol. 145:79-99 abstract (1991).
Burgal et al., "Metabolic engineering of hydroxy fatty acid production in plants: RcDGAT2 drives dramatic increases in ricinoleate levels in seed oil," Plant Biotechnol J., 6(8):819-831, (2008).
Campbell et al., "Codon Usage in Higher Plants, Green Algae, and Cyanobacteria," Plant Physiol., (92):1-11, (1990).
Chasan, "Engineering Fatty Acids—The Long and Short of It," Plant Cell, 7:235-237, (1995).
Chattopadhyay et al., "Effect of single amino acid mutations in the conserved GDNQ motif of L protein of Rinderpest virus on RNA synthesis in vitro and in vivo," Virus Research, 99:139-145, (2004).
Chen et al., "Recognition of prokaryotic transcription terminators by spinach chloroplast RNA polymerase," Nucleic Acids Research, 16(17):8411-8431, (1988).
Chen et al., "Effect of C/N ratio and aeration on the fatty acid composition of heterotrophic Chlorella sorokiniana," Journal of Applied Phycology, 3:203-209, (1991).
Chen et al., "Highly Effective Expression of Rabbit Neutrophil Peptide-1 Gene in Chlorella Ellipsoidea Cells," Current Genetics, 39:365-370, (2001).
Chica et al., "Semi-rational approaches to engineering enzyme activity: combining the benefits of directed evolution and rational design ," Current Opinion in Biotechnology, 16:378-384, (2005).
Chow et al., "Electroformation of Chlorella Vulgaris," Plant Cell Reports, 18:778-780, (1999).
Ciferri, "Thiamine-deficiency of Prototheca, a Yeast-like Achloric Alga," Nature, 178:1475-1476.
Co et al., "Matching the Functionality of Single-Cell Algal Oils with Different Molecular Compositions," J Am Oil Chem Soc, doi:10.1007/s11746-013-2405-y, 16 pages, (2014).
Cobley et al., "CpeR is an activator required for expression of the phycoerythrin operon (cpeBA) in the cyanobacterium *Fremyella diplosiphon* and is encoded in the phycoerythrin linker-polypeptide operon (cpeCDESTR)," Molecular Microbiology, 44(6):1517-153.
Cobley et al., Construction of Shuttle Plasmids Which Can Be Efficiently Mobilized From *Escherichia Coli* Into the Chromatically Adapting Cyanobacterium, Plasmid, 30:90-105, (1993).
Cohen et al., "The Heterotrophic Connection in a Photoautotrophic Chlorella Vulgaris Dominant in W Astew Ater Oxidation Ponds," War. Sci. Tech., 27(7-8):151-155, (1993).
Comai et al., "Chloroplast Transport of a Ribulose Biphosphate Carboxylase Small Subunit-5-Enolypyruvyl 3-Phosphoshikimate Synthase Chimeric Protein Requires Part of the Mature Small Subunit in Addition to the Transit Peptide," Journal of Biological Chemic.
Cordy et al., "Chlorellasis in a Lamb," Vet. Path., 10:171-176, (1973).
Courchesne et al., "Enhancement of Lipid Production Using Biochemical, Genetic and Transcription Factor Engineering Approaches," J Biotechnol. Epub, 141(1-431-41, (2009).
Davies et al.,"Expression of the Arylsulfatase Gene from the Beta 2-Tubulin Promoter in Chlamydomonas reinhardtii," Nucleic Acids Research, 20(12):2959-2965, (1992).
Dawson et al., "Stable Transformation of Chlorella: Rescue of Nitrate Reductase-Deficient Mutants with the Nitrate Reductase Gene," Current Microbiology, 35:356-362, (1997).
Day, Al. et al., "Safety evaluation of a high-lipid algal biomass from Chlorella protorhecoides," Rego!. Toxicol. Pharmacol., doi:10.1016/j.yrtph.2009.06.014, 15 pages, (2009).
De Cock, "Structure development in confectionery products: importance of triacylglycerol composition," Master Thesis, Masters in Bioscience Engineering, Ghent University, 73 pages, (2011).
Debuchy et al., "The argininosuccinate lyase gene of Chlamydomonas reinhardtii: an important tool for nuclear transformation and for correlating the genetic and molecular maps of the ARG7 locus," EMBO J., 8(10):2803-2809, (1989).
Dehesh et al., "KAS IV: a 3-ketoacyl-ACP synthase from *Cuphea* sp. is a medium chain specific condensing enzyme," The Plant Journal, 15:383-390, (1998).
Dehesh et al., "Production of high levels of 8:0 and 10:0 fatty acids in transgenic canola by overexpression of Ch FatB2, a thioesterase cDNA from Cuphea hookeriana," The Plant Journal, 9(2):167-172, (1996).
Demirbas et al., "Importance of algae oil as a source of biodiesel," Energy Conversion and Management, 52:163-170, (2011).
Deshnium et al., "Transformation of Synechococcus with a gene for choline oxidase enhances tolerance to salt stress," Plant Mol Biol, 29(5):897-907, (1995).
Desmond et al., "Phylogenomics of Sterol Synthesis: Insights into the Origin, Evolution, and Diversity of a Key Eukaryotic Feature," Genome. Biol. Evol., 1:364-381, (2009).
Devos et al., "Practical Limits of Function Prediction," Proteins: Structure, Function, and Genetics, 41:98-107, (2000).
Dormann et al., "Cloning and Expression in *Escherichia coli* of a Novel Thioesterase from Arabidopsis thaliana Specific for Long-Chain Acyl-Acyl Carrier Proteins," Archives of Biochemistry and Biophysics, 316(1):612-618, (1995).
Dunahay et al., "Genetic Engineering of Microalgae for Fuel Production," Applied Biochemistry and Biotechnology, 34/35:331-339 (1992).
Dunahay et al., "Manipulation of Microalgal Lipid Production Using Genetic Engineering," Applied Biochemistry and Biotechnology, 57/58:223-231, (1996).
Eccleston et al., "Medium-chain Fatty Acid Biosynthesis and Utilization in Brassica Mapus Plants Expressing Lauroyl-Acyl Carrier Protein Thioesterase," Planta 198:46-53, (1996)
El-Fadaly et al., "Single Cell Oil Production by an Oleaginous Yeast Strain in a Low Cost Cultivation Medium," Research Journal of Microbiology, 4(8):301-313, (2009).
El-Sheekh, MM., "Stable Transformation of the Intact Cells of Chlorella Kessleri With High Velocity Microprojectiles," Biologic Plantarium 42(2): 209-216, (1999).
EPO Supplementary European Search Report and European Search Opinion for application EP 12782478.7 dated Oct. 22, 2014.
EPO Supplementary European Search Report and European Search Opinion for application EP08769988.0 dated Jul. 1, 2011.
EPO Supplementary European Search Report and European Search Opinion for application EP11158642.6 dated Jul. 1, 2011.
EPO Supplementary European Search Report and European Search Opinion for application EP12741997.6 dated Aug. 31, 2015.
EPO Supplementary European Search Report and European Search Opinion for application EP 09829850.8 dated May 16, 2014.

(56) References Cited

OTHER PUBLICATIONS

Erhan, "Vegetable Oils as Lubricants, Hydraulic Fluids, and Inks," Bailey's Industrial Oil and Fat Products, 6:259-278, (2005).
Evans et al., "A comparison of the oleaginous yeast, *Candida curvata*, grown on different carbon sources in continuous and batch culture," Lipids, 18(09):623-629, (1983).
Facciotti et al., "Improved stearate phenotype in transgenic canola expressing a modified acyl-acyl carrier protein thioesterase," Nat Biotechnol., 17(6):593-597, (1999).
Falciatore et al., "Transformation of Nonselectable Reporter Genes in Marine Diatoms," Marine Biotechnology; 1:239-251, (1999).
Fall et al., "Bioconversion of Xylan to Triglycerides by Oil-Rich Yeasts," Applied and Environmental Microbiology, 47(5):1130-1134, (1984).
Fernandez-Reiriz et al., "Biomass Production and Variation in the Biochemical Profile (Total Protein, Carbohydrates, RNA, Lipids and Fatty Acids) of Seven Species of Marine Microalgae," Aquaculture, 83:17-37, (1989).
Ferrentino, "Microalgal oil extraction and in situ transesterification," University of New Hampshire, Pub. No. MT 1447885, 8 pages, (2007).
Ferrentino, et al., "Microalgal Oil Extraction and In-situ Transesterification," AIChE Annual Mtg, San Francisco, CA, Nov. 11-13, 2006. Abstract.
Franklin et al., "Prospects for molecular farming in the green alga *Chlamydomonas reinhardtii*," Current Opinion in Plant Biology, 7:159-165, (2004).
Franzen et al., "Chloroplast transit peptides from the green alga *Chlamydomonas reinhardtii* share features with both mitochondrial and higher plant chloroplast presequences," FEBS Letters, 260(2):165-168, (1990).
Frenz et al., "Hydrocarbon recovery by extraction with a biocompatible solvent from free and immobilized cultures of Botryococcus braunii," Enzyme Microb Technol, 11(11):717-724, (1989).
Frohns et al., "Potassium ion channels of Chlorella viruses cause rapid depolarization of host cells during infection," J Virol, 80(5):2437-2444, (2006).
Fromm et al., "Expression of Genes Transferred into Monocot and Dicot Plant Cells by Electroporation," Proc Natl Acad Sci, 82:5824-5828, (1985).
Funes et al., "The typically mitochondrial DNA-encoded ATP6 subunit of the F1F0-ATPase is encoded by a nuclear gene in Chlamydomonas reinhardtii," J Biol Chem, 277(8):6051-6058, (2002).
Gabay et al., "Stigmasterol: a phytosterol with potential anti-osteoarthritic properties," Osteoarthritis and Cartilage,18:106-116, (2010).
GenBank: "Codon Usage Database file for Chlorella vulgaris," Jun. 2007. [Retrieved from the Internet Aug. 26, 2010: <URL: http://www.kazusa.or.jp/codon/cgi-bin/showcodon.cgi?species=3077 >].
GenBank: Accession No. AAC49001.1, May 1995. [Retrieved from the Internet Oct. 14, 2014: <URL: http://www.ncbi.nlrrtnih.gov/protein/595955?sat=13&satkey=6522409>].
Gill et al., "Lipid Accumulation in an Oleaginous Yeast (*Candida* 107) Growing on Glucose in Single-Stage Continuous Culture," Applied and Environmental Microbiology, 33(02):231-239, (1977).
Igouveia et al., "Microalgae in Novel Food Products," Food Chemistry Research Developments, Chapter 2, Nova Science Publishers, Inc., ISBN 978-1-60456-262-0, 37 pages, (2008).
Graves et al., "Hyaluronan synthesis in virus PBCV-1-infected chiorella-like green algae," Virology, 257(1):15-23, (1999).
Grima et al., "Recovery of microalgal biomass and metabolites: process options and economics," Biotechnology Advances, 20:491-515, (2003).
Gruber et al., "*Escherichia coli*—Anacystis nidulans plasmid shuttle vectors containing the PL promoter from bacteriophage lambda," Current Microbiology, 22(1)15-19, (1991).
Guiry et al., "How Many Species of Algae are There?," J. Phycol., 48:1057-1063, (2012).
Gul et al., "Sterols and the Phytosterol Content in Oilseed Rape (*Brassica napus* L.)," Journal of Cell and Molecular Biology, 5:71-79 (2006).
Gunstone, "Enzymes as biocatalysts in the modification of natural lipids," Journal of the Science of Food and Agriculture, 79:1535-1549, (1999).
Guo-Zhong et al., "The Actin Gene Promoter-driven Bar as a Dominant Selectable Marker for Nuclear Transformation of Dunaliella Salina," Acta Genetica Sinica, 32(4): 424-433, (2005).
Guschina et al., "Lipids and lipid metabolism in eukaryotic algae," Progress in Lipid Research, 45:160-186, (2006).
Hall et al., "Expression of a foreign gene in Chlamydomonas reinhardtii," Gene, 124(1):75-81, (1993).
Hall et al., "Lipid Accumulation in an Oleaginous Yeast (*Candida* 107) Growing on Glucose Under Various Conditions in a One- and Two-Stage Continuous Culture," Applied and Environmental Microbiology, 33(3):577-584, (1977).
Hallmann et al., "Reporter Genes and Highly Regulated Promoters as Tools for Transformation Experiements in Volvox Carteri," Proc Natl Acad Sci U S A., 91(24):11562-11566, (1994).
Hanley-Bowdoin et al., "Chloroplast promoters," Trends in Biochemical Sciences, 12:67-70, (1987).
Hawkins et al., "Expression of Human Growth Hormone by the Eukaryotic Alga, *Chlorella*," Current Microbiology, 38:335-341, (1999).
Heifetz, "Genetic Engineering of the Chloroplast," Biochimie, 82:655-666, (2000).
Heise et al., "Factors Controlling Medium-Chain Fatty Acid Synthesis in Plastids From Cuphea Embryos," Prog. Lipid Res., 33(1/2):87-95, (1994).
Henderson et al., "Lipid Composition and Biosynthesis in the Marine Dinoflagellate *Crypthecodznzum Cohnii*," Phytochem. 27(6)1679-1683 (1988).
Henikff et al., "Amino Acid Substitution Matrices from Protein Blocks," Proc Natl Acad of Sci, 89(22):10915-10919. (1992).
Heredia et al., "Simultaneous utilization of glucose and xylose by Candida curvata D in continuous culture," Biotechnology Letters, 10(01):25-30, (1988).
Heredia-Arroyo et al., "Oil Accumulation via Heterotrophic/Mixotrophic Chlorella protothecoides," Appl Biochem Biotechnol, 162:1978-1995, (2010).
Hillen et al., "Hydrocracking of the Oils of Botryococcus braunii to Transport Fuels," Biotechnology and Bioengineering, 24(1):193-205, (1982).
Hiramatsu et al., "Expression of a chitinase gene and lysis of the host cell wall during Chlorella virus CVK2 infection," Virology, 260(2):308-315, (1999).
Hitz et al.,"Cloning of a Higher-Plant Plastid Omega-6 Fatty Acid Desaturase cDNA and Its Expression in a Cyanobacterium," Plant Physiology, 105(2):635-641, (1994).
Hu et al., "Microalgal Triacylglycerols as Feedstocks for Biofuel Production: Perspectives and Advances," The Plant Journal 54:621-639, (2008).
Huang et al., "Sterols as ecological indicators," Geochimica et Cosmochimica Acta, 43:739-745, (1979).
Huang et al., "Expression of Mercuric Reductase From Bacillus Megaterium MB1 in Eukaryotic *Microalga chlorella* sp. DT: An Approach for Mercury Phytoremediation," Appl. Microbiol. Biotechnol., 72:197-205, (2006).
Huss et al., "Deoxyribonucleic acid reassociation in the taxonomy of the genus *Chlorella*," Arch Microbiol, 150:509-511, (1988).
Inoue et al., "Analysis of oil derived from liquefaction of Botryococcus Braunii," Biomass and Bioenergy, 6(4):269-274, (1994).
Itoh et al., "Sterol Compositoin of 19 Vegetable Oils," Journal of The American Oil Chmists' Society, 50:122-125, (1973).
Iturriaga et al. "Heterologous transformation of Mucor circinelfoides with the Phycomyces blakesleeanus leu1 gene," Current Genetics, 21(3):215-223, (1992).
Jakobiak et al, "The Bacterial Paromomycin Resistance Gene, aphH, as a Dominant Selectable Marker in Volvox carteri," Protist, 55: 381-393, (2004).

(56) References Cited

OTHER PUBLICATIONS

Jarvis et al. "Transient Expression of Firefly Luciferase in Protoplasts of the Green Alga *Chlorella ellipsoidea*," Current Genet., 19: 317-322, (1991).
Jaworski et al., "Industrial oils from transgenic plants," Current Opinion in Plant Biology, 6:178-184, (2003).
Jha et al., "Cloning and functional expression of an acyl-ACP thioesterase FatB type from Diploknema (*Madhuca*) butyracea seeds in *Escherichia coli*," Plant Physiology and Biochemistry, 44:645-655, (2006).
Jiang et al., "The actin gene promoter-driven bar as a dominant selectable marker for nuclear transformation of Dunaliella saline," Yi Chuan Xue Bao, 32(4):424-433, (2005).
Jones et al., "Palmitoyl-Acyl Carrier Protein (ACP) Thioesterase and the Evolutionary Origin of Plant Acyl-ACP Thioesterases," 7:359-371, (1995).
Kalscheuer et al., "Establishment of a Gene Transfer System for Rhodococcus Opacus PD630 Based on Electroporation and its Application for Recombinant Biosynthesis of Poly(3-hyroxyalkanoic acids)," Applied Microbiology and Biotechnology, 52(4):508-515, (1999).
Kamiya, "Effects of Blue Light and Ammonia on Nitrogen Metabolism in a Colorless Mutant of Chlorella," Plant Celll Physiol., 30(4):513-521, (1989).
Kamurthy et al., "Antinocieptive Activity of Stigmosterol-3-Glyceryl-2-Linoleiate, Campesterol and Daucosterol Isolated From Aerva Lanata Linn. Aerial Parts," Asian J Pharm Clin Res, 6(1):149-152, (2013).
Kang et al., "Genetic diversity in chlorella viruses flanking kcv, a gene that encodes a potassium ion channel protein," Virology, 326(1):150-159 (2004).
Kang et al., "The regulation activity of Chlorella virus gene 5' upstream sequence in *Escherichia coli* and eucaryotic alage," Institute of Microbiology, Chinese Academy of Sciences, Beijing, 16(4):443-6, (2000). Abstract only.
Karabulut et al., "Determination of changes in some physical and chemical properties of soybean oil during hydrogenation," Food Chemistry, 81:453-456, (2003).
Karlin et al., "Applications and statistics for multiple high-scoring segments in molecular sequences," Proc Natl Acad Sci, 90(12):5873-5877, (1993).
Katayama et al., "Alpha-Linolenate and Photosynethetic Activity in Chlorella Protothecoides," Plant Physiol., 42:308-313, (1967).
Kawasaki et al., "Characterization of Immediate Early Genes Expressed in Chlorovirus Infections," Nucleic Acids Symp Ser, 44:161-162, (2000).
Kawasaki et al., "Immediate Early Genes Expressed in Chlorovirus Infections," Virology 318(1):214-223, (2004).
Kenyon, "Fatty Acid Composition of Unicellular Strains of Blue-Green Algae," J. Bacteriology 109(2):827-834 (1972).
Kim et al. "Stable Integraion and Functional Expression of Flounder Growth Hormone Gene in Tranformed Microalga, *Chlorella ellipsoidea*," Mar. Biotechnol. 4:63-73 (2002).
Kimchi-Sarfaty et al., "A 'Siient' Polymorphism in the MDR1 Gene Changes Substrate Specificity," Science, 315:525-528, (2007). [Retrieved from the Internet Nov. 1, 2007: <URL: http://www.sciencemag.org>].
Kindle, "High-Frequency Nuclear Transformation of Chlamydomonas reinhardtii," Proc Natl Acad Sci, 87(3):1228-1232, (1990).
Kisselev, "Polypeptide Release Factors in Prokaryotes and Eukaryotes: Same Function, Different Structure," Structure, 10:8-9, (2002).
Klein et al., "High-velocity microprojectiles for delivering nucleic acids into living cells," Nature, 327:70-73, (1987).
Klosty et al., "Sterols of Algae. The Occurrence of Ergosterol in Chiorelia pyrarwidosa," J. Am. Chem. Soc. Notes, 74(6):1601-1601, (1952).
Knauf, "The application of genetic engineering to oilseed crops," Trends in Biotechnology, 5(2):40-47, (1987).
Knothe, "'Designer' Biodiesel: Optimizing Fatty Ester Composition to Improve Fuel Properties," Energy & Fuels, 22:1358-1364, (2008).
Knothe, "Analyzing Biodiesel: Standards and Other Methods," JAOCS, 83(10):823-833, (2006).
Kohler et al., "The green fluorescent protein as a marker to visualize plant mitochondria in vivo," Plant J, 11(3):613-621, (1997).
Koksharova, "Genetic Tools for Cyanobacteria," Appl Microbiol Biotechnol, 58(2):123-37, (2002).
Kong et al., "Microbial production of lipids by cofermentation of glucose and xylose with Lipomyces starkeyi 2#," Chinese Journal of Bioprocess Engineering, 05(02):36, (2007). Abstract.
Krebbers et al., "The maize chloroplast genes for the beta and epsilon subunits of the photosynthetic coupling factor CF1 are fused," Nucleic Acids Res, 10(16): 4985-5002, (1982).
Kris-Etherton et al., "Monounsaturated Fatty Acids and Risk of Cardiovascular Disease," Circulation, 100:1253-1258, (1999).
La Scala et al., "The effect of fatty acid composition on the acrylation kinetics of epoxidized triacylglycerols," Journal of the American Oil Chemists' Society, 79(1):59-63, (2002).
Lapidot et al., "Stable Chloroplast Transformation of the Unicellular Red Alga Porphyridium Species," Plant Physiol, 129:7-12, (2002).
Larson et al., "Acyl CoA profilesof transgenic plants that accumulate medium-chain fatty acids indicate inefficient storage lipid synthesis in developing oilseeds," The Plant Journal, 32(4):519-527, (2002).
Lawford et al., "Performance Testing of Zymomonas Mobilis Metabolically Engeineered for Confermation of Glucose, Xylose, and Arabinose," Appl Biochem Biotechnol., 98-100:429-48, (2002).
Leema et al., "Heterotrophic Production of Lutein and Biomass by Chlorella Vulgaris with Different Nitrogen Sources," Algae Biofuel, Studium Press (India) Pvt. Ltd., pp. 91-101, (2011).
Leon-Banares et al., "Transgenic microalgae as green cell-factories," TRENDS in Biotechnology, 22(1):45-52, (2004).
Levitan et al., "Dual targeting of the protein disulfide isomerase R660 to the chloroplast and the endoplasmic reticulum," Proc Nati Aced Sci, 102(17):6225-6230, (2005).
Li et al., "Broad-spectrum oil-producing yeast carbon filter," China Biotechnology, 25(12):39-44 (2005), and machine translation.
Li et al., "High-density cultivation of oleaginous yeast Rhodosporidium toruloides Y4 in fed-batch culture," Enzyme and Microbial Technology, 41:312-317, (2007).
Lindley, "The impact of food processing antioxidants in vegetable oils, fruits, and vegetables," Trends in Food Science & Technology. 9:336-340, (1998).
List et al., "Melting properties of some structured lipids native to high stearic acid soybean oil," Grasas y Aceites, 55(Fasc. 2):135-137, (2004).
Lu, "Biosynthesis and Gene Engineering of Plant Fatty Acids," Chinese Bulletin of Botany, 17(6):481-491, (2000). Abstract only.
Lubitz, "The Protein Quality, Digestibility, and Composition of Algae, Chlorella 71105," J. Food Sci. 28(2):229-232 (1963).
Lumbreras et al., "Efficient Foreign Gene Expression in Chlamydomonas Reinhardtii Mediated by an Endogenous Intron," Plant Journal, 14(4):441-447, (1998).
Madzak et al., "Functional analysis of upstream regulating regions from Yarrowia lipolytica XPR2 promoter," Microbiology, 145:75-87, (1999).
Manuell et al., "Robust Expression of a bioactive mammalian protein in Chlamydomonas chloroplast," Plant Biotech J, 5(3):402-412, (2007).
Maruyama et al., "Introduction of Foreign DNA Into Chlorella Saccharophila by Electroporation," Biotechnology Techniques, 8:821-826, (1994).
Mayer et al., "A Structural Model of the Plant Acyl-Acyl Carrier Protein Thioesterase FatB Comprises Two Helix/4-Stranded Sheet Domains, the N-terminal Domain Containing Residues That Affect Specificity and the C-terminal Domain Containing Catalytic Residues," The Journal of Biological Chemistry, 280(5):3621-3627, (2005).
Mayer et al., "Identification of amino acid residues involved in substrate specificity of plant acyl-ACP thioesterases using a bioinformatics-guided approach," BMC Plant Biology, 7(1):1-11, (2007).

(56) References Cited

OTHER PUBLICATIONS

Mayfield et al., "Expression and Assembly of a Fully Active Antibody in Algae," Proc Nati Aced Sci, 100(2):438-442, (2003).
Mayfield et al., "Stable nuclear transformation of Chlamydomonas reinhardtii by using a C. reinhardtii gene as the selectable marker," Proc. Natl. Acad. Sci. USA, Cell Biology, 87:2087-2091, (1990).
Meesters et al., "High-cell-density cultivation of the lipid accumulating yeast *Cryptococcus curvatus* using using glycerol as a carbon source," Applied Microbiology and Biotechnology, 45:575-579, (1996).
Meguro et al., "Original Communication Solubilization of phytosterols in diacylglycerol versus triacylglycerol improves the serum cholesterol-lowering effect," European Journal of Clinical Nutrition, 55:513-517, (2001).
Mekhedov et al., "Toward a Functional Catalog of the Plant Genome. A Survey of Genes for Lipid Biosynthesis," Plant Physiology, 122:389-401, (2000).
Mendes et al., "Supercritical Carbon Dioxide Extraction of Compounds With Pharmaceutical Importance from Microalgae," Inorganica Chimica Acta, 356:328-334, (2003).
Menget al., "Biodiesel production from oleaginous microorganisms," Renewable Energy, 34:1-5, (2009).
Metzger et al., "Botryococcus braunii: A Rich Source for Hydrocarbons and Related Ether Lipids," Applied Microbiology and Biotechnology, 66(5):486-496, (2005).
Miao et al., "High Yield Bio-Oil Production from Fast Pyrolysis by Metabolic Controlling of Chlorella Protothecoides," J. Biotech., 110:85-93, (2004).
Minowa et al., "Oil Production from Algal Cells of Dunaliella tertiolecta by Direct Thermochemical Liquefaction," Fuel, 74(12):1735-1738, (1995).
Mitra et al., "A Chlorella Virus Gene Promoter Functions as a Strong Promoter Both in Plants and Bacteria," Biochemical and Biophysical Research Communications, 204(1)189-194, (1994).
Mitra et al., "The Chlorella Virus Adenine Methyltransferase Gene Promoter is a Strong Promoter in Plants," Plant Molecular Biology, 26(1):85-93, (1994).
Moreno-Perez et al., "Reduced expression of FatA thioesterases in Arabidopsis affects the oil content and fatty acid composition of the seeds," Planta, 235:629-639, (2012).
Morris, "Effect of Growth Temperature on the Cryopreservation of Prototheca," Journal of General Microbiology, 94:395-399, (1976).
Mullet et al., "Multiple transcripts for higher plantrbcL andatpB genes and localization of the transcription initiation site of therbcL gene," Plant Molecular Biology, 4(1):39-54, (1985).
Murakami et al., "Lipid Composition of Commercial Bakers' Yeasts Having Different Freeze-tolerance in Frozen Dough," Biosci. Biotechnol. Biochem., 60(11)1874-1876, (1996).
Murakami et al., "Lipids and Fatty Acid Custipvsi lions of Chlorella," Nihon Yuka gakkai-shi, 46(4):423-427, (1997).
Nackley et al., "Human Catechol-O-Methyltransferase Haplotypes Modulate Protein Expression by Altering mRNA Secondary Structure," Science, 314:1930-1933, (2006).[Retrieved from the Internet Nov. 1 , 2007: <URL: http://www.sciencemag.org>].
Nahm, "Quality Characteristics of West African Shea Butter (*Vitellaria paradoxa*) and Approaches to Extend Shelf-Life," Master Thesis, Master of Science in Food Service, Rutgers, The State University of New Jersey, 133 pages, (2011).
Napier et al., "Tailoring plant lipid composition: designer oilseeds come of age," Current Opinion in Plant Biology, 13:330-337, (2010).
Nazaruddin et al., "The Effect of Enzymatic Alcoholysis on the Physicochemical Properties of Commercial Cocoa Butter Substitutes," Pakistan Journal of Nutrition, 10(8):718-723, (2011).
Needleman et al., "A general method applicable to the search for similarities in the amino acid sequence of two proteins," Journal of Molecular Biology, 48(3):443-453, (1970).
Nes et al., "Biosynthesis of Cholesterol and Other Sterols," Chem. Rev., 111:6423-6451, (2011).
Norton et al., "Identification of Ergosta-6(7),8(14),25(27)-trien-3β-ol and Ergosta-5(6),7(8),25(27)-trien-3β-ol, Two New Steroidal Trienes Synthesized by Prototheca wickerhamii," Lipids, 26: 247-249, (1991).
Onai et al., "Natural Tranformation of the Termophillic Cyanbacterium Thermosynechococcus Elongatus BP-1: A Simple and Efficicent Method for Gene Transfer," Mol Genet Genomics, 271(1):50-9, (2004).
Papanikolaou et al., "Single cell oil production by Yarrowia lipolytica growing on an industrial derivative of animal fat in batch cultures," Appl. Microbiol. Biotechnol., 58:308-312, (2002).
Papanikolaou et al., "Lipid production by Yarrowia lipolytica growing on industrial glycerol in a single-stage continuous culture," Bioresource Technology, 82:43-49, (2002).
Park et al., "Isolation and Characterization of Chiorella Virus From Fresh Water in Korea and Application in Chiorella Transformation System," Plant Pathol. J., 21(1):13-20, (2005).
Patil et al., "Fatty acid composition of 12 microalgae for possible use in aquaculture feed," Aquacult Int , 15:1-9, (2007).
Patterson et al., "Sterols of Clorella. II. The Occurrence of an Unusual Sterol Mixture in Chlorella vulgaris," Plant Physiol., 42:1457-I 1459, (1967).
Patterson et al., "Sterols of Chlorella-III. Species Containing Ergosterol," Comp. Biochem. Physiol., 31:391-394, (1969).
PCT International Preliminary Report on Patentability (Chapter I) dated May 31, 2011 for application PCT/US09/066142.
PCT International Preliminary Report on Patentability (Chapter I) dated Aug. 13, 2012 for application PCT/US11/38463.
PCT International Preliminary Report on Patentability (Chapter I) dated Dec. 7, 2009 for application PCT/US08/65563.
PCT International Preliminary Report on Patentability for application PCT/US2011/059224 dated May 16, 2013.
PCT International Search Report and Written Opinion of the International Searching Authority for application PCT/US2013/037261 dated Aug. 23, 2013.
PCT International Search Report and Written Opinion of the International Searching Authority for application PCT/US2014/035476 dated Feb. 18, 2015.
PCT International Search Report and Written Opinion of the International Searching Authority for application PCT/US2014/059161 dated Jun. 1, 2015.
PCT International Search Report and Written Opinion of the International Searching Authority for application PCT/US2015/023181 dated Jul. 28, 2015.
PCT International Search Report for application PCT/US2011/032582 dated Aug. 9, 2011.
PCT International Search Report for application PCT/US2011/038463 dated Jan. 18, 2012.
PCT International Search Report for application PCT/US2011/059224 dated Jun. 27, 2012.
PCT International Search Report for application PCT/US2012/023696 dated May 23, 2012.
PCT International Search Report for application PCT/US2012/036690 dated Aug. 30, 2012.
PCT International Search Report dated Aug. 20, 2010 for application PCT/US2009/066142.
PCT International Search Report dated Nov. 5, 2010 for application PCT/US2009/066141.
PCT International Search Report dated Nov. 6, 2008 for application PCT/US2008/065563.
PCT Invitation to Pay Additional Fees for application PCT/US2014/059161 dated Mar. 9, 2015.
PCT Invitation to Pay Additional Fees from the International Searching Authority for application PCT/US2014/035476 dated Dec. 1, 2014.
PCT Written Opinion of the International Search Authority dated Aug. 20, 2010 for application PCT/US2009/066142.
PCT Written Opinion of the International Searching Authority for application PCT/US2011/032582 dated Aug. 9, 2011.
PCT Written Opinion of the International Searching Authority for application PCT/US2011/038463 dated Jan. 18, 2012.
PCT Written Opinion of the International Searching Authority for application PCT/US2012/023696 dated May 23, 2012.

(56) References Cited

OTHER PUBLICATIONS

PCT Written Opinion of the International Searching Authority for application PCT/US2012/036690 dated Aug. 30, 2012.
PCT Written Opinion of the International Searching Authority dated Nov. 5, 2010 for application PCT/US2009/066141.
PCT Written Opinion of the International Searching Authority dated Nov. 6, 2008 for application PCT/US2008/065563.
Pearson et al., "Improved tools for biological sequence comparison," Proc Nati Acad Sci, 85(8):2444-2448, (1988).
Petkov et al., "Which are fatty acids of the green alga *Chlorella*?," Biochemical Systematics and Ecology, 35:281 (2007).
Phippen et al., "Total seed oil and fatty acid methyl ester contents of Cuphea accessions," Industrial Crops and Products, 24:52-59, (2006).
Powell et al., "Algae Feeding in Humans," J. Nutrition, 75:7-12, (1961).
Pratoomyot et al., "Fatty acids composition of 10 microalgal species," Songklanakarin J. Sci. Technol., 27(6):1179-1187, (2005).
Proschold et al, "Portrait of a Species: *Chlamydomonas reinhardtii*," Genetics, 170(4):1601-1610, (2005).
Puglia et al., "In viva spectrophotometric evaluation of skin barrier recovery after topical application of soybean phytosterols," J. Cosmet. Sci., 59:217-224, (2008).
Qingyu et al., "Fine Cell Structure and Biochemical Compositions of Chlorella Protothecoides after Transferring from Autotrophic to Heterotrophic Metabolism," Journal of Nanjing University, Natural Sciences Edition, 29(4):622-630, (1993). Abstract.
Radakovits et al., "Genetic Engineering of Algae for Enhanced Biofuel Production," Eukaryotic Cell, 9(04): 486-501, (2010).
Radmer et al., "Commercial applications of algae: opportunities and constraints," Journal of Applied Phycology, 6:93-98, (1994).
Randolph-Anderson et al., "Further characterization of the respiratory deficient dum-1 mutation of Chlamydomonas reinhardtii and its use as a recipient for mitochondrial transformation," Mol Gen Genet, 236(2-3):235-244, (1993).
Ratledge, "Regulation of lipid accumulation in oleaginous microorganisms," Biochem Soc Trans., 30(Pt 6):1047-1050, (2002).
Rehm et al., "Heterologous expression of the acyl—acyl carrier protein thioesterase gene from the plant *Umbellularia californica* mediates polyhydroxyalkanoate biosynthesis in recombinant *Escherichia coli*," Appl Microbial Biotechnol, 55:205-209, (2001).
Rismani-Yazdi et al., "Transcriptome sequencing and annotation of the microalgae Dunaliella tertiolecta: Pathway description and gene discovery for production of next-generation biofuels," BMC Genomics, 12:148, 17 pages; doi:10.1186/1471-2164-12-148, (2011).
Roessler et al., "Genetic Engineering Approaches for Enhanced Production of Biodiesel Fuel from Microalgae," Enzymatic Conversion of Biomass for Fuels Production, Chapter 13, American Chemical Society, doi: 10.1021/bk-1994-0566.ch013, pp. 255-270, (1994).
Rosenberg et al., "A Green Light for Engineered Algae: Redirecting Metabolism to Fuel a Biotechnology Revolution," Current Opinion in Biotechnology. Tissue, Cell and Pathyway Engineering, E-Pub 19:430-436, (2008).
Roy et al., "Production of Intracellular Fat by the Yeast *Lipomyces starkeyi*," Indian Journal of Experimental Biology, 16(4):511-512, (1978).
Ruiz et al., "Lipids accumulation in Chlorella protothecoides through mixotrophic and heterotrophic cultures for biodiesel production," New Biotechnology, 255:S266-S266, (2009).
Running et al., "Extracellular production of L-ascorbic acid by Chlorella protothecoides, *Prototheca* species, and mutants of *P. moriformis* during aerobic culturing at low pH," Journal of Industrial Microbiology & Biotechnology, 29:93-98, (2002).
Saha et al., "Transformation in Aspergillus ochraceus," Current Microbioligy, 30(2):83-86, (1995).
Sakuradani, "Studies of Metabolic Engineering of Useful Lipid-producing Microorganisms," NISR Research Grant, (2004).
Sanchez et al., "Mixotrophic culture of Chlorella pyrenoidosa with olive-mill wastewater as the nutrient medium," Journal of Applied Phycology, 13:443-449, (2001).
Sanford, "The biolistic process," Trends in Biotechnology, 6(12):299-302, (1988).
Sauna et al., "Silent Polymorphisms Speak: How They Affect Pharmacogenomics and the Treatment of Cancer," Cancer Res, 67(20):9609-9612 , (2007).
Sawayama et al., "Possibility of renewable energy production and CO2 mitigation by thermochemical liquefaction of microalgae," Biomass and Bioenergy, 17(1):33-39, (1999).
Schreier et al., "The use of nuclear-encoded sequences to direct the light-regulated synthesis and transport of a foreign protein into plant chloroplasts," EMBO J, 4(1):25-32, (1985).
Schultz et al., "A common core of secondary structure of the internal transcribed spacer 2 (ITS2) throughout the Eukaryota," RNA, 11(4):361-364, (2005).
Schutt et al., "The role of acyl carrier protein isoforms from Cuphea lanceolata seeds in the de-novo biosynthesis of medium-chain fatty acids," Publication, Planta, 205:263-268, (1998).
Seffernick et al., "Melamine Deaminase and Atrazine Chlorohydrolase: 98 Percent Identical but Functionally Different," Journal of Bacteriology, 183(8):2405-2410, (2001).
Sen et al., "Developments in Directed Evolution for Improving Enzyme Functions," Appl Biochem Biotechnol, 143:212-223, (2007).
Shao et al., "Cloning and expression of metallothionein mutant α-Kks-α in *Anabaena* sp. PCC 7120," Marine Pollution Bulletin, 45(1012):163-167, (2002).
Shi et al., "High-Yield Production of Lutein by the Green Microalga Chlorella protothecoides in Heterotrophic Fed-Batch Culture," Biotechnol. Prog., 18(4): 723-727 (2002).
Shi et al., "Production and rapid extraction of lutein and the other lipid-soluble pigments from Chlorella protothecoides grown under heterotrophic and mixotrophic conditions," Nahrung, 43:109-113, (1999).
Skolnick et al., "From genes to protein structure and function: novel applications of computational approaches in the genomic era," TIBTECH, 18: 34-39, (2000).
Smallwood et al., "Different Substitutions at Conserved Amino Acids in Domains II and III in the *Sendai* L RNA Polymerase Protein Inactivate Viral RNA Synthesis," Virology, 304:135-145, (2002).
Smith et al., "Comparison of Biosequences," Adv Appl Math, 2(4):482-489, (1981).
Smith et al., "Production of hydroxy fatty acids in the seeds of Arabidopsis thaliana," Biochemical Society Transactions, 28(6):947-950, (2000).
Sorger et al., "Triacylglycerol biosynthesis in yeast," AppL Microbiol Biotechnol, 61:289-299, (2003).
Spolaore et al., "Commercial Applications of Microalgae," J. Biosci. Bioeng. 101(2):87-96 (2006).
Stemmer et al., "Single-Step Assembly of a Gene and Entire Plasmid from Large Numbers of Oligodeoxyribonucleotides," Gene, 164:49-53, (1995).
Sud et al., "Lipid Composition and Sensitivity of Prototecha wickerhamii to Membrane-Active Antimicrobial Agents," Antimicrobial Agents and Chemotherapy, 16:486-490, (1979).
Suda, et al., "Evidence for a novel Chlorella virus-encoded alginate lyase," FEMS Microbiology Letters, 180(1):45-53, (1999).
Suh et al., "What limits production of unusual monenoic fatty acids in transgenic plants?," Planta, 215:584-595, (2002).
Sun et al., "Characterization of two chitinase genes and one chitosanase gene encoded by Chlorella virus PBCV-1," Virology, 263(2):376-387, (1999).
Sung et al., "The research on the lipid content and composition of microalgae and their impact factors," Marine Science, 12(33)122-128, (2009). (English translation of first two pages).
Swern et al. "Fractionation of tallow fatty acids:Preparation of purified oleic acid and an inedible olive oil substitute," Oil & Soap, 22(11):302-304 (1945).

(56) References Cited

OTHER PUBLICATIONS

Szabo et al., "Safety evaluation of a high lipid Whole Algalin Flour (WAF) from Chlorella protothecoides," Regulatory Toxicology and Pharmacology, 63:155-165, (2012).
Szabo et al., "Safety evaluation of Whole Algalin Protein (WAP) from Chlorella protothecoides," Food and Chemical Toxicology, 59:34-45, (2013).
Takaku et al., "Isolation of an Antitumor Compound from Agaricus blazei Murill and Its Mechanism of Action," J. Nutr., 131:1409-1413, (2001). [Retrieved from the Internet May 14, 2013: <URL: http://jn.nutrition.org>].
Takeno et al., "Establishment of an overall transformation system for an oil-producing filamentous fungus, *Mortierella alpine* 1S-4," Appl Microbiol Biotechnol, 65:419-425, (2004).
Talbot et al., "Formulation and Production of Confectionery Fats," OFI Middle East 2007 Conference and Exhibition, 378 pages, (2007).
Talebi et al., "Genetic manipulation, a feasible tool to enhance unique characteristic of Chlarella vulgaris as a feedstock for bio-diesel production," Mol Biol Rep, 40:4421-4428, (2013).
Tan et al., "Establishment of a Micro-Particle Bombardment Transformation System for Dunaliella Salina," J Microbiol.;43(4):361-365, (2005).
Tan et al., "Fatty acid production by heterotrophic Chlorella saccharophila," Hydrobiologia, 215:13-19, (1991).
Tang et al., "Insertion mutagenesis of Chlamydomonas reinhardtii by electroporation and heterologous DNA," Biochem Mol Biol Int, 36(5)1 025-1035, (1995).
Tomasinsig et al., "The Cathelicidins—Structure, Function and Evolution," Current Protein and Peptide Science, 6: 23-34, (2005).
Tornabene et al., "Lipid composition of the nitrogen starved green alga *Neochloris oleoabundans*," Enzyme Microb. Technol., 5:435-440, (1983).
U.S. Appl. No. 12/131,766, Advisory Action dated Oct. 13, 2011.
U.S. Appl. No. 12/131,766, Non-Final Office Action dated Aug. 1, 2011.
U.S. Appl. No. 12/131,766, Non-Final Office Action dated Nov. 23, 2010.
U.S. Appl. No. 12/131,766, Non-Final Office Action dated Dec. 10, 2009.
U.S. Appl. No. 12/131,766, Requirement for Restriction/Election dated Aug. 5, 2009.
U.S. Appl. No. 12/131,766, Requirement for Restriction/Election dated Aug. 17, 2010.
U.S. Appl. No. 12/131,773, Advisory Action dated Jan. 27, 2014.
U.S. Appl. No. 12/131,773, Final Office Action dated Mar. 21, 2011.
U.S. Appl. No. 12/131,773, Final Office Action dated Oct. 15, 2013.
U.S. Appl. No. 12/131,773, Non-Final Office Action dated Jun. 5, 2013.
U.S. Appl. No. 12/131,773, Non-Final Office Action dated Jun. 25, 2010.
U.S. Appl. No. 12/131,773, Non-Final Office Action dated Dec. 15, 2009.
U.S. Appl. No. 12/131,773, Notice of Allowance and Examiner Initiated Interview Summary dated Apr. 1, 2014.
U.S. Appl. No. 12/131,773, Requirement for Restriction/Election dated Aug. 6, 2009.
U.S. Appl. No. 12/131,783, Final Office Action dated Jan. 12, 2012.
U.S. Appl. No. 12/131,783, Final Office Action dated Dec. 13, 2013.
U.S. Appl. No. 12/131,783, Non-Final Office Action dated Jun. 6, 2011.
U.S. Appl. No. 12/131,783, Non-Final Office Action dated Jul. 18, 2013.
U.S. Appl. No. 12/131,783, Notice of Allowance and Examiner Initiated Interview Summary dated Mar. 24, 2014.
U.S. Appl. No. 12/131,783, Requirement for Restriction/Election dated Apr. 19, 2011.
U.S. Appl. No. 12/131,793, Final Office Action dated Mar. 30, 2010.
U.S. Appl. No. 12/131,793, Non-Final Office Action dated Jun. 21, 2012.
U.S. Appl. No. 12/131,793, Non-Final Office Action dated Sep. 16, 2009.
U.S. Appl. No. 12/131,793, Non-Final Office Action dated Nov. 13, 2012.
U.S. Appl. No. 12/131,793, Notice of Allowance dated Apr. 3, 2013.
U.S. Appl. No. 12/131,793, Requirement for Restriction/Election dated Aug. 6, 2009.
U.S. Appl. No. 12/131,804, Final Office Action dated Feb. 2, 2011.
U.S. Appl. No. 12/131,804, Non-Final Office Action dated Oct. 26, 2012.
U.S. Appl. No. 12/131,804, Non-Final Office Action dated Mar. 3, 2010.
U.S. Appl. No. 12/131,804, Non-Final Office Action dated Jun. 7, 2012.
U.S. Appl. No. 12/131,804, Requirement for Restriction/Election dated Sep. 17, 2009.
U.S. Appl. No. 12/131,804, Requirement for Restriction/Election dated Nov. 18, 2009.
U.S. Appl. No. 12/194,389, Final Office Action dated Jan. 5, 2011.
U.S. Appl. No. 12/194,389, Non-Final Office Action dated Feb. 4, 2010.
U.S. Appl. No. 12/194,389, Notice of Allowance dated Jan. 15, 2014.
U.S. Appl. No. 12/194,389, Requirement for Restriction/Election dated Oct. 5, 2010.
U.S. Appl. No. 12/194,389, Requirement for Restriction/Election dated Nov. 2, 2009.
U.S. Appl. No. 12/628,140, Final Office Action dated Mar. 15, 2013.
U.S. Appl. No. 12/628,140, Final Office Action dated May 22, 2014.
U.S. Appl. No. 12/628,140, Final Office Action dated Sep. 12, 2013.
U.S. Appl. No. 12/628,140, Final Office Action dated Oct. 8, 2014.
U.S. Appl. No. 12/628,140, Non-Final Office Action dated Jul. 17, 2015.
U.S. Appl. No. 12/628,140, Non-Final Office Action dated Oct. 30, 2012.
U.S. Appl. No. 12/628,144, Final Office Action dated Nov. 16, 2010.
U.S. Appl. No. 12/628,144, Final Office Action dated Dec. 5, 2011.
U.S. Appl. No. 12/628,144, Final Office Action dated Dec. 12, 2014.
U.S. Appl. No. 12/628,144, Non-Final Office Action dated May 16, 2014.
U.S. Appl. No. 12/628,144, Non-Final Office Action dated Jun. 7, 2011.
U.S. Appl. No. 12/628,144, Non-Final Office Action dated Jul. 8, 2010.
U.S. Appl. No. 12/628,144, Requirement Requirement for Restriction/Election and Examiner Initiated Interview Summary dated Oct. 7, 2014.
U.S. Appl. No. 12/628,147, Examiner Interview Summary Record dated Mar. 3, 2013.
U.S. Appl. No. 12/627,147, Final Office Action dated Jul. 12, 2012.
U.S. Appl. No. 12/627,147, Final Office Action dated Oct. 1, 2010.
U.S. Appl. No. 12/627,147, Non-Final Office Action dated May 25, 2010.
U.S. Appl. No. 12/627,147, Non-Final Office Action dated Oct. 25, 2011.
U.S. Appl. No. 12/627,147, Notice of Allowance and Examiner Intiated Interview Summary dated Aug. 7, 2012.
U.S. Appl. No. 12/627,149, Non-Final Office Action dated Jun. 25, 2010.
U.S. Appl. No. 12/627,149, Non-Final Office Action dated Sep. 16, 2010.
U.S. Appl. No. 12/627,149, Notice of Allowance dated Dec. 15, 2010.
U.S. Appl. No. 12/627,150, Non-Final Office Action dated Apr. 29, 2010.
U.S. Appl. No. 12/627,150, Non-Final Office Action dated Oct. 13, 2010.
U.S. Appl. No. 12/627,150, Notice of Allowance dated Mar. 21, 2011.
U.S. Appl. No. 12/772,163, Non-Final Office Action dated May 25, 2012.
U.S. Appl. No. 12/772,163, Non-Final Office Action dated Dec. 12, 2012.

(56) References Cited

OTHER PUBLICATIONS

U.S. Appl. No. 12/772,163, Notice of Allowance dated May 28, 2013.
U.S. Appl. No. 12/772,163, Requirement for Restriction/Election dated Jun. 24, 2011.
U.S. Appl. No. 12/772,164, Final Office Action dated May 24, 2012.
U.S. Appl. No. 12/772,164, Non-Final Office Action dated Oct. 12, 2011.
U.S. Appl. No. 12/772,164, Requirement for Restriction/Election dated Jul. 20, 2011.
U.S. Appl. No. 12/772,170, Final Office Action dated Feb. 21, 2012.
U.S. Appl. No. 12/772,170, Non-Final Office Action dated Sep. 13, 2012.
U.S. Appl. No. 12/772,170, Non-Final Office Action dated Dec. 17, 2013.
U.S. Appl. No. 12/772,170, Notice of Allowance and Examiner-Initiated Interview Summary dated Jul. 11, 2014.
U.S. Appl. No. 12/772,170, Requirement for Restriction/Election dated Jul. 13, 2011.
U.S. Appl. No. 12/772,173, Final Office Action dated May 7, 2012.
U.S. Appl. No. 12/772,173, Non-Final Office Action dated Dec. 16, 2011.
U.S. Appl. No. 12/772,173, Notice of Allowance dated Mar. 29, 2013.
U.S. Appl. No. 12/772,173, Notice of Allowance dated Jul. 10, 2013.
U.S. Appl. No. 12/772,173, Requirement for Restriction/Election dated Oct. 26, 2011.
U.S. Appl. No. 12/772,174, Non-Final Office Action dated Nov. 29, 2011.
U.S. Appl. No. 12/772,174, Requirement for Restriction/Election dated Aug. 10, 2011.
U.S. Appl. No. 12/960,388, Notice of Allowance dated May 28, 2013.
U.S. Appl. No. 12/960,388, Requirement for Restriction/Election dated Apr. 1, 2013.
U.S. Appl. No. 12/981,409, Non-Final Office Action dated Jan. 6, 2012.
U.S. Appl. No. 12/981,409, Notice of Allowance dated May 29, 2012.
U.S. Appl. No. 12/981,409, Requirement for Restriction/Election dated Apr. 19, 2012.
U.S. Appl. No. 12/981,409, Requirement for Restriction/Election dated Oct. 28, 2011.
U.S. Appl. No. 13/029,061, Requirement for Restriction/Election dated Nov. 29, 2011.
U.S. Appl. No. 13/045,500, Non-Final Office Action dated Mar. 9, 2012.
U.S. Appl. No. 13/045,500, Non-Final Office Action dated Jun. 5, 2014.
U.S. Appl. No. 13/045.500, Final Office Action dated Sep. 26, 2012.
U.S. Appl. No. 13/073,757, Non-Final Office Action dated Aug. 15, 2011.
U.S. Appl. No. 13/073,757, Non-Final Office Action dated Dec. 29, 2011.
U.S. Appl. No. 13/073,757, Notice of Allowance dated Apr. 17, 2012.
U.S. Appl. No. 13/087,311, Final Office Action dated Dec. 16, 2013.
U.S. Appl. No. 13/087,311, Non-Final Office Action dated Apr. 23, 2013.
U.S. Appl. No. 13/087,311, Non-Final Office Action dated Jun. 24, 2014.
U.S. Appl. No. 13/118,365, Final Office Action dated Jul. 22, 2013.
U.S. Appl. No. 13/118,365, Non-Final Office Action dated Feb. 11, 2013.
U.S. Appl. No. 13/118,365, Requirement for Restriction/Election dated Oct. 11, 2012.
U.S. Appl. No. 13/273,179, Non-Final Office Action dated Jan. 28, 2014.
U.S. Appl. No. 13/273,179, Notice of Allowance dated Jul. 11, 2014.
U.S. Appl. No. 13/273,179, Requirement for Restriction/Election dated Nov. 14, 2013.
U.S. Appl. No. 13/288,815, Final Office Action dated Oct. 22, 2014.
U.S. Appl. No. 13/288,815, Non-Final Office Action dated Jun. 18, 2014.
U.S. Appl. No. 13/288,815, Notice of Allowance dated Feb. 26, 2015.
U.S. Appl. No. 13/288,815, Requirement for Restriction/Election dated Jan. 30, 2014.
U.S. Appl. No. 13/365,253, Requirement for Restriction/Election dated Dec. 16, 2014.
U.S. Appl. No. 13/406,417, Non-Final Office Action dated Nov. 5, 2012.
U.S. Appl. No. 13/406,417, Requirement for Restriction/Election dated Apr. 30, 2012.
U.S. Appl. No. 13/464,948, Final Office Action dated Feb. 13, 2014.
U.S. Appl. No. 13/464,948, Non-Final Office Action dated Oct. 9, 2013.
U.S. Appl. No. 13/464,948, Notice of Allowance dated May 25, 2014.
U.S. Appl. No. 13/464,948, Requirement for Restriction/Election dated Aug. 21, 2013.
U.S. Appl. No. 13/479,194, Non-Final Office Action dated Mar. 26, 2014.
U.S. Appl. No. 13/479,200, Non-Final Office Action dated Apr. 10, 2013.
U.S. Appl. No. 13/479,200, Non-Final Office Action dated Sep. 9, 2013.
U.S. Appl. No. 13/479,200, Notice of Allowance dated Nov. 25, 2013.
U.S. Appl. No. 13/479,200, Requirement for Restriction/Election dated Jan. 15, 2013.
U.S. Appl. No. 13/527,480, Final Office Action dated Jan. 16, 2014.
U.S. Appl. No. 13/527,480, Non-Final Office Action dated Jun. 26, 2013.
U.S. Appl. No. 13/527,480, Requirement for Restriction/Election dated May 3, 2013.
U.S. Appl. No. 13/543,666, Non-Final Office Action dated Sep. 5, 2013.
U.S. Appl. No. 13/543,666, Notice of Allowance dated Feb. 10, 2014.
U.S. Appl. No. 13/543,666, Requirement for Restriction/Election dated Jan. 3, 2013.
U.S. Appl. No. 13/547,457, Final Office Action dated Mar. 20, 2014.
U.S. Appl. No. 13/547,457, Non-Final Office Action dated Jul. 8, 2013.
U.S. Appl. No. 13/547,457, Notice of Allowance and Examiner-Initiated Interview Summary dated May 29, 2014.
U.S. Appl. No. 13/550,412, Non-Final Office Action dated Oct. 29, 2012.
U.S. Appl. No. 13/550,412, Notice of Allowance dated Feb. 21, 2013.
U.S. Appl. No. 13/555,009, Notice of Allowance dated Jan. 9, 2015.
U.S. Appl. No. 13/555,009, Requirement for Restriction/Election dated Jun. 16, 2014.
U.S. Appl. No. 13/558,252, Final Office Action dated Jul. 9, 2013.
U.S. Appl. No. 13/558,252, Non-Final Office Action dated Jan. 18, 2013.
U.S. Appl. No. 13/558,252, Notice of Allowance dated Oct. 23, 2013.
U.S. Appl. No. 13/601,928, Non-Final Office Action dated Jan. 31, 2013.
U.S. Appl. No. 13/601,928, Notice of Allowance dated Feb. 26, 2013.
U.S. Appl. No. 13/621,722, Requirement for Restriction/Election dated Jan. 31, 2013.
U.S. Appl. No. 13/621,722, Final Office Action dated Oct. 25, 2013.
U.S. Appl. No. 13/621,722, Non-Final Office Action dated May 9, 2013.
U.S. Appl. No. 13/621,722, Notice of Allowance and Examiner Initiated Interview Summary dated Jan. 10, 2014.

(56) References Cited

OTHER PUBLICATIONS

U.S. Appl. No. 13/628,039, Non-Final Office Action dated Jun. 4, 2013.
U.S. Appl. No. 13/628,039, Notice of Allowance and Examiner-Initiated Interview Summary dated Feb. 20, 2014.
U.S. Appl. No. 13/628,039, Requirement for Restriction/Election dated Mar. 7, 2013.
U.S. Appl. No. 13/630,757, Non-Final Office Action dated Apr. 23, 2015.
U.S. Appl. No. 13/630,757, Non-Final Office Action dated Oct. 27, 2014.
U.S. Appl. No. 13/630,757, Requirement for Restriction/Election dated Jun. 12, 2014.
U.S. Appl. No. 13/650,018, Non-Final Office Action dated Dec. 23, 2013.
U.S. Appl. No. 13/650,018, Notice of Allowance dated Apr. 1, 2015.
U.S. Appl. No. 13/650,018, Notice of Allowance dated Apr. 10, 2015.
U.S. Appl. No. 13/650,018, Notice of Allowance dated Aug. 14, 2014.
U.S. Appl. No. 13/650,018, Requirement for Restriction/Election dated Aug. 22, 2013.
U.S. Appl. No. 13/650,024, Non-Final Office Action dated Jul. 2, 2013.
U.S. Appl. No. 13/650,024, Notice of Allowance dated Oct. 17, 2013.
U.S. Appl. No. 13/804,185, Non-Final Office Action dated Jun. 1, 2015.
U.S. Appl. No. 13/804,185, Requirement for Restriction/Election dated Mar. 16, 2015.
U.S. Appl. No. 13/849,330, Requirement for Restriction/Election dated Jan. 21, 2015.
U.S. Appl. No. 13/852,116, Final Office Action dated Aug. 18, 2014.
U.S. Appl. No. 13/852,116, Non-Final Office Action dated Mar. 26, 2014.
U.S. Appl. No. 13/852,116, Notice of Allowance dated Nov. 7, 2014.
U.S. Appl. No. 13/865,974, Non-Final Office Action dated May 2, 2014.
U.S. Appl. No. 13/865,974, Notice of Allowance dated Oct. 22, 2014.
U.S. Appl. No. 13/865,974, Requirement for Restriction/Election dated Jan. 29, 2014.
U.S. Appl. No. 13/889,214, Non-Final Office Action dated Sep. 18, 2013.
U.S. Appl. No. 13/889,214, Notice of Allowance dated Apr. 28, 2014.
U.S. Appl. No. 13/889,221, Non-Final Office Action dated Sep. 6, 2013.
U.S. Appl. No. 13/889,221, Notice of Allowance dated Apr. 24, 2014.
U.S. Appl. No. 13/941,342, Notice of Allowance dated Jul. 24, 2015.
U.S. Appl. No. 13/941,342, Requirement for Restriction/Election dated Apr. 13, 2015.
U.S. Appl. No. 13/941,346, Final Office Action dated Jun. 26, 2014.
U.S. Appl. No. 13/941,346, Non-Final Office Action dated Jan. 21, 2014.
U.S. Appl. No. 13/941,346, Non-Final Office Action dated Nov. 3, 2014.
U.S. Appl. No. 13/941,346, Notice of Allowance dated Feb. 23, 2015.
U.S. Appl. No. 13/941,353, Requirement for Restriction/Election dated Jan. 16, 2014.
U.S. Appl. No. 13/941,357, Final Office Action dated Nov. 6, 2014.
U.S. Appl. No. 13/941,357, Non-Final Office Action dated Jun. 3, 2014.
U.S. Appl. No. 13/941,357, Notice of Allowance dated Mar. 30, 2015.
U.S. Appl. No. 13/941,357, Requirement for Restriction/Election dated Jan. 7, 2014.
U.S. Appl. No. 14/184,288, Non-Final Office Action dated Sep. 11, 2015.
U.S. Appl. No. 14/184,288, Requirement for Restriction/Election dated Jun. 9, 2015.
U.S. Appl. No. 14/262,070, Non-Final Office Action dated Jul. 10, 2015.
U.S. Appl. No. 14/276,943, Requirement for Restriction/Election dated Jun. 4, 2015.
U.S. Appl. No. 14/285,354, Requirement for Restriction/Election dated Jul. 20, 2015.
U.S. Appl. No. 14/474,244, Final Office Action dated Jul. 30, 2015.
U.S. Appl. No. 14/474,244, Non-Final Office Action dated Apr. 24, 2015.
Ueno et al., "Optimization of heterotrophic culture conditions for n-alkane utilization and phylogenetic position based on the 188 rDNA sequence of a thermotolerant Prototheca zopfii strain," J Biosci Bioeng, 94(2):160-165, (2002). Abstract. [Retrieved from the Internet Dec. 1, 2014: <URL: http://www.ncbi.nlm.nih.gov/pubmed/16233286>].
Urano, et al., "Effect of Osmotic Stabilizers on Protoplast Generation of Chlorella ellipsoidea Yellow/White Color Mutants," Journal of Bioscience and Bioengineering, 90(5):567-569, (2000).
Van Etten et al., "Giant viruses infecting algae," Annu Rev Microbiol, 53:447-494, (1999).
Vazquez-Bermudez et al., "Carbon Supply and 2-Oxoglutarate Effects on Expression of Nitrate Reductase and Nitrogen-Regulated Genes in *Synechococcus* sp. strain PCC 7942," FEMS Microbiology Letters, 221(2)155-159, (2003).
Vazquez-Bermudez et al., "Uptake of 2-Oxoglutarate in Synechococcus Strains Transformed with the *Escherichia coli* kgtP Gene," Journal of Bacteriology, 182(1):211-215, (2000).
Voelker et al., "Alteration of the Specificity and Regulation of Fatty Acid Synthesis of *Escherichia coli* by Expression of a Plant Medium Chain Acyl-Acyl Carrier Protein Thioesterase," Journal of Bacteriology, 176(23):7320-7327, (1994).
Voelker et al., "Broad-Range and Binary-Range Acyl-Acyl-Carrier-Protein Thioesterases Suggest an Alternative Mechanism for Medium-Chain Production in Seeds," Plant Physiol., 114:669-677, (1997).
Voetz et al., "Three Different cDNAs Encoding Acyl Carrier Proteins from Cuphea lanceolate'," Plant Physiol., 106:785-786, (1994).
Volkman et al., "Sterols in microorganisms," Appl Microbial Biotechnol, 60:495-506, (2003).
Walker et al., "Characterization of the Dunaliella tertiolecta RbcS Genes and Their Promoter Activity in Chlamydomonas reinhardtii," Plant Cell Rep, 23(10-11):727-735, (2005).
Wang et al., "Rapid isolation and functional analysis of promoter sequences of the nitrate reductase gene from Chlorella ellipsoidea," J. Appl. Phycol., 16:11-16, (2004).
Warner et al., "Analysis of Tocopherols and Phytosterols in Vegetable Oils by HPLC with Evaporative Light-Scattering Detection," JAOCS, 67(11):827-831 (1990).
Westphal, et al., "Vippl Deletion Mutant of Synechocystis; A Connection Between Bacterial Phage Shock and Thylakoid Biogenesis," Proc Natl Acad Sci U S A., 98(7):4243-4248, (2001).
Whisstock et al., "Prediction of protein function from protein sequence and structure," Quarterly Reviews of Biophysics, 36(3)307-340, (2003).
Wiberg et al., "The distribution of caprylate, caprate and laurate in lipids from developing and mature seeds of transgeni*Brassica napus* L.," Planta, 212:33-40, (2000).
Wirth et al., "Transforamtion of Various Species of Gram-Negitive Bacteria Belonging to 11 Difference Genera by Electroporation," Mol Gen Genet.; 216(1):175-177, (1989).
Wishart et al., "A Single Mutation Converts a Novel Phosphotyrosine Binding Domain into a Dual-specificity Phosphatase," The Journal of Biological Chemistry, 270(45):26782-26785, (1995).

(56) References Cited

OTHER PUBLICATIONS

Witkowski et al., "Conversion of a β-Ketoacyl Synthase to a Malonyl Decarboxylase by Replacement of the Active-Site Cysteine with Glutamine," Biochemistry, 38:11643-11650, (1999).
Wolk et al., "Construction of Shuttle Vectors Capable of Conjugative Transfer From *Escherichia Coli* to Nitrogen-Fixing Filamentous Cyanobacteria," Proc Natl Aced Sci U S A., 81(5):1561-1565, (1984).
Wong et al., "Arabidopsis thaliana small subunit leader and transit peptide enhance the expression of Bacillus thuringiensis proteins in transgenic plants," Plant Mol Biol, 20(1):81-93, (1992).
Wu et al., "A Comparative Study of Gases Generated from Simulant Thermal Degradation of Autotrophic and Heterotrophic Chlorella," Progress in Natural Science, 2(4):311-318, (1992).
Wu et al., "Comparative study on Liposoluble Compounds in Autotrophic and Heterotrophic Chlorella Protothecoides," Acta Botanica Sinica, 35(11):849-858, (1992).
Wu et al., "New Discoveries in Study on Hydrocarbons From Thermal Degradation of Heterotrophically Yellowing Algae," Science in China, 37(3):326-35, (1994).
Xiong et al., "High-density fermentation of microalga Chlorella protothecoides in bioreactor for microbio-diesel production,"Appl. Microbiol. Biotechnol., 78:29-36, (2008).
Yamada et al., "Alternative expression of a chitosanase gene produces two different proteins in cells infected with Chlorella virus CVK2," Virology, 230(2):361-368, (1997).
Yamada et al., "Chlorella viruses," Adv Virus Res, 66:293-336, (2006).
Yu et al., "Modifications of the metabolic pathways of lipid and triacylglycerol production in microalgae," Microbial Cell Factories, 10:91, (2011). [Retrieved from the Internet Jul. 24, 2012: <URL: http://www.microbialcellfactories.com/content/10/1/91>].
Yuan et al., "Modification of the substrate specificity of an acyl-acyl carrier protein thioesterase by protein engineering," Proc. NatL Acad. Sci. USA, Biochemistry, 92:10639-10643, (1995).
Zaidul et al., "Supercritical carbon dioxide (SC-0O2) extraction and fractionation of palm kernel oil from palm kernel as cocoa butter replacers blend," Journal of Food Engineering, 73:210-216, (2006).
Zhang et al., "Malic enzyme: the controlling activity for lipid production? Overexpression of malic enzyme in Mucor circinelloides leads to a 2.5-fold increase in lipid accumulation," Microbiology, 153(7):2013-2025, (2007).
Zhang et al., Geneseq Database, Accession No. AED66345, CN1618976, May 25, 2005.
Zhao et al., "Medium optimization for lipid production through co-fermentation of glucose and xylose by the oleaginous yeast *Lipomyces starkeyi*," Eur. J. Lipid Sci. Technol., 110:405-412, (2008).
Zurawski et al., "Nucleotide sequence of the gene for the Mr 32,000 thylakoid membrane protein from Spinacia oleracea and Nicotania debneyi predicts a totally conserved primary product of Mr 38,950," Proc Natl Acad Sci, 79(24):7699-7703, (1982).
U.S. Appl. No. 14/184,288, Notice of Allowance dated Feb. 3, 2016.
U.S. Appl. No. 15/173,335, Requirement for Restriction/Election dated Jul. 5, 2017.
U.S. Appl. No. 12/628,140, Final Office Action dated Feb. 2, 2016.
U.S. Appl. No. 12/628,140, Non-Final Office Action dated Nov. 21, 2016.
U.S. Appl. No. 12/628,144, Final Office Action dated Mar. 1, 2016.
U.S. Appl. No. 12/628,144, Notice of Allowance dated Jun. 13, 2016.
U.S. Appl. No. 14/285,354, Notice of Allowance dated Feb. 1, 2016.
U.S. Appl. No. 13/555,009, Non-Final Office Action dated Sep. 16, 2014.
U.S. Appl. No. 14/626,505, Requirement for Restriction/Election dated Apr. 26, 2016.
U.S. Appl. No. 14/626,505, Non-Final Office Action dated Jul. 19, 2016.
U.S. Appl. No. 13/118,365, Notice of Allowance dated Sep. 20, 2013.
U.S. Appl. No. 14/276,943, Notice of Allowance dated Sep. 22, 2015.
U.S. Appl. No. 14/975,016, Notice of Allowance dated Jan. 10, 2017.
U.S. Appl. No. 14/975,016, Notice of Allowance dated Jan. 31, 2017.
U.S. Appl. No. 14/975,016, Notice of Allowance dated Feb. 24, 2017.
U.S. Appl. No. 13/118,369, Requirement for Restriction/Election dated Dec. 13, 2012.
U.S. Appl. No. 13/118,369, Non-Final Office Action dated Mar. 28, 2013.
U.S. Appl. No. 13/118,369, Final Office Action dated Mar. 28, 2014.
U.S. Appl. No. 13/630,757, Notice of Allowance dated Oct. 23, 2015.
U.S. Appl. No. 13/630,757, Supplemental Notice of Allowance dated Dec. 3, 2015.
U.S. Appl. No. 13/630,757, Miscellaneous Communication dated Dec. 17, 2015.
U.S. Appl. No. 13/630,757, Notice of Allowance (Supplemental Notice of Allowability) dated Jan. 15, 2016.
U.S. Appl. No. 14/819,117, Requirement for Restriction/Election dated Apr. 11, 2016.
U.S. Appl. No. 14/819,117, Non-Final Office Action dated Nov. 2, 2016.
U.S. Appl. No. 14/819,117, Final Office Action dated Mar. 22, 2017.
U.S. Appl. No. 14/819,117, Notice of Allowance dated Sep. 7, 2017.
U.S. Appl. No. 13/288,815, Requirement for Restriction/Election dated Feb. 11, 2014.
U.S. Appl. No. 14/730,671, Notice of Allowance dated Mar. 21, 2016.
U.S. Appl. No. 13/365,253, Non-Final Office Action dated Mar. 25, 2015.
U.S. Appl. No. 13/365,253, Notice of Allowance dated Sep. 24, 2015.
U.S. Appl. No. 13/365,253, Notice of Allowance (Notice of Allowability) dated Nov. 6, 2015.
U.S. Appl. No. 14/974,983, Requirement for Restriction/Election dated Jul. 28, 2016.
U.S. Appl. No. 14/974,983, Non-Final Office Action dated Dec. 5, 2016.
U.S. Appl. No. 14/974,983, Final Office Action dated Jul. 19, 2017.
U.S. Appl. No. 13/804,185, Final Office Action dated Dec. 11, 2015.
U.S. Appl. No. 13/804,185, Non-Final Office Action dated Jul. 20, 2016.
U.S. Appl. No. 13/804,185, Notice of Allowance dated Jan. 27, 2017.
U.S. Appl. No. 13/941,353, Notice of Allowance dated May 21, 2014.
U.S. Appl. No. 14/474,244, Notice of Allowance dated Sep. 18, 2015.
U.S. Appl. No. 14/975,137, Notice of Allowance dated Sep. 6, 2016.
U.S. Appl. No. 15/369,557, Non-Final Office Action dated Jun. 23, 2017.
U.S. Appl. No. 14/506,491, Requirement for Restriction/Election dated Jan. 19, 2017.
U.S. Appl. No. 14/506,491, Non-Final Office Action dated Jun. 1, 2017.
U.S. Appl. No. 13/087,305, Non-Final Office Action dated Aug. 15, 2012.
U.S. Appl. No. 13/087,305, Final Office Action dated Mar. 18, 2013.
Australian Patent Examination Report No. 1 dated Jan. 23, 2013 issued in AU 2008259834.
Australian Patent Examination Report No. 1 dated May 4, 2015 issued in AU 2013251198.
Canadian Examination Report dated Nov. 30, 2015 issued in Application No. CA 2,689,724.
Chinese First Office Action dated Apr. 23, 2012 issued in Application No. CN 200880100976.9.
Chinese Second Office Action dated Jan. 21, 2013 issued in Application No. CN 200880100976.9.
Chinese Third Office Action dated May 28, 2013 issued in Application No. CN 200880100976.9.

(56) References Cited

OTHER PUBLICATIONS

Chinese Fourth Office Action dated Sep. 11, 2013 issued in Application No. CN 200880100976.9.
Chinese Fifth Office Action dated Jan. 23, 2014 issued in Application No. CN 200880100976.9.
Chinese First Office Action dated May 18, 2016 issued in Application No. CN 201410321130.5.
Columbian Opposition dated Sep. 5, 2011 [Brief Communication dated Sep. 5, 2011 re Application No. EP 06 075 479.3, D50-Declaration of Dr. Matthias Staufenbiel; D51-WO-A-2004/016282; D52-Sturchler-Pierrat et al. Proc Natl. Acad. Sci. USA, 94:13287-13292 (1997)].
European Office Action dated Mar. 9, 2012 issued in Application No. EP 08 769 988.0.
Indonesian first Office Action dated Apr. 13, 2016 issued in Application No. W00200903371.
Indonesian second Office Action dated Aug. 4, 2016 issued in Application No. W00200903371.
Indian Examination Report dated Oct. 4, 2016 issued in Application No. IN 8573/DELNP/2009.
Korean Office Action dated Aug. 25, 2014 [no translation] issued in Application No. KR 10-2009-7027618.
Australian Patent Examination Report No. 1 dated Dec. 9, 2014 issued in AU 2009319722.
Canadian Examination Report dated Oct. 3, 2016 issued in Application No. CA 2,745,129.
Chinese First Office Action dated Apr. 26, 2013 issued in CN 200980155465.1.
Chinese Second Office Action dated Jan. 16, 2014 issued in CN 200980155465.1.
Chinese Third Office Action dated Aug. 28, 2014 issued in CN 200980155465.1.
Chinese Rejection Decision dated Mar. 24, 2015 issued in CN 200980155465.1.
Columbian Office Action dated Feb. 13, 2013 issued in CO 11.080. 882.
Columbian Office Action dated Nov. 24, 2014 issued in CO 11.080. 882.
Columbian Office Action dated Mar. 16, 2015 issued in CO 11.080. 882.
Columbian Office Action dated Mar. 1, 2016 issued in CO 11.080. 882.
European Extended Search Report dated Sep. 12, 2014 issued in EP 09 829 851.6.
European Office Action dated Jun. 25, 2015 issued in EP 09 829 851.6.
European Partial Search Report dated Sep. 12, 2016 issued in EP 16 16 6059.2.
European Extended Search Report dated Dec. 14, 2016 issued in EP 16 16 6059.2.
Israel Office Action dated Sep. 30, 2013 issued in IL 213157.
Japanese Office Action dated Jul. 1, 2016 issued in JP 2011-538719.
Japanese Office Action dated Oct. 31, 2016 issued in JP 2011-538719.
Japanese Office Action [no translation] dated May 9, 2016 issued in JP 2015-126360.
Japanese Final Office Action [no translation] dated Nov. 24, 2016 issued in JP 2015-126360.
Korean Office Action dated Nov. 14, 2015 issued in KR 10-2011-7014923.
Korean Office Action dated Oct. 5, 2016 issued in KR 10-2011-7014923.
Malaysian Examination Report dated Mar. 31, 2016 issued in MY PI2011002435.
Mexican Office Action dated Sep. 21, 2012 issued in MX/a/2010/011065.
Australian Patent Examination Report No. 1 dated Feb. 25, 2014 issued in AU 2009319721.
Australian Patent Examination Report No. 2 dated Oct. 29, 2015 issued in AU 2009319721.
Canadian Office Action dated Dec. 1, 2015 issued in CA 2,745,040.
Chinese First Office Action dated Dec. 23, 2013 issued in CN 200980155463.2.
Chinese Second Office Action dated Oct. 20, 2014 issued in CN 200980155463.2.
Columbian Office Action dated Mar. 21, 2013 issued in CO 11.080. 835.
European Office Action dated Mar. 21, 2016 issued in EP 09 829 850.8.
European Extended Search Report dated May 16, 2016 issued in EP 09 829 850.8.
Israel Office Action dated Apr. 8, 2014 issued in IL 213154.
Israel Office Action dated Jun. 30, 2015 issued in IL 213154.
Israel Office Action dated Sep. 14, 2016 issued in IL 213154.
Japanese Office Action dated May 13, 2014 issued in JP 2011-538718.
Japanese Office Action dated Jun. 1, 2015 issued in JP 2011-538718.
Japanese Office Action dated Oct. 16, 2016 issued in JP 2014-227718.
Japanese Final Office Action [no translation] dated Jul. 13, 2016 issued in JP 2014-227718.
Korean Office Action dated Jan. 4, 2016 issued in KR 10-2011-7014925.
Korean Office Action dated Jul. 18, 2016 issued in KR 10-2011-7014925.
Korean Office Action dated Feb. 23, 2017 issued in KR 10-2011-7014925.
Mexican Office Action [no translation] dated Dec. 6, 2012 issued in MX/a/2011/005630.
Mexican Office Action [no translation] dated May 14, 2013 issued in MX/a/2011/005630.
Australian Patent Examination Report No. 1 dated Jul. 21, 2016 issued in Application No. AU 2011257982.
Canadian Examination Report dated Feb. 23, 2017 issued in Application No. CA 2,801,057.
Chinese First Office Action dated May 29, 2014 issued in Application No. CN 201180036870.9 .
Chinese Second Office Action dated Apr. 15, 2015 issued in Application No. CN201180036870.9.
Chinese Third Office Action dated Nov. 4, 2015 issued in Application No. CN 201180036870.9.
Chinese Rejection Decision dated Apr. 14, 2016 issued in Application No. CN 201180036870.9.
Chinese Notification of Reexamination dated Jan. 26, 2017 issued in Application No. CN 201180036870.9.
European Extended Search Report dated Jun. 9, 2016 issued in Application No. EP 11 787 551.8.
European Office Action dated Jan. 25, 2017 issued in Application No. EP 11 787 551.8.
Japanese Office Action dated Jul. 7, 2015 issued in Application No. JP 2013-512064.
Japanese Office Action dated Dec. 16, 2016 issued in Application No. JP 2016-001030.
Mexican Office Action dated Aug. 11, 2015 issued in Application No. MX/a/2012/013777.
Mexican Office Action dated Jan. 15, 2016 issued in Application No. MX/a/2012/013777.
Malaysian Examination Report dated Sep. 15, 2015 issued in MY PI 2012005117.
PCT International Search Report dated Nov. 3, 2011 issued in PCT/US2011/038464.
PCT Written Opinion of the International Searching Authority dated Nov. 3, 2011 issued in PCT/US2011/038464.
PCT International Preliminary Report on Patentability dated Jun. 28, 2012 issued in PCT/US2011/038464.
Australian Patent Examination Report No. 1 dated Feb. 26, 2015 issued in Application No. AU 2011257983.
Australian Examination Report dated Feb. 1, 2017 issued in Application No. AU 2016202905.
Canadian Examination Report dated May 17, 2017 issued in Application No. CA 2,801,024.
Chinese First Office Action dated Oct. 29, 2013 issued in Application No. CN 201180036696.8.

(56) References Cited

OTHER PUBLICATIONS

Chinese Second Office Action dated Jun. 5, 2014 issued in Application No. CN 201180036696.8.
Chinese Rejection Decision dated Jan. 14, 2015 issued in Application No. CN 201180036696.8.
Chinese Re-examination Decision dated May 26, 2015 issued in Application No. CN 201180036696.8.
Chinese Third Office Action dated Jul. 31, 2015 issued in Application No. CN 201180036696.8.
Chinese Fourth Office Action dated Dec. 30, 2015 issued in Application No. CN 201180036696.8.
European Extended Search Report dated Feb. 19, 2016 issued in Application No. EP 11 787 552.6.
European Office Action dated Oct. 11, 2016 issued in Application No. EP 11 787 552.6.
Japanese Office Action dated Jul. 7, 2015 issued in Application No. JP 2013-512605.
Japanese Final Office Action dated Feb. 29, 2016 issued in Application No. JP 2013-512605.
Japanese Office Action [no translation] dated Jul. 8, 2016 issued in Application No. JP 2013-512605.
Japanese Office Action [no translation] dated Sep. 6, 2016 issued in Application No. JP 2015-199078.
Malaysian Examination Report dated Sep. 15, 2015 issued in Application No. MY PI 2012005120.
Australian Patent Examination Report No. 1 dated Jul. 22, 2015 issued in Application No. AU 2012212079.
Chinese First Office Action dated Apr. 7, 2015 issued in Application No. CN 201280007593.3.
Chinese Second Office Action dated Nov. 17, 2015 issued in Application No. CN 201280007593.3.
Chinese Third Office Action dated Apr. 26, 2016 issued in Application No. CN 201280007593.3.
Chinese Fourth Office Action dated Oct. 17, 2016 issued in Application No. CN 201280007593.3.
Chinese Rejection Decision dated May 26, 2017 issued in Application No. CN 201280007593.3.
European Partial Supplementary Search Report dated May 8, 2015 issued in Application No. EP 12 741 997.6.
European Office Action dated Feb. 6, 2017 issued in Application No. EP 12 741 997.6.
Japanese Office Action dated Jan. 25, 2016 issued in Application No. JP 2013-552645.
Japanese Office Action [no translation] dated Apr. 20, 2016 issued in Application No. JP 2016-145348.
Mexican First Office Action dated Nov. 6, 2015 issued in Application No. MX/a/2013/008651.
Mexican Second Office Action dated Mar. 23, 2016 issued in Application No. MX/a/2013/008651.
Mexican Third Office Action dated Jul. 25, 2016 issued in Application No. MX/a/2013/008651.
Mexican First Office Action dated Apr. 24, 2017 issued in Application No. MX/a/2016/015902.
Malaysia Office Action dated Sep. 30, 2016 issued in Application No. MY PI2013002880.
PCT International Preliminary Report on Patentability dated Oct. 30, 2014 issued in PCT/US2013/037261.
Australian Patent Examination Report No. 1 dated Apr. 20, 2016 issued in Application No. AU 2013249172.
Australian Examination Report No. 2 dated Jan. 25, 2017 issued in Application No. AU 2013249172.
Chinese First Office Action dated Jul. 7, 2016 issued in Application No. CN 201380031877.0.
Chinese Second Office Action dated Mar. 24, 2017 issued in Application No. CN 201380031877.0.
European Supplementary Search Report dated Jan. 25, 2016 issued in Application No. EP 13 778 920.2.
European Examination Report dated Mar. 6, 2017 issued in Application No. EP 13 778 920.2.
Japanese First Office Action dated Mar. 10, 2017 issued in Application No. JP 2015-507197.
Mexican First Office Action dated Jul. 27, 2017 issued in Application No. MX/a/2014/012552.
Singapore Search Report and Written Opinion dated Mar. 24, 2016 issued in Application No. SG 11201406711T.
PCT International Report on Patentability and Written Opinion of the International Searching Authority dated Apr. 5, 2016 issued in PCT/US2014/059161.
Singapore Search Report and Written Opinion dated Aug. 7, 2017 issued in Application No. SG 11201602638S.
PCT Invitation to Pay Additional Fees dated Nov. 20, 2015 issued in PCT/US2015/039951.
PCT International Search Report and Written Opinion of the International Searching Authority dated Jan. 29, 2016 issued in Application No. PCT/US2015/039951.
PCT International Preliminary Report on Patentability and Written Opinion dated Jan. 10, 2017 issued in PCT/US2015/039951.
PCT International Search Report and Written Opinion of the International Searching Authority dated Jan. 3, 2017 issued in PCT/US2016/053979.
PCT International Search Report and Written Opinion of the International Searching Authority dated Jul. 18, 2016 issued in PCT/US2016/026265.
Geneseq: Database Accession No. AXE01814, "Palmitic acid production-related gene, SEQ:20024," XP002750550, Oct. 14, 2010.
Geneseq: Database Accession No. ADJ49365, "Oil-associated gene related protein #865," XP002750551, Jun. 15, 2007.
Blatti, Jillian L. et al. (Jun. 2013) "Engineering fatty acid biosynthesis in microalgae for sustainable biodiesel," *Current Opinion in Chemical Biology*, 17(3):496-505.
Dehesh et al., (2001) "Overexpression of 3-Ketoacyl-Acyl-Carrier Protein Synthase IIIs in Plants Reduces the Rate of Lipid Synthesis," *Plant Physiology*, 125:1103-1114.
Facciotti et al., (May 1998) "Molecular dissection of the plant acyl-acyl carrier protein thioesterases," *Fett/Lipid, Lipid-Weinheim*, 100(4-5), S.:167-172 [<URL:http://www.researchgate.net/publication/247961590>].
Hsieh et al., (2012) "Accumulation of Lipid Production in *Chlorella minutissima* by Triacylglycerol Biosynthesis-Related Genes Cloned from *Saccharomyces cerevisiae and Yarrowia lipolytica*," *The Journal of Microbiology*, 50(3):526-534.
Khozin-Goldberg et al. (2011) "Unravelling algal lipid metabolism: Recent advances in gene identification," *Biochemie*, 93:91-100.
Kosa et al., (Feb. 2011) "Lipids from heterotrophic microbes: advances in metabolism research," *Trends in Biotechnology*, 29(2):53-61.
Leonard et al., (Mar. 1998) A *Cuphea* β-ketoacyl-ACP synthase shifts the synthesis of fatty acids toward shorter chains in *Arabidopsis* seeds expressing *Cuphea* FatB thioesterases, *The Plant Journal*, 13(5):621-628.
Lu et al., (2008) "Overproduction of free fatty acids in *E. coli*: Implications for biodiesel production," *Metabolic Engineering*, 10:333-339.
Pidkowich et al., (Mar. 13, 2007) "Modulating seed β-ketoacyl-acyl carrier protein synthase II level converts the composition of a temperate seed oil to that of a palm-like tropical oil," *PNAS*, 104(11):4742-4747.
Radakovits et al., (2011) "Genetic engineering of fatty acid chain length in *Phaeodactylum tricornutum*," *Metabolic Engineering*, 13:89-95.
Schütt et al., (2002) "β-Ketoacyl-acyl carrier protein synthase IV: a key enzyme for regulation of medium-chain fatty acid synthesis in Cuphea lanceolata seeds," *Planta*, 215:847-854.
U.S. Appl. No. 15/443,209, filed Feb. 27, 2017, Franklin et al.
U.S. Appl. No. 15/173,335, Non-Final Office Action dated Oct. 12, 2017.
U.S. Appl. No. 14/819,117, Supplemental Notice of Allowance dated Nov. 13, 2017.
U.S. Appl. No. 15/179,253, Requirement for Restriction/Election dated Sep. 28, 2017.
U.S. Appl. No. 14/974,983, Non-Final Office Action dated Oct. 26, 2017.

(56) References Cited

OTHER PUBLICATIONS

U.S. Appl. No. 15/369,557, Notice of Allowance dated Oct. 17, 2017.
U.S. Appl. No. 14/506,491, Final Office Action dated Dec. 5, 2017.
U.S. Appl. No. 15/092,538, Requirement for Restriction/Election dated Oct. 6, 2017.
Declaration of Dr. Matthias Staufenbiel, Opposition Document for European Patent No. EP-B-1679080 dated Aug. 2, 2011; Patentee: Janssen Alzheimer Immunotherapy; Opponent: Dr. Alexander Esslinger, 19 pp.
Colombian Office Action dated Jan. 28, 2013 issued in Application No. CO 09149183.
Colombian Office Action dated Jun. 13, 2013 issued in Application No. CO 09149183.
Colombian Office Action dated Sep. 25, 2013 issued in Application No. CO 09149183.
Japanese Notice of Reason for Denial [no translation] dated May 24, 2016 issued in Application No. JP 2016-095504.
Korean Office Action dated Aug. 25, 2014 issued in Application No. KR 10-2009-7027618.
Mexican Office Action dated Oct. 13, 2011 issued in Application No. MX/a/2009/012850.
Mexican First Office Action dated Sep. 30, 2013 issued in Application No. MX/a/2012/000844.
Mexican Second Office Action dated Jan. 22, 2014 issued in Application No. MX/a/2012/000844.
Mexican Third Office Action dated Oct. 13, 2014 issued in Application No. MX/a/2012/000844.
Mexican Fourth Office Action dated Apr. 1, 2015 issued in Application No. MX/a/2012/000844.
Mexican Office Action dated Feb. 23, 2017 issued in Application No. MX/a/2015/008626
Malaysian Examination and Search Report dated Dec. 31, 2013 issued in Application No. PI20095102.
Malaysian Examination and Adverse Report dated Dec. 31, 2014 issued in Application No. PI20095102.
Malaysian Examination and Clear Report dated Jul. 15, 2015 issued in Application No. PI20095102.
Malaysian Examination and Search Report dated May 15, 2017 issued in Application No. PI2014000965.
New Zealand First Examination Report dated Oct. 19, 2010 issued in Application No. NZ 581700.
New Zealand Examination Report dated Sep. 22, 2011 issued in Application No. NZ 581700.
New Zealand Examination Report dated Sep. 8, 2011 issued in Application No. NZ 595029.
New Zealand Examination Report dated Dec. 19, 2012 issued in Application No. NZ 595029.
Philippines Examination Report dated Apr. 7, 2014 issued in Application No. PH 1-2009-502294.
Philippines Examination Report dated Nov. 18, 2014 issued in Application No. PH 1-2009-502294.
Singapore Written Opinion and Search Report dated Apr. 29, 2011 issued in Application No. SG 200907978-1.
Thailand Office Action dated Feb. 22, 2011 issued in Application No. TH 0901005340.
Thailand Office Action dated Jul. 26, 2017 issued in Application No. TH 0901005340.
Australian Patent Examination Report No. 1 dated Jul. 20, 2017 issued in Application No. AU 2016250460.
Canadian Examination Report dated Aug. 18, 2015 issued in Application No. CA 2,745,129.
Canadian Examination Report dated Nov. 16, 2017 issued in Application No. CA 2,745,129.
Chinese Reexamination notification dated Nov. 10, 2016 issued in Application No. CN 200980155465.1.
Chinese Reexamination Decision dated Apr. 27, 2017 issued in Application No. CN 200980155465.1.
Chinese Fourth Office Action dated Sep. 25, 2017 issued in Application No. CN 200980155465.1.
Colombian Office Action dated Jun. 18, 2013 issued in Application No. CO 11.080.882.
Indonesia Substantive Examination Report Stage 1 dated Aug. 5, 2015 issued in Application No. ID W-00 2011 02343.
Japanese Office Action dated May 27, 2014 issued in Application No. JP 2011-538719.
Japanese Final Office Action dated Feb. 24, 2015 issued in Application No. JP 2011-538719.
Japanese Pre-Appeal Examination Report dated Aug. 27, 2015 issued in Application No. JP 2011-538719.
PCT International Search Report dated Nov. 5, 2010 issued in PCT/US2009/066141.
PCT International Preliminary Report on Patentability and Written Opinion dated Oct. 26, 2012 issued in PCT/US2009/066141.
Indonesian Examination Report dated Feb. 22, 2017 issued in Application No. W-00201102342.
Indian Examination Report dated Sep. 1, 2017 issued in Application No. IN 4959/DELNP/2011.
Mexican Office Action [no translation] dated Dec. 9, 2013 issued in Application No. MX/a/2011/005630.
Malaysian Examination Report dated Mar. 15, 2017 issued in Application No. MY PI2011002435.
European Consultation by telephone dated May 29, 2017 issued in Application No. EP 11 787 551.8.
European Office Action dated Aug. 23, 2017 issued in Application No. EP 11 787 551.8.
Indonesian Office Action dated Sep. 21, 2017 issued in Application No. W00201205280.
Korean Office Action dated Nov. 29, 2017 issued in Application No. KR 10-2012-7034232.
Australian Examination Report No. 2 dated Aug. 28, 2017 issued in Application No. AU 2016202905.
Korean Office action [no translation] dated Dec. 11, 2017 issued in Application No. KR 10-2012-7034225.
Mexican Office Action dated Sep. 12, 2017 issued in Application No. MX/a/2012/013756.
Australian Patent Examination Report No. 1 dated May 20, 2015 issued in Application No. AU 2011323288.
Australian Patent Examination Report No. 2 dated Mar. 23, 2016 issued in Application No. AU 2011323288.
Australian Patent Examination Report No. 1 dated Aug. 21, 2017 issued in Application No. AU 2016202999.
Canadian Office Action dated Aug. 8, 2017 issued in Application No. CA 2,816,125.
Chinese First Office Action dated Apr. 15, 2014 issued in Application No. CN 201180053258.2.
Chinese Second Office Action dated Feb. 2, 2015 issued in Application No. CN 201180053258.2.
Chinese Third Office Action dated Jul. 3, 2015 issued in Application No. CN 201180053258.2.
Chinese Fourth Office Action dated Dec. 16, 2015 issued in Application No. CN 201180053258.2.
Chinese Fifth Office Action dated Jun. 6, 2016 issued in Application No. CN 201180053258.2.
Chinese Sixth Office Action (Rejection Decision) dated Nov. 2, 2016 issued in Application No. CN 201180053258.2.
Chinese Notification of Reexamination dated Aug. 31, 2017 issued in Application No. CN 201180053258.2.
European Office Action dated Aug. 15, 2014 issued in Application No. EP 11 785 851.4.
European Office Action dated Apr. 11, 2017 issued in Application No. EP 11 785 851.4.
Japanese Office Action dated Oct. 21, 2015 issued in Application No. JP 2013537836.
Japanese Office Action dated Feb. 12, 2016 issued in Application No. JP 2013537836.
Japanese Office Action dated Apr. 3, 2017 issued in Application No. JP 2016-009933.
Mexican First Office Action dated Jul. 19, 2016 issued in Application No. MX/a/2013/004631.
Mexican Second Office Action dated Jan. 16, 2017 issued in Application No. MX/a/2013/004631.

(56) References Cited

OTHER PUBLICATIONS

Mexican Third Office Action dated May 10, 2017 issued in Application No. MX/a/2013/004631.
Mexican Fourth Office Action dated Jul. 18, 2017 issued in Application No. MX/a/2013/004631.
Malaysian Examination Report dated May 31, 2016 issued in Application No. MY PI2013001587.
Canadian Examination Report dated Nov. 22, 2017 issued in Application No. CA 2,825,691.
European Examination Report dated Oct. 10, 2017 issued in Application No. EP 12 741 997.6.
Japanese Office Action dated Dec. 1, 2017 issued in Application No. JP 2016-145348.
Chinese Rejection Decision dated Oct. 10, 2017 issued in Application No. CN 201380031877.0.
PCT International Preliminary Report on Patentability and Written Opinion of the International Searching Authority dated Oct. 19, 2017 issued in PCT/US2016/026265.
GenBank Accession No. M94159.1 "California Bay Tree thioesterase mRNA, complete cds", (Apr. 27, 1993), 2pp.
GenBank: U31813 "Cinnamomum camphora acyl-ACP thioesterase mRNA, complete cds," Jan. 31, 1996, 2pp.
Abbadi et al., (2000) "Knockout of the regulatory site of 3-ketoacyl-ACP synthase III enhances short- and medium-chain acyl-ACP synthesis," *The Plant Journal*, 24(1): 1-9.
Blatti, Jillian L. et al., (Sep. 2012) "Manipulating Fatty Acid Biosynthesis in Microalgae for Biofuel through Protein-Protein Interactions," *PLoS ONE*, 7(9):e42949, 12 pp.
Chen et al., (2011) "Structural classification and properties of ketoacyl synthases," *Protein Science*, 20(10):1659-1667.
Gimpel et al., (Dec. 15, 2015) "In Metabolic Engineering of Eukaryotic Microalgae: Potential and Challenges Come with Great Diversity," *Metabolic Engineering of Eukaryotic Microalgae, Frontiers in Microbiology*, 6(Article 1376):14pp.
Snyder et al., (2009) "Acyltransferase action in the modification of seed oil biosynthesis," *New Biotechnology*, 26(1/2):11-16.
U.S. Appl. No. 15/725,222, filed Oct. 4, 2017, Moseley et al.

* cited by examiner

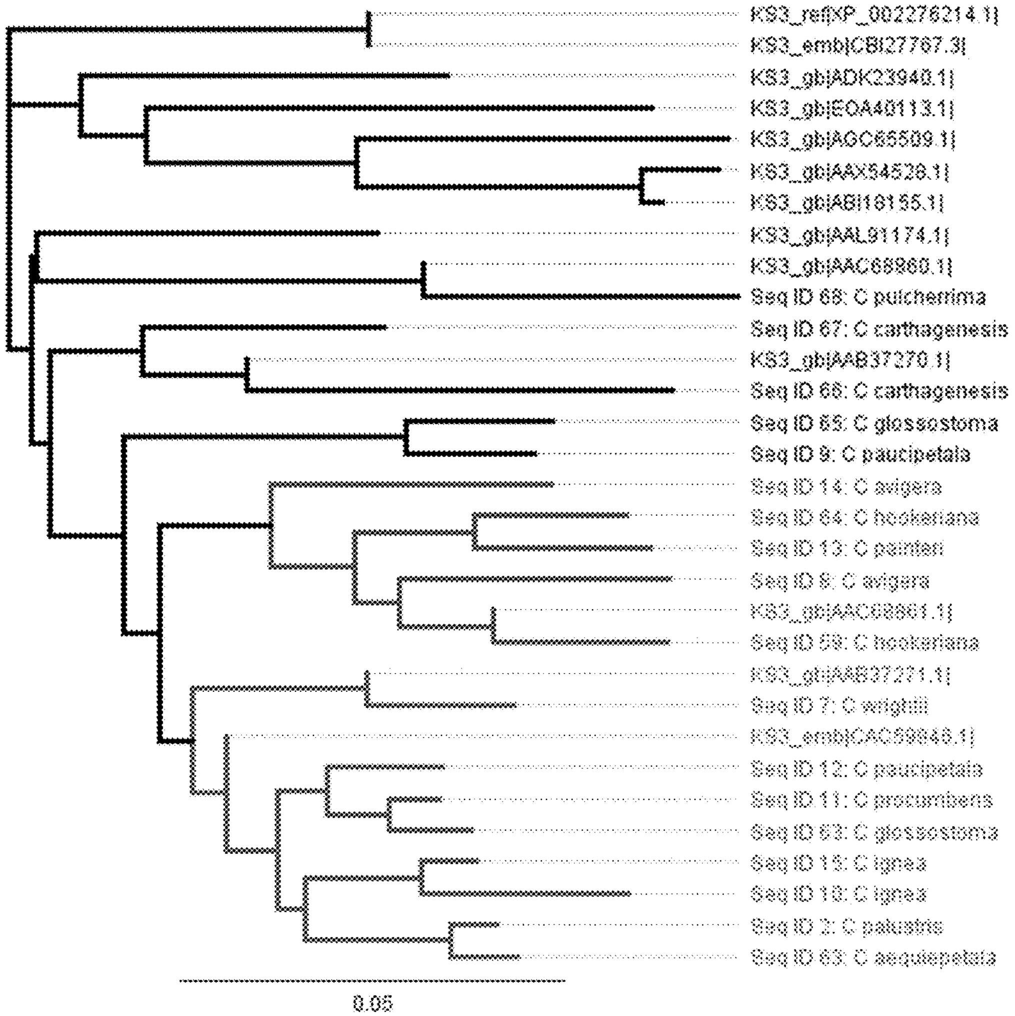
KS3_ref|XP_002276214.1|
KS3_emb|CBI27767.3|
KS3_gb|ADK23940.1|
KS3_gb|EOA40113.1|
KS3_gb|AGC65509.1|
KS3_gb|AAX54526.1|
KS3_gb|ABI18155.1|
KS3_gb|AAL91174.1|
KS3_gb|AAC68860.1|
Seq ID 68: C pulcherrima
Seq ID 67: C carthagenesis
KS3_gb|AAB37270.1|
Seq ID 66: C carthagenesis
Seq ID 65: C glossostoma
Seq ID 9: C paucipetala
Seq ID 14: C avigera
Seq ID 64: C hookeriana
Seq ID 13: C painteri
Seq ID 8: C avigera
KS3_gb|AAC68861.1|
Seq ID 59: C hookeriana
KS3_gb|AAB37271.1|
Seq ID 7: C wrightii
KS3_emb|CAC59848.1|
Seq ID 12: C paucipetala
Seq ID 11: C procumbens
Seq ID 63: C glossostoma
Seq ID 15: C lignea
Seq ID 10: C lignea
Seq ID 2: C palustris
Seq ID 63: C aequipetala
0.05

SEQUENCE LISTING

<160> NUMBER OF SEQ ID NOS: 72

<210> SEQ ID NO 1
<211> LENGTH: 411
<212> TYPE: PRT
<213> ORGANISM: Cuphea palustris
<220> FEATURE:
<221> NAME/KEY: MISC_FEATURE
<223> OTHER INFORMATION: FATB2

<400> SEQUENCE: 1

```
Met Val Ala Ala Ala Ala Ser Ala Ala Phe Phe Ser Val Ala Thr Pro
1               5                   10                  15

Arg Thr Asn Ile Ser Pro Ser Ser Leu Ser Val Pro Phe Lys Pro Lys
            20                  25                  30

Ser Asn His Asn Gly Gly Phe Gln Val Lys Ala Asn Ala Ser Ala His
        35                  40                  45

Pro Lys Ala Asn Gly Ser Ala Val Ser Leu Lys Ser Gly Ser Leu Glu
    50                  55                  60

Thr Gln Glu Asp Lys Thr Ser Ser Ser Ser Pro Pro Pro Arg Thr Phe
65                  70                  75                  80

Ile Asn Gln Leu Pro Val Trp Ser Met Leu Leu Ser Ala Val Thr Thr
                85                  90                  95

Val Phe Gly Val Ala Glu Lys Gln Trp Pro Met Leu Asp Arg Lys Ser
            100                 105                 110

Lys Arg Pro Asp Met Leu Val Glu Pro Leu Gly Val Asp Arg Ile Val
        115                 120                 125

Tyr Asp Gly Val Ser Phe Arg Gln Ser Phe Ser Ile Arg Ser Tyr Glu
    130                 135                 140

Ile Gly Ala Asp Arg Thr Ala Ser Ile Glu Thr Leu Met Asn Met Phe
145                 150                 155                 160

Gln Glu Thr Ser Leu Asn His Cys Lys Ile Ile Gly Leu Leu Asn Asp
                165                 170                 175

Gly Phe Gly Arg Thr Pro Glu Met Cys Lys Arg Asp Leu Ile Trp Val
            180                 185                 190

Val Thr Lys Met Gln Ile Glu Val Asn Arg Tyr Pro Thr Trp Gly Asp
```

-continued

```
        195                 200                 205

Thr Ile Glu Val Asn Thr Trp Val Ser Ala Ser Gly Lys His Gly Met
    210                 215                 220

Gly Arg Asp Trp Leu Ile Ser Asp Cys His Thr Gly Glu Ile Leu Ile
225                 230                 235                 240

Arg Ala Thr Ser Val Trp Ala Met Met Asn Gln Lys Thr Arg Arg Leu
                245                 250                 255

Ser Lys Ile Pro Tyr Glu Val Arg Gln Glu Ile Glu Pro Gln Phe Val
            260                 265                 270

Asp Ser Ala Pro Val Ile Val Asp Asp Arg Lys Phe His Lys Leu Asp
        275                 280                 285

Leu Lys Thr Gly Asp Ser Ile Cys Asn Gly Leu Thr Pro Arg Trp Thr
    290                 295                 300

Asp Leu Asp Val Asn Gln His Val Asn Asn Val Lys Tyr Ile Gly Trp
305                 310                 315                 320

Ile Leu Gln Ser Val Pro Thr Glu Val Phe Glu Thr Gln Glu Leu Cys
                325                 330                 335

Gly Leu Thr Leu Glu Tyr Arg Arg Glu Cys Gly Arg Asp Ser Val Leu
            340                 345                 350

Glu Ser Val Thr Ala Met Asp Pro Ser Lys Glu Gly Asp Arg Ser Leu
        355                 360                 365

Tyr Gln His Leu Leu Arg Leu Glu Asp Gly Ala Asp Ile Val Lys Gly
    370                 375                 380

Arg Thr Glu Trp Arg Pro Lys Asn Ala Gly Ala Lys Gly Ala Ile Leu
385                 390                 395                 400

Thr Gly Lys Thr Ser Asn Gly Asn Ser Ile Ser
                405                 410
```

<210> SEQ ID NO 2
<211> LENGTH: 525
<212> TYPE: PRT
<213> ORGANISM: Cuphea palustris
<220> FEATURE:
<221> NAME/KEY: MISC_FEATURE
<223> OTHER INFORMATION: KASIV

<400> SEQUENCE: 2

```
Met Ala Ser Ala Ala Phe Thr Met Ser Ala Cys Pro Ala Met Thr Gly
1               5                   10                  15

Arg Ala Pro Gly Ala Arg Arg Ser Gly Arg Pro Val Ala Thr Arg Leu
            20                  25                  30

Arg Gly Ser Thr Phe Gln Cys Leu Val Thr Ser Tyr Ile Asp Pro Cys
        35                  40                  45

Asn Gln Phe Ser Ser Ser Ala Ser Leu Ser Phe Leu Gly Asp Asn Gly
    50                  55                  60

Phe Ala Ser Leu Phe Gly Ser Lys Pro Phe Arg Ser Asn Arg Gly His
65                  70                  75                  80

Arg Arg Leu Gly Arg Ala Ser His Ser Gly Glu Ala Met Ala Val Ala
                85                  90                  95

Leu Glu Pro Ala Gln Glu Val Ala Thr Lys Lys Lys Pro Leu Val Lys
            100                 105                 110

Gln Arg Arg Val Val Val Thr Gly Met Gly Val Val Thr Pro Leu Gly
        115                 120                 125

His Glu Pro Asp Val Tyr Tyr Asn Asn Leu Leu Asp Gly Val Ser Gly
    130                 135                 140
```

-continued

```
Ile Ser Glu Ile Glu Ala Phe Asp Cys Thr Gln Phe Pro Thr Arg Ile
145                 150                 155                 160

Ala Gly Glu Ile Lys Ser Phe Ser Thr Asp Gly Trp Val Ala Pro Lys
                165                 170                 175

Leu Ser Lys Arg Met Asp Lys Phe Met Leu Tyr Leu Leu Thr Ala Gly
            180                 185                 190

Lys Lys Ala Leu Ala Asp Gly Gly Ile Thr Asp Asp Val Met Lys Glu
        195                 200                 205

Leu Asp Lys Arg Lys Cys Gly Val Leu Ile Gly Ser Gly Leu Gly Gly
    210                 215                 220

Met Lys Leu Phe Ser Asp Ser Ile Glu Ala Leu Arg Ile Ser Tyr Lys
225                 230                 235                 240

Lys Met Asn Pro Phe Cys Val Pro Phe Ala Thr Thr Asn Met Gly Ser
                245                 250                 255

Ala Met Leu Ala Met Asp Leu Gly Trp Met Gly Pro Asn Tyr Ser Ile
            260                 265                 270

Ser Thr Ala Cys Ala Thr Ser Asn Phe Cys Ile Leu Asn Ser Ala Asn
        275                 280                 285

His Ile Val Arg Gly Glu Ala Asp Met Met Leu Cys Gly Gly Ser Asp
    290                 295                 300

Ala Val Ile Ile Pro Ile Gly Leu Gly Gly Phe Val Ala Cys Arg Ala
305                 310                 315                 320

Leu Ser Gln Arg Asn Asn Asp Pro Thr Lys Ala Ser Arg Pro Trp Asp
                325                 330                 335

Ser Asn Arg Asp Gly Phe Val Met Gly Glu Gly Ala Gly Val Leu Leu
            340                 345                 350

Leu Glu Glu Leu Glu His Ala Lys Lys Arg Gly Ala Thr Ile Tyr Ala
        355                 360                 365

Glu Phe Leu Gly Gly Ser Phe Thr Cys Asp Ala Tyr His Met Thr Glu
    370                 375                 380

Pro His Pro Glu Gly Ala Gly Val Ile Leu Cys Ile Glu Lys Ala Leu
385                 390                 395                 400

Ala Gln Ala Gly Val Ser Arg Glu Asp Val Asn Tyr Ile Asn Ala His
                405                 410                 415

Ala Thr Ser Thr Pro Ala Gly Asp Ile Lys Glu Tyr Gln Ala Leu Ala
            420                 425                 430

His Cys Phe Gly Gln Asn Ser Glu Leu Arg Val Asn Ser Thr Lys Ser
        435                 440                 445

Met Ile Gly His Leu Ile Gly Ala Ala Gly Gly Val Glu Ala Val Thr
    450                 455                 460

Val Val Gln Ala Ile Arg Thr Gly Trp Ile His Pro Asn Leu Asn Leu
465                 470                 475                 480

Glu Asp Pro Asp Lys Ala Val Asp Ala Lys Val Leu Val Gly Pro Lys
                485                 490                 495

Lys Glu Arg Leu Asn Val Lys Val Gly Leu Ser Asn Ser Phe Gly Phe
            500                 505                 510

Gly Gly His Asn Ser Ser Ile Leu Phe Ala Pro Tyr Asn
        515                 520                 525
```

<210> SEQ ID NO 3
<211> LENGTH: 492
<212> TYPE: PRT
<213> ORGANISM: Cinnamonum camphora
<220> FEATURE:
<221> NAME/KEY: MISC_FEATURE

<223> OTHER INFORMATION: KASIV

<400> SEQUENCE: 3

Met Ala Met Met Ala Gly Ser Cys Ser Asn Leu Val Ile Gly Asn Arg
1 5 10 15

Glu Leu Gly Gly Asn Gly Pro Ser Leu Leu His Tyr Asn Gly Leu Arg
20 25 30

Pro Leu Glu Asn Ile Gln Thr Ala Ser Ala Val Lys Lys Pro Asn Gly
35 40 45

Leu Phe Ala Ser Ser Thr Ala Arg Lys Ser Lys Ala Val Arg Ala Met
50 55 60

Val Leu Pro Thr Val Thr Ala Pro Lys Arg Glu Lys Asp Pro Lys Lys
65 70 75 80

Arg Ile Val Ile Thr Gly Met Gly Leu Val Ser Val Phe Gly Asn Asp
85 90 95

Ile Asp Thr Phe Tyr Ser Lys Leu Leu Glu Gly Glu Ser Gly Ile Gly
100 105 110

Pro Ile Asp Arg Phe Asp Ala Ser Ser Phe Ser Val Arg Phe Ala Gly
115 120 125

Gln Ile His Asn Phe Ser Ser Lys Gly Tyr Ile Asp Gly Lys Asn Asp
130 135 140

Arg Arg Leu Asp Asp Cys Trp Arg Tyr Cys Leu Val Ala Gly Arg Arg
145 150 155 160

Ala Leu Glu Asp Ala Asn Leu Gly Pro Glu Val Leu Glu Lys Met Asp
165 170 175

Arg Ser Arg Ile Gly Val Leu Ile Gly Thr Gly Met Gly Gly Leu Ser
180 185 190

Ala Phe Ser Asn Gly Val Glu Ser Leu Ile Gln Lys Gly Tyr Lys Lys
195 200 205

Ile Thr Pro Phe Phe Ile Pro Tyr Ser Ile Thr Asn Met Gly Ser Ala
210 215 220

Leu Leu Ala Ile Asp Thr Gly Val Met Gly Pro Asn Tyr Ser Ile Ser
225 230 235 240

Thr Ala Cys Ala Thr Ala Asn Tyr Cys Phe His Ala Ala Ala Asn His
245 250 255

Ile Arg Arg Gly Glu Ala Glu Ile Met Val Thr Gly Gly Thr Glu Ala
260 265 270

Ala Val Ser Ala Thr Gly Val Gly Gly Phe Ile Ala Cys Arg Ala Leu
275 280 285

Ser His Arg Asn Asp Glu Pro Gln Thr Ala Ser Arg Pro Trp Asp Lys
290 295 300

Asp Arg Asp Gly Phe Val Met Gly Glu Gly Ala Gly Val Leu Val Met
305 310 315 320

Glu Ser Leu His His Ala Arg Lys Arg Gly Ala Asn Ile Ile Ala Glu
325 330 335

Tyr Leu Gly Gly Ala Val Thr Cys Asp Ala His His Met Thr Asp Pro
340 345 350

Arg Ala Asp Gly Leu Gly Val Ser Ser Cys Ile Thr Lys Ser Leu Glu
355 360 365

Asp Ala Gly Val Ser Pro Glu Glu Val Asn Tyr Val Asn Ala His Ala
370 375 380

Thr Ser Thr Leu Ala Gly Asp Leu Ala Glu Val Asn Ala Ile Lys Lys
385 390 395 400

```
Val Phe Lys Asp Thr Ser Glu Met Lys Met Asn Gly Thr Lys Ser Met
                405                 410                 415

Ile Gly His Cys Leu Gly Ala Ala Gly Gly Leu Glu Ala Ile Ala Thr
            420                 425                 430

Ile Lys Ala Ile Asn Thr Gly Trp Leu His Pro Thr Ile Asn Gln Phe
        435                 440                 445

Asn Ile Glu Pro Ala Val Thr Ile Asp Thr Val Pro Asn Val Lys Lys
    450                 455                 460

Lys His Asp Ile His Val Gly Ile Ser Asn Ser Phe Gly Phe Gly Gly
465                 470                 475                 480

His Asn Ser Val Val Val Phe Ala Pro Phe Met Pro
                485                 490


<210> SEQ ID NO 4
<211> LENGTH: 482
<212> TYPE: PRT
<213> ORGANISM: Cinnamonum camphora
<220> FEATURE:
<221> NAME/KEY: MISC_FEATURE
<223> OTHER INFORMATION: KASI

<400> SEQUENCE: 4

Met Gln Ile Leu Gln Thr Pro Ser Ser Ser Ser Ser Ser Leu Arg Met
1               5                   10                  15

Ser Ser Met Glu Ser Leu Ser Leu Thr Pro Lys Ser Leu Pro Leu Lys
            20                  25                  30

Thr Leu Leu Pro Leu Arg Pro Arg Pro Lys Asn Leu Ser Arg Arg Lys
        35                  40                  45

Ser Gln Asn Pro Arg Pro Ile Ser Ser Ser Ser Ser Pro Glu Arg Glu
    50                  55                  60

Thr Asp Pro Lys Lys Arg Val Val Ile Thr Gly Met Gly Leu Val Ser
65                  70                  75                  80

Val Phe Gly Asn Asp Val Asp Ala Tyr Tyr Asp Arg Leu Leu Ser Gly
                85                  90                  95

Glu Ser Gly Ile Ala Pro Ile Asp Arg Phe Asp Ala Ser Lys Phe Pro
            100                 105                 110

Thr Arg Phe Ala Gly Gln Ile Arg Gly Phe Thr Ser Asp Gly Tyr Ile
        115                 120                 125

Asp Gly Lys Asn Asp Arg Arg Leu Asp Asp Cys Leu Arg Tyr Cys Ile
    130                 135                 140

Val Ser Gly Lys Lys Ala Leu Glu Asn Ala Gly Leu Gly Pro His Leu
145                 150                 155                 160

Met Asp Gly Lys Ile Asp Lys Glu Arg Ala Gly Val Leu Val Gly Thr
                165                 170                 175

Gly Met Gly Gly Leu Thr Val Phe Ser Asn Gly Val Gln Thr Leu His
            180                 185                 190

Glu Lys Gly Tyr Arg Lys Met Thr Pro Phe Phe Ile Pro Tyr Ala Ile
        195                 200                 205

Thr Asn Met Gly Ser Ala Leu Leu Ala Ile Glu Leu Gly Phe Met Gly
    210                 215                 220

Pro Asn Tyr Ser Ile Ser Thr Ala Cys Ala Thr Ser Asn Tyr Cys Phe
225                 230                 235                 240

Tyr Ala Ala Ala Asn His Ile Arg Arg Gly Glu Ala Asp Leu Met Leu
                245                 250                 255

Ala Gly Gly Thr Glu Ala Ala Ile Ile Pro Ile Gly Leu Gly Gly Phe
            260                 265                 270
```

Val Ala Cys Arg Ala Leu Ser Gln Arg Asn Asp Asp Pro Gln Thr Ala
275 280 285

Ser Arg Pro Trp Asp Lys Asp Arg Asp Gly Phe Val Met Gly Glu Gly
290 295 300

Ala Gly Val Leu Val Met Glu Ser Leu Glu His Ala Met Lys Arg Asp
305 310 315 320

Ala Pro Ile Ile Ala Glu Tyr Leu Gly Gly Ala Val Asn Cys Asp Ala
325 330 335

Tyr His Met Thr Asp Pro Arg Ala Asp Gly Leu Gly Val Ser Thr Cys
340 345 350

Ile Glu Arg Ser Leu Glu Asp Ala Gly Val Ala Pro Glu Glu Val Asn
355 360 365

Tyr Ile Asn Ala His Ala Thr Ser Thr Leu Ala Gly Asp Leu Ala Glu
370 375 380

Val Asn Ala Ile Lys Lys Val Phe Thr Asn Thr Ser Glu Ile Lys Ile
385 390 395 400

Asn Ala Thr Lys Ser Met Ile Gly His Cys Leu Gly Ala Ala Gly Gly
405 410 415

Leu Glu Ala Ile Ala Thr Ile Lys Ala Ile Asn Thr Gly Trp Leu His
420 425 430

Pro Ser Ile Asn Gln Phe Asn Pro Glu Pro Ser Val Glu Phe Asp Thr
435 440 445

Val Ala Asn Lys Lys Gln Gln His Glu Val Asn Val Ala Ile Ser Asn
450 455 460

Ser Phe Gly Phe Gly Gly His Asn Ser Val Val Val Phe Ser Ala Phe
465 470 475 480

Lys Pro

<210> SEQ ID NO 5
<211> LENGTH: 464
<212> TYPE: PRT
<213> ORGANISM: Umbellularia californica
<220> FEATURE:
<221> NAME/KEY: MISC_FEATURE
<223> OTHER INFORMATION: KASI

<400> SEQUENCE: 5

Met Glu Ser Leu Ser Leu Thr Pro Lys Ser Leu Pro Leu Lys Thr Leu
1 5 10 15

Leu Pro Phe Arg Pro Arg Pro Lys Asn Leu Ser Arg Arg Lys Ser Gln
20 25 30

Asn Pro Lys Pro Ile Ser Ser Ser Ser Ser Pro Glu Arg Glu Thr Asp
35 40 45

Pro Lys Lys Arg Val Val Ile Thr Gly Met Gly Leu Val Ser Val Phe
50 55 60

Gly Asn Asp Val Asp Ala Tyr Tyr Asp Arg Leu Leu Ser Gly Glu Ser
65 70 75 80

Gly Ile Ala Pro Ile Asp Arg Phe Asp Ala Ser Lys Phe Pro Thr Arg
85 90 95

Phe Ala Gly Gln Ile Arg Gly Phe Thr Ser Asp Gly Tyr Ile Asp Gly
100 105 110

Lys Asn Asp Arg Arg Leu Asp Asp Cys Leu Arg Tyr Cys Ile Val Ser
115 120 125

Gly Lys Lys Ala Leu Glu Asn Ala Gly Leu Gly Pro Asp Leu Met Asp
130 135 140

```
Gly Lys Ile Asp Lys Glu Arg Ala Gly Val Leu Val Gly Thr Gly Met
145                 150                 155                 160

Gly Gly Leu Thr Val Phe Ser Asn Gly Val Gln Thr Leu His Glu Lys
                165                 170                 175

Gly Tyr Arg Lys Met Thr Pro Phe Phe Ile Pro Tyr Ala Ile Thr Asn
            180                 185                 190

Met Gly Ser Ala Leu Leu Ala Ile Asp Leu Gly Phe Met Gly Pro Asn
        195                 200                 205

Tyr Ser Ile Ser Thr Ala Cys Ala Thr Ser Asn Tyr Cys Phe Tyr Ala
    210                 215                 220

Ala Ala Asn His Ile Arg Arg Gly Glu Ala Asp Val Met Leu Ala Gly
225                 230                 235                 240

Gly Thr Glu Ala Ala Ile Ile Pro Ile Gly Leu Gly Gly Phe Val Ala
                245                 250                 255

Cys Arg Ala Leu Ser Gln Arg Asn Asp Asp Pro Gln Thr Ala Ser Arg
            260                 265                 270

Pro Trp Asp Lys Asp Arg Asp Gly Phe Val Met Gly Glu Gly Ala Gly
        275                 280                 285

Val Leu Val Met Glu Ser Leu Glu His Ala Met Lys Arg Asp Ala Pro
    290                 295                 300

Ile Ile Ala Glu Tyr Leu Gly Gly Ala Val Asn Cys Asp Ala Tyr His
305                 310                 315                 320

Met Thr Asp Pro Arg Ala Asp Gly Leu Gly Val Ser Thr Cys Ile Glu
                325                 330                 335

Arg Ser Leu Glu Asp Ala Gly Val Ala Pro Glu Glu Val Asn Tyr Ile
            340                 345                 350

Asn Ala His Ala Thr Ser Thr Leu Ala Gly Asp Leu Ala Glu Val Asn
        355                 360                 365

Ala Ile Lys Lys Val Phe Thr Asn Thr Ser Glu Ile Lys Ile Asn Ala
    370                 375                 380

Thr Lys Ser Met Ile Gly His Cys Leu Gly Ala Ala Gly Gly Leu Glu
385                 390                 395                 400

Ala Ile Ala Thr Ile Lys Ala Ile Asn Thr Gly Trp Leu His Pro Ser
                405                 410                 415

Ile Asn Gln Phe Asn Pro Glu Pro Ser Val Glu Phe Asp Thr Val Ala
            420                 425                 430

Asn Lys Lys Gln Gln His Glu Val Asn Val Ala Ile Ser Asn Ser Phe
        435                 440                 445

Gly Phe Gly Gly His Asn Ser Val Val Val Phe Ser Ala Phe Lys Pro
    450                 455                 460


<210> SEQ ID NO 6
<211> LENGTH: 472
<212> TYPE: PRT
<213> ORGANISM: Umbellularia californica
<220> FEATURE:
<221> NAME/KEY: MISC_FEATURE
<223> OTHER INFORMATION: KASIV

<400> SEQUENCE: 6

Met Thr Gln Thr Leu Ile Cys Pro Ser Ser Met Glu Thr Leu Ser Leu
1               5                   10                  15

Thr Lys Gln Ser His Phe Arg Leu Arg Leu Pro Thr Pro Pro His Ile
            20                  25                  30

Arg Arg Gly Gly Gly His Arg His Pro Pro Pro Phe Ile Ser Ala Ser
```

-continued

```
        35                  40                  45

Ala Ala Pro Arg Arg Glu Thr Asp Pro Lys Lys Arg Val Val Ile Thr
    50                  55                  60

Gly Met Gly Leu Val Ser Val Phe Gly Thr Asn Val Asp Val Tyr Tyr
65                  70                  75                  80

Asp Arg Leu Leu Ala Gly Glu Ser Gly Val Gly Thr Ile Asp Arg Phe
                85                  90                  95

Asp Ala Ser Met Phe Pro Thr Arg Phe Gly Gly Gln Ile Arg Arg Phe
            100                 105                 110

Thr Ser Glu Gly Tyr Ile Asp Gly Lys Asn Asp Arg Arg Leu Asp Asp
        115                 120                 125

Tyr Leu Arg Tyr Cys Leu Val Ser Gly Lys Lys Ala Ile Glu Ser Ala
    130                 135                 140

Gly Phe Asp Leu His Asn Ile Thr Asn Lys Ile Asp Lys Glu Arg Ala
145                 150                 155                 160

Gly Ile Leu Val Gly Ser Gly Met Gly Gly Leu Lys Val Phe Ser Asp
                165                 170                 175

Gly Val Glu Ser Leu Ile Glu Lys Gly Tyr Arg Lys Ile Ser Pro Phe
            180                 185                 190

Phe Ile Pro Tyr Met Ile Pro Asn Met Gly Ser Ala Leu Leu Gly Ile
        195                 200                 205

Asp Leu Gly Phe Met Gly Pro Asn Tyr Ser Ile Ser Thr Ala Cys Ala
    210                 215                 220

Thr Ser Asn Tyr Cys Ile Tyr Ala Ala Ala Asn His Ile Arg Gln Gly
225                 230                 235                 240

Asp Ala Asp Leu Met Val Ala Gly Gly Thr Glu Ala Pro Ile Ile Pro
                245                 250                 255

Ile Gly Leu Gly Gly Phe Val Ala Cys Arg Ala Leu Ser Thr Arg Asn
            260                 265                 270

Asp Asp Pro Gln Thr Ala Ser Arg Pro Trp Asp Ile Asp Arg Asp Gly
        275                 280                 285

Phe Val Met Gly Glu Gly Ala Gly Ile Leu Val Leu Glu Ser Leu Glu
    290                 295                 300

His Ala Met Lys Arg Asp Ala Pro Ile Leu Ala Glu Tyr Leu Gly Gly
305                 310                 315                 320

Ala Val Asn Cys Asp Ala His His Met Thr Asp Pro Arg Ala Asp Gly
                325                 330                 335

Leu Gly Val Ser Thr Cys Ile Glu Ser Ser Leu Glu Asp Ala Gly Val
            340                 345                 350

Ala Ala Glu Glu Val Asn Tyr Ile Asn Ala His Ala Thr Ser Thr Pro
        355                 360                 365

Thr Gly Asp Leu Ala Glu Met Lys Ala Ile Lys Asn Val Phe Arg Asn
    370                 375                 380

Thr Ser Glu Ile Lys Ile Asn Ala Thr Lys Ser Met Ile Gly His Cys
385                 390                 395                 400

Leu Gly Ala Ser Gly Gly Leu Glu Ala Ile Ala Thr Leu Lys Ala Ile
                405                 410                 415

Thr Thr Gly Trp Leu His Pro Thr Ile Asn Gln Phe Asn Pro Glu Pro
            420                 425                 430

Ser Val Asp Phe Asp Thr Val Ala Lys Lys Lys Lys Gln His Glu Val
        435                 440                 445

Asn Val Ala Ile Ser Asn Ser Phe Gly Phe Gly Gly His Asn Ser Val
    450                 455                 460
```

```
Leu Val Phe Ser Ala Phe Lys Pro
465                 470


<210> SEQ ID NO 7
<211> LENGTH: 525
<212> TYPE: PRT
<213> ORGANISM: Cuphea wrightii
<220> FEATURE:
<221> NAME/KEY: MISC_FEATURE
<223> OTHER INFORMATION: KASAI

<400> SEQUENCE: 7

Met Ala Ser Ala Ala Phe Thr Met Ser Ala Cys Pro Ala Met Thr Gly
1               5                   10                  15

Arg Ala Pro Gly Ala Arg Arg Ser Gly Arg Pro Val Ala Thr Arg Leu
            20                  25                  30

Arg Tyr Val Phe Gln Cys Leu Val Ala Ser Cys Ile Asp Pro Cys Asp
        35                  40                  45

Gln Tyr Arg Ser Ser Ala Ser Leu Ser Phe Leu Gly Asp Asn Gly Phe
    50                  55                  60

Ala Ser Leu Phe Gly Ser Lys Pro Phe Met Ser Asn Arg Gly His Arg
65                  70                  75                  80

Arg Leu Arg Arg Ala Ser His Ser Gly Glu Ala Met Ala Val Ala Leu
                85                  90                  95

Gln Pro Ala Gln Glu Ala Gly Thr Lys Lys Lys Pro Val Ile Lys Gln
            100                 105                 110

Arg Arg Val Val Val Thr Gly Met Gly Val Val Thr Pro Leu Gly His
        115                 120                 125

Glu Pro Asp Val Phe Tyr Asn Asn Leu Leu Asp Gly Val Ser Gly Ile
    130                 135                 140

Ser Glu Ile Glu Thr Phe Asp Cys Thr Gln Phe Pro Thr Arg Ile Ala
145                 150                 155                 160

Gly Glu Ile Lys Ser Phe Ser Thr Asp Gly Trp Val Ala Pro Lys Leu
                165                 170                 175

Ser Lys Arg Met Asp Lys Phe Met Leu Tyr Leu Leu Thr Ala Gly Lys
            180                 185                 190

Lys Ala Leu Ala Asp Gly Gly Ile Thr Asp Glu Val Met Lys Glu Leu
        195                 200                 205

Asp Lys Arg Lys Cys Gly Val Leu Ile Gly Ser Gly Met Gly Gly Met
    210                 215                 220

Lys Val Phe Asn Asp Ala Ile Glu Ala Leu Arg Val Ser Tyr Lys Lys
225                 230                 235                 240

Met Asn Pro Phe Cys Val Pro Phe Ala Thr Thr Asn Met Gly Ser Ala
                245                 250                 255

Met Leu Ala Met Asp Leu Gly Trp Met Gly Pro Asn Tyr Ser Ile Ser
            260                 265                 270

Thr Ala Cys Ala Thr Ser Asn Phe Cys Ile Leu Asn Ala Ala Asn His
        275                 280                 285

Ile Ile Arg Gly Glu Ala Asp Met Met Leu Cys Gly Gly Ser Asp Ala
    290                 295                 300

Val Ile Ile Pro Ile Gly Leu Gly Gly Phe Val Ala Cys Arg Ala Leu
305                 310                 315                 320

Ser Gln Arg Asn Ser Asp Pro Thr Lys Ala Ser Arg Pro Trp Asp Ser
                325                 330                 335

Asn Arg Asp Gly Phe Val Met Gly Glu Gly Ala Gly Val Leu Leu Leu
```

340 345 350

Glu Glu Leu Glu His Ala Lys Lys Arg Gly Ala Thr Ile Tyr Ala Glu
355 360 365

Phe Leu Gly Gly Ser Phe Thr Cys Asp Ala Tyr His Met Thr Glu Pro
370 375 380

His Pro Glu Gly Ala Gly Val Ile Leu Cys Ile Glu Lys Ala Leu Ala
385 390 395 400

Gln Ala Gly Val Ser Lys Glu Asp Val Asn Tyr Ile Asn Ala His Ala
405 410 415

Thr Ser Thr Ser Ala Gly Asp Ile Lys Glu Tyr Gln Ala Leu Ala Arg
420 425 430

Cys Phe Gly Gln Asn Ser Glu Leu Arg Val Asn Ser Thr Lys Ser Met
435 440 445

Ile Gly His Leu Leu Gly Ala Ala Gly Gly Val Glu Ala Val Thr Val
450 455 460

Val Gln Ala Ile Arg Thr Gly Trp Ile His Pro Asn Leu Asn Leu Glu
465 470 475 480

Asp Pro Asp Lys Ala Val Asp Ala Lys Leu Leu Val Gly Pro Lys Lys
485 490 495

Glu Arg Leu Asn Val Lys Val Gly Leu Ser Asn Ser Phe Gly Phe Gly
500 505 510

Gly His Asn Ser Ser Ile Leu Phe Ala Pro Cys Asn Val
515 520 525

<210> SEQ ID NO 8
<211> LENGTH: 502
<212> TYPE: PRT
<213> ORGANISM: Cuphea avigera
<220> FEATURE:
<221> NAME/KEY: MISC_FEATURE
<223> OTHER INFORMATION: KASIVb

<400> SEQUENCE: 8

Met Ala Ser Ala Ala Phe Thr Met Ser Ala Cys Pro Ala Met Thr Gly
1 5 10 15

Arg Ala Pro Gly Ala Arg Arg Ser Gly Arg Pro Val Ala Thr Arg Leu
20 25 30

Arg Gly Ser Thr Phe Gln Cys Tyr Ile Gly Asp Asn Gly Phe Gly Ser
35 40 45

Lys Pro Pro Arg Ser Asn Arg Gly His Leu Arg Leu Gly Arg Thr Ser
50 55 60

His Ser Gly Glu Val Met Ala Val Ala Met Gln Ser Ala Gln Glu Val
65 70 75 80

Ser Thr Lys Glu Lys Pro Ala Thr Lys Gln Arg Arg Val Val Val Thr
85 90 95

Gly Met Gly Val Val Thr Ala Leu Gly His Asp Pro Asp Val Tyr Tyr
100 105 110

Asn Asn Leu Leu Asp Gly Val Ser Gly Ile Ser Glu Ile Glu Asn Phe
115 120 125

Asp Cys Ser Gln Leu Pro Thr Arg Ile Ala Gly Glu Ile Lys Ser Phe
130 135 140

Ser Ala Asp Gly Trp Val Ala Pro Lys Phe Ser Arg Arg Met Asp Lys
145 150 155 160

Phe Met Leu Tyr Ile Leu Thr Ala Gly Lys Lys Ala Leu Val Asp Gly
165 170 175

```
Gly Ile Thr Glu Asp Val Met Lys Glu Leu Asp Lys Arg Lys Cys Gly
            180                 185                 190

Val Leu Ile Gly Ser Gly Leu Gly Gly Met Lys Val Phe Ser Glu Ser
        195                 200                 205

Ile Glu Ala Leu Arg Thr Ser Tyr Lys Lys Ile Ser Pro Phe Cys Val
    210                 215                 220

Pro Phe Ser Thr Thr Asn Met Gly Ser Ala Ile Leu Ala Met Asp Leu
225                 230                 235                 240

Gly Trp Met Gly Pro Asn Tyr Ser Ile Ser Thr Ala Cys Ala Thr Ser
                245                 250                 255

Asn Phe Cys Ile Leu Asn Ala Ala Asn His Ile Thr Lys Gly Glu Ala
            260                 265                 270

Asp Met Met Leu Cys Gly Gly Ser Asp Ser Val Ile Leu Pro Ile Gly
        275                 280                 285

Met Gly Gly Phe Val Ala Cys Arg Ala Leu Ser Gln Arg Asn Asn Asp
    290                 295                 300

Pro Thr Lys Ala Ser Arg Pro Trp Asp Ser Asn Arg Asp Gly Phe Val
305                 310                 315                 320

Met Gly Glu Gly Ala Gly Val Leu Leu Leu Glu Glu Leu Glu His Ala
                325                 330                 335

Lys Lys Arg Gly Ala Thr Ile Tyr Ala Glu Phe Leu Gly Gly Ser Phe
            340                 345                 350

Thr Cys Asp Ala Tyr His Met Thr Glu Pro His Pro Glu Gly Ala Gly
        355                 360                 365

Val Ile Leu Cys Ile Glu Lys Ala Leu Ala Gln Ser Gly Val Ser Arg
    370                 375                 380

Glu Asp Val Asn Tyr Ile Asn Ala His Ala Thr Ser Thr Pro Ala Gly
385                 390                 395                 400

Asp Ile Lys Glu Tyr Gln Ala Leu Ala His Cys Phe Gly Gln Asn Ser
                405                 410                 415

Glu Leu Arg Val Asn Ser Thr Lys Ser Met Ile Gly His Leu Leu Gly
            420                 425                 430

Gly Ala Gly Gly Val Glu Ala Val Thr Val Val Gln Ala Ile Arg Thr
        435                 440                 445

Gly Trp Ile His Pro Asn Ile Asn Leu Asp Asp Pro Asp Glu Gly Val
    450                 455                 460

Asp Ala Lys Leu Leu Val Gly Pro Lys Lys Glu Lys Leu Lys Val Lys
465                 470                 475                 480

Val Gly Leu Ser Asn Ser Phe Gly Phe Gly Gly His Asn Ser Ser Ile
                485                 490                 495

Leu Phe Ala Pro Cys Asn
            500
```

<210> SEQ ID NO 9
<211> LENGTH: 505
<212> TYPE: PRT
<213> ORGANISM: Cuphea paucipetala
<220> FEATURE:
<221> NAME/KEY: MISC_FEATURE
<223> OTHER INFORMATION: KASIVb

<400> SEQUENCE: 9

```
Met Ala Ser Ala Ala Phe Thr Met Ser Ala Cys Pro Ala Met Thr Gly
1               5                   10                  15

Arg Ala Pro Gly Ala Arg Arg Ser Gly Arg Pro Val Ala Thr Arg Leu
            20                  25                  30
```

-continued

Arg Gly Ser Thr Phe Gln Cys Leu Gly Asp Ile Gly Phe Ala Ser Leu
35 40 45

Ile Gly Ser Lys Pro Pro Arg Ser Asn Arg Asn His Arg Arg Leu Gly
50 55 60

Arg Thr Ser His Ser Gly Glu Val Met Ala Val Ala Met Gln Pro Ala
65 70 75 80

His Glu Ala Ser Thr Lys Asn Lys Pro Val Thr Lys Gln Arg Arg Val
85 90 95

Val Val Thr Gly Met Gly Val Ala Thr Pro Leu Gly His Asp Pro Asp
100 105 110

Val Tyr Tyr Asn Asn Leu Leu Asp Gly Val Ser Gly Ile Ser Gln Ile
115 120 125

Glu Asn Phe Asp Cys Thr Gln Phe Pro Thr Arg Ile Ala Gly Glu Ile
130 135 140

Lys Ser Phe Ser Thr Glu Gly Tyr Val Ile Pro Lys Phe Ala Lys Arg
145 150 155 160

Met Asp Lys Phe Met Leu Tyr Leu Leu Thr Ala Gly Lys Lys Ala Leu
165 170 175

Glu Asp Gly Gly Ile Thr Glu Asp Val Met Lys Glu Leu Asp Lys Arg
180 185 190

Lys Cys Gly Val Leu Ile Gly Ser Gly Met Gly Gly Met Lys Ile Ile
195 200 205

Asn Asp Ser Ile Ala Ala Leu Asn Val Ser Tyr Lys Lys Met Thr Pro
210 215 220

Phe Cys Val Pro Phe Ser Thr Thr Asn Met Gly Ser Ala Met Leu Ala
225 230 235 240

Ile Asp Leu Gly Trp Met Gly Pro Asn Tyr Ser Ile Ser Thr Ala Cys
245 250 255

Ala Thr Ser Asn Tyr Cys Ile Leu Asn Ala Ala Asn His Ile Val Arg
260 265 270

Gly Glu Ala Asp Met Met Leu Cys Gly Gly Ser Asp Ala Val Ile Ile
275 280 285

Pro Val Gly Leu Gly Gly Phe Val Ala Cys Arg Ala Leu Ser Gln Arg
290 295 300

Asn Asn Asp Pro Thr Lys Ala Ser Arg Pro Trp Asp Ser Asn Arg Asp
305 310 315 320

Gly Phe Val Met Gly Glu Gly Ala Gly Val Leu Leu Leu Glu Glu Leu
325 330 335

Glu His Ala Lys Lys Arg Gly Ala Thr Ile Tyr Ala Glu Phe Leu Gly
340 345 350

Gly Ser Phe Thr Cys Asp Ala Tyr His Met Thr Glu Pro His Pro Asp
355 360 365

Gly Ala Gly Val Ile Leu Cys Ile Glu Lys Ala Leu Ala Gln Ser Gly
370 375 380

Val Ser Arg Glu Asp Val Asn Tyr Ile Asn Ala His Ala Thr Ser Thr
385 390 395 400

Pro Ala Gly Asp Ile Lys Glu Tyr Gln Ala Leu Ala His Cys Phe Gly
405 410 415

Gln Asn Ser Glu Leu Arg Val Asn Ser Thr Lys Ser Met Ile Gly His
420 425 430

Leu Leu Gly Ala Ala Gly Gly Val Glu Ala Val Thr Val Val Gln Ala
435 440 445

```
Ile Arg Thr Gly Trp Ile His Pro Asn Ile Asn Leu Glu Asn Pro Asp
    450                 455                 460

Glu Ala Val Asp Ala Lys Leu Leu Val Gly Pro Lys Lys Glu Lys Leu
465                 470                 475                 480

Lys Val Lys Val Gly Leu Ser Asn Ser Phe Gly Phe Gly Gly His Asn
                485                 490                 495

Ser Ser Ile Leu Phe Ala Pro Tyr Asn
            500                 505


<210> SEQ ID NO 10
<211> LENGTH: 525
<212> TYPE: PRT
<213> ORGANISM: Cuphea ignea
<220> FEATURE:
<221> NAME/KEY: MISC_FEATURE
<223> OTHER INFORMATION: KASIVb

<400> SEQUENCE: 10

Met Ala Ser Ala Ala Phe Thr Met Ser Ala Cys Pro Ala Met Thr Gly
1               5                   10                  15

Arg Ala Pro Gly Ala Arg Arg Ser Gly Arg Pro Val Ala Thr Arg Leu
            20                  25                  30

Arg Gly Ser Thr Ser Gln Cys Leu Val Thr Ser Tyr Ile Asp Pro Cys
        35                  40                  45

Asn Lys Tyr Cys Ser Ser Ala Ser Leu Ser Phe Leu Gly Asp Asn Gly
    50                  55                  60

Phe Ala Ser Leu Phe Gly Ser Lys Pro Phe Arg Ser Asn Arg Gly His
65                  70                  75                  80

Arg Arg Leu Gly Arg Ala Ser His Ser Gly Glu Ala Met Ala Val Ala
                85                  90                  95

Leu Gln Pro Ala Gln Glu Val Thr Thr Lys Lys Lys Pro Val Ile Lys
            100                 105                 110

Gln Arg Arg Val Val Val Thr Gly Met Gly Val Val Thr Pro Leu Gly
        115                 120                 125

His Glu Pro Asp Val Tyr Tyr Asn Asn Leu Leu Asp Gly Val Ser Gly
    130                 135                 140

Ile Ser Glu Ile Glu Thr Phe Asp Cys Thr Gln Phe Pro Thr Arg Ile
145                 150                 155                 160

Ala Gly Glu Ile Lys Ser Phe Ser Thr Asp Gly Trp Val Ala Pro Lys
                165                 170                 175

Leu Ser Lys Arg Met Asp Lys Phe Met Leu Tyr Leu Leu Thr Ala Gly
            180                 185                 190

Lys Lys Ala Leu Ala Asp Gly Gly Ile Thr Asp Asp Val Met Lys Glu
        195                 200                 205

Leu Asp Lys Arg Lys Cys Gly Val Leu Ile Gly Ser Gly Met Gly Gly
    210                 215                 220

Met Lys Leu Phe Asn Asp Ser Ile Glu Ala Leu Arg Ile Ser Tyr Lys
225                 230                 235                 240

Lys Met Asn Pro Phe Cys Val Pro Phe Ala Thr Thr Asn Met Gly Ser
                245                 250                 255

Ala Met Leu Ala Met Asp Leu Gly Trp Met Gly Pro Asn Tyr Ser Ile
            260                 265                 270

Ser Thr Ala Cys Ala Thr Ser Asn Phe Cys Ile Leu Asn Ala Ser Asn
        275                 280                 285

His Ile Val Arg Gly Glu Ala Asp Met Met Leu Cys Gly Gly Ser Asp
    290                 295                 300
```

Ser Val Thr Val Pro Leu Gly Val Gly Gly Phe Val Ala Cys Arg Ala
305 310 315 320

Leu Ser Gln Arg Asn Asn Asp Pro Thr Lys Ala Ser Arg Pro Trp Asp
325 330 335

Ser Asn Arg Asp Gly Phe Val Met Gly Glu Gly Ala Gly Val Leu Leu
340 345 350

Leu Glu Glu Leu Glu His Ala Lys Lys Arg Gly Ala Thr Ile Tyr Ala
355 360 365

Glu Phe Leu Gly Gly Ser Phe Thr Ser Asp Ala Tyr His Met Thr Glu
370 375 380

Pro His Pro Glu Gly Ala Gly Val Ile Leu Cys Ile Glu Lys Ala Leu
385 390 395 400

Ala Gln Ser Gly Val Ser Arg Glu Asp Val Asn Tyr Ile Asn Ala His
405 410 415

Ala Thr Ser Thr Pro Ala Gly Asp Ile Lys Glu Tyr Gln Ala Leu Ala
420 425 430

Arg Cys Phe Gly Gln Asn Ser Glu Leu Arg Val Asn Ser Thr Lys Ser
435 440 445

Met Ile Gly His Leu Leu Gly Ala Ala Gly Gly Val Glu Ala Val Ala
450 455 460

Val Ile Gln Ala Ile Arg Thr Gly Trp Ile His Pro Asn Ile Asn Leu
465 470 475 480

Glu Asp Pro Asp Glu Ala Val Asp Pro Lys Leu Leu Val Gly Pro Lys
485 490 495

Lys Glu Lys Leu Lys Val Lys Val Ala Leu Ser Asn Ser Phe Gly Phe
500 505 510

Gly Gly His Asn Ser Ser Ile Leu Phe Ala Pro Cys Asn
515 520 525

<210> SEQ ID NO 11
<211> LENGTH: 521
<212> TYPE: PRT
<213> ORGANISM: Cuphea procumbens
<220> FEATURE:
<221> NAME/KEY: MISC_FEATURE
<223> OTHER INFORMATION: KASIV

<400> SEQUENCE: 11

Met Ala Ser Ala Ala Phe Thr Met Ser Ala Cys Pro Ala Met Thr Gly
1 5 10 15

Arg Ala Pro Gly Ala Arg Arg Ser Gly Arg Pro Val Ala Thr Arg Leu
20 25 30

Arg Gly Ser Thr Phe Gln Cys Leu Val Thr Ser His Asn Asp Pro Cys
35 40 45

Asn Gln Tyr Cys Ser Ser Ala Ser Leu Ser Phe Leu Gly Asp Asn Gly
50 55 60

Phe Gly Ser Lys Pro Phe Arg Ser Asn Arg Gly His Arg Arg Leu Gly
65 70 75 80

Arg Ala Ser His Ser Gly Glu Ala Met Ala Val Ala Leu Gln Pro Ala
85 90 95

Gln Glu Val Ala Thr Lys Lys Lys Pro Ala Met Lys Gln Arg Arg Val
100 105 110

Val Val Thr Gly Met Gly Val Val Thr Pro Leu Gly His Glu Pro Asp
115 120 125

Val Tyr Tyr Asn Asn Leu Leu Asp Gly Val Ser Gly Ile Ser Glu Ile

-continued

```
    130                 135                 140

Glu Thr Phe Asp Cys Thr Gln Phe Pro Thr Arg Ile Ala Gly Glu Ile
145                 150                 155                 160

Lys Ser Phe Ser Thr Asp Gly Trp Val Ala Pro Lys Leu Ser Lys Arg
                165                 170                 175

Met Asp Lys Phe Met Leu Tyr Leu Leu Thr Ala Gly Lys Lys Ala Leu
            180                 185                 190

Ala Asp Gly Gly Ile Thr Asp Asp Val Met Lys Glu Leu Asp Lys Arg
        195                 200                 205

Lys Cys Gly Val Leu Ile Gly Ser Gly Met Gly Gly Met Lys Leu Phe
    210                 215                 220

Asn Asp Ser Ile Glu Ala Leu Arg Val Ser Tyr Lys Lys Met Asn Pro
225                 230                 235                 240

Phe Cys Val Pro Phe Ala Thr Thr Asn Met Gly Ser Ala Met Leu Ala
                245                 250                 255

Met Asp Leu Gly Trp Met Gly Pro Asn Tyr Ser Ile Ser Thr Ala Cys
            260                 265                 270

Ala Thr Ser Asn Phe Cys Ile Leu Asn Ala Ala Asn His Ile Val Arg
        275                 280                 285

Gly Glu Ala Asp Met Met Leu Cys Gly Gly Ser Asp Ala Val Ile Ile
    290                 295                 300

Pro Ile Gly Leu Gly Gly Phe Val Ala Cys Arg Ala Leu Ser Gln Arg
305                 310                 315                 320

Asn Asn Asp Pro Thr Lys Ala Ser Arg Pro Trp Asp Ser Asn Arg Asp
                325                 330                 335

Gly Phe Val Met Gly Glu Gly Ala Gly Val Leu Leu Leu Glu Glu Leu
            340                 345                 350

Glu His Ala Lys Lys Arg Gly Ala Thr Ile Tyr Ala Glu Phe Leu Gly
        355                 360                 365

Gly Ser Phe Thr Cys Asp Ala Tyr His Met Thr Glu Pro His Pro Glu
    370                 375                 380

Gly Ala Gly Val Ile Leu Cys Ile Glu Lys Ala Leu Ala Gln Ser Gly
385                 390                 395                 400

Val Ser Arg Glu Asp Val Asn Tyr Ile Asn Ala His Ala Thr Ser Thr
                405                 410                 415

Pro Ala Gly Asp Ile Lys Glu Tyr Gln Ala Leu Ala His Cys Phe Gly
            420                 425                 430

Gln Asn Ser Glu Leu Arg Val Asn Ser Thr Lys Ser Met Ile Gly His
        435                 440                 445

Leu Leu Gly Ala Ala Gly Gly Val Glu Ala Val Thr Val Ile Gln Ala
    450                 455                 460

Ile Arg Thr Gly Trp Ile His Pro Asn Leu Asn Leu Glu Asp Pro Asp
465                 470                 475                 480

Lys Ala Val Asp Ala Lys Phe Leu Val Gly Pro Lys Lys Glu Arg Leu
                485                 490                 495

Asn Val Lys Val Gly Leu Ser Asn Ser Phe Gly Phe Gly Gly His Asn
            500                 505                 510

Ser Ser Ile Leu Phe Ala Pro Cys Asn
        515                 520
```

<210> SEQ ID NO 12
<211> LENGTH: 521
<212> TYPE: PRT
<213> ORGANISM: Cuphea paucipetala
<220> FEATURE:
<221> NAME/KEY: MISC_FEATURE
<223> OTHER INFORMATION: KASIVa

<400> SEQUENCE: 12

```
Met Ala Ser Ala Ala Phe Thr Met Ser Ala Cys Pro Ala Met Thr Gly
1               5                   10                  15

Arg Ala Pro Gly Ala Arg Arg Ser Gly Arg Pro Val Ala Thr Arg Leu
            20                  25                  30

Arg Gly Ser Thr Phe Gln Cys Leu Val Asn Ser His Ile Asp Pro Cys
        35                  40                  45

Asn Gln Asn Val Ser Ser Ala Ser Leu Ser Phe Leu Gly Asp Asn Gly
    50                  55                  60

Phe Gly Ser Asn Pro Phe Arg Ser Asn Arg Gly His Arg Arg Leu Gly
65                  70                  75                  80

Arg Ala Ser His Ser Gly Glu Ala Met Ala Val Ala Leu Gln Pro Ala
                85                  90                  95

Gln Glu Val Ala Thr Lys Lys Lys Pro Ala Ile Lys Gln Arg Arg Val
            100                 105                 110

Val Val Thr Gly Met Gly Val Val Thr Pro Leu Gly His Glu Pro Asp
        115                 120                 125

Val Phe Tyr Asn Asn Leu Leu Asp Gly Val Ser Gly Ile Ser Glu Ile
    130                 135                 140

Glu Thr Phe Asp Cys Thr Gln Phe Pro Thr Arg Ile Ala Gly Glu Ile
145                 150                 155                 160

Lys Ser Phe Ser Thr Asp Gly Trp Val Ala Pro Lys Leu Ser Lys Arg
                165                 170                 175

Met Asp Lys Phe Met Leu Tyr Leu Leu Thr Ala Gly Lys Lys Ala Leu
            180                 185                 190

Ala Asp Ala Gly Ile Thr Glu Asp Val Met Lys Glu Leu Asp Lys Arg
        195                 200                 205

Lys Cys Gly Val Leu Ile Gly Ser Gly Met Gly Gly Met Lys Leu Phe
    210                 215                 220

Asn Asp Ser Ile Glu Ala Leu Arg Val Ser Tyr Lys Lys Met Asn Pro
225                 230                 235                 240

Phe Cys Val Pro Phe Ala Thr Thr Asn Met Gly Ser Ala Met Leu Ala
                245                 250                 255

Met Asp Leu Gly Trp Met Gly Pro Asn Tyr Ser Ile Ser Thr Ala Cys
            260                 265                 270

Ala Thr Ser Asn Phe Cys Ile Leu Asn Ala Ala Asn His Ile Ile Arg
        275                 280                 285

Gly Glu Ala Asp Met Met Leu Cys Gly Gly Ser Asp Ala Val Ile Ile
    290                 295                 300

Pro Ile Gly Leu Gly Gly Phe Val Ala Cys Arg Ala Leu Ser Gln Arg
305                 310                 315                 320

Asn Ser Asp Pro Thr Lys Ala Ser Arg Pro Trp Asp Ser Asn Arg Asp
                325                 330                 335

Gly Phe Val Met Gly Glu Gly Ala Gly Val Leu Leu Leu Glu Glu Leu
            340                 345                 350

Glu His Ala Lys Lys Arg Gly Ala Thr Ile Tyr Ala Glu Phe Leu Gly
        355                 360                 365

Gly Ser Phe Thr Cys Asp Ala Tyr His Met Thr Glu Pro His Pro Asp
    370                 375                 380

Gly Ala Gly Val Ile Leu Cys Ile Glu Lys Ala Leu Ala Gln Ser Gly
```

```
385                 390                 395                 400

Val Ser Arg Glu Asp Val Asn Tyr Ile Asn Ala His Ala Thr Ser Thr
                405                 410                 415

Pro Ala Gly Asp Ile Lys Glu Tyr Gln Ala Leu Ala His Cys Phe Gly
            420                 425                 430

Gln Asn Ser Glu Leu Arg Val Asn Ser Thr Lys Ser Met Ile Gly His
        435                 440                 445

Leu Leu Gly Ala Ala Gly Gly Val Glu Ala Val Thr Val Ile Gln Ala
    450                 455                 460

Ile Arg Thr Gly Trp Ile His Pro Asn Leu Asn Leu Glu Asp Pro Asp
465                 470                 475                 480

Glu Ala Val Asp Ala Lys Phe Leu Val Gly Pro Lys Lys Glu Arg Leu
                485                 490                 495

Asn Val Lys Val Gly Leu Ser Asn Ser Phe Gly Phe Gly Gly His Asn
            500                 505                 510

Ser Ser Ile Leu Phe Ala Pro Tyr Asn
        515                 520


<210> SEQ ID NO 13
<211> LENGTH: 510
<212> TYPE: PRT
<213> ORGANISM: Cuphea painteri
<220> FEATURE:
<221> NAME/KEY: MISC_FEATURE
<223> OTHER INFORMATION: KASIV

<400> SEQUENCE: 13

Met Ala Ser Ala Ala Phe Thr Met Ser Ala Cys Pro Ala Met Thr Gly
1               5                   10                  15

Arg Ala Pro Gly Ala Arg Arg Ser Gly Arg Pro Val Ala Thr Arg Leu
            20                  25                  30

Arg Gly Ser Thr Pro Gln Cys Leu Asp Pro Cys Asn Gln His Cys Phe
        35                  40                  45

Leu Gly Asp Asn Gly Phe Ala Ser Leu Ile Gly Ser Lys Pro Pro Arg
    50                  55                  60

Ser Asn Leu Gly His Leu Arg Leu Gly Arg Thr Ser His Ser Gly Glu
65                  70                  75                  80

Val Met Ala Val Ala Gln Glu Val Ser Thr Asn Lys Lys His Ala Thr
                85                  90                  95

Lys Gln Arg Arg Val Val Val Thr Gly Met Gly Val Val Thr Pro Leu
            100                 105                 110

Gly His Asp Pro Asp Val Tyr Tyr Asn Asn Leu Leu Glu Gly Val Ser
        115                 120                 125

Gly Ile Ser Glu Ile Glu Asn Phe Asp Cys Ser Gln Leu Pro Thr Arg
    130                 135                 140

Ile Ala Gly Glu Ile Lys Ser Phe Ser Thr Asp Gly Leu Val Ala Pro
145                 150                 155                 160

Lys Leu Ser Lys Arg Met Asp Lys Phe Met Leu Tyr Ile Leu Thr Ala
                165                 170                 175

Gly Lys Lys Ala Leu Ala Asp Gly Gly Ile Thr Glu Asp Val Met Lys
            180                 185                 190

Glu Leu Asp Lys Arg Lys Cys Gly Val Leu Ile Gly Ser Gly Leu Gly
        195                 200                 205

Gly Met Lys Val Phe Ser Asp Ser Val Glu Ala Leu Arg Ile Ser Tyr
    210                 215                 220
```

-continued

Lys Lys Ile Ser Pro Phe Cys Val Pro Phe Ser Thr Thr Asn Met Gly
225 230 235 240

Ser Ala Met Leu Ala Met Asp Leu Gly Trp Met Gly Pro Asn Tyr Ser
245 250 255

Ile Ser Thr Ala Cys Ala Thr Ser Asn Phe Cys Ile Leu Asn Ala Ala
260 265 270

Asn His Ile Thr Lys Gly Glu Ala Asp Met Met Leu Cys Gly Gly Ser
275 280 285

Asp Ala Ala Ile Leu Pro Ile Gly Met Gly Gly Phe Val Ala Cys Arg
290 295 300

Ala Leu Ser Gln Arg Asn Asn Asp Pro Thr Lys Ala Ser Arg Pro Trp
305 310 315 320

Asp Ser Asn Arg Asp Gly Phe Val Met Gly Glu Gly Ala Gly Val Leu
325 330 335

Leu Leu Glu Glu Leu Glu His Ala Lys Lys Arg Gly Ala Thr Ile Tyr
340 345 350

Ala Glu Phe Leu Gly Gly Ser Phe Thr Cys Asp Ala Tyr His Met Thr
355 360 365

Glu Pro His Pro Asp Gly Ala Gly Val Ile Leu Cys Ile Glu Lys Ala
370 375 380

Leu Ala Gln Ser Gly Val Ser Arg Glu Glu Val Asn Tyr Ile Asn Ala
385 390 395 400

His Ala Thr Ser Thr Pro Ala Gly Asp Ile Lys Glu Tyr Gln Ala Leu
405 410 415

Ala His Cys Phe Gly Gln Asn Ser Glu Leu Arg Val Asn Ser Thr Lys
420 425 430

Ser Met Ile Gly His Leu Leu Gly Gly Ala Gly Gly Val Glu Ala Val
435 440 445

Thr Val Val Gln Ala Ile Arg Thr Gly Trp Ile His Pro Asn Ile Asn
450 455 460

Leu Glu Asp Pro Asp Lys Gly Val Asp Ala Lys Leu Leu Val Gly Pro
465 470 475 480

Lys Lys Glu Lys Leu Lys Val Lys Val Gly Leu Ser Asn Ser Phe Gly
485 490 495

Phe Gly Gly His Asn Ser Ser Ile Leu Phe Ala Pro Cys Asn
500 505 510

<210> SEQ ID NO 14
<211> LENGTH: 525
<212> TYPE: PRT
<213> ORGANISM: Cuphea avigera
<220> FEATURE:
<221> NAME/KEY: MISC_FEATURE
<223> OTHER INFORMATION: KASIVa

<400> SEQUENCE: 14

Met Ala Ser Ala Ala Phe Thr Met Ser Ala Cys Pro Ala Met Thr Gly
1 5 10 15

Arg Ala Pro Gly Ala Arg Arg Ser Gly Arg Pro Val Ala Thr Arg Leu
20 25 30

Arg Gly Ser Thr Phe Gln Cys Leu Val Thr Ser Tyr Asn Asp Pro Cys
35 40 45

Glu Gln Tyr Arg Ser Ser Ala Ser Leu Ser Phe Leu Gly Asp Asn Gly
50 55 60

Phe Ala Ser Leu Phe Gly Ser Lys Pro Phe Arg Ser Asn Arg Gly His
65 70 75 80

-continued

```
Arg Arg Leu Gly Arg Ala Ser His Ser Gly Glu Ala Met Ala Val Ala
                85                  90                  95

Leu Gln Pro Ala Gln Glu Val Gly Thr Lys Lys Lys Pro Val Ile Lys
            100                 105                 110

Gln Arg Arg Val Val Val Thr Gly Met Gly Val Val Thr Pro Leu Gly
        115                 120                 125

His Glu Pro Asp Val Tyr Tyr Asn Asn Leu Leu Asp Gly Val Ser Gly
    130                 135                 140

Ile Ser Glu Ile Glu Thr Phe Asp Cys Thr Gln Phe Pro Thr Arg Ile
145                 150                 155                 160

Ala Gly Glu Ile Lys Ser Phe Ser Thr Asp Gly Trp Val Ala Pro Lys
                165                 170                 175

Leu Ser Lys Arg Met Asp Lys Phe Met Leu Tyr Leu Leu Thr Ala Gly
            180                 185                 190

Lys Lys Ala Leu Ala Asp Gly Gly Ile Thr Asp Asp Val Met Lys Glu
        195                 200                 205

Leu Asp Lys Arg Lys Cys Gly Val Leu Ile Gly Ser Gly Leu Gly Gly
    210                 215                 220

Met Lys Val Phe Ser Glu Ser Ile Glu Ala Leu Arg Thr Ser Tyr Lys
225                 230                 235                 240

Lys Ile Ser Pro Phe Cys Val Pro Phe Ser Thr Thr Asn Met Gly Ser
                245                 250                 255

Ala Ile Leu Ala Met Asp Leu Gly Trp Met Gly Pro Asn Tyr Ser Ile
            260                 265                 270

Ser Thr Ala Cys Ala Thr Ser Asn Phe Cys Ile Leu Asn Ala Ala Asn
        275                 280                 285

His Ile Thr Lys Gly Glu Ala Asp Met Met Leu Cys Gly Gly Ser Asp
    290                 295                 300

Ser Val Ile Leu Pro Ile Gly Met Gly Gly Phe Val Ala Cys Arg Ala
305                 310                 315                 320

Leu Ser Gln Arg Asn Asn Asp Pro Thr Lys Ala Ser Arg Pro Trp Asp
                325                 330                 335

Ser Asn Arg Asp Gly Phe Val Met Gly Glu Gly Ala Gly Val Leu Leu
            340                 345                 350

Leu Glu Glu Leu Glu His Ala Lys Lys Arg Gly Ala Thr Ile Tyr Ala
        355                 360                 365

Glu Phe Leu Gly Gly Ser Phe Thr Cys Asp Ala Tyr His Met Thr Glu
    370                 375                 380

Pro His Pro Glu Gly Ala Gly Val Ile Leu Cys Ile Glu Lys Ala Leu
385                 390                 395                 400

Ala Gln Ser Gly Val Ser Arg Glu Asp Val Asn Tyr Ile Asn Ala His
                405                 410                 415

Ala Thr Ser Thr Pro Ala Gly Asp Ile Lys Glu Tyr Gln Ala Leu Ala
            420                 425                 430

His Cys Phe Gly Gln Asn Ser Glu Leu Arg Val Asn Ser Thr Lys Ser
        435                 440                 445

Met Ile Gly His Leu Leu Gly Gly Ala Gly Gly Val Glu Ala Val Thr
    450                 455                 460

Val Val Gln Ala Ile Arg Thr Gly Trp Ile His Pro Asn Ile Asn Leu
465                 470                 475                 480

Asp Asp Pro Asp Glu Gly Val Asp Ala Lys Leu Leu Val Gly Pro Lys
                485                 490                 495
```

```
Lys Glu Lys Leu Lys Val Lys Val Gly Leu Ser Asn Ser Phe Gly Phe
            500                 505                 510

Gly Gly His Asn Ser Ser Ile Leu Phe Ala Pro Cys Asn
        515                 520                 525


<210> SEQ ID NO 15
<211> LENGTH: 525
<212> TYPE: PRT
<213> ORGANISM: Cuphea ignea
<220> FEATURE:
<221> NAME/KEY: MISC_FEATURE
<223> OTHER INFORMATION: KASIVa

<400> SEQUENCE: 15

Met Ala Ser Ala Ala Phe Thr Met Ser Ala Cys Pro Ala Met Thr Gly
1               5                   10                  15

Arg Ala Pro Gly Ala Arg Arg Ser Gly Arg Pro Val Ala Thr Arg Leu
            20                  25                  30

Arg Gly Ser Thr Ser Gln Cys Leu Val Thr Ser Tyr Ile Asp Pro Cys
        35                  40                  45

Asn Lys Tyr Cys Ser Ser Ala Ser Leu Ser Phe Leu Gly Asp Asn Gly
    50                  55                  60

Phe Ala Ser Leu Phe Gly Ser Lys Pro Phe Arg Ser Asn Arg Gly His
65                  70                  75                  80

Arg Arg Leu Gly Arg Ala Ser His Ser Gly Glu Ala Met Ala Val Ala
                85                  90                  95

Leu Gln Pro Ala Gln Glu Val Thr Thr Lys Lys Lys Pro Val Ile Lys
            100                 105                 110

Gln Arg Arg Val Val Val Thr Gly Met Gly Val Val Thr Pro Leu Gly
        115                 120                 125

His Glu Pro Asp Val Tyr Tyr Asn Asn Leu Leu Asp Gly Val Ser Gly
    130                 135                 140

Ile Ser Glu Ile Glu Thr Phe Asp Cys Thr Gln Phe Pro Thr Arg Ile
145                 150                 155                 160

Ala Gly Glu Ile Lys Ser Phe Ser Thr Asp Gly Trp Val Ala Pro Lys
                165                 170                 175

Leu Ser Lys Arg Met Asp Lys Phe Met Leu Tyr Leu Leu Thr Ala Gly
            180                 185                 190

Lys Lys Ala Leu Ala Asp Gly Gly Ile Thr Asp Asp Val Met Lys Glu
        195                 200                 205

Leu Asp Lys Arg Lys Cys Gly Val Leu Ile Gly Ser Gly Met Gly Gly
    210                 215                 220

Met Lys Leu Phe Asn Asp Ser Ile Glu Ala Leu Arg Ile Ser Tyr Lys
225                 230                 235                 240

Lys Met Asn Pro Phe Cys Val Pro Phe Ala Thr Thr Asn Met Gly Ser
                245                 250                 255

Ala Met Leu Ala Met Asp Leu Gly Trp Met Gly Pro Asn Tyr Ser Ile
            260                 265                 270

Ser Thr Ala Cys Ala Thr Ser Asn Phe Cys Ile Leu Asn Ala Ser Asn
        275                 280                 285

His Ile Val Arg Gly Glu Ala Asp Met Met Leu Cys Gly Gly Ser Asp
    290                 295                 300

Ala Val Ile Ile Pro Ile Gly Leu Gly Gly Phe Val Ala Cys Arg Ala
305                 310                 315                 320

Leu Ser Gln Arg Asn Asn Asp Pro Thr Lys Ala Ser Arg Pro Trp Asp
                325                 330                 335
```

```
Ser Asn Arg Asp Gly Phe Val Met Gly Glu Gly Ala Gly Val Leu Leu
            340                 345                 350

Leu Glu Glu Leu Glu His Ala Lys Lys Arg Gly Ala Thr Ile Tyr Ala
        355                 360                 365

Glu Phe Leu Gly Gly Ser Phe Thr Cys Asp Ala Tyr His Met Thr Glu
    370                 375                 380

Pro His Pro Glu Gly Ala Gly Val Ile Leu Cys Ile Glu Lys Ala Leu
385                 390                 395                 400

Ala Gln Ala Gly Val Ser Lys Glu Asp Val Asn Tyr Ile Asn Ala His
                405                 410                 415

Ala Thr Ser Thr Pro Ala Gly Asp Ile Lys Glu Tyr Gln Ala Leu Ala
            420                 425                 430

Gln Cys Phe Gly Gln Asn Ser Glu Leu Arg Val Asn Ser Thr Lys Ser
        435                 440                 445

Met Ile Gly His Leu Leu Gly Ala Ala Gly Gly Val Glu Ala Val Thr
    450                 455                 460

Val Val Gln Ala Ile Arg Thr Gly Trp Ile His Pro Asn Leu Asn Leu
465                 470                 475                 480

Glu Asp Pro Asp Lys Ala Val Asp Ala Lys Leu Leu Val Gly Pro Lys
                485                 490                 495

Lys Glu Arg Leu Asn Val Lys Val Gly Leu Ser Asn Ser Phe Gly Phe
            500                 505                 510

Gly Gly His Asn Ser Ser Ile Leu Phe Ala Pro Tyr Asn
        515                 520                 525


<210> SEQ ID NO 16
<211> LENGTH: 473
<212> TYPE: PRT
<213> ORGANISM: Cuphea avigera
<220> FEATURE:
<221> NAME/KEY: MISC_FEATURE
<223> OTHER INFORMATION: KASIa

<400> SEQUENCE: 16

Met Gln Ser Leu His Ser Pro Ala Leu Arg Ala Ser Pro Leu Asp Pro
1               5                   10                  15

Leu Arg Leu Lys Ser Ser Ala Asn Gly Pro Ser Ser Thr Ala Ala Phe
            20                  25                  30

Arg Pro Leu Arg Arg Ala Thr Leu Pro Asn Ile Arg Ala Ala Ser Pro
        35                  40                  45

Thr Val Ser Ala Pro Lys Arg Glu Thr Asp Pro Lys Lys Arg Val Val
    50                  55                  60

Ile Thr Gly Met Gly Leu Val Ser Val Phe Gly Ser Asp Val Asp Ala
65                  70                  75                  80

Tyr Tyr Glu Lys Leu Leu Ser Gly Glu Ser Gly Ile Ser Leu Ile Asp
                85                  90                  95

Arg Phe Asp Ala Ser Lys Phe Pro Thr Arg Phe Gly Gly Gln Ile Arg
            100                 105                 110

Gly Phe Asn Ala Thr Gly Tyr Ile Asp Gly Lys Asn Asp Arg Arg Leu
        115                 120                 125

Asp Asp Cys Leu Arg Tyr Cys Ile Val Ala Gly Lys Lys Ala Leu Glu
    130                 135                 140

Asn Ser Asp Leu Gly Gly Asp Ser Leu Ser Lys Ile Asp Lys Glu Arg
145                 150                 155                 160

Ala Gly Val Leu Val Gly Thr Gly Met Gly Gly Leu Thr Val Phe Ser
```

-continued

```
                165                 170                 175

Asp Gly Val Gln Asn Leu Ile Glu Lys Gly His Arg Lys Ile Ser Pro
            180                 185                 190

Phe Phe Ile Pro Tyr Ala Ile Thr Asn Met Gly Ser Ala Leu Leu Ala
        195                 200                 205

Ile Asp Leu Gly Leu Met Gly Pro Asn Tyr Ser Ile Ser Thr Ala Cys
    210                 215                 220

Ala Thr Ser Asn Tyr Cys Phe Tyr Ala Ala Ala Asn His Ile Arg Arg
225                 230                 235                 240

Gly Glu Ala Asp Leu Met Ile Ala Gly Gly Thr Glu Ala Ala Ile Ile
                245                 250                 255

Pro Ile Gly Leu Gly Gly Phe Val Ala Cys Arg Ala Leu Ser Gln Arg
            260                 265                 270

Asn Asp Asp Pro Gln Thr Ala Ser Arg Pro Trp Asp Lys Asp Arg Asp
        275                 280                 285

Gly Phe Val Met Gly Glu Gly Ala Gly Val Leu Val Met Glu Ser Leu
    290                 295                 300

Glu His Ala Met Lys Arg Gly Ala Pro Ile Ile Ala Glu Tyr Leu Gly
305                 310                 315                 320

Gly Ala Val Asn Cys Asp Ala Tyr His Met Thr Asp Pro Arg Ala Asp
                325                 330                 335

Gly Leu Gly Val Ser Ser Cys Ile Glu Ser Ser Leu Glu Asp Ala Gly
            340                 345                 350

Val Ser Pro Glu Glu Val Asn Tyr Ile Asn Ala His Ala Thr Ser Thr
        355                 360                 365

Leu Ala Gly Asp Leu Ala Glu Ile Asn Ala Ile Lys Lys Val Phe Lys
    370                 375                 380

Asn Thr Lys Asp Ile Lys Ile Asn Ala Thr Lys Ser Met Ile Gly His
385                 390                 395                 400

Cys Leu Gly Ala Ser Gly Gly Leu Glu Ala Ile Ala Thr Ile Lys Gly
                405                 410                 415

Ile Thr Thr Gly Trp Leu His Pro Ser Ile Asn Gln Phe Asn Pro Glu
            420                 425                 430

Pro Ser Val Glu Phe Asp Thr Val Ala Asn Lys Lys Gln Gln His Glu
        435                 440                 445

Val Asn Val Ala Ile Ser Asn Ser Phe Gly Phe Gly Gly His Asn Ser
    450                 455                 460

Val Val Ala Phe Ser Ala Phe Lys Pro
465                 470
```

<210> SEQ ID NO 17
<211> LENGTH: 465
<212> TYPE: PRT
<213> ORGANISM: Cuphea pulcherima
<220> FEATURE:
<221> NAME/KEY: MISC_FEATURE
<223> OTHER INFORMATION: KASI

<400> SEQUENCE: 17

```
Met His Ser Leu Gln Ser Pro Ser Leu Arg Ala Ser Pro Leu Asp Pro
1               5                   10                  15

Phe Arg Pro Lys Ser Ser Thr Val Arg Pro Leu His Arg Ala Ser Ile
            20                  25                  30

Pro Asn Val Arg Ala Ala Ser Pro Thr Val Ser Ala Pro Lys Arg Glu
        35                  40                  45
```

-continued

```
Thr Asp Pro Lys Lys Arg Val Val Ile Thr Gly Met Gly Leu Val Ser
    50                  55                  60

Val Phe Gly Ser Asp Val Asp Ala Tyr Tyr Asp Lys Leu Leu Ser Gly
65                  70                  75                  80

Glu Ser Gly Ile Gly Pro Ile Asp Arg Phe Asp Ala Ser Lys Phe Pro
                85                  90                  95

Thr Arg Phe Gly Gly Gln Ile Arg Gly Phe Asn Ser Met Gly Tyr Ile
            100                 105                 110

Asp Gly Lys Asn Asp Arg Arg Leu Asp Asp Cys Leu Arg Tyr Cys Ile
        115                 120                 125

Val Ala Gly Lys Lys Ser Leu Glu Asp Ala Asp Leu Gly Ala Asp Arg
    130                 135                 140

Leu Ser Lys Ile Asp Lys Glu Arg Ala Gly Val Leu Val Gly Thr Gly
145                 150                 155                 160

Met Gly Gly Leu Thr Val Phe Ser Asp Gly Val Gln Ser Leu Ile Glu
                165                 170                 175

Lys Gly His Arg Lys Ile Thr Pro Phe Phe Ile Pro Tyr Ala Ile Thr
            180                 185                 190

Asn Met Gly Ser Ala Leu Leu Ala Ile Glu Leu Gly Leu Met Gly Pro
        195                 200                 205

Asn Tyr Ser Ile Ser Thr Ala Cys Ala Thr Ser Asn Tyr Cys Phe His
    210                 215                 220

Ala Ala Ala Asn His Ile Arg Arg Gly Glu Ala Asp Leu Met Ile Ala
225                 230                 235                 240

Gly Gly Thr Glu Ala Ala Ile Ile Pro Ile Gly Leu Gly Gly Phe Val
                245                 250                 255

Ala Cys Arg Ala Leu Ser Gln Arg Asn Asp Asp Pro Gln Thr Ala Ser
            260                 265                 270

Arg Pro Trp Asp Lys Asp Arg Asp Gly Phe Val Met Gly Glu Gly Ala
        275                 280                 285

Gly Val Leu Val Leu Glu Ser Leu Glu His Ala Met Lys Arg Gly Ala
    290                 295                 300

Pro Ile Ile Ala Glu Tyr Leu Gly Gly Ala Ile Asn Cys Asp Ala Tyr
305                 310                 315                 320

His Met Thr Asp Pro Arg Ala Asp Gly Leu Gly Val Ser Ser Cys Ile
                325                 330                 335

Glu Ser Ser Leu Glu Asp Ala Gly Val Ser Pro Glu Glu Val Asn Tyr
            340                 345                 350

Ile Asn Ala His Ala Thr Ser Thr Leu Ala Gly Asp Leu Ala Glu Ile
        355                 360                 365

Asn Ala Ile Lys Lys Val Phe Lys Asn Thr Lys Asp Ile Lys Ile Asn
    370                 375                 380

Ala Thr Lys Ser Met Ile Gly His Cys Leu Gly Ala Ser Gly Gly Leu
385                 390                 395                 400

Glu Ala Ile Ala Thr Ile Lys Gly Ile Asn Thr Gly Trp Leu His Pro
                405                 410                 415

Ser Ile Asn Gln Phe Asn Pro Glu Pro Ser Val Glu Phe Asp Thr Val
            420                 425                 430

Ala Asn Lys Lys Gln Gln His Glu Val Asn Val Ala Ile Ser Asn Ser
        435                 440                 445

Phe Gly Phe Gly Gly His Asn Ser Val Val Ala Phe Ser Ala Phe Lys
    450                 455                 460

Pro
```

465

<210> SEQ ID NO 18
<211> LENGTH: 466
<212> TYPE: PRT
<213> ORGANISM: Cuphea avigera
<220> FEATURE:
<221> NAME/KEY: MISC_FEATURE
<223> OTHER INFORMATION: mitochondrial KAS

<400> SEQUENCE: 18

```
Met Val Phe Leu Pro Trp Arg Lys Met Leu Cys Pro Ser Gln Tyr Arg
1               5                   10                  15

Phe Leu Arg Pro Leu Ser Ser Ser Thr Thr Phe Asp Pro Arg Arg Val
            20                  25                  30

Val Val Thr Gly Leu Gly Met Val Thr Pro Leu Gly Cys Gly Val Asn
        35                  40                  45

Thr Thr Trp Lys Gln Leu Ile Glu Gly Lys Cys Gly Ile Arg Ala Ile
    50                  55                  60

Ser Leu Glu Asp Leu Lys Met Asp Ala Phe Asp Ile Asp Thr Gln Ala
65                  70                  75                  80

Tyr Val Phe Asp Gln Leu Thr Ser Lys Val Ala Ala Thr Val Pro Thr
                85                  90                  95

Gly Val Asn Pro Gly Glu Phe Asn Glu Asp Leu Trp Phe Asn Gln Lys
            100                 105                 110

Glu His Arg Ala Ile Ala Arg Phe Ile Ala Tyr Ala Leu Cys Ala Ala
        115                 120                 125

Asp Glu Ala Leu Lys Asp Ala Asn Trp Glu Pro Thr Glu Pro Glu Glu
    130                 135                 140

Arg Glu Met Thr Gly Val Ser Ile Gly Gly Gly Thr Gly Ser Ile Ser
145                 150                 155                 160

Asp Val Leu Asp Ala Gly Arg Met Ile Cys Glu Lys Lys Leu Arg Arg
                165                 170                 175

Leu Ser Pro Phe Phe Ile Pro Arg Ile Leu Ile Asn Met Ala Ser Gly
            180                 185                 190

His Val Ser Met Lys Tyr Gly Phe Gln Gly Pro Asn His Ala Ala Val
        195                 200                 205

Thr Ala Cys Ala Thr Gly Ala His Ser Ile Gly Asp Ala Ala Arg Met
    210                 215                 220

Ile Gln Phe Gly Asp Ala Asp Val Met Val Ala Gly Gly Thr Glu Ser
225                 230                 235                 240

Ser Ile Asp Ala Leu Ser Ile Ala Gly Phe Cys Arg Ser Arg Ala Leu
                245                 250                 255

Thr Thr Lys Tyr Asn Ser Cys Pro Gln Glu Ala Ser Arg Pro Phe Asp
            260                 265                 270

Thr Asp Arg Asp Gly Phe Val Ile Gly Glu Gly Ser Gly Val Leu Val
        275                 280                 285

Leu Glu Glu Leu Asp His Ala Arg Lys Arg Gly Ala Lys Met Tyr Ala
    290                 295                 300

Glu Phe Cys Gly Tyr Gly Met Ser Gly Asp Ala His His Ile Thr Gln
305                 310                 315                 320

Pro His Ser Asp Gly Arg Gly Ala Ile Leu Ala Met Thr Arg Ala Leu
                325                 330                 335

Lys Gln Ser Asn Leu His Pro Asp Gln Val Asp Tyr Val Asn Ala His
            340                 345                 350
```

-continued

Ala Thr Ser Thr Ser Leu Gly Asp Ala Ile Glu Ala Lys Ala Ile Lys
355 360 365

Thr Val Phe Ser Asp His Ala Met Ser Gly Ser Leu Ala Leu Ser Ser
370 375 380

Thr Lys Gly Ala Ile Gly His Leu Leu Gly Ala Ala Gly Ala Val Glu
385 390 395 400

Ala Ile Phe Ser Ile Leu Ala Ile Lys Asn Gly Leu Ala Pro Leu Thr
405 410 415

Leu Asn Val Ala Arg Pro Asp Pro Val Phe Thr Glu Arg Phe Val Pro
420 425 430

Leu Thr Ala Ser Lys Glu Met His Val Arg Ala Ala Leu Ser Asn Ser
435 440 445

Phe Gly Phe Gly Gly Thr Asn Thr Thr Leu Leu Phe Thr Ser Pro Pro
450 455 460

Gln Asn
465

<210> SEQ ID NO 19
<211> LENGTH: 402
<212> TYPE: PRT
<213> ORGANISM: Cuphea avigera
<220> FEATURE:
<221> NAME/KEY: MISC_FEATURE
<223> OTHER INFORMATION: KASIII

<400> SEQUENCE: 19

Met Ala Asn Ala Tyr Gly Phe Val Gly Ser Ser Val Pro Thr Val Gly
1 5 10 15

Arg Ala Ala Gln Phe Gln Gln Met Gly Ser Gly Phe Cys Ser Val Asp
20 25 30

Phe Ile Ser Lys Arg Val Phe Cys Cys Ser Ala Val Gln Gly Ala Asp
35 40 45

Lys Pro Ala Ser Gly Asp Ser Arg Ala Glu Tyr Arg Thr Pro Arg Leu
50 55 60

Val Ser Arg Gly Cys Lys Leu Ile Gly Ser Gly Ser Ala Ile Pro Thr
65 70 75 80

Leu Gln Val Ser Asn Asp Asp Leu Ala Lys Ile Val Asp Thr Asn Asp
85 90 95

Glu Trp Ile Ser Val Arg Thr Gly Ile Arg Asn Arg Arg Val Leu Thr
100 105 110

Gly Lys Asp Ser Leu Thr Asn Leu Ala Thr Glu Ala Ala Arg Lys Ala
115 120 125

Leu Glu Met Ala Gln Val Asp Ala Glu Asp Val Asp Met Val Leu Met
130 135 140

Cys Thr Ser Thr Pro Glu Asp Leu Phe Gly Ser Ala Pro Gln Ile Gln
145 150 155 160

Lys Ala Leu Gly Cys Lys Lys Asn Pro Leu Ser Tyr Asp Ile Thr Ala
165 170 175

Ala Cys Ser Gly Phe Val Leu Gly Leu Val Ser Ala Ala Cys His Ile
180 185 190

Arg Gly Gly Gly Phe Asn Asn Val Leu Val Ile Gly Ala Asp Ser Leu
195 200 205

Ser Arg Tyr Val Asp Trp Thr Asp Arg Gly Thr Cys Ile Leu Phe Gly
210 215 220

Asp Ala Ala Gly Ala Val Leu Val Gln Ser Cys Asp Ala Glu Glu Asp
225 230 235 240

Gly Leu Phe Ala Phe Asp Leu His Ser Asp Gly Asp Gly Gln Arg His
245 250 255

Leu Arg Ala Val Ile Thr Glu Asn Glu Thr Asp His Ala Val Gly Thr
260 265 270

Asn Gly Ser Val Ser Asp Phe Pro Pro Arg Arg Ser Ser Tyr Ser Cys
275 280 285

Ile Gln Met Asn Gly Lys Glu Val Phe Arg Phe Ala Cys Arg Ser Val
290 295 300

Pro Gln Ser Ile Glu Leu Ala Leu Gly Lys Ala Gly Leu Asn Gly Ser
305 310 315 320

Asn Ile Asp Trp Leu Leu Leu His Gln Ala Asn Gln Arg Ile Ile Asp
325 330 335

Ala Val Ala Thr Arg Leu Glu Val Pro Gln Glu Arg Val Ile Ser Asn
340 345 350

Leu Ala Asn Tyr Gly Asn Thr Ser Ala Ala Ser Ile Pro Leu Ala Leu
355 360 365

Asp Glu Ala Val Arg Gly Gly Lys Val Lys Pro Gly His Leu Ile Ala
370 375 380

Thr Ala Gly Phe Gly Ala Gly Leu Thr Trp Gly Ser Ala Ile Val Arg
385 390 395 400

Trp Gly

<210> SEQ ID NO 20
<211> LENGTH: 11
<212> TYPE: PRT
<213> ORGANISM: Artificial Sequence
<220> FEATURE:
<223> OTHER INFORMATION: HA Epitope TAG

<400> SEQUENCE: 20

Thr Met Tyr Pro Tyr Asp Val Pro Asp Tyr Ala
1 5 10

<210> SEQ ID NO 21
<211> LENGTH: 1632
<212> TYPE: DNA
<213> ORGANISM: Cuphea palustris
<220> FEATURE:
<221> NAME/KEY: misc_feature
<223> OTHER INFORMATION: KASIV

<400> SEQUENCE: 21
atggcggccg ccgcttccat ggttgcgtcc ccactctgta cgtggctcgt agccgcttgc 60
atgtccactt ccttcgacaa cgacccacgt tccccgtcca tcaagcgtct cccccgccgg 120
aggaggactc tctcccaatc ctccctccgc ggcggatcca ccttccaatg cctcgtcacc 180
tcatacatcg acccttgcaa tcagttctcc tcctccgcct cccttagctt cctcggggat 240
aacggattcg catccctttt cggatccaag cctttccggt ccaatcgcgg ccaccggagg 300
ctcggccgtg cttcccattc cggggaggcc atggccgtgg ctttggaacc tgcacaggaa 360
gtcgccacga agaagaaacc tcttgtcaag caaaggcgag tagttgttac aggaatgggc 420
gtggtgactc ctctaggcca tgaacctgat gtttactaca acaatctcct agatggagta 480
agcggcataa gtgagataga ggccttcgac tgcactcagt ttcccacgag aattgccgga 540
gagatcaagt ctttttccac agatggatgg gtggccccaa agctctccaa gaggatggac 600
aagttcatgc tttacttgtt gactgctggc aagaaagcat tagcggatgg tggaatcacc 660

-continued

```
gatgatgtga tgaaagagct tgataaaaga aagtgtggag ttctcattgg ctccggattg     720

ggcggcatga agctgttcag tgattccatt gaagctctga ggatttcata taagaagatg     780

aatccctttt gtgtaccttt tgctactaca aatatgggat cagctatgct tgcaatggac     840

ttgggatgga tgggtcctaa ctactcgata tcaactgcct gtgctacaag taatttctgt     900

atactgaatt ctgcaaatca catagtcaga ggcgaagctg acatgatgct ttgtggtggc     960

tcggatgcgg tcattatacc tattggtttg ggaggttttg tggcgtgccg agctttgtca    1020

cagaggaata atgaccctac caaagcttcg agaccatggg acagtaatcg tgatggattt    1080

gtaatgggcg aaggagctgg agtgttactt ctcgaggagt tagagcatgc aaagaaaaga    1140

ggtgccacca tttatgcgga atttttaggg ggcagtttca cttgcgatgc ctaccatatg    1200

accgagcctc accctgaagg tgctggagtg atcctctgca tagagaaggc cttggctcag    1260

gccggagtct ctagagaaga cgtaaattac ataaatgcgc atgcaacttc cactcctgct    1320

ggagatatca aggaatacca agctctcgca cactgcttcg gccaaaacag tgagctgaga    1380

gtgaattcca ctaaatcgat gatcggtcat cttattggag cagctggtgg tgtagaagca    1440

gttaccgtag ttcaggcgat aaggactggg tggatccatc caaatcttaa tttggaggac    1500

ccggacaaag ccgtggatgc aaaagtgctc gtaggaccta agaaggagag actaaatgtc    1560

aaggtcggtt tgtccaattc atttgggttc ggtggtcata actcgtccat actcttcgcc    1620

ccttacaatt ag                                                        1632
```

```
<210> SEQ ID NO 22
<211> LENGTH: 1479
<212> TYPE: DNA
<213> ORGANISM: Cinnamonum camphora
<220> FEATURE:
<221> NAME/KEY: misc_feature
<223> OTHER INFORMATION: KASIV

<400> SEQUENCE: 22

atggcaatga tggcaggttc ttgttccaat ttggtgattg gaaacagaga attgggtggg      60

aatgggcctt ctttgcttca ctacaatggc ctcagaccat tggaaaatat tcaaacagcc     120

tcagctgtga aaaagccaaa tgggttattt gcatcttcta cagctcgaaa atccaaagct     180

gtcagagcca tggtattgcc cactgtaaca gctccaaaac gcgaaaaaga tcccaagaag     240

cggattgtaa taacaggaat gggcctggtt tccgtctttg gaaatgacat tgatacattt     300

tatagtaaac tactggaagg agagagcggg attggcccaa tcgacagatt tgatgcttct     360

tccttctcag tgagatttgc tggtcagatt cacaatttct catccaaagg atacattgat     420

gggaagaatg atcgtcggct agatgactgc tggaggtatt gccttgtggc tggaagaaga     480

gcccttgaag atgccaatct tggaccagag gtattggaaa aaatggaccg atctcgaata     540

ggggtgctga tagggacagg aatgggtggg ttgtcagcct ttagcaatgg agttgagtct     600

ctgatccaga agggctacaa gaaaatcact ccatttttta ttccttactc catcaccaat     660

atgggctctg ctcttttagc aatcgacacg ggcgtaatgg gaccaaacta ctccatttca     720

acagcatgtg caaccgcaaa ctattgcttc catgctgctg caaatcatat aagaaggggt     780

gaagctgaaa tcatggtgac tggagggaca gaggcagcag tctcagctac tggagttggc     840

ggattcatag catgtagagc cttatcgcac aggaatgatg agccccagac ggcctcgaga     900

ccatgggata aagatcggga tggtttcgtc atgggcgaag gcgctggtgt gctggtgatg     960

gagagcttgc atcatgcaag aaagagagga gcaaacataa ttgcagagta tttaggagga    1020
```

```
gcagtaacat gtgatgcaca tcacatgaca gatcctcgag ctgatggtct cggggtttct   1080

tcttgcataa ccaagagctt agaagatgca ggagtctccc cagaagaggt gaactatgtg   1140

aatgctcatg caacatcaac acttgcagga gatttagcag aggttaatgc cataaagaag   1200

gtcttcaagg acacatctga aatgaaaatg aatggaacta agtcaatgat tggacactgt   1260

cttggagcag ctggtggatt agaagccatt gcgaccatca aagctatcaa tactggctgg   1320

ctacatccaa ccatcaatca atttaacata gaaccagcgg taactatcga cacggtccca   1380

aatgtgaaga aaaagcatga tatccatgtt ggcatctcta actcatttgg ctttggtggg   1440

cacaactcgg tggtcgtttt tgctcccttc atgccatga                          1479


<210> SEQ ID NO 23
<211> LENGTH: 1449
<212> TYPE: DNA
<213> ORGANISM: Cinnamonum camphora
<220> FEATURE:
<221> NAME/KEY: misc_feature
<223> OTHER INFORMATION: KASI

<400> SEQUENCE: 23

atgcaaatcc tccaaacccc atcatcatca tcgtcttctc tccgcatgtc gtccatggaa     60

tctctctctc tcacccctaa atctctccct ctcaaaaccc ttcttcccct tcgtcctcgc    120

cctaaaaacc tctccagacg caaatcccaa aaccctagac ccatctcctc ctcttcctcc    180

cccgagagag agacggatcc caagaagcga gtcgtcatca ccgggatggg cctcgtctcc    240

gtcttcggca acgatgtcga tgcctactac gaccgcctcc tctcgggaga gagcggcatc    300

gcccccatcg atcgcttcga cgcctccaag ttccccacca gattcgccgg tcagatccga    360

gggttcacct ccgacggcta cattgacggg aagaacgacc gccggttaga cgattgtctc    420

agatactgta ttgttagtgg gaagaaggcg ctcgagaatg ccggcctcgg accccatctc    480

atggacggaa agattgacaa ggagagagct ggtgtgcttg tcgggacagg catgggtggt    540

cttacagttt tctctaatgg ggtccagact ctacatgaga aaggttacag gaaaatgact    600

ccgtttttca tcccttatgc cataacaaac atgggttctg ccttgcttgc aattgaactt    660

ggttttatgg gcccaaacta ttctatctca actgcatgtg ctacctccaa ttattgcttt    720

tatgctgctg ctaaccatat acggagaggt gaggctgatc tgatgcttgc tggtggaact    780

gaagctgcaa ttattcctat tggattagga ggctttgttg catgtagagc tttatcacag    840

agaaatgatg acccccagac agcttcaaga ccatgggaca aagatcgaga cggttttgtt    900

atgggtgaag gtgctggagt attggtaatg gagagcttgg agcatgctat gaaacgtgat    960

gcaccaatta ttgctgagta tttaggaggt gcagtgaact gtgatgcgta tcatatgacg   1020

gatcctagag ctgatgggct cggggtttca acatgcatag aaagaagtct tgaagatgct   1080

ggtgtggcac ctgaagaggt taactacata aatgcacatg caacttccac tcttgcagga   1140

gacctggctg aggtgaatgc gatcaaaaag gtttttacaa acacttcaga gatcaaaatc   1200

aatgcaacca agtctatgat agggcactgc cttggagcgg ccggggggtt agaagccatt   1260

gccacaatca aagcaataaa tactggttgg ctgcaccctt ctataaacca atttaatcca   1320

gagccctctg ttgagtttga cactgtagca aataaaaagc agcagcatga agtgaatgtt   1380

gccatttcca actctttcgg gtttggcgga cacaactcag tcgtggtgtt ttcggcattc   1440

aagccttga                                                           1449


<210> SEQ ID NO 24
```

<211> LENGTH: 1395
<212> TYPE: DNA
<213> ORGANISM: Umbellularia californica
<220> FEATURE:
<221> NAME/KEY: misc_feature
<223> OTHER INFORMATION: KASI

<400> SEQUENCE: 24

```
atggaatctc tctctctcac ccctaaatct ctccctctca aaacccttct tccctttcgt     60

cctcgcccta aaaacctctc cagacgcaaa tcccaaaacc ctaaacccat ctcctcctct    120

tcctccccgg agagagagac ggatcccaag aagcgagtcg tcatcaccgg gatgggcctc    180

gtctccgtct tcggcaacga cgtcgatgcc tactacgacc gcctcctctc cggagagagc    240

ggcatcgccc ccatcgatcg cttcgacgcc tccaagttcc ccaccagatt cgccggtcag    300

atccgagggt tcacctccga cggctacatt gacgggaaga acgaccgccg gttagacgat    360

tgtctcagat actgtatcgt tagtgggaag aaggcgctcg agaatgccgg cctcggaccc    420

gatctcatgg acggaaagat tgacaaggag cgagctggtg tgcttgtcgg gacaggcatg    480

ggtggtctta cagttttctc taatggggtt cagactctcc atgagaaagg ttacaggaaa    540

atgactccgt ttttcatccc ttatgccata acaaacatgg gttctgcctt gcttgcaatt    600

gaccttggtt ttatgggccc aaactattct atctcaactg catgtgctac ctccaattat    660

tgcttttatg ctgctgctaa ccatatacgg agaggtgagg ctgatgtgat gcttgctggt    720

ggaactgaag ctgcaattat tcctattggc ttaggaggct ttgttgcatg tagagcttta    780

tcacagcgaa atgatgaccc ccagacagct tcaagaccat gggacaaaga tcgagacggt    840

tttgttatgg gtgaaggtgc tggagtattg gtaatggaga gcttggagca tgctatgaaa    900

cgtgatgcac caattattgc tgagtattta ggaggtgcag tgaactgtga tgcgtatcat    960

atgacggatc ctagagctga tgggctcggg gtttcaacat gcatagaaag aagtcttgaa   1020

gatgctggtg tggcacctga agaggttaac tacataaatg cacatgcaac ttccacactt   1080

gcaggtgacc tggccgaggt gaatgccatc aaaaaggttt ttacaaacac ttcagagatc   1140

aaaatcaatg caaccaagtc tatgataggg cactgccttg gagcggccgg gggtttagaa   1200

gccattgcca caatcaaagc aataaatact ggttggctgc acccttctat aaaccaattt   1260

aatccagagc cctctgttga gtttgacact gtagcaaata aaaagcagca gcatgaagtg   1320

aatgttgcca tttccaactc tttcgggttt ggtggacaca actcggtcgt ggtgttttcg   1380

gcattcaagc cttga                                                    1395
```

<210> SEQ ID NO 25
<211> LENGTH: 1419
<212> TYPE: DNA
<213> ORGANISM: Umbellularia californica
<220> FEATURE:
<221> NAME/KEY: misc_feature
<223> OTHER INFORMATION: KASIV

<400> SEQUENCE: 25

```
atgacgcaaa ccctcatctg cccatcctcc atggaaaccc tctctcttac caaacaatcc     60

catttcagac tcaggctacc cactcctcct cacatcagac gcggcggcgg ccatcgccat    120

cctcctccct tcatctccgc ctccgccgcc cctaggagag agaccgatcc gaagaagaga    180

gtcgtcatca cgggaatggg cctcgtctcc gtcttcggca ccaacgtcga tgtctactac    240

gatcgcctcc tcgccggcga gagcggcgtt ggcactatcg atcgcttcga cgcgtcgatg    300

ttcccgacga gattcggcgg ccagatccgg aggttcacgt cggaggggta catcgacggg    360
```

-continued

```
aagaacgacc ggcggctgga tgactacctc cggtactgcc tcgtcagcgg gaagaaggcg    420

atcgagagtg ctggcttcga tctccataac atcaccaaca agattgacaa ggagcgagct    480

gggatacttg ttgggtcagg catgggcggt cttaaagttt tctctgatgg tgttgagtct    540

cttatcgaga aaggttacag gaaaataagt ccatttttca tcccttatat gataccaaac    600

atgggttctg ctttgcttgg aattgacctt ggtttcatgg gaccaaacta ctcaatttca    660

actgcttgtg ctacgtcaaa ttattgcatt tatgctgctg caaatcatat ccgacaaggt    720

gatgccgacc taatggttgc tggtggaact gaggctccaa ttattccaat tggcttaggg    780

ggctttgtag catgtagagc tttgtcaaca agaaatgatg atccccagac agcttcaagg    840

ccatgggaca tagaccgaga tggttttgtt atgggcgaag gagctggaat attggtattg    900

gagagcttgg aacatgcaat gaaacgtgat gcaccaattc ttgctgagta tttaggaggt    960

gcagttaact gtgatgctca tcatatgaca gatcctcgag ctgatgggct tggggtttca   1020

acatgcattg aaagcagtct tgaagatgcc ggcgtggcag cagaagaggt taactatata   1080

aatgcacacg cgacttcaac acctacaggt gacctggctg agatgaaggc tataaaaaat   1140

gtatttagga acacttctga gatcaaaatc aatgcaacca agtctatgat tgggcattgc   1200

cttggagcgt ctgggggct agaagccatt gccacattga aagcgattac aactggttgg    1260

cttcatccaa ctataaacca atttaatcca gagccttctg ttgactttga tacggtggca   1320

aagaaaaaga agcagcatga agttaatgtt gccatttcaa actcttttgg attcggagga   1380

cacaactcag tgttggtgtt ttcggcattc aagccttga                          1419
```

```
<210> SEQ ID NO 26
<211> LENGTH: 1578
<212> TYPE: DNA
<213> ORGANISM: Cuphea wrightii
<220> FEATURE:
<221> NAME/KEY: misc_feature
<223> OTHER INFORMATION: KASAI

<400> SEQUENCE: 26

atggcttccg cggcattcac catgtcggcg tgccccgcga tgactggcag ggcccctggg     60

gcacgtcgct ccggacggcc agtcgccacc cgcctgaggt acgtattcca gtgcctggtg    120

gccagctgca tcgacccctg cgaccagtac cgcagcagcg ccagcctgag cttcctgggc    180

gacaacggct tcgccagcct gttcggcagc aagcccttca tgagcaaccg cggccaccgc    240

cgcctgcgcc gcgccagcca cagcggcgag gccatggccg tggccctgca gcccgcccag    300

gaggccggca ccaagaagaa gcccgtgatc aagcagcgcc gcgtggtggt gaccggcatg    360

ggcgtggtga ccccctggg ccacgagccc gacgtgttct acaacaacct gctggacggc     420

gtgagcggca tcagcgagat cgagaccttc gactgcaccc agttccccac ccgcatcgcc    480

ggcgagatca agagcttcag caccgacggc tgggtggccc ccaagctgag caagcgcatg    540

gacaagttca tgctgtacct gctgaccgcc ggcaagaagg ccctggccga cggcggcatc    600

accgacgagg tgatgaagga gctggacaag cgcaagtgcg gcgtgctgat cggcagcggc    660

atgggcggca tgaaggtgtt caacgacgcc atcgaggccc tgcgcgtgag ctacaagaag    720

atgaacccct tctgcgtgcc cttcgccacc accaacatgg gcagcgccat gctggccatg    780

gacctgggct ggatgggccc caactacagc atcagcaccg cctgcgccac cagcaacttc    840

tgcatcctga acgccgccaa ccacatcatc cgcggcgagg ccgacatgat gctgtgcggc    900

ggcagcgacg ccgtgatcat ccccatcggc ctgggcggct tcgtggcctg ccgcgccctg    960
```

agccagcgca acagcgaccc caccaaggcc agccgcccct gggacagcaa ccgcgacggc 1020
ttcgtgatgg gcgagggcgc cggcgtgctg ctgctggagg agctggagca cgccaagaag 1080
cgcggcgcca ccatctacgc cgagttcctg ggcggcagct tcacctgcga cgcctaccac 1140
atgaccgagc ccaccccga gggcgccggc gtgatcctgt gcatcgagaa ggccctggcc 1200
caggccggcg tgagcaagga ggacgtgaac tacatcaacg cccacgccac cagcaccagc 1260
gccggcgaca tcaaggagta ccaggccctg gcccgctgct tcggccagaa cagcgagctg 1320
cgcgtgaaca gcaccaagag catgatcggc cacctgctgg gcgccgccgg cggcgtggag 1380
gccgtgaccg tggtgcaggc catccgcacc ggctggattc accccaacct gaacctggag 1440
gaccccgaca aggccgtgga cgccaagctg ctggtgggcc ccaagaagga gcgcctgaac 1500
gtgaaggtgg gcctgagcaa cagcttcggc ttcggcggcc acaacagcag catcctgttc 1560
gccccctgca acgtgtga 1578

<210> SEQ ID NO 27
<211> LENGTH: 1515
<212> TYPE: DNA
<213> ORGANISM: Cuphea avigera
<220> FEATURE:
<221> NAME/KEY: misc_feature
<223> OTHER INFORMATION: KASIVb

<400> SEQUENCE: 27
atggcggccg cttcttgcat ggctgcgtcc cctttctgta cgtcgctcgt ggctgcatgc 60
atgtcgactt catccgacaa cgacccatgt cccctttccc gccgcggatc caccttccaa 120
tgctacatcg ggataacgg attcggatcg aagcctcccc gttcaaatcg tggccacctg 180
aggctcggcc gcacttcaca ttccggagag gtgatggctg tggctatgca atctgcacaa 240
gaagtctcca caaaggagaa acctgctacc aagcaaaggc gagttgttgt cacgggtatg 300
ggtgtggtga ctgctctagg ccatgacccc gatgtttact acaacaatct cctagacgga 360
gtaagcggca taagcgagat agaaaacttt gactgttctc agcttcccac gagaattgcc 420
ggagagatca agtctttttc tgcagatggg tgggtggccc cgaagttctc caggaggatg 480
gacaagttta tgctttacat tctgactgca ggcaagaaag cattagtaga tggtggaatc 540
actgaagatg tgatgaaaga gctcgataaa agaaagtgtg gagttctcat tggctccgga 600
ttgggcggta tgaaggtatt tagcgagtcc attgaagctc tgaggacttc atataagaag 660
atcagtccct tttgtgtacc tttttctacc acgaatatgg gatccgctat tcttgcaatg 720
gacttgggat ggatgggccc taactattcg atatcgactg cctgtgcaac aagtaacttc 780
tgtatactga atgctgcgaa ccacataacc aaaggcgaag cagacatgat gctttgtggt 840
ggctcggatt cggtcatttt acctattggt atgggaggtt tcgtagcatg ccgagctttg 900
tcacagagga ataatgaccc taccaaagct tcgagaccat gggacagtaa tcgtgatgga 960
tttgtgatgg gagaaggtgc tggagtttta cttctcgagg agttagagca tgcaaagaaa 1020
agaggcgcaa ccatttatgc ggaatttctt ggtgggagtt tcacttgcga tgcctaccac 1080
atgaccgagc ctcaccctga aggagctgga gtgatcctct gcatagagaa ggccttggct 1140
cagtccggag tctcgaggga agacgtaaat tacataaatg cgcatgcaac ttccactccc 1200
gctggagata tcaaagaata ccaagctctc gcccactgtt tcggccaaaa cagtgagtta 1260
agagtgaatt ccaccaagtc gatgatcggt caccttcttg gaggagccgg tggcgtagaa 1320
gcagttacag tcgttcaggc aataaggact ggatggatcc atccaaatat taatttggac 1380
gacccggacg aaggcgtgga tgcaaaactg ctcgtcggcc ctaagaagga gaaactgaag 1440
gtcaaggtcg gtttgtccaa ttcattcggg ttcggcggcc ataactcatc catactcttt 1500
gccccatgca attag 1515

<210> SEQ ID NO 28
<211> LENGTH: 1539
<212> TYPE: DNA
<213> ORGANISM: Cuphea paucipetala
<220> FEATURE:
<221> NAME/KEY: misc_feature
<223> OTHER INFORMATION: KASIVb

<400> SEQUENCE: 28
atggcggccg cttcatcaat ggttgcctcc ccattctcta cgtccctcgt agccgcctgc 60
atgtccactt cattcgacaa cgacccacgt tccctttccc acaaccgcat ccgcctccgc 120
ggatccacct tccaatgcct cggggatatc ggattcgctt ccctcatcgg atccaagcct 180
ccgcgttcaa atcgcaacca ccggaggctc ggccgcactt cccattccgg ggaggtcatg 240
gctgtggcta tgcaacctgc acatgaagct tccacaaaga ataaacctgt taccaagcaa 300
aggcgagtag ttgtgacagg tatgggcgtg gcgactcctc taggccatga ccccgatgtt 360
tactacaaca atctcctaga cggagtaagt ggcataagtc agatagagaa cttcgactgc 420
actcagtttc ccacgagaat tgccggagag atcaagtctt tctccacaga agggtatgtg 480
atcccgaagt tcgccaagag gatggacaag ttcatgcttt acttgctgac tgcaggcaag 540
aaagcattag aagatggtgg aatcactgaa gatgtgatga aagagctcga taaaagaaag 600
tgtggagttc tcattggctc cggaatgggc ggtatgaaga taatcaacga ttccattgca 660
gctctgaatg tttcatataa gaagatgact cccttttgtg tacccttttc caccacaaat 720
atgggatccg ctatgcttgc gatagacttg ggatggatgg gcccgaacta ttcgatatca 780
actgcctgtg caacaagtaa ctactgtata ctgaatgctg cgaaccacat agtcagaggc 840
gaagcagata tgatgctttg tggtggctcg gatgcggtca ttatacctgt tggtttggga 900
ggtttcgtag catgccgagc tttgtcacag aggaacaatg accctaccaa agcttcgaga 960
ccttgggaca gtaaccgtga tggatttgtg atgggagaag gagccggagt gttacttctc 1020
gaggagttag agcatgcaaa gaaaagaggt gcaaccattt atgcggaatt tctaggtggg 1080
agtttcactt gcgatgccta ccacatgacc gagcctcacc ctgatggagc tggagtgatc 1140
ctctgcatag agaaggcttt ggcacagtcc ggagtctcga gggaagacgt caattacata 1200
aatgcgcatg caacttctac tcctgctgga gatatcaagg aataccaagc tctcgcccac 1260
tgtttcggcc aaaacagtga gttaagagtg aattccacca aatcgatgat cggtcacctt 1320
cttggagctg ctggtggcgt agaagcagtt acagtagttc aggcaataag gactgggtgg 1380
atccatccaa atattaattt ggaaaacccg gacgaagctg tggatgcaaa attgctcgtc 1440
ggccctaaga aggagaaact gaaggtcaag gtcggtttgt ccaattcatt tgggttcggt 1500
gggcataact catccatact cttcgcccct tacaattag 1539

<210> SEQ ID NO 29
<211> LENGTH: 1629
<212> TYPE: DNA
<213> ORGANISM: Cuphea ignea
<220> FEATURE:
<221> NAME/KEY: misc_feature
<223> OTHER INFORMATION: KASIVb -continued

<400> SEQUENCE: 29
atggcggcgg ccgcttccat gtttacgtcc ccactctgta cgtggctcgt agcctcttgc 60
atgtcgactt ccttcgacaa cgacccacgt tcgccgtccg tcaagcgtct cccccgccgg 120
aggaggattc tctcccaatg ctccctccgc ggatccacct cccaatgcct cgtcacctca 180
tacatcgacc cttgcaataa gtactgctcc tccgcctccc ttagcttcct cggggataac 240
ggattcgcat ccccttttcgg atctaagcca ttccggtcca atcgcggcca ccggaggctc 300
ggccgtgctt cccattccgg ggaggccatg gctgtggctc tgcaacctgc acaggaagtc 360
accacgaaga agaaacctgt gatcaagcaa aggcgagtag ttgttacagg aatgggcgtg 420
gtgactcctc taggccatga acctgatgtt tactacaaca atctcctaga tggagtaagc 480
ggcataagtg agatagagac cttcgactgc actcagtttc ccacgagaat cgccggagag 540
atcaagtctt tttccacaga tgggtgggtg gccccaaagc tctccaagag gatggacaag 600
ttcatgcttt acttgttgac tgctggcaag aaagcattag cagatggtgg aatcaccgat 660
gatgtgatga aagagcttga taaaagaaag tgtggggttc tcattggctc tggaatgggc 720
ggcatgaagt tgttcaacga ttccattgaa gctctgagga tttcatataa aaagatgaat 780 ccccttttgtg taccttttgc taccacaaat atgggatcag ctatgcttgc aatggacttg 840
ggatggatgg gtcctaacta ctcgatatca actgcctgtg caacaagtaa tttctgtata 900
ctgaatgctt caaaccacat agtcagaggc gaagctgaca tgatgctttg tggtggctcg 960
gattctgtca ctgtaccttt aggtgtggga ggtttcgtag catgccgagc tttgtcacag 1020
aggaataatg accctaccaa agcttcgaga ccttgggaca gtaatcggga tggatttgtg 1080
atgggagaag gagctggagt gttacttctt gaggagttag agcatgcaaa gaaaagaggt 1140
gcaaccattt atgcggaatt tctcggtggg agctttactt ctgatgccta ccacatgacc 1200
gagcctcacc ccgaaggagc tggagtgatt ctctgcattg agaaggcctt ggctcagtcc 1260
ggagtctcga gggaagacgt gaattatata aatgcgcatg caacttccac tcctgctggt 1320
gatataaagg aataccaagc tctcgcccgc tgtttcggcc aaaacagtga gttaagagtg 1380
aattccacca aatcgatgat cggtcacctt cttggagcag ctggtggcgt agaagcagtt 1440
gcagtaattc aggcaataag gactggatgg atccatccaa atattaattt ggaagacccc 1500
gacgaagccg tggatccaaa attgctcgtc ggccctaaga aggagaaact gaaggtcaag 1560
gtagctttgt ccaattcatt cgggttcggc gggcataact catccatact ctttgcccct 1620
tgcaattag 1629

<210> SEQ ID NO 30
<211> LENGTH: 1608
<212> TYPE: DNA
<213> ORGANISM: Cuphea procumbens
<220> FEATURE:
<221> NAME/KEY: misc_feature
<223> OTHER INFORMATION: KASIV

<400> SEQUENCE: 30
atggcggcgg cgccctcttc cccactctgt acgtggctcg tagccgcttg catgtccact 60
tccttcgaca acaacccacg ttcgccctcc atcaagcgtc tcccccgccg gaggagggtt 120
ctctcccaat gctccctccg tggatccacc ttccaatgcc tcgtcacctc acacaacgac 180
ccttgcaatc agtactgctc ctccgcctcc cttagcttcc tcggggataa cggattcgga 240
tccaagccat tccggtccaa tcgcggccac cggaggctcg gccgtgcttc gcattccggg 300

```
gaggccatgg ctgtggcctt gcaacctgca caggaagtcg ccacgaagaa gaaacctgct    360

atgaagcaaa ggcgagtagt tgttacagga atgggcgtgg tgactcctct gggccatgaa    420

cctgatgttt actacaacaa tctcctagat ggagtaagcg gcataagtga gatagagacc    480

ttcgactgca ctcagtttcc cacgagaatc gccggagaga tcaagtcttt ttccacagat    540

ggatgggtgg ccccaaagct ctccaagagg atggacaagt tcatgcttta cttgttgact    600

gctggcaaga aagcattagc agatggtgga atcactgatg atgtgatgaa agagcttgat    660

aaaagaaagt gtggagttct cattggctct ggaatgggcg gcatgaagtt gttcaacgat    720

tccattgaag ctctgagagt ttcatataag aagatgaatc ccttttgtgt accttttgct    780

accacaaata tgggatcagc tatgcttgca atggacttgg gatggatggg tcctaactac    840

tcgatatcaa ctgcctgtgc aacaagtaat ttctgtatac tgaatgctgc aaaccacata    900

gtcagaggcg aagctgacat gatgctttgt ggtggctcgg atgcggtcat tatacctatt    960

ggtttgggag gttttgtggc gtgccgagct ttgtcacaga ggaataatga ccctaccaag   1020

gcttcgagac catgggatag taatcgtgat ggatttgtaa tgggcgaagg agctggagtg   1080

ttacttctcg aggagttaga gcatgcaaag aaaagaggtg caaccattta tgcggaattt   1140

ttagggggca gtttcacttg cgatgcctac catatgaccg agcctcaccc tgaaggagct   1200

ggagtgatcc tctgcataga gaaggccttg gctcagtccg gagtctctag agaagacgta   1260

aattacataa atgcgcatgc aacttccact cctgctggag atatcaaaga ataccaagct   1320

ctcgcccact gtttcggcca aaacagtgag ctgagagtga attccactaa atcgatgatc   1380

ggtcatcttc ttggagcagc tggtggtgta gaagcagtta ccgtaattca ggcgataagg   1440

actgggtgga tccatccaaa tcttaatttg gaagacccgg acaaagccgt ggatgcaaaa   1500

tttctcgtgg gacctaagaa ggagagactg aatgtcaagg tcggtttgtc caattcattt   1560

gggttcgggg ggcataactc atccatactc tttgcccctt gcaattag                1608
```

<210> SEQ ID NO 31
<211> LENGTH: 1608
<212> TYPE: DNA
<213> ORGANISM: Cuphea paucipetala
<220> FEATURE:
<221> NAME/KEY: misc_feature
<223> OTHER INFORMATION: KASIVa

<400> SEQUENCE: 31

```
atggcggcgg cggcctcttc ccccactctgc acatggctcg tagccgcttg catgtccact     60

tcattcgaca acaacccacg ttcgccctcc atcaagcgtc tcccccgccg gaggagggtt    120

ctctcccaat gctccctccg cggatccacc ttccaatgcc tcgtcaactc acacatcgac    180

ccttgcaatc agaacgtctc ctccgcctcc cttagcttcc tcggggataa cggattcgga    240

tccaatccat tccggtccaa tcgcggccac cggaggctcg gccgggcttc ccattccggg    300

gaggccatgg ctgttgctct gcaacctgca caggaagtcg ccacgaagaa gaaacctgct    360

atcaagcaaa ggcgagtagt tgttacagga atgggcgtgg tgactcctct aggccatgag    420

cctgatgttt tctacaacaa tctcctagat ggagtaagcg gcataagtga gatagagacc    480

ttcgactgca ctcagtttcc cacgagaatt gccggagaga tcaagtcttt ttccacagat    540

gggtgggtgg ccccaaagct ctccaagagg atggacaagt tcatgcttta cttgttgact    600

gctggcaaga aagcattagc agatgctgga attaccgagg atgtgatgaa agagcttgat    660

aaaagaaagt gtggagttct cattggctcc ggaatgggcg gcatgaagtt gttcaacgat    720
```

-continued

```
tccattgaag ctctgagggt ttcatataag aagatgaatc ccttttgtgt accttttgct    780

accacaaata tgggatcagc tatgcttgca atggacttgg gatggatggg tcctaactac    840

tcgatatcga ctgcctgtgc aacaagtaat ttctgtatac tgaatgctgc aaaccacata    900

atcagaggcg aagctgacat gatgctttgt ggtggttcgg atgcggtcat tatacctatt    960

ggtttgggag gttttgtggc gtgccgagct ttgtcacaga ggaatagtga ccctaccaaa   1020

gcttcgagac catgggatag taatcgtgat ggatttgtaa tgggcgaagg agctggagtg   1080

ttacttctcg aggagttaga gcatgcaaag aaaagaggtg caaccattta tgcggaattt   1140

ttagggggca gcttcacttg cgatgcctac cacatgaccg agcctcaccc tgatggagct   1200

ggagtgatcc tctgcataga gaaggctttg gcacagtccg gagtctcgag ggaagacgtc   1260

aattacataa atgcgcatgc aacttctact cctgctggag atatcaagga ataccaagct   1320

ctcgcccact gtttcggcca aaacagtgag ctgagagtga attccactaa atcgatgatc   1380

ggtcatcttc ttggtgcagc tggtggtgta gaagctgtta ctgtaattca ggcgataagg   1440

actgggtgga ttcatccaaa tcttaatttg gaagacccgg acgaagccgt ggatgcaaaa   1500

tttctcgtgg gacctaagaa ggagagattg aatgtcaagg tcggtttgtc caattcattt   1560

gggttcggtg ggcataactc atccatactc ttcgcccctt acaattag                1608


<210> SEQ ID NO 32
<211> LENGTH: 1593
<212> TYPE: DNA
<213> ORGANISM: Cuphea painteri
<220> FEATURE:
<221> NAME/KEY: misc_feature
<223> OTHER INFORMATION: KASIV

<400> SEQUENCE: 32

atggcggcct cctcttgcat ggttgcgtcc ccgttctgta cgtggctcgt atccgcatgc     60

atgtctactt cattcgacaa cgacccacgt tccctttccc acaagcggct ccgcctctcc    120

cgtcgccgga ggcctctctc ctctcattgc tccctccgcg gatccactcc ccaatgcctc    180

gacccttgca atcagcactg cttcctcggg gataacggat tcgcttccct catcggatcc    240

aagcctcccc gttccaatct cggccacctg aggctcggcc gcacttccca ttccggggag    300

gtcatggctg tggcacagga agtctccaca aataagaaac atgctaccaa gcaaaggcga    360

gtagttgtga caggtatggg cgtggtgact cctctaggcc atgaccccga tgtttactac    420

aacaatctcc tagaaggagt aagtggcatc agtgagatag agaacttcga ctgctctcag    480

cttcccacga gaattgccgg agagatcaag tctttttcca cagatgggtt ggtggccccg    540

aagctctcca agaggatgga caagttcatg ctttacatcc tgactgcagg caagaaagca    600

ttagcagatg gtggaatcac tgaagatgtg atgaaagagc tcgataaaag aaagtgtgga    660

gttctcattg gctccggatt gggcggtatg aaggtattca gcgactccgt tgaagctctg    720

aggatttcat ataagaagat cagtcccttt tgtgtacctt tttctaccac aaatatggga    780

tccgctatgc ttgcaatgga cttgggatgg atgggcccta actattcgat atcaactgcc    840

tgtgcaacaa gtaacttctg tatactgaat gctgcgaacc acataaccaa aggcgaagct    900

gacatgatgc tttgtggtgg ctcggatgcg gccattttac ctattggtat gggaggtttc    960

gtggcatgcc gagctttgtc acagaggaat aatgacccta ccaaagcttc gagaccatgg   1020

gacagtaatc gtgatggatt tgtgatggga gaaggagctg gagtgttact tctcgaggag   1080

ttagagcatg caaagaaaag aggtgcaacc atttatgcgg aatttctagg tgggagtttc   1140
```

```
acttgcgatg cctaccacat gaccgagcct caccctgatg gagctggagt gatcctctgc   1200

atagagaagg ccttggctca gtccggagtc tcgagggaag aagtaaatta cataaatgcg   1260

catgcaactt ccactcctgc tggagatatc aaggaatacc aagctctcgc ccattgtttc   1320

ggccaaaaca gtgagttaag agtgaattcc accaaatcga tgatcggtca ccttcttgga   1380

ggagctggtg gcgtagaagc agttacagta gttcaggcaa taaggactgg atggatccat   1440

ccaaatatta atttggaaga cccggacaaa ggcgtggatg caaaactgct cgtcggccct   1500

aagaaggaga aactgaaggt caaggtcggt ttgtccaatt catttgggtt cggcggccat   1560

aactcatcca tactctttgc cccatgcaat tag                                 1593
```

<210> SEQ ID NO 33
<211> LENGTH: 1629
<212> TYPE: DNA
<213> ORGANISM: Cuphea avigera
<220> FEATURE:
<221> NAME/KEY: misc_feature
<223> OTHER INFORMATION: KASIVa

<400> SEQUENCE: 33

```
atggcggccg ccgcttccat ggttgcgtcc ccattctgta cgtggctcgt agccgcttgc     60

atgtccactt ccgtcgacaa agacccacgt tcgccgtcta tcaagcgtct cccccgccgg    120

aagaggattc attcccaatg ctccctccgc ggatccacct tccaatgcct cgtcacctca    180

tacaacgacc cttgcgaaca ataccgctca tccgcctccc ttagcttcct cggggataac    240

ggattcgcat cccttttcgg atccaagcca ttccggtcca atcgcggcca ccggaggctc    300

ggccgtgctt cccattccgg ggaggccatg gccgtggcac tgcaacctgc acaggaagtt    360

ggcacgaaga agaaacctgt tatcaagcaa aggcgagtag ttgttacagg aatgggcgtg    420

gtgactcctc taggccatga acctgatgtt tactacaaca atctcctaga cggagtaagc    480

ggcataagtg agatagagac cttcgactgc actcagtttc ccacgagaat tgccggagag    540

atcaagtctt tttccacaga tgggtgggtg gctccaaagc tctctaagag gatggacaag    600

ttcatgcttt acttgttgac tgctggcaag aaagcattgg cagatggtgg aatcaccgat    660

gatgtgatga aagagcttga taaaagaaag tgtggagttc tcattggctc cggattgggc    720

ggtatgaagg tatttagcga gtccattgaa gctctgagga cttcatataa gaagatcagt    780

ccctttttgtg taccttttttc taccacgaat atgggatccg ctattcttgc aatggacttg    840

ggatggatgg gccctaacta ttcgatatcg actgcctgtg caacaagtaa cttctgtata    900

ctgaatgctg cgaaccacat aaccaaaggc gaagcagaca tgatgctttg tggtggctcg    960

gattcggtca ttttacctat tggtatggga ggtttcgtag catgccgagc tttgtcacag   1020

aggaataatg accctaccaa agcttcgaga ccatgggaca gtaatcgtga tggatttgtg   1080

atgggagaag gtgctggagt tttacttctc gaggagttag agcatgcaaa gaaaagaggc   1140

gcaaccattt atgcggaatt tcttggtggg agtttcactt gcgatgccta ccacatgacc   1200

gagcctcacc ctgaaggagc tggagtgatc ctctgcatag agaaggcctt ggctcagtcc   1260

ggagtctcga gggaagacgt aaattacata aatgcgcatg caacttccac tcccgctgga   1320

gatatcaaag aataccaagc tctcgcccac tgtttcggcc aaaacagtga gttaagagtg   1380

aattccacca agtcgatgat cggtcacctt cttggaggag ccggtggcgt agaagcagtt   1440

acagtcgttc aggcaataag gactggatgg atccatccaa atattaattt ggacgacccg   1500

gacgaaggcg tggatgcaaa actgctcgtc ggccctaaga aggagaaact gaaggtcaag   1560
```

gtcggtttgt ccaattcatt cgggttcggc ggccataact catccatact ctttgcccca 1620
tgcaattag 1629

<210> SEQ ID NO 34
<211> LENGTH: 1629
<212> TYPE: DNA
<213> ORGANISM: Cuphea ignea
<220> FEATURE:
<221> NAME/KEY: misc_feature
<223> OTHER INFORMATION: KASIVa

<400> SEQUENCE: 34
atggcggcgg ccgcttccat gtttacgtcc ccactctgta cgtggctcgt agcctcttgc 60
atgtcgactt ccttcgacaa cgacccacgt tcgccgtccg tcaagcgtct cccccgccgg 120
aggaggattc tctcccaatg ctccctccgc ggatccacct cccaatgcct cgtcacctca 180
tacatcgacc cttgcaataa gtactgctcc tccgcctccc ttagcttcct cggggataac 240
ggattcgcat cccttttcgg atctaagcca ttccggtcca atcgcggcca ccggaggctc 300
ggccgtgctt cccattccgg ggaggccatg gctgtggctc tgcaacctgc acaggaagtc 360
accacgaaga agaaacctgt gatcaagcaa aggcgagtag ttgttacagg aatgggcgtg 420
gtgactcctc taggccatga acctgatgtt tactacaaca atctcctaga tggagtaagc 480
ggcataagtg agatagagac cttcgactgc actcagtttc ccacgagaat cgccggagag 540
atcaagtctt tttccacaga tgggtgggtg gccccaaagc tctccaagag gatggacaag 600
ttcatgcttt acttgttgac tgctggcaag aaagcattag cagatggtgg aatcaccgat 660
gatgtgatga aagagcttga taaaagaaag tgtggggttc tcattggctc tggaatgggc 720
ggcatgaagt tgttcaacga ttccattgaa gctctgagga tttcatataa aaagatgaat 780
cccttttgtg taccttttgc taccacaaat atgggatcag ctatgcttgc aatggacttg 840
ggatggatgg gtcctaacta ctcgatatca actgcctgtg caacaagtaa tttctgtata 900
ctgaatgctt caaaccacat agtcagaggc gaagctgaca tgatgctttg tggtggctcg 960
gatgcggtta ttatacctat tggtttggga ggttttgtgg cgtgccgagc tttgtcacag 1020
aggaataatg accctaccaa agcttcgagg ccatgggata gtaatcgtga tggatttgta 1080
atgggcgaag gagctggagt gttacttctc gaggagttag agcatgcaaa gaaaagaggt 1140
gcaaccattt atgcggaatt tttagggggc agtttcactt gcgatgccta ccacatgacc 1200
gagcctcacc ctgaaggagc tggagtgatc ctctgcatag agaaggcctt ggctcaggcc 1260
ggagtctcta aagaagatgt aaattacata aatgcgcatg caacttctac tcctgctgga 1320
gatatcaagg aataccaagc tctcgcccaa tgtttcggcc aaaacagtga gctgagagtg 1380
aattccacta aatcgatgat cggtcatctt cttggagcag ctggtggtgt agaagcagtt 1440
actgtggttc aggcgataag gactgggtgg atccatccaa atcttaattt ggaagacccg 1500
gacaaagccg tggatgcaaa gttgctcgtg ggacctaaga aggagagact gaatgtcaag 1560
gtcggtttgt ccaattcatt tgggttcggt gggcataatt cgtccatact cttcgcccct 1620
tacaattag 1629

<210> SEQ ID NO 35
<211> LENGTH: 1422
<212> TYPE: DNA
<213> ORGANISM: Cuphea avigera
<220> FEATURE:
<221> NAME/KEY: misc_feature
<223> OTHER INFORMATION: KASIa

<400> SEQUENCE: 35
atgcaatccc tccattcccc tgccctccgg gcctcccctc tcgaccctct ccgactcaaa 60
tcctccgcca atggcccctc ttccaccgcc gctttccgtc ccctccgccg cgccaccctc 120
cccaacattc gggccgcctc cccaccgtc tccgccccca agcgcgagac cgaccccaag 180
aagcgtgtcg tcatcaccgg catgggcctc gtctccgtct tcggctccga tgtcgacgct 240
tattacgaaa agctcctctc cggcgagagc gggatcagct taatcgaccg cttcgacgct 300
tccaagttcc ccacgaggtt cggcggccag atccggggat tcaacgccac gggatacatc 360
gacggcaaaa acgacaggag gctcgacgat tgcctccgct actgcattgt cgccgggaag 420
aaggctctcg aaaattccga tctcggcggc gatagtctct caaagattga taaggagaga 480
gctggagtgc tagttggaac tggcatgggt ggcctaaccg tcttctctga cggggttcag 540
aatctaatcg agaaaggtca ccggaagatc tccccgtttt tcattccata tgccattaca 600
aacatggggt ctgccctgct tgccatcgat ttgggtctga tgggcccaaa ttattcgatt 660
tcaactgcat gtgctacttc caactactgc ttttatgctg ctgctaatca tatccgccga 720
ggcgaggctg acctcatgat tgctggagga actgaggctg caatcattcc aattgggtta 780
ggaggattcg ttgcttgcag ggctttatct caaaggaatg atgaccctca gactgcctca 840
aggccgtggg ataaggaccg tgatggtttt gtgatgggtg aaggggctgg agtattggtt 900
atggagagct tagaacatgc aatgaaacga ggagcgccga ttattgcaga atatttggga 960
ggtgcagtca actgtgatgc ttatcatatg actgatccaa gggctgatgg gcttggtgtc 1020
tcctcgtgca ttgagagcag tctcgaagat gccggggtct cacctgaaga ggtcaattac 1080
ataaatgctc atgcgacttc tactcttgct ggggatcttg ccgagataaa tgccatcaag 1140
aaggttttca agaacaccaa ggatatcaaa atcaatgcaa ctaagtcgat gattggacac 1200
tgtcttggag catcaggggg tcttgaagcc attgcgacaa ttaagggaat aaccactggc 1260
tggcttcatc ccagcataaa ccaattcaat cccgagccat cagtggaatt tgacactgtt 1320
gccaacaaga agcagcaaca tgaagtcaat gttgctatct caaattcatt cggattcgga 1380
ggccacaact cagttgtagc tttctcagct ttcaagccat ga 1422

<210> SEQ ID NO 36
<211> LENGTH: 1398
<212> TYPE: DNA
<213> ORGANISM: Cuphea pulcherrima
<220> FEATURE:
<221> NAME/KEY: misc_feature
<223> OTHER INFORMATION: KASI

<400> SEQUENCE: 36
atgcattccc tccagtcacc ctcccttcgg gcctccccgc tcgacccctt ccgccccaaa 60
tcatccaccg tccgcccccct ccaccgagca tcaattccca acgtccgggc cgcttccccc 120
accgtctccg ctcccaagcg cgagaccgac cccaagaagc gcgtcgtgat caccggaatg 180
ggccttgtct ccgttttcgg ctccgacgtc gatgcgtact acgacaagct cctgtcaggc 240
gagagcggga tcggcccaat cgaccgcttc gacgcctcca agttccccac caggttcggc 300
ggccagattc gtggcttcaa ctccatggga tacattgacg gcaaaaacga caggcggctt 360
gatgattgcc ttcgctactg cattgtcgcc gggaagaagt ctcttgagga cgccgatctc 420
ggtgccgacc gcctctccaa gatcgacaag gagagagccg gagtgctggt tgggacagga 480
atgggtggtc tgactgtctt ctctgacggg gttcaatctc ttatcgagaa gggtcaccgg 540

-continued

```
aaaatcaccc ctttcttcat cccctatgcc attacaaaca tggggtctgc cctgctcgct    600

attgaactcg gtctgatggg cccaaactat tcaatttcca ctgcatgtgc cacttccaac    660

tactgcttcc atgctgctgc taatcatatc cgccgtggtg aggctgatct tatgattgct    720

ggaggcactg aggccgcaat cattccaatt gggttgggag gctttgtggc ttgcagggct    780

ctgtctcaaa ggaacgatga ccctcagact gcctctaggc cctgggataa agaccgtgat    840

ggttttgtga tgggtgaagg tgctggagtg ttggtgctgg agagcttgga acatgcaatg    900

aaacgaggag cacctattat tgcagagtat ttgggaggtg caatcaactg tgatgcttat    960

cacatgactg acccaagggc tgatggtctc ggtgtctcct cttgcattga gagtagcctt   1020

gaagatgctg gcgtctcacc tgaagaggtc aattacataa atgctcatgc gacttctact   1080

ctagctgggg atctcgccga gataaatgcc atcaagaagg ttttcaagaa cacaaaggat   1140

atcaaaatta atgcaactaa gtcaatgatc ggacactgtc ttggagcctc tggaggtctt   1200

gaagctatag cgactattaa gggaataaac accggctggc ttcatcccag cattaatcaa   1260

ttcaatcctg agccatccgt ggagttcgac actgttgcca acaagaagca gcaacacgaa   1320

gttaatgttg cgatctcgaa ttcatttgga ttcggaggcc acaactcagt cgtggctttc   1380

tcggctttca agccatga                                                 1398
```

<210> SEQ ID NO 37
<211> LENGTH: 1401
<212> TYPE: DNA
<213> ORGANISM: Cuphea avigera
<220> FEATURE:
<221> NAME/KEY: misc_feature
<223> OTHER INFORMATION: mitochondrial KAS

<400> SEQUENCE: 37

```
atggtgtttc ttccttggcg aaaaatgctc tgtccatctc aataccgttt tttgcggccc     60

ttatcttcat ctacaacttt tgatcctcgt agggttgttg ttacaggcct gggtatggtg    120

actccattag gatgcggggt gaacaccaca tggaaacaac tcatagaggg gaaatgtggg    180

ataagagcaa tatcccttga agacctaaag atggatgctt ttgatattga tactcaggcc    240

tatgtatttg atcagctgac ctcgaaggtc gctgccaccg tgcccaccgg agtgaatccc    300

ggagaattta atgaagattt atggttcaat cagaaggagc accgtgctat tgcaaggttc    360

atagcttatg cactctgtgc agctgatgaa gctcttaaag atgcaaattg ggaacctact    420

gaacctgaag agagagaaat gacgggtgtc tccattggtg gagggactgg aagcattagc    480

gatgtattag atgctggtcg gatgatttgt gagaagaaat tgcgtcgcct aagtccattc    540

ttcattccac gcatattgat aaatatggcc tctggtcatg tgagcatgaa atatggtttc    600

cagggaccca accatgctgc tgtgacagct tgtgcaacag ggctcattc gataggtgat    660

gctgcaagga tgatacagtt tggagatgca gatgtcatgg tcgctggagg cacagaatct    720

agcatagacg ccttatccat tgcaggattt tgcaggtcaa gggctcttac aacaaagtat    780

aattcttgcc cacaagaagc ttcacgaccc tttgataccg atagagatgg gtttgtaata    840

ggtgaagggt ctggcgtctt ggtattggag gaactagatc atgcaagaaa acgtggtgca    900

aagatgtatg ccgagttctg tggatatgga atgtctggtg atgcgcatca tataacccaa    960

cctcatagcg atggaagagg tgccatttta gcaatgaccc gtgcattgaa gcagtcaaat   1020

ctacatccgg atcaggtgga ttatgtaaat gctcacgcta cgtctacttc tttaggtgat   1080

gcaattgaag ctaaggcgat taaaacagtt ttctcggatc atgcgatgtc aggttcgctc   1140
```

-continued gccctttcct ccaccaaggg agctattggg catctcctcg gagcagcggg tgctgtggaa 1200
gccattttct ccattctggc tataaaaaac ggacttgcgc ctttgacgct aaatgtcgca 1260
agaccagacc ctgtgtttac cgagcggttt gtgcctttga ctgcttcaaa agagatgcat 1320
gtaagggcgg cgttgtcaaa ctcttttggc tttggaggta caaatactac acttcttttc 1380
acttcacctc ctcaaaacta a 1401

<210> SEQ ID NO 38
<211> LENGTH: 6169
<212> TYPE: DNA
<213> ORGANISM: Artificial Sequence
<220> FEATURE:
<223> OTHER INFORMATION: Cuphea palustris KAS IV codon optimized for Prototheca with cloning sequence and tags

<400> SEQUENCE: 38
aacggaggtc tgtcaccaaa tggaccccgt ctattgcggg aaaccacggc gatggcacgt 60
ttcaaaactt gatgaaatac aatattcagt atgtcgcggg cggcgacggc ggggagctga 120
tgtcgcgctg ggtattgctt aatcgccagc ttcgcccccg tcttggcgcg aggcgtgaac 180
aagccgaccg atgtgcacga gcaaatcctg acactagaag ggctgactcg cccggcacgg 240
ctgaattaca caggcttgca aaaataccag aatttgcacg caccgtattc gcggtatttt 300
gttggacagt gaatagcgat gcggcaatgg cttgtggcgt tagaaggtgc gacgaaggtg 360
gtgccaccac tgtgccagcc agtcctggcg gctcccaggg ccccgatcaa gagccaggac 420
atccaaacta cccacagcat caacgccccg gcctatactc gaaccccact tgcactctgc 480
aatggtatgg gaaccacggg gcagtcttgt gtgggtcgcg cctatcgcgg tcggcgaaga 540
ccgggaaggt accccgctcc cgtctggtcc tcacgttcgt gtacggcctg gatcccggaa 600
agggcggatg cacgtggtgt tgccccgcca ttggcgccca cgtttcaaag tccccggcca 660
gaaatgcaca ggaccggccc ggctcgcaca ggccatgacg aatgcccaga tttcgacagc 720
aaaacaatct ggaataatcg caaccattcg cgttttgaac gaaacgaaaa gacgctgttt 780
agcacgtttc cgatatcgtg gggccgaag catgattggg gggaggaaag cgtggcccca 840
aggtagccca ttctgtgcca cacgccgacg aggaccaatc cccggcatca gccttcatcg 900
acggctgcgc cgcacatata aagccggacg ccttcccgac acgttcaaac agttttattt 960
cctccacttc ctgaatcaaa caaatcttca aggaagatcc tgctcttgag caactagtat 1020
gttcgcgttc tacttcctga cggcctgcat ctccctgaag ggcgtgttcg gcgtctcccc 1080
ctcctacaac ggcctgggcc tgacgcccca gatgggctgg gacaactgga acacgttcgc 1140
ctgcgacgtc tccgagcagc tgctgctgga cacggccgac cgcatctccg acctgggcct 1200
gaaggacatg ggctacaagt acatcatcct ggacgactgc tggtcctccg gccgcgactc 1260
cgacggcttc ctggtcgccg acgagcagaa gttccccaac ggcatgggcc acgtcgccga 1320
ccacctgcac aacaactcct tcctgttcgg catgtactcc tccgcgggcg agtacacgtg 1380
cgccggctac cccggctccc tgggccgcga ggaggaggac gcccagttct tcgcgaacaa 1440
ccgcgtggac tacctgaagt acgacaactg ctacaacaag ggccagttcg gcacgcccga 1500
gatctcctac caccgctaca aggccatgtc cgacgccctg aacaagacgg gccgccccat 1560
cttctactcc ctgtgcaact ggggccagga cctgaccttc tactggggct ccggcatcgc 1620
gaactcctgg cgcatgtccg gcgacgtcac ggcggagttc acgcgccccg actcccgctg 1680
cccctgcgac ggcgacgagt acgactgcaa gtacgccggc ttccactgct ccatcatgaa 1740

-continued

```
catcctgaac aaggccgccc ccatgggcca gaacgcgggc gtcggcggct ggaacgacct   1800

ggacaacctg gaggtcggcg tcggcaacct gacggacgac gaggagaagg cgcacttctc   1860

catgtgggcc atggtgaagt ccccctgat catcggcgcg aacgtgaaca acctgaaggc    1920

ctcctcctac tccatctact cccaggcgtc cgtcatcgcc atcaaccagg actccaacgg   1980

catccccgcc acgcgcgtct ggcgctacta cgtgtccgac acggacgagt acggccaggg   2040

cgagatccag atgtggtccg gcccccctgga caacggcgac caggtcgtgg cgctgctgaa  2100

cggcggctcc gtgtcccgcc ccatgaacac gaccctggag gagatcttct tcgactccaa   2160

cctgggctcc aagaagctga cctccacctg ggacatctac gacctgtggg cgaaccgcgt   2220

cgacaactcc acggcgtccg ccatcctggg ccgcaacaag accgccaccg gcatcctgta   2280

caacgccacc gagcagtcct acaaggacgg cctgtccaag aacgacaccc gcctgttcgg   2340

ccagaagatc ggctccctgt cccccaacgc gatcctgaac acgaccgtcc ccgcccacgg   2400

catcgcgttc taccgcctgc gcccctcctc ctgatacaac ttattacgta ttctgaccgg   2460

cgctgatgtg gcgcggacgc cgtcgtactc tttcagactt tactcttgag gaattgaacc   2520

tttctcgctt gctggcatgt aaacattggc gcaattaatt gtgtgatgaa gaaagggtgg   2580

cacaagatgg atcgcgaatg tacgagatcg acaacgatgg tgattgttat gaggggccaa   2640

acctggctca atcttgtcgc atgtccggcg caatgtgatc cagcggcgtg actctcgcaa   2700

cctggtagtg tgtgcgcacc gggtcgcttt gattaaaact gatcgcattg ccatcccgtc   2760

aactcacaag cctactctag ctcccattgc gcactcgggc gcccggctcg atcaatgttc   2820

tgagcggagg gcgaagcgtc aggaaatcgt ctcggcagct ggaagcgcat ggaatgcgga   2880

gcggagatcg aatcaggatc ccgcgtctcg aacagagcgc gcagaggaac gctgaaggtc   2940

tcgcctctgt cgcacctcag cgcggcatac accacaataa ccacctgacg aatgcgcttg   3000

gttcttcgtc cattagcgaa gcgtccggtt cacacacgtg ccacgttggc gaggtggcag   3060

gtgacaatga tcggtggagc tgatggtcga aacgttcaca gcctagggat atcgcctgct   3120

caagcgggcg ctcaacatgc agagcgtcag cgagacgggc tgtggcgatc gcgagacgga   3180

cgaggccgcc tctgccctgt ttgaactgag cgtcagcgct ggctaagggg agggagactc   3240

atccccaggc tcgcgccagg gctctgatcc cgtctcgggc ggtgatcggc gcgcatgact   3300

acgacccaac gacgtacgag actgatgtcg gtcccgacga ggagcgccgc gaggcactcc   3360

cgggccaccg accatgttta caccgaccga aagcactcgc tcgtatccat tccgtgcgcc   3420

cgcacatgca tcatcttttg gtaccgactt cggtcttgtt ttacccctac gacctgcctt   3480

ccaaggtgtg agcaactcgc ccggacatga ccgagggtga tcatccggat ccccaggccc   3540

cagcagcccc tgccagaatg gctcgcgctt tccagcctgc aggcccgtct cccaggtcga   3600

cgcaacctac atgaccaccc caatctgtcc cagaccccaa acaccctcct tccctgcttc   3660

tctgtgatcg ctgatcagca acacatatgg cttccgcggc attcaccatg tcggcgtgcc   3720

ccgcgatgac tggcagggcc cctggggcac gtcgctccgg acggccagtc gccacccgcc   3780

tgaggggctc caccttccag tgcctggtga cctcctacat cgacccctgc aaccagttct   3840

cctcctccgc ctccctgtcc ttcctgggcg acaacggctt cgcctccctg ttcggctcca   3900

agcccttccg ctccaaccgc ggccaccgcc gcctgggccg cgcctcccac tccggcgagg   3960

ccatggccgt ggccctggag cccgcccagg aggtggccac caagaagaag cccctggtga   4020

agcagcgccg cgtggtggtg accggcatgg gcgtggtgac cccccctgggc cacgagcccg  4080
```

```
acgtgtacta caacaacctg ctggacggcg tgtccggcat ctccgagatc gaggccttcg   4140

actgcaccca gttccccacc cgcatcgccg gcgagatcaa gtccttctcc accgacggct   4200

gggtggcccc caagctgtcc aagcgcatgg acaagttcat gctgtacctg ctgaccgccg   4260

gcaagaaggc cctggccgac ggcggcatca ccgacgacgt gatgaaggag ctggacaagc   4320

gcaagtgcgg cgtgctgatc ggctccggcc tgggcggcat gaagctgttc tccgactcca   4380

tcgaggccct gcgcatctcc tacaagaaga tgaacccctt ctgcgtgccc ttcgccacca   4440

ccaacatggg ctccgccatg ctggccatgg acctgggctg gatgggcccc aactactcca   4500

tctccaccgc ctgcgccacc tccaacttct gcatcctgaa ctccgccaac cacatcgtgc   4560

gcggcgaggc cgacatgatg ctgtgcggcg gctccgacgc cgtgatcatc cccatcggcc   4620

tgggcggctt cgtggcctgc cgcgccctgt cccagcgcaa caacgacccc accaaggcct   4680

cccgcccctg ggactccaac cgcgacggct tcgtgatggg cgagggcgcc ggcgtgctgc   4740

tgctggagga gctggagcac gccaagaagc gcggcgccac catctacgcc gagttcctgg   4800

gcggctcctt cacctgcgac gcctaccaca tgaccgagcc ccacccgag ggcgccggcg   4860

tgatcctgtg catcgagaag gccctggccc aggccggcgt gtcccgcgag gacgtgaact   4920

acatcaacgc ccacgccacc tccacccccg ccggcgacat caaggagtac caggccctgg   4980

cccactgctt cggccagaac tccgagctgc gcgtgaactc caccaagtcc atgatcggcc   5040

acctgatcgg cgccgccggc ggcgtggagg ccgtgaccgt ggtgcaggcc atccgcaccg   5100

gctggatcca ccccaacctg aacctggagg accccgacaa ggccgtggac gccaaggtgc   5160

tggtgggccc caagaaggag cgcctgaacg tgaaggtggg cctgtccaac tccttcggct   5220

tcggcggcca caactcctcc atcctgttcg ccccctacaa caccatgtac ccctacgacg   5280

tgcccgacta cgcctgatat cgaggcagca gcagctcgga tagtatcgac acactctgga   5340

cgctggtcgt gtgatggact gttgccgcca cacttgctgc cttgacctgt gaatatccct   5400

gccgctttta tcaaacagcc tcagtgtgtt tgatcttgtg tgtacgcgct tttgcgagtt   5460

gctagctgct tgtgctattt gcgaatacca cccccagcat ccccttccct cgtttcatat   5520

cgcttgcatc ccaaccgcaa cttatctacg ctgtcctgct atccctcagc gctgctcctg   5580

ctcctgctca ctgcccctcg cacagccttg gtttgggctc cgcctgtatt ctcctggtac   5640

tgcaacctgt aaaccagcac tgcaatgctg atgcacggga agtagtggga tgggaacaca   5700

aatggaaagc ttgagctcag cggcgacggt cctgctaccg tacgacgttg ggcacgccca   5760

tgaaagtttg tataccgagc ttgttgagcg aactgcaagc gcggctcaag gatacttgaa   5820

ctcctggatt gatatcggtc caataatgga tggaaaatcc gaacctcgtg caagaactga   5880

gcaaacctcg ttacatggat gcacagtcgc cagtccaatg aacattgaag tgagcgaact   5940

gttcgcttcg gtggcagtac tactcaaaga atgagctgct gttaaaaatg cactctcgtt   6000

ctctcaagtg agtggcagat gagtgctcac gccttgcact tcgctgcccg tgtcatgccc   6060

tgcgccccaa aatttgaaaa aagggatgag attattgggc aatggacgac gtcgtcgctc   6120

cgggagtcag gaccggcgga aaataagagg caacacactc cgcttctta               6169
```

<210> SEQ ID NO 39
<211> LENGTH: 1611
<212> TYPE: DNA
<213> ORGANISM: Artificial Sequence
<220> FEATURE:
<223> OTHER INFORMATION: Cuphea palustris KAS IV codon optimized for
Prototheca

<400> SEQUENCE: 39

```
atggcttccg cggcattcac catgtcggcg tgccccgcga tgactggcag ggcccctggg     60
gcacgtcgct ccggacggcc agtcgccacc cgcctgaggg gctccacctt ccagtgcctg    120
gtgacctcct acatcgaccc ctgcaaccag ttctcctcct ccgcctccct gtccttcctg    180
ggcgacaacg gcttcgcctc cctgttcggc tccaagccct tccgctccaa ccgcggccac    240
cgccgcctgg gccgcgcctc ccactccggc gaggccatgg ccgtggccct ggagcccgcc    300
caggaggtgg ccaccaagaa gaagcccctg gtgaagcagc gccgcgtggt ggtgaccggc    360
atgggcgtgg tgaccccct gggccacgag cccgacgtgt actacaacaa cctgctggac     420
ggcgtgtccg gcatctccga gatcgaggcc ttcgactgca cccagttccc cacccgcatc    480
gccggcgaga tcaagtcctt ctccaccgac ggctgggtgg cccccaagct gtccaagcgc    540
atggacaagt tcatgctgta cctgctgacc gccggcaaga aggccctggc cgacggcggc    600
atcaccgacg acgtgatgaa ggagctggac aagcgcaagt gcggcgtgct gatcggctcc    660
ggcctgggcg gcatgaagct gttctccgac tccatcgagg ccctgcgcat ctcctacaag    720
aagatgaacc ccttctgcgt gcccttcgcc accaccaaca tgggctccgc catgctggcc    780
atggacctgg gctggatggg ccccaactac tccatctcca ccgcctgcgc cacctccaac    840
ttctgcatcc tgaactccgc caaccacatc gtgcgcggcg aggccgacat gatgctgtgc    900
ggcggctccg acgccgtgat catccccatc ggcctgggcg gcttcgtggc ctgccgcgcc    960
ctgtcccagc gcaacaacga ccccaccaag gcctcccgcc cctgggactc caaccgcgac   1020
ggcttcgtga tgggcgaggg cgccggcgtg ctgctgctgg aggagctgga gcacgccaag   1080
aagcgcggcg ccaccatcta cgccgagttc ctgggcggct ccttcacctg cgacgcctac   1140
cacatgaccg agccccaccc cgagggcgcc ggcgtgatcc tgtgcatcga gaaggccctg   1200
gcccaggccg gcgtgtcccg cgaggacgtg aactacatca acgcccacgc cacctccacc   1260
cccgccggcg acatcaagga gtaccaggcc ctggcccact gcttcggcca gaactccgag   1320
ctgcgcgtga actccaccaa gtccatgatc ggccacctga tcggcgccgc cggcggcgtg   1380
gaggccgtga ccgtggtgca ggccatccgc accggctgga tccaccccaa cctgaacctg   1440
gaggaccccg acaaggccgt ggacgccaag gtgctggtgg gccccaagaa ggagcgcctg   1500
aacgtgaagg tgggcctgtc caactccttc ggcttcggcg gccacaactc ctccatcctg   1560
ttcgcccccct acaacaccat gtacccctac gacgtgcccg actacgcctg a           1611
```

<210> SEQ ID NO 40
<211> LENGTH: 1512
<212> TYPE: DNA
<213> ORGANISM: Artificial Sequence
<220> FEATURE:
<223> OTHER INFORMATION: C. camphora KASIV codon optimized for Prototheca

<400> SEQUENCE: 40

```
atggccatga tggccggctc ctgctccaac ctggtgatcg gcaaccgcga gctgggcggc     60
aacggcccct ccctgctgca ctacaacggc ctgcgccccc tggagaacat ccagaccgcc    120
tccgccgtga agaagcccaa cggcctgttc gcctcctcca ccgcccgcaa gtccaaggcc    180
gtgcgcgcca tggtgctgcc caccgtgacc gcccccaagc gcgagaagga ccccaagaag    240
cgcatcgtga tcaccggcat gggcctggtg tccgtgttcg gcaacgacat cgacaccttc    300
tactccaagc tgctggaggg cgagtccggc atcggcccca tcgaccgctt cgacgcctcc    360
```

```
tccttctccg tgcgcttcgc cggccagatc cacaacttct cctccaaggg ctacatcgac    420

ggcaagaacg accgccgcct ggacgactgc tggcgctact gcctggtggc cggccgccgc    480

gccctggagg acgccaacct gggccccgag gtgctggaga agatggaccg ctcccgcatc    540

ggcgtgctga tcggcaccgg catgggcggc ctgtccgcct tctccaacgg cgtggagtcc    600

ctgatccaga agggctacaa gaagatcacc ccctcttca tcccctactc catcaccaac    660

atgggctccg ccctgctggc catcgacacc ggcgtgatgg gccccaacta ctccatctcc    720

accgcctgcg ccaccgccaa ctactgcttc cacgccgccg ccaaccacat ccgccgcggc    780

gaggccgaga tcatggtgac cggcggcacc gaggccgccg tgtccgccac cggcgtgggc    840

ggcttcatcg cctgccgcgc cctgtcccac cgcaacgacg agccccagac cgcctcccgc    900

ccctgggaca aggaccgcga cggcttcgtg atgggcgagg gcgccggcgt gctggtgatg    960

gagtccctgc accacgcccg caagcgcggc gccaacatca tcgccgagta cctgggcggc   1020

gccgtgacct gcgacgccca ccacatgacc gacccccgcg ccgacggcct gggcgtgtcc   1080

tcctgcatca ccaagtccct ggaggacgcc ggcgtgtccc ccgaggaggt gaactacgtg   1140

aacgcccacg ccacctccac cctggccggc gacctggccg aggtgaacgc catcaagaag   1200

gtgttcaagg acacctccga gatgaagatg aacggcacca agtccatgat cggccactgc   1260

ctgggcgccg ccggcggcct ggaggccatc gccaccatca aggccatcaa caccggctgg   1320

ctgcacccca ccatcaacca gttcaacatc gagcccgccg tgaccatcga caccgtgccc   1380

aacgtgaaga agaagcacga catccacgtg ggcatctcca actccttcgg cttcggcggc   1440

cacaactccg tggtggtgtt cgccccctc atgcccacca tgtaccccta cgacgtgccc   1500

gactacgcct ga                                                        1512
```

<210> SEQ ID NO 41
<211> LENGTH: 1482
<212> TYPE: DNA
<213> ORGANISM: Artificial Sequence
<220> FEATURE:
<223> OTHER INFORMATION: C. camphora KASI (D3148, pSZ4339) codon optimized for Prototheca

<400> SEQUENCE: 41

```
atgcagatcc tgcagacccc ctcctcctcc tcctcctccc tgcgcatgtc ctccatggag     60

tccctgtccc tgacccccaa gtccctgccc ctgaagaccc tgctgcccct gcgcccccgc    120

cccaagaacc tgtcccgccg caagtcccag aacccccgcc ccatctcctc ctcctcctcc    180

cccgagcgcg agaccgaccc caagaagcgc gtggtgatca ccggcatggg cctggtgtcc    240

gtgttcggca acgacgtgga cgcctactac gaccgcctgc tgtccggcga gtccggcatc    300

gcccccatcg accgcttcga cgcctccaag ttccccaccc gcttcgccgg ccagatccgc    360

ggcttcacct ccgacggcta catcgacggc aagaacgacc gccgcctgga cgactgcctg    420

cgctactgca tcgtgtccgg caagaaggcc ctggagaacg ccggcctggg cccccacctg    480

atggacggca agatcgacaa ggagcgcgcc ggcgtgctgg tgggcaccgg catgggcggc    540

ctgaccgtgt tctccaacgg cgtgcagacc ctgcacgaga agggctaccg caagatgacc    600

cccttcttca tcccctacgc catcaccaac atgggctccg ccctgctggc catcgagctg    660

ggcttcatgg gccccaacta ctccatctcc accgcctgcg ccacctccaa ctactgcttc    720

tacgccgccg ccaaccacat ccgccgcggc gaggccgacc tgatgctggc cggcggcacc    780

gaggccgcca tcatccccat cggcctgggc ggcttcgtgg cctgccgcgc cctgtcccag    840
```

```
cgcaacgacg acccccagac cgcctcccgc ccctgggaca aggaccgcga cggcttcgtg    900
atgggcgagg gcgccggcgt gctggtgatg gagtccctgg agcacgccat gaagcgcgac    960
gcccccatca tcgccgagta cctgggcggc gccgtgaact gcgacgccta ccacatgacc   1020
gacccccgcg ccgacggcct gggcgtgtcc acctgcatcg agcgctccct ggaggacgcc   1080
ggcgtggccc ccgaggaggt gaactacatc aacgcccacg ccacctccac cctggccggc   1140
gacctggccg aggtgaacgc catcaagaag gtgttcacca acacctccga gatcaagatc   1200
aacgccacca agtccatgat cggccactgc ctgggcgccg ccggcggcct ggaggccatc   1260
gccaccatca aggccatcaa caccggctgg ctgcacccct ccatcaacca gttcaacccc   1320
gagccctccg tggagttcga caccgtggcc aacaagaagc agcagcacga ggtgaacgtg   1380
gccatctcca actccttcgg cttcggcggc cacaactccg tggtggtgtt ctccgccttc   1440
aagcccacca tgtaccccta cgacgtgccc gactacgcct ga                      1482
```

<210> SEQ ID NO 42
<211> LENGTH: 1428
<212> TYPE: DNA
<213> ORGANISM: Artificial Sequence
<220> FEATURE:
<223> OTHER INFORMATION: U. californica KASI (D3150, pSZ4341) codon optimized for Prototheca

<400> SEQUENCE: 42

```
atggagtccc tgtccctgac ccccaagtcc ctgcccctga agaccctgct gcccttccgc      60
ccccgcccca agaacctgtc ccgccgcaag tcccagaacc ccaagcccat ctcctcctcc     120
tcctcccccg agcgcgagac cgaccccaag aagcgcgtgg tgatcaccgg catgggcctg     180
gtgtccgtgt tcggcaacga cgtggacgcc tactacgacc gcctgctgtc cggcgagtcc     240
ggcatcgccc ccatcgaccg cttcgacgcc tccaagttcc ccacccgctt cgccggccag     300
atccgcggct tcacctccga cggctacatc gacggcaaga acgaccgccg cctggacgac     360
tgcctgcgct actgcatcgt gtccggcaag aaggccctgg agaacgccgg cctgggcccc     420
gacctgatgg acggcaagat cgacaaggag cgcgccggcg tgctggtggg caccggcatg     480
ggcggcctga ccgtgttctc caacggcgtg cagaccctgc acgagaaggg ctaccgcaag     540
atgaccccct tcttcatccc ctacgccatc accaacatgg gctccgccct gctggccatc     600
gacctgggct tcatgggccc caactactcc atctccaccg cctgcgccac ctccaactac     660
tgcttctacg ccgccgccaa ccacatccgc cgcggcgagg ccgacgtgat gctggccggc     720
ggcaccgagg ccgccatcat ccccatcggc ctgggcggct tcgtggcctg ccgcgccctg     780
tcccagcgca acgacgaccc ccagaccgcc tcccgcccct gggacaagga ccgcgacggc     840
ttcgtgatgg gcgagggcgc cggcgtgctg gtgatggagt ccctggagca cgccatgaag     900
cgcgacgccc ccatcatcgc cgagtacctg ggcggcgccg tgaactgcga cgcctaccac     960
atgaccgacc cccgcgccga cggcctgggc gtgtccacct gcatcgagcg ctccctggag    1020
gacgccggcg tggcccccga ggaggtgaac tacatcaacg cccacgccac ctccaccctg    1080
gccggcgacc tggccgaggt gaacgccatc aagaaggtgt tcaccaacac ctccgagatc    1140
aagatcaacg ccaccaagtc catgatcggc cactgcctgg gcgccgccgg cggcctggag    1200
gccatcgcca ccatcaaggc catcaacacc ggctggctgc acccctccat caaccagttc    1260
aaccccgagc cctccgtgga gttcgacacc gtggccaaca agaagcagca gcacgaggtg    1320
aacgtggcca tctccaactc cttcggcttc ggcggccaca actccgtggt ggtgttctcc    1380
```

gccttcaagc ccaccatgta cccctacgac gtgcccgact acgcctga 1428

<210> SEQ ID NO 43
<211> LENGTH: 1452
<212> TYPE: DNA
<213> ORGANISM: Artificial Sequence
<220> FEATURE:
<223> OTHER INFORMATION: U. californica KASIV (D3152, pSZ4343) codon optimized for Prototheca

<400> SEQUENCE: 43
atgacccaga ccctgatctg cccctcctcc atggagaccc tgtccctgac caagcagtcc 60
cacttccgcc tgcgcctgcc caccccccc cacatccgcc gcggcggcgg ccaccgccac 120
ccccccccct tcatctccgc ctccgccgcc ccccgccgcg agaccgaccc caagaagcgc 180
gtggtgatca ccggcatggg cctggtgtcc gtgttcggca ccaacgtgga cgtgtactac 240
gaccgcctgc tggccggcga gtccggcgtg ggcaccatcg accgcttcga cgcctccatg 300
ttccccaccc gcttcggcgg ccagatccgc cgcttcacct ccgagggcta catcgacggc 360
aagaacgacc gccgcctgga cgactacctg cgctactgcc tggtgtccgg caagaaggcc 420
atcgagtccg ccggcttcga cctgcacaac atcaccaaca agatcgacaa ggagcgcgcc 480
ggcatcctgg tgggctccgg catgggcggc ctgaaggtgt tctccgacgg cgtggagtcc 540
ctgatcgaga agggctaccg caagatctcc cccttcttca tcccctacat gatccccaac 600
atgggctccg ccctgctggg catcgacctg ggcttcatgg gccccaacta ctccatctcc 660
accgcctgcg ccacctccaa ctactgcatc tacgccgccg ccaaccacat ccgccagggc 720
gacgccgacc tgatggtggc cggcggcacc gaggccccca tcatccccat cggcctgggc 780
ggcttcgtgg cctgccgcgc cctgtccacc cgcaacgacg acccccagac cgcctcccgc 840
ccctgggaca tcgaccgcga cggcttcgtg atgggcgagg gcgccggcat cctggtgctg 900
gagtccctgg agcacgccat gaagcgcgac gcccccatcc tggccgagta cctgggcggc 960
gccgtgaact gcgacgccca ccacatgacc gacccccgcg ccgacggcct gggcgtgtcc 1020
acctgcatcg agtcctccct ggaggacgcc ggcgtggccg ccgaggaggt gaactacatc 1080
aacgcccacg ccacctccac ccccaccggc gacctggccg agatgaaggc catcaagaac 1140
gtgttccgca acacctccga gatcaagatc aacgccacca agtccatgat cggccactgc 1200
ctgggcgcct ccggcggcct ggaggccatc gccaccctga aggccatcac caccggctgg 1260
ctgcacccca ccatcaacca gttcaacccc gagccctccg tggacttcga caccgtggcc 1320
aagaagaaga agcagcacga ggtgaacgtg gccatctcca actccttcgg cttcggcggc 1380
cacaactccg tgctggtgtt ctccgccttc aagcccacca tgtaccccta cgacgtgccc 1440
gactacgcct ga 1452

<210> SEQ ID NO 44
<211> LENGTH: 1578
<212> TYPE: DNA
<213> ORGANISM: Artificial Sequence
<220> FEATURE:
<223> OTHER INFORMATION: C. wrightii KASAI (D3153, pSZ4379) codon optimized for Prototheca

<400> SEQUENCE: 44
atggcttccg cggcattcac catgtcggcg tgccccgcga tgactggcag ggcccctggg 60
gcacgtcgct ccggacggcc agtcgccacc cgcctgaggt acgtattcca gtgcctggtg 120
gccagctgca tcgacccctg cgaccagtac cgcagcagcg ccagcctgag cttcctgggc 180

```
gacaacggct tcgccagcct gttcggcagc aagcccttca tgagcaaccg cggccaccgc    240

cgcctgcgcc gcgccagcca cagcggcgag gccatggccg tggccctgca gcccgcccag    300

gaggccggca ccaagaagaa gcccgtgatc aagcagcgcc gcgtggtggt gaccggcatg    360

ggcgtggtga cccccctggg ccacgagccc gacgtgttct acaacaacct gctggacggc    420

gtgagcggca tcagcgagat cgagaccttc gactgcaccc agttccccac ccgcatcgcc    480

ggcgagatca agagcttcag caccgacggc tgggtggccc ccaagctgag caagcgcatg    540

gacaagttca tgctgtacct gctgaccgcc ggcaagaagg ccctggccga cggcggcatc    600

accgacgagg tgatgaagga gctggacaag cgcaagtgcg gcgtgctgat cggcagcggc    660

atgggcggca tgaaggtgtt caacgacgcc atcgaggccc tgcgcgtgag ctacaagaag    720

atgaacccct tctgcgtgcc cttcgccacc accaacatgg gcagcgccat gctggccatg    780

gacctgggct ggatgggccc caactacagc atcagcaccg cctgcgccac cagcaacttc    840

tgcatcctga acgccgccaa ccacatcatc cgcggcgagg ccgacatgat gctgtgcggc    900

ggcagcgacg ccgtgatcat ccccatcggc ctgggcggct tcgtggcctg ccgcgccctg    960

agccagcgca acagcgaccc caccaaggcc agccgcccct gggacagcaa ccgcgacggc   1020

ttcgtgatgg gcgagggcgc cggcgtgctg ctgctggagg agctggagca cgccaagaag   1080

cgcggcgcca ccatctacgc cgagttcctg ggcggcagct tcacctgcga cgcctaccac   1140

atgaccgagc cccaccccga gggcgccggc gtgatcctgt gcatcgagaa ggccctggcc   1200

caggccggcg tgagcaagga ggacgtgaac tacatcaacg cccacgccac cagcaccagc   1260

gccggcgaca tcaaggagta ccaggccctg gcccgctgct tcggccagaa cagcgagctg   1320

cgcgtgaaca gcaccaagag catgatcggc cacctgctgg gcgccgccgg cggcgtggag   1380

gccgtgaccg tggtgcaggc catccgcacc ggctggattc accccaacct gaacctggag   1440

gaccccgaca aggccgtgga cgccaagctg ctggtgggcc ccaagaagga gcgcctgaac   1500

gtgaaggtgg gcctgagcaa cagcttcggc ttcggcggcc acaacagcag catcctgttc   1560

gcccccctgca acgtgtga                                                 1578
```

<210> SEQ ID NO 45
<211> LENGTH: 1542
<212> TYPE: DNA
<213> ORGANISM: Artificial Sequence
<220> FEATURE:
<223> OTHER INFORMATION: C. avigera KASIVb (D3287, pSZ4453) codon
      optimized for Prototheca

<400> SEQUENCE: 45

```
atggcttccg cggcattcac catgtcggcg tgccccgcga tgactggcag ggcccctggg     60

gcacgtcgct ccggacggcc agtcgccacc cgcctgaggg gctccacctt ccagtgctac    120

atcggcgaca acggcttcgg ctccaagccc ccccgctcca accgcggcca cctgcgcctg    180

ggccgcacct cccactccgg cgaggtgatg gccgtggcca tgcagtccgc ccaggaggtg    240

tccaccaagg agaagcccgc caccaagcag cgccgcgtgg tggtgaccgg catgggcgtg    300

gtgaccgccc tgggccacga ccccgacgtg tactacaaca acctgctgga cggcgtgtcc    360

ggcatctccg agatcgagaa cttcgactgc tcccagctgc ccacccgcat cgccggcgag    420

atcaagtcct tctccgccga cggctgggtg gcccccaagt tctcccgccg catggacaag    480

ttcatgctgt acatcctgac cgccggcaag aaggccctgg tggacggcgg catcaccgag    540

gacgtgatga aggagctgga caagcgcaag tgcggcgtgc tgatcggctc cggcctgggc    600
```

```
ggcatgaagg tgttctccga gtccatcgag gccctgcgca cctcctacaa gaagatctcc    660

cccttctgcg tgcccttctc caccaccaac atgggctccg ccatcctggc catggacctg    720

ggctggatgg gccccaacta ctccatctcc accgcctgcg ccacctccaa cttctgcatc    780

ctgaacgccg ccaaccacat caccaagggc gaggccgaca tgatgctgtg cggcggctcc    840

gactccgtga tcctgcccat cggcatgggc ggcttcgtgg cctgccgcgc cctgtcccag    900

cgcaacaacg accccaccaa ggcctcccgc ccctgggact ccaaccgcga cggcttcgtg    960

atgggcgagg gcgccggcgt gctgctgctg gaggagctgg agcacgccaa gaagcgcggc   1020

gccaccatct acgccgagtt cctgggcggc tccttcacct gcgacgccta ccacatgacc   1080

gagccccacc ccgagggcgc cggcgtgatc ctgtgcatcg agaaggccct ggcccagtcc   1140

ggcgtgtccc gcgaggacgt gaactacatc aacgcccacg ccacctccac ccccgccggc   1200

gacatcaagg agtaccaggc cctggcccac tgcttcggcc agaactccga gctgcgcgtg   1260

aactccacca agtccatgat cggccacctg ctgggcggcg ccggcggcgt ggaggccgtg   1320

accgtggtgc aggccatccg caccggctgg atccaccccca acatcaacct ggacgacccc   1380

gacgagggcg tggacgccaa gctgctggtg ggccccaaga aggagaagct gaaggtgaag   1440

gtgggcctgt ccaactcctt cggcttcggc ggccacaact cctccatcct gttcgccccc   1500

tgcaacacca tgtaccccta cgacgtgccc gactacgcct ga                      1542
```

```
<210> SEQ ID NO 46
<211> LENGTH: 1551
<212> TYPE: DNA
<213> ORGANISM: Artificial Sequence
<220> FEATURE:
<223> OTHER INFORMATION: C. paucipetala KASIVb codon optimized for
      Prototheca

<400> SEQUENCE: 46
```

```
atggcttccg cggcattcac catgtcggcg tgccccgcga tgactggcag ggcccctggg      60

gcacgtcgct ccggacggcc agtcgccacc cgcctgaggg gctccacctt ccagtgcctg     120

ggcgacatcg gcttcgcctc cctgatcggc tccaagcccc cccgctccaa ccgcaaccac     180

cgccgcctgg gccgcacctc ccactccggc gaggtgatgg ccgtggccat gcagcccgcc     240

cacgaggcct ccaccaagaa caagcccgtg accaagcagc gccgcgtggt ggtgaccggc     300

atgggcgtgg ccacccccct gggccacgac cccgacgtgt actacaacaa cctgctggac     360

ggcgtgtccg gcatctccca gatcgagaac ttcgactgca cccagttccc cacccgcatc     420

gccggcgaga tcaagtcctt ctccaccgag ggctacgtga tccccaagtt cgccaagcgc     480

atggacaagt tcatgctgta cctgctgacc gccggcaaga aggccctgga ggacggcggc     540

atcaccgagg acgtgatgaa ggagctggac aagcgcaagt gcggcgtgct gatcggctcc     600

ggcatgggcg gcatgaagat catcaacgac tccatcgccg ccctgaacgt gtcctacaag     660

aagatgaccc ccttctgcgt gcccttctcc accaccaaca tgggctccgc catgctggcc     720

atcgacctgg gctggatggg ccccaactac tccatctcca ccgcctgcgc cacctccaac     780

tactgcatcc tgaacgccgc caaccacatc gtgcgcggcg aggccgacat gatgctgtgc     840

ggcggctccg acgccgtgat catccccgtg ggcctgggcg gcttcgtggc ctgccgcgcc     900

ctgtcccagc gcaacaacga ccccaccaag gcctcccgcc cctgggactc caaccgcgac     960

ggcttcgtga tgggcgaggg cgccggcgtg ctgctgctgg aggagctgga gcacgccaag    1020

aagcgcggcg ccaccatcta cgccgagttc ctgggcggct ccttcacctg cgacgcctac    1080
```

```
cacatgaccg agccccaccc cgacggcgcc ggcgtgatcc tgtgcatcga gaaggccctg   1140

gcccagtccg gcgtgtcccg cgaggacgtg aactacatca acgcccacgc cacctccacc   1200

cccgccggcg acatcaagga gtaccaggcc ctggcccact gcttcggcca gaactccgag   1260

ctgcgcgtga actccaccaa gtccatgatc ggccacctgc tgggcgccgc cggcggcgtg   1320

gaggccgtga ccgtggtgca ggccatccgc accggctgga tccaccccaa catcaacctg   1380

gagaaccccg acgaggccgt ggacgccaag ctgctggtgg gccccaagaa ggagaagctg   1440

aaggtgaagg tgggcctgtc caactccttc ggcttcggcg gccacaactc ctccatcctg   1500

ttcgcccccct acaacaccat gtacccctac gacgtgcccg actacgcctg a           1551
```

<210> SEQ ID NO 47
<211> LENGTH: 1611
<212> TYPE: DNA
<213> ORGANISM: Artificial Sequence
<220> FEATURE:
<223> OTHER INFORMATION: C. ignea KASIVb (D3289, pSZ4455) codon
      optimized for Prototheca

<400> SEQUENCE: 47

```
atggcttccg cggcattcac catgtcggcg tgccccgcga tgactggcag ggcccctggg     60

gcacgtcgct ccggacggcc agtcgccacc cgcctgaggg gctccacctc ccagtgcctg    120

gtgacctcct acatcgaccc ctgcaacaag tactgctcct ccgcctccct gtccttcctg    180

ggcgacaacg gcttcgcctc cctgttcggc tccaagccct tccgctccaa ccgcggccac    240

cgccgcctgg gccgcgcctc ccactccggc gaggccatgg ccgtggccct gcagcccgcc    300

caggaggtga ccaccaagaa gaagcccgtg atcaagcagc gccgcgtggt ggtgaccggc    360

atgggcgtgg tgaccccct gggccacgag cccgacgtgt actacaacaa cctgctggac    420

ggcgtgtccg gcatctccga gatcgagacc ttcgactgca cccagttccc cacccgcatc    480

gccggcgaga tcaagtcctt ctccaccgac ggctgggtgg cccccaagct gtccaagcgc    540

atggacaagt tcatgctgta cctgctgacc gccggcaaga aggccctggc cgacggcggc    600

atcaccgacg acgtgatgaa ggagctggac aagcgcaagt gcggcgtgct gatcggctcc    660

ggcatgggcg gcatgaagct gttcaacgac tccatcgagg ccctgcgcat ctcctacaag    720

aagatgaacc ccttctgcgt gcccttcgcc accaccaaca tgggctccgc catgctggcc    780

atggacctgg gctggatggg ccccaactac tccatctcca ccgcctgcgc cacctccaac    840

ttctgcatcc tgaacgcctc caaccacatc gtgcgcggcg aggccgacat gatgctgtgc    900

ggcggctccg actccgtgac cgtgcccctg ggcgtgggcg gcttcgtggc ctgccgcgcc    960

ctgtcccagc gcaacaacga ccccaccaag gcctcccgcc cctgggactc caaccgcgac   1020

ggcttcgtga tgggcgaggg cgccggcgtg ctgctgctgg aggagctgga gcacgccaag   1080

aagcgcggcg ccaccatcta cgccgagttc ctgggcggct ccttcacctc cgacgcctac   1140

cacatgaccg agccccaccc cgagggcgcc ggcgtgatcc tgtgcatcga gaaggccctg   1200

gcccagtccg gcgtgtcccg cgaggacgtg aactacatca acgcccacgc cacctccacc   1260

cccgccggcg acatcaagga gtaccaggcc ctggcccgct gcttcggcca gaactccgag   1320

ctgcgcgtga actccaccaa gtccatgatc ggccacctgc tgggcgccgc cggcggcgtg   1380

gaggccgtgg ccgtgatcca ggccatccgc accggctgga tccaccccaa catcaacctg   1440

gaggaccccg acgaggccgt ggaccccaag ctgctggtgg gccccaagaa ggagaagctg   1500

aaggtgaagg tggccctgtc caactccttc ggcttcggcg gccacaactc ctccatcctg   1560
```

ttcgcccct gcaacaccat gtacccctac gacgtgcccg actacgcctg a 1611

<210> SEQ ID NO 48
<211> LENGTH: 1599
<212> TYPE: DNA
<213> ORGANISM: Artificial Sequence
<220> FEATURE:
<223> OTHER INFORMATION: Cuphea procumbens KASIV (D3290, pSZ4456) codon optimized for Prototheca

<400> SEQUENCE: 48
atggcttccg cggcattcac catgtcggcg tgccccgcga tgactggcag ggcccctggg 60
gcacgtcgct ccggacggcc agtcgccacc cgcctgaggg gctccacctt ccagtgcctg 120
gtgacctccc acaacgaccc ctgcaaccag tactgctcct ccgcctccct gtccttcctg 180
ggcgacaacg gcttcggctc caagcccttc cgctccaacc gcggccaccg ccgcctgggc 240
cgcgcctccc actccggcga ggccatggcc gtggccctgc agcccgccca ggaggtggcc 300
accaagaaga agcccgccat gaagcagcgc cgcgtggtgg tgaccggcat gggcgtggtg 360 accccctgg gccacgagcc cgacgtgtac tacaacaacc tgctggacgg cgtgtccggc 420
atctccgaga tcgagacctt cgactgcacc cagttcccca cccgcatcgc cggcgagatc 480
aagtccttct ccaccgacgg ctgggtggcc cccaagctgt ccaagcgcat ggacaagttc 540
atgctgtacc tgctgaccgc cggcaagaag gccctggccg acggcggcat caccgacgac 600
gtgatgaagg agctggacaa gcgcaagtgc ggcgtgctga tcggctccgg catgggcggc 660
atgaagctgt tcaacgactc catcgaggcc ctgcgcgtgt cctacaagaa gatgaacccc 720
ttctgcgtgc ccttcgccac caccaacatg ggctccgcca tgctggccat ggacctgggc 780
tggatgggcc ccaactactc catctccacc gcctgcgcca cctccaactt ctgcatcctg 840
aacgccgcca accacatcgt gcgcggcgag gccgacatga tgctgtgcgg cggctccgac 900
gccgtgatca tccccatcgg cctgggcggc ttcgtggcct gccgcgccct gtcccagcgc 960
aacaacgacc ccaccaaggc ctcccgcccc tgggactcca accgcgacgg cttcgtgatg 1020
ggcgagggcg ccggcgtgct gctgctggag gagctggagc acgccaagaa gcgcggcgcc 1080
accatctacg ccgagttcct gggcggctcc ttcacctgcg acgcctacca catgaccgag 1140
ccccaccccg agggcgccgg cgtgatcctg tgcatcgaga aggccctggc ccagtccggc 1200
gtgtcccgcg aggacgtgaa ctacatcaac gcccacgcca cctccacccc cgccggcgac 1260
atcaaggagt accaggccct ggcccactgc ttcggccaga actccgagct gcgcgtgaac 1320
tccaccaagt ccatgatcgg ccacctgctg ggcgccgccg gcggcgtgga ggccgtgacc 1380
gtgatccagg ccatccgcac cggctggatc caccccaacc tgaacctgga ggaccccgac 1440
aaggccgtgg acgccaagtt cctggtgggc cccaagaagg agcgcctgaa cgtgaaggtg 1500
ggcctgtcca actccttcgg cttcggcggc cacaactcct ccatcctgtt cgccccctgc 1560
aacaccatgt acccctacga cgtgcccgac tacgcctga 1599

<210> SEQ ID NO 49
<211> LENGTH: 1599
<212> TYPE: DNA
<213> ORGANISM: Artificial Sequence
<220> FEATURE:
<223> OTHER INFORMATION: C paucipetala KASIVa (D3291, pSZ4457) codon optimized for Prototheca

<400> SEQUENCE: 49

-continued

```
atggcttccg cggcattcac catgtcggcg tgccccgcga tgactggcag ggcccctggg      60
gcacgtcgct ccggacggcc agtcgccacc cgcctgaggg gctccacctt ccagtgcctg     120
gtgaactccc acatcgaccc ctgcaaccag aacgtgtcct ccgcctccct gtccttcctg     180
ggcgacaacg gcttcggctc caaccccttc cgctccaacc gcggccaccg ccgcctgggc     240
cgcgcctccc actccggcga ggccatggcc gtggccctgc agcccgccca ggaggtggcc     300
accaagaaga agcccgccat caagcagcgc cgcgtggtgg tgaccggcat gggcgtggtg     360
acccccctgg gccacgagcc cgacgtgttc tacaacaacc tgctggacgg cgtgtccggc     420
atctccgaga tcgagacctt cgactgcacc cagttcccca cccgcatcgc cggcgagatc     480
aagtccttct ccaccgacgg ctgggtggcc cccaagctgt ccaagcgcat ggacaagttc     540
atgctgtacc tgctgaccgc cggcaagaag gccctggccg acgccggcat caccgaggac     600
gtgatgaagg agctggacaa gcgcaagtgc ggcgtgctga tcggctccgg catgggcggc     660
atgaagctgt tcaacgactc catcgaggcc ctgcgcgtgt cctacaagaa gatgaacccc     720
ttctgcgtgc ccttcgccac caccaacatg ggctccgcca tgctggccat ggacctgggc     780
tggatgggcc ccaactactc catctccacc gcctgcgcca cctccaactt ctgcatcctg     840
aacgccgcca accacatcat ccgcggcgag gccgacatga tgctgtgcgg cggctccgac     900
gccgtgatca tccccatcgg cctgggcggc ttcgtggcct gccgcgccct gtcccagcgc     960
aactccgacc ccaccaaggc ctcccgcccc tgggactcca accgcgacgg cttcgtgatg    1020
ggcgagggcg ccggcgtgct gctgctggag gagctggagc acgccaagaa gcgcggcgcc    1080
accatctacg ccgagttcct gggcggctcc ttcacctgcg acgcctacca catgaccgag    1140
ccccaccccg acggcgccgg cgtgatcctg tgcatcgaga aggccctggc ccagtccggc    1200
gtgtcccgcg aggacgtgaa ctacatcaac gcccacgcca cctccacccc cgccggcgac    1260
atcaaggagt accaggccct ggcccactgc ttcggccaga actccgagct gcgcgtgaac    1320
tccaccaagt ccatgatcgg ccacctgctg ggcgccgccg gcggcgtgga ggccgtgacc    1380
gtgatccagg ccatccgcac cggctggatc caccccaacc tgaacctgga ggaccccgac    1440
gaggccgtgg acgccaagtt cctggtgggc cccaagaagg agcgcctgaa cgtgaaggtg    1500
ggcctgtcca actccttcgg cttcggcggc cacaactcct ccatcctgtt cgccccctac    1560
aacaccatgt accccctacga cgtgcccgac tacgcctga                           1599
```

<210> SEQ ID NO 50
<211> LENGTH: 1566
<212> TYPE: DNA
<213> ORGANISM: Artificial Sequence
<220> FEATURE:
<223> OTHER INFORMATION: Cuphea painteri KASIV (D3292, pSZ4458) codon
optimized for Prototheca

<400> SEQUENCE: 50

```
atggcttccg cggcattcac catgtcggcg tgccccgcga tgactggcag ggcccctggg      60
gcacgtcgct ccggacggcc agtcgccacc cgcctgaggg gctccacccc ccagtgcctg     120
gacccctgca accagcactg cttcctgggc gacaacggct tcgcctccct gatcggctcc     180
aagccccccc gctccaacct gggccacctg cgcctgggcc gcacctccca ctccggcgag     240
gtgatggccg tggcccagga ggtgtccacc aacaagaagc acgccaccaa gcagcgccgc     300
gtggtggtga ccggcatggg cgtggtgacc cccctgggcc acgaccccga cgtgtactac     360
aacaacctgc tggagggcgt gtccggcatc tccgagatcg agaacttcga ctgctcccag     420
```

```
ctgcccaccc gcatcgccgg cgagatcaag tccttctcca ccgacggcct ggtggccccc    480
aagctgtcca agcgcatgga caagttcatg ctgtacatcc tgaccgccgg caagaaggcc    540
ctggccgacg gcggcatcac cgaggacgtg atgaaggagc tggacaagcg caagtgcggc    600
gtgctgatcg gctccggcct gggcggcatg aaggtgttct ccgactccgt ggaggccctg    660
cgcatctcct acaagaagat ctcccccttc tgcgtgccct tctccaccac caacatgggc    720
tccgccatgc tggccatgga cctgggctgg atgggcccca actactccat ctccaccgcc    780
tgcgccacct ccaacttctg catcctgaac gccgccaacc acatcaccaa gggcgaggcc    840
gacatgatgc tgtgcggcgg ctccgacgcc gccatcctgc ccatcggcat gggcggcttc    900
gtggcctgcc gcgccctgtc ccagcgcaac aacgacccca ccaaggcctc ccgcccctgg    960
gactccaacc gcgacggctt cgtgatgggc gagggcgccg gcgtgctgct gctggaggag   1020
ctggagcacg ccaagaagcg cggcgccacc atctacgccg agttcctggg cggctccttc   1080
acctgcgacg cctaccacat gaccgagccc caccccgacg gcgccggcgt gatcctgtgc   1140
atcgagaagg ccctggccca gtccggcgtg tcccgcgagg aggtgaacta catcaacgcc   1200
cacgccacct ccacccccgc cggcgacatc aaggagtacc aggccctggc ccactgcttc   1260
ggccagaact ccgagctgcg cgtgaactcc accaagtcca tgatcggcca cctgctgggc   1320
ggcgccggcg gcgtggaggc cgtgaccgtg gtgcaggcca tccgcaccgg ctggatccac   1380
cccaacatca acctggagga ccccgacaag ggcgtggacg ccaagctgct ggtgggcccc   1440
aagaaggaga agctgaaggt gaaggtgggc ctgtccaact ccttcggctt cggcggccac   1500
aactcctcca tcctgttcgc cccctgcaac accatgtacc cctacgacgt gcccgactac   1560
gcctga                                                              1566
```

<210> SEQ ID NO 51
<211> LENGTH: 1611
<212> TYPE: DNA
<213> ORGANISM: Artificial Sequence
<220> FEATURE:
<223> OTHER INFORMATION: C. avigera KASIVa (D3293, pSZ4459) codon optimized for Prototheca

<400> SEQUENCE: 51

```
atggcttccg cggcattcac catgtcggcg tgccccgcga tgactggcag ggcccctggg     60
gcacgtcgct ccggacggcc agtcgccacc cgcctgaggg gctccacctt ccagtgcctg    120
gtgacctcct acaacgaccc ctgcgagcag taccgctcct ccgcctccct gtccttcctg    180
ggcgacaacg gcttcgcctc cctgttcggc tccaagccct tccgctccaa ccgcggccac    240
cgccgcctgg gccgcgcctc ccactccggc gaggccatgg ccgtggccct gcagcccgcc    300
caggaggtgg gcaccaagaa gaagcccgtg atcaagcagc gccgcgtggt ggtgaccggc    360
atgggcgtgg tgaccccct gggccacgag cccgacgtgt actacaacaa cctgctggac    420
ggcgtgtccg gcatctccga gatcgagacc ttcgactgca cccagttccc cacccgcatc    480
gccggcgaga tcaagtcctt ctccaccgac ggctgggtgg cccccaagct gtccaagcgc    540
atggacaagt tcatgctgta cctgctgacc gccggcaaga aggccctggc cgacggcggc    600
atcaccgacg acgtgatgaa ggagctggac aagcgcaagt gcggcgtgct gatcggctcc    660
ggcctgggcg gcatgaaggt gttctccgag tccatcgagg ccctgcgcac ctcctacaag    720
aagatctccc ccttctgcgt gcccttctcc accaccaaca tgggctccgc catcctggcc    780
atggacctgg gctggatggg ccccaactac tccatctcca ccgcctgcgc cacctccaac    840
```

ttctgcatcc tgaacgccgc caaccacatc accaagggcg aggccgacat gatgctgtgc 900
ggcggctccg actccgtgat cctgcccatc ggcatgggcg gcttcgtggc ctgccgcgcc 960
ctgtcccagc gcaacaacga ccccaccaag gcctcccgcc cctgggactc caaccgcgac 1020
ggcttcgtga tgggcgaggg cgccggcgtg ctgctgctgg aggagctgga gcacgccaag 1080
aagcgcggcg ccaccatcta cgccgagttc ctgggcggct ccttcacctg cgacgcctac 1140
cacatgaccg agccccaccc cgagggcgcc ggcgtgatcc tgtgcatcga gaaggccctg 1200
gcccagtccg gcgtgtcccg cgaggacgtg aactacatca acgcccacgc cacctccacc 1260
cccgccggcg acatcaagga gtaccaggcc ctggcccact gcttcggcca gaactccgag 1320
ctgcgcgtga actccaccaa gtccatgatc ggccacctgc tgggcggcgc cggcggcgtg 1380
gaggccgtga ccgtggtgca ggccatccgc accggctgga tccaccccaa catcaacctg 1440
gacgaccccg acgagggcgt ggacgccaag ctgctggtgg gccccaagaa ggagaagctg 1500
aaggtgaagg tgggcctgtc caactccttc ggcttcggcg gccacaactc ctccatcctg 1560
ttcgccccct gcaacaccat gtacccctac gacgtgcccg actacgcctg a 1611

<210> SEQ ID NO 52
<211> LENGTH: 1611
<212> TYPE: DNA
<213> ORGANISM: Artificial Sequence
<220> FEATURE:
<223> OTHER INFORMATION: C ignea KASIVa (D3294, pSZ4460) codon optimized for Prototheca

<400> SEQUENCE: 52
atggcttccg cggcattcac catgtcggcg tgccccgcga tgactggcag ggcccctggg 60
gcacgtcgct ccggacggcc agtcgccacc cgcctgaggg gctccacctc ccagtgcctg 120
gtgacctcct acatcgaccc ctgcaacaag tactgctcct ccgcctccct gtccttcctg 180
ggcgacaacg gcttcgcctc cctgttcggc tccaagccct tccgctccaa ccgcggccac 240
cgccgcctgg gccgcgcctc ccactccggc gaggccatgg ccgtggccct gcagcccgcc 300
caggaggtga ccaccaagaa gaagcccgtg atcaagcagc gccgcgtggt ggtgaccggc 360
atgggcgtgg tgacccccct gggccacgag cccgacgtgt actacaacaa cctgctggac 420
ggcgtgtccg gcatctccga gatcgagacc ttcgactgca cccagttccc cacccgcatc 480
gccggcgaga tcaagtcctt ctccaccgac ggctgggtgg cccccaagct gtccaagcgc 540
atggacaagt tcatgctgta cctgctgacc gccggcaaga aggccctggc cgacggcggc 600
atcaccgacg acgtgatgaa ggagctggac aagcgcaagt gcggcgtgct gatcggctcc 660
ggcatgggcg gcatgaagct gttcaacgac tccatcgagg ccctgcgcat ctcctacaag 720
aagatgaacc ccttctgcgt gcccttcgcc accaccaaca tgggctccgc catgctggcc 780
atggacctgg gctggatggg ccccaactac tccatctcca ccgcctgcgc cacctccaac 840
ttctgcatcc tgaacgcctc caaccacatc gtgcgcggcg aggccgacat gatgctgtgc 900
ggcggctccg acgccgtgat catccccatc ggcctgggcg gcttcgtggc ctgccgcgcc 960
ctgtcccagc gcaacaacga ccccaccaag gcctcccgcc cctgggactc caaccgcgac 1020
ggcttcgtga tgggcgaggg cgccggcgtg ctgctgctgg aggagctgga gcacgccaag 1080
aagcgcggcg ccaccatcta cgccgagttc ctgggcggct ccttcacctg cgacgcctac 1140
cacatgaccg agccccaccc cgagggcgcc ggcgtgatcc tgtgcatcga gaaggccctg 1200
gcccaggccg gcgtgtccaa ggaggacgtg aactacatca acgcccacgc cacctccacc 1260

-continued cccgccggcg acatcaagga gtaccaggcc ctggcccagt gcttcggcca gaactccgag 1320
ctgcgcgtga actccaccaa gtccatgatc ggccacctgc tgggcgccgc cggcggcgtg 1380
gaggccgtga ccgtggtgca ggccatccgc accggctgga tccaccccaa cctgaacctg 1440
gaggaccccg acaaggccgt ggacgccaag ctgctggtgg gccccaagaa ggagcgcctg 1500
aacgtgaagg tgggcctgtc caactccttc ggcttcggcg gccacaactc ctccatcctg 1560
ttcgccccct acaacaccat gtacccctac gacgtgcccg actacgcctg a 1611

<210> SEQ ID NO 53
<211> LENGTH: 1455
<212> TYPE: DNA
<213> ORGANISM: Artificial Sequence
<220> FEATURE:
<223> OTHER INFORMATION: C. avigera KASIa (D3342, pSZ4511) codon optimized for Prototheca

<400> SEQUENCE: 53
atgcagtccc tgcactcccc cgccctgcgc gcctcccccc tggaccccct gcgcctgaag 60
tcctccgcca acggcccctc ctccaccgcc gccttccgcc ccctgcgccg cgccaccctg 120
cccaacatcc gcgccgcctc ccccaccgtg tccgccccca agcgcgagac cgaccccaag 180
aagcgcgtgg tgatcaccgg catgggcctg gtgtccgtgt tcggctccga cgtggacgcc 240
tactacgaga agctgctgtc cggcgagtcc ggcatctccc tgatcgaccg cttcgacgcc 300
tccaagttcc ccacccgctt cggcggccag atccgcggct tcaacgccac cggctacatc 360
gacggcaaga acgaccgccg cctggacgac tgcctgcgct actgcatcgt ggccggcaag 420
aaggccctgg agaactccga cctgggcggc gactccctgt ccaagatcga caaggagcgc 480
gccggcgtgc tggtgggcac cggcatgggc ggcctgaccg tgttctccga cggcgtgcag 540
aacctgatcg agaagggcca ccgcaagatc tccccctttct tcatccccta cgccatcacc 600
aacatgggct ccgccctgct ggccatcgac ctgggcctga tgggccccaa ctactccatc 660
tccaccgcct gcgccacctc caactactgc ttctacgccg ccgccaacca catccgccgc 720
ggcgaggccg acctgatgat cgccggcggc accgaggccg ccatcatccc catcggcctg 780
ggcggcttcg tggcctgccg cgccctgtcc cagcgcaacg acgaccccca gaccgcctcc 840
cgcccctggg acaaggaccg cgacggcttc gtgatgggcg agggcgccgg cgtgctggtg 900
atggagtccc tggagcacgc catgaagcgc ggcgccccca tcatcgccga gtacctgggc 960
ggcgccgtga actgcgacgc ctaccacatg accgaccccc gcgccgacgg cctgggcgtg 1020
tcctcctgca tcgagtcctc cctggaggac gccggcgtgt cccccgagga ggtgaactac 1080
atcaacgccc acgccacctc caccctggcc ggcgacctgg ccgagatcaa cgccatcaag 1140
aaggtgttca agaacaccaa ggacatcaag atcaacgcca ccaagtccat gatcggccac 1200
tgcctgggcg cctccggcgg cctggaggcc atcgccacca tcaagggcat caccaccggc 1260
tggctgcacc cctccatcaa ccagttcaac cccgagccct ccgtggagtt cgacaccgtg 1320
gccaacaaga agcagcagca cgaggtgaac gtggccatct ccaactcctt cggcttcggc 1380
ggccacaact ccgtggtggc cttctccgcc ttcaagccca ccatgtaccc ctacgacgtg 1440
cccgactacg cctga 1455

<210> SEQ ID NO 54
<211> LENGTH: 1431
<212> TYPE: DNA
<213> ORGANISM: Artificial Sequence
<220> FEATURE:

<223> OTHER INFORMATION: C. pulcherrima KASI (D3343, pSZ4512) codon
optimized for Prototheca

<400> SEQUENCE: 54
atgcactccc tgcagtcccc ctccctgcgc gcctcccccc tggacccctt ccgccccaag 60
tcctccaccg tgcgcccct gcaccgcgcc tccatcccca acgtgcgcgc cgcctccccc 120
accgtgtccg cccccaagcg cgagaccgac cccaagaagc gcgtggtgat caccggcatg 180
ggcctggtgt ccgtgttcgg ctccgacgtg gacgcctact acgacaagct gctgtccggc 240
gagtccggca tcggccccat cgaccgcttc gacgcctcca agttccccac ccgcttcggc 300
ggccagatcc gcggcttcaa ctccatgggc tacatcgacg gcaagaacga ccgccgcctg 360
gacgactgcc tgcgctactg catcgtggcc ggcaagaagt ccctggagga cgccgacctg 420
ggcgccgacc gcctgtccaa gatcgacaag gagcgcgccg gcgtgctggt gggcaccggc 480
atgggcggcc tgaccgtgtt ctccgacggc gtgcagtccc tgatcgagaa gggccaccgc 540
aagatcaccc ccttcttcat cccctacgcc atcaccaaca tgggctccgc cctgctggcc 600
atcgagctgg gcctgatggg ccccaactac tccatctcca ccgcctgcgc cacctccaac 660
tactgcttcc acgccgccgc caaccacatc cgccgcggcg aggccgacct gatgatcgcc 720
ggcggcaccg aggccgccat catccccatc ggcctgggcg gcttcgtggc ctgccgcgcc 780
ctgtcccagc gcaacgacga cccccagacc gcctcccgcc cctgggacaa ggaccgcgac 840
ggcttcgtga tgggcgaggg cgccggcgtg ctggtgctgg agtccctgga gcacgccatg 900
aagcgcggcg cccccatcat cgccgagtac ctgggcggcg ccatcaactg cgacgcctac 960
cacatgaccg acccccgcgc cgacggcctg ggcgtgtcct cctgcatcga gtcctccctg 1020
gaggacgccg gcgtgtcccc cgaggaggtg aactacatca acgcccacgc cacctccacc 1080
ctggccggcg acctggccga gatcaacgcc atcaagaagg tgttcaagaa caccaaggac 1140
atcaagatca acgccaccaa gtccatgatc ggccactgcc tgggcgcctc cggcggcctg 1200
gaggccatcg ccaccatcaa gggcatcaac accggctggc tgcacccctc catcaaccag 1260
ttcaaccccg agccctccgt ggagttcgac accgtggcca acaagaagca gcagcacgag 1320
gtgaacgtgg ccatctccaa ctccttcggc ttcggcggcc acaactccgt ggtggccttc 1380
tccgccttca agcccaccat gtacccctac gacgtgcccg actacgcctg a 1431

<210> SEQ ID NO 55
<211> LENGTH: 1434
<212> TYPE: DNA
<213> ORGANISM: Artificial Sequence
<220> FEATURE:
<223> OTHER INFORMATION: C. avigera mitochondrial KAS (D3344, pSZ4513)
codon optimized for Prototheca

<400> SEQUENCE: 55
atggtgttcc tgccctggcg caagatgctg tgcccctccc agtaccgctt cctgcgcccc 60
ctgtcctcct ccaccacctt cgacccccgc cgcgtggtgg tgaccggcct gggcatggtg 120 accccctgg gctgcggcgt gaacaccacc tggaagcagc tgatcgaggg caagtgcggc 180
atccgcgcca tctccctgga ggacctgaag atggacgcct tcgacatcga cacccaggcc 240
tacgtgttcg accagctgac ctccaaggtg gccgccaccg tgcccaccgg cgtgaacccc 300
ggcgagttca acgaggacct gtggttcaac cagaaggagc accgcgccat cgcccgcttc 360
atcgcctacg ccctgtgcgc cgccgacgag gccctgaagg acgccaactg ggagcccacc 420
gagcccgagg agcgcgagat gaccggcgtg tccatcggcg gcggcaccgg ctccatctcc 480

```
gacgtgctgg acgccggccg catgatctgc gagaagaagc tgcgccgcct gtccccccttc    540

ttcatccccc gcatcctgat caacatggcc tccggccacg tgtccatgaa gtacggcttc    600

cagggcccca accacgccgc cgtgaccgcc tgcgccaccg gcgcccactc catcggcgac    660

gccgcccgca tgatccagtt cggcgacgcc gacgtgatgg tggccggcgg caccgagtcc    720

tccatcgacg ccctgtccat cgccggcttc tgccgctccc gcgccctgac caccaagtac    780

aactcctgcc cccaggaggc ctcccgcccc ttcgacaccg accgcgacgg cttcgtgatc    840

ggcgagggct ccggcgtgct ggtgctggag gagctggacc acgcccgcaa gcgcggcgcc    900

aagatgtacg ccgagttctg cggctacggc atgtccggcg acgcccacca catcacccag    960

ccccactccg acggccgcgg cgccatcctg gccatgaccc gcgccctgaa gcagtccaac   1020

ctgcaccccg accaggtgga ctacgtgaac gcccacgcca cctccacctc cctgggcgac   1080

gccatcgagg ccaaggccat caagaccgtg ttctccgacc acgccatgtc cggctccctg   1140

gccctgtcct ccaccaaggg cgccatcggc cacctgctgg gcgccgccgg cgccgtggag   1200

gccatcttct ccatcctggc catcaagaac ggcctggccc ccctgaccct gaacgtggcc   1260

cgcccccgacc ccgtgttcac cgagcgcttc gtgcccctga ccgcctccaa ggagatgcac   1320

gtgcgcgccg ccctgtccaa ctccttcggc ttcggcggca ccaacaccac cctgctgttc   1380

acctcccccc cccagaacac catgtacccc tacgacgtgc ccgactacgc ctga         1434
```

<210> SEQ ID NO 56
<211> LENGTH: 1242
<212> TYPE: DNA
<213> ORGANISM: Artificial Sequence
<220> FEATURE:
<223> OTHER INFORMATION: C. avigera KASIII (D3345, pSZ4514) Codon optimized for Prototheca

<400> SEQUENCE: 56

```
atggccaacg cctacggctt cgtgggctcc tccgtgccca ccgtgggccg cgccgcccag     60

ttccagcaga tgggctccgg cttctgctcc gtggacttca tctccaagcg cgtgttctgc    120

tgctccgccg tgcagggcgc cgacaagccc gcctccggcg actcccgcgc cgagtaccgc    180

accccccgcc tggtgtcccg cggctgcaag ctgatcggct ccggctccgc catccccacc    240

ctgcaggtgt ccaacgacga cctggccaag atcgtggaca ccaacgacga gtggatctcc    300

gtgcgcaccg gcatccgcaa ccgccgcgtg ctgaccggca aggactccct gaccaacctg    360

gccaccgagg ccgcccgcaa ggccctggag atggcccagg tggacgccga ggacgtggac    420

atggtgctga tgtgcacctc cacccccgag gacctgttcg gctccgcccc ccagatccag    480

aaggccctgg gctgcaagaa gaacccctg tcctacgaca tcaccgccgc ctgctccggc    540

ttcgtgctgg gcctggtgtc cgccgcctgc cacatccgcg gcggcggctt caacaacgtg    600

ctggtgatcg gcgccgactc cctgtcccgc tacgtggact ggaccgaccg cggcacctgc    660

atcctgttcg gcgacgccgc cggcgccgtg ctggtgcagt cctgcgacgc cgaggaggac    720

ggcctgttcg ccttcgacct gcactccgac ggcgacggcc agcgccacct gcgcgccgtg    780

atcaccgaga acgagaccga ccacgccgtg ggcaccaacg gctccgtgtc cgacttcccc    840

ccccgccgct cctcctactc ctgcatccag atgaacggca aggaggtgtt ccgcttcgcc    900

tgccgctccg tgccccagtc catcgagctg gccctgggca aggccggcct gaacggctcc    960

aacatcgact ggctgctgct gcaccaggcc aaccagcgca tcatcgacgc cgtggccacc   1020

cgcctggagg tgccccagga gcgcgtgatc tccaacctgg ccaactacgg caacacctcc   1080
```

gccgcctcca tccccctggc cctggacgag gccgtgcgcg gcggcaaggt gaagcccggc 1140
cacctgatcg ccaccgccgg cttcggcgcc ggcctgacct ggggctccgc catcgtgcgc 1200
tggggcacca tgtaccccta cgacgtgccc gactacgcct ga 1242

<210> SEQ ID NO 57
<211> LENGTH: 415
<212> TYPE: PRT
<213> ORGANISM: Cuphea hookeriana
<220> FEATURE:
<221> NAME/KEY: MISC_FEATURE
<223> OTHER INFORMATION: FATB2

<400> SEQUENCE: 57

Met Val Ala Ala Ala Ala Ser Ser Ala Phe Phe Pro Val Pro Ala Pro
1 5 10 15

Gly Ala Ser Pro Lys Pro Gly Lys Phe Gly Asn Trp Pro Ser Ser Leu
20 25 30

Ser Pro Ser Phe Lys Pro Lys Ser Ile Pro Asn Gly Gly Phe Gln Val
35 40 45

Lys Ala Asn Asp Ser Ala His Pro Lys Ala Asn Gly Ser Ala Val Ser
50 55 60

Leu Lys Ser Gly Ser Leu Asn Thr Gln Glu Asp Thr Ser Ser Ser Pro
65 70 75 80

Pro Pro Arg Thr Phe Leu His Gln Leu Pro Asp Trp Ser Arg Leu Leu
85 90 95

Thr Ala Ile Thr Thr Val Phe Val Lys Ser Lys Arg Pro Asp Met His
100 105 110

Asp Arg Lys Ser Lys Arg Pro Asp Met Leu Val Asp Ser Phe Gly Leu
115 120 125

Glu Ser Thr Val Gln Asp Gly Leu Val Phe Arg Gln Ser Phe Ser Ile
130 135 140

Arg Ser Tyr Glu Ile Gly Thr Asp Arg Thr Ala Ser Ile Glu Thr Leu
145 150 155 160

Met Asn His Leu Gln Glu Thr Ser Leu Asn His Cys Lys Ser Thr Gly
165 170 175

Ile Leu Leu Asp Gly Phe Gly Arg Thr Leu Glu Met Cys Lys Arg Asp
180 185 190

Leu Ile Trp Val Val Ile Lys Met Gln Ile Lys Val Asn Arg Tyr Pro
195 200 205

Ala Trp Gly Asp Thr Val Glu Ile Asn Thr Arg Phe Ser Arg Leu Gly
210 215 220

Lys Ile Gly Met Gly Arg Asp Trp Leu Ile Ser Asp Cys Asn Thr Gly
225 230 235 240

Glu Ile Leu Val Arg Ala Thr Ser Ala Tyr Ala Met Met Asn Gln Lys
245 250 255

Thr Arg Arg Leu Ser Lys Leu Pro Tyr Glu Val His Gln Glu Ile Val
260 265 270

Pro Leu Phe Val Asp Ser Pro Val Ile Glu Asp Ser Asp Leu Lys Val
275 280 285

His Lys Phe Lys Val Lys Thr Gly Asp Ser Ile Gln Lys Gly Leu Thr
290 295 300

Pro Gly Trp Asn Asp Leu Asp Val Asn Gln His Val Ser Asn Val Lys
305 310 315 320

Tyr Ile Gly Trp Ile Leu Glu Ser Met Pro Thr Glu Val Leu Glu Thr

```
                325                 330                 335

Gln Glu Leu Cys Ser Leu Ala Leu Glu Tyr Arg Arg Glu Cys Gly Arg
            340                 345                 350

Asp Ser Val Leu Glu Ser Val Thr Ala Met Asp Pro Ser Lys Val Gly
        355                 360                 365

Val Arg Ser Gln Tyr Gln His Leu Leu Arg Leu Glu Asp Gly Thr Ala
    370                 375                 380

Ile Val Asn Gly Ala Thr Glu Trp Arg Pro Lys Asn Ala Gly Ala Asn
385                 390                 395                 400

Gly Ala Ile Ser Thr Gly Lys Thr Ser Asn Gly Asn Ser Val Ser
                405                 410                 415


<210> SEQ ID NO 58
<211> LENGTH: 573
<212> TYPE: DNA
<213> ORGANISM: Prototheca moriformis
<220> FEATURE:
<221> NAME/KEY: misc_feature
<223> OTHER INFORMATION: 23S rRNA for UTEX 1439, UTEX 1441, UTEX 1435,
      UTEX 1437 Prototheca moriformis

<400> SEQUENCE: 58

tgttgaagaa tgagccggcg acttaaaata aatggcaggc taagagaatt aataactcga     60

aacctaagcg aaagcaagtc ttaatagggc gctaatttaa caaaacatta aataaaatct    120

aaagtcattt attttagacc cgaacctgag tgatctaacc atggtcagga tgaaacttgg    180

gtgacaccaa gtggaagtcc gaaccgaccg atgttgaaaa atcggcggat gaactgtggt    240

tagtggtgaa ataccagtcg aactcagagc tagctggttc tccccgaaat gcgttgaggc    300

gcagcaatat atctcgtcta tctaggggta aagcactgtt tcggtgcggg ctatgaaaat    360

ggtaccaaat cgtggcaaac tctgaatact agaaatgacg atatattagt gagactatgg    420

gggataagct ccatagtcga gagggaaaca gcccagacca ccagttaagg ccccaaaatg    480

ataatgaagt ggtaaaggag gtgaaaatgc aaatacaacc aggaggttgg cttagaagca    540

gccatccttt aaagagtgcg taatagctca ctg                                  573


<210> SEQ ID NO 59
<211> LENGTH: 514
<212> TYPE: PRT
<213> ORGANISM: Cuphea hookeriana
<220> FEATURE:
<221> NAME/KEY: MISC_FEATURE
<223> OTHER INFORMATION: KASIV

<400> SEQUENCE: 59

Met Ala Ser Ala Ala Phe Thr Met Ser Ala Cys Pro Ala Met Thr Gly
1               5                   10                  15

Arg Ala Pro Gly Ala Arg Arg Ser Gly Arg Pro Val Ala Thr Arg Leu
            20                  25                  30

Arg Gly Ser Thr Phe Gln Cys Leu Asp Pro Cys Asn Gln Gln Arg Phe
        35                  40                  45

Leu Gly Asp Asn Gly Phe Ala Ser Leu Phe Gly Ser Lys Pro Leu Arg
    50                  55                  60

Ser Asn Arg Gly His Leu Arg Leu Gly Arg Thr Ser His Ser Gly Glu
65                  70                  75                  80

Val Met Ala Val Ala Met Gln Pro Ala Gln Glu Val Ser Thr Asn Lys
                85                  90                  95

Lys Pro Ala Thr Lys Gln Arg Arg Val Val Val Thr Gly Met Gly Val
```

-continued

```
            100                 105                 110

Val Thr Pro Leu Gly His Asp Pro Asp Val Tyr Tyr Asn Asn Leu Leu
        115                 120                 125

Asp Gly Ile Ser Gly Ile Ser Glu Ile Glu Asn Phe Asp Cys Ser Gln
    130                 135                 140

Phe Pro Thr Arg Ile Ala Gly Glu Ile Lys Ser Phe Ser Thr Asp Gly
145                 150                 155                 160

Trp Val Ala Pro Lys Phe Ser Glu Arg Met Asp Lys Phe Met Leu Tyr
                165                 170                 175

Met Leu Thr Ala Gly Lys Lys Ala Leu Ala Asp Gly Gly Ile Thr Glu
            180                 185                 190

Asp Ala Met Lys Glu Leu Asn Lys Arg Lys Cys Gly Val Leu Ile Gly
        195                 200                 205

Ser Gly Leu Gly Gly Met Lys Val Phe Ser Asp Ser Ile Glu Ala Leu
    210                 215                 220

Arg Thr Ser Tyr Lys Lys Ile Ser Pro Phe Cys Val Pro Phe Ser Thr
225                 230                 235                 240

Thr Asn Met Gly Ser Ala Ile Leu Ala Met Asp Leu Gly Trp Met Gly
                245                 250                 255

Pro Asn Tyr Ser Ile Ser Thr Ala Cys Ala Thr Ser Asn Phe Cys Ile
            260                 265                 270

Leu Asn Ala Ala Asn His Ile Ile Lys Gly Glu Ala Asp Met Met Leu
        275                 280                 285

Cys Gly Gly Ser Asp Ala Ala Val Leu Pro Val Gly Leu Gly Gly Phe
    290                 295                 300

Val Ala Cys Arg Ala Leu Ser Gln Arg Asn Asn Asp Pro Thr Lys Ala
305                 310                 315                 320

Ser Arg Pro Trp Asp Ser Asn Arg Asp Gly Phe Val Met Gly Glu Gly
                325                 330                 335

Ala Gly Val Leu Leu Leu Glu Glu Leu Glu His Ala Lys Lys Arg Gly
            340                 345                 350

Ala Thr Ile Tyr Ala Glu Phe Leu Gly Gly Ser Phe Thr Cys Asp Ala
        355                 360                 365

Tyr His Met Thr Glu Pro His Pro Glu Gly Ala Gly Val Ile Leu Cys
    370                 375                 380

Ile Glu Lys Ala Leu Ala Gln Ser Gly Val Ser Arg Glu Asp Val Asn
385                 390                 395                 400

Tyr Ile Asn Ala His Ala Thr Ser Thr Pro Ala Gly Asp Ile Lys Glu
                405                 410                 415

Tyr Gln Ala Leu Ala His Cys Phe Gly Gln Asn Ser Glu Leu Arg Val
            420                 425                 430

Asn Ser Thr Lys Ser Met Ile Gly His Leu Leu Gly Gly Ala Gly Gly
        435                 440                 445

Val Glu Ala Val Ala Val Val Gln Ala Ile Arg Thr Gly Trp Ile His
    450                 455                 460

Pro Asn Ile Asn Leu Glu Asp Pro Asp Glu Gly Val Asp Ala Lys Leu
465                 470                 475                 480

Leu Val Gly Pro Lys Lys Glu Lys Leu Lys Val Lys Val Gly Leu Ser
                485                 490                 495

Asn Ser Phe Gly Phe Gly Gly His Asn Ser Ser Ile Leu Phe Ala Pro
            500                 505                 510

Cys Asn
```

<210> SEQ ID NO 60
<211> LENGTH: 6227
<212> TYPE: DNA
<213> ORGANISM: Artificial Sequence
<220> FEATURE:
<223> OTHER INFORMATION: C. hookeriana KASIV (D3668, pSZ4756) expression vector

<400> SEQUENCE: 60

```
gccggtcacc acccgcatgc tcgtactaca gcgcacgcac cgcttcgtga tccaccgggt     60
gaacgtagtc ctcgacggaa acatctggtt cgggcctcct gcttgcactc ccgcccatgc    120
cgacaacctt tctgctgtta ccacgaccca caatgcaacg cgacacgacc gtgtgggact    180
gatcggttca ctgcacctgc atgcaattgt cacaagcgct tactccaatt gtattcgttt    240
gttttctggg agcagttgct cgaccgcccg cgtcccgcag gcagcgatga cgtgtgcgtg    300
gcctgggtgt ttcgtcgaaa ggccagcaac cctaaatcgc aggcgatccg gagattggga    360
tctgatccga gtttggacca gatccgcccc gatgcggcac gggaactgca tcgactcggc    420
gcggaaccca gctttcgtaa atgccagatt ggtgtccgat acctggattt gccatcagcg    480
aaacaagact tcagcagcga gcgtatttgg cgggcgtgct accagggttg catacattgc    540
ccatttctgt ctggaccgct ttactggcgc agagggtgag ttgatggggt tggcaggcat    600
cgaaacgcgc gtgcatggtg tgcgtgtctg ttttcggctg cacgaattca atagtcggat    660
gggcgacggt agaattgggt gtggcgctcg cgtgcatgcc tcgccccgtc gggtgtcatg    720
accgggactg gaatcccccc tcgcgaccat cttgctaacg ctcccgactc tcccgaccgc    780
gcgcaggata gactcttgtt caaccaatcg acaggtacca tggcttccgc ggcattcacc    840
atgtcggcgt gccccgcgat gactggcagg gcccctgggg cacgtcgctc cggacggcca    900
gtcgccaccc gcctgagggg cagcaccttc cagtgcctgg acccctgcaa ccagcagcgc    960
ttcctgggcg acaacggctt cgcgtcgctg ttcggctcca agcccctgcg cagcaaccgc   1020
ggccacctgc gcctgggccg cacctcgcac tccggcgagg tgatggccgt cgcgatgcag   1080
cccgcccagg aggtgagcac caacaagaag cccgcgacca agcagcgccg cgtggtcgtg   1140
accggcatgg gcgtcgtgac ccccctgggc cacgaccccg acgtgtatta taacaacctg   1200
ctggacggca tctcgggcat ctccgagatc gagaacttcg actgcagcca gttccccacc   1260
cgcatcgccg gcgagatcaa gtcgttctcc accgacggct gggtcgcgcc caagttcagc   1320
gagcgcatgg acaagttcat gctgtatatg ctgaccgccg gcaagaaggc gctggccgac   1380
ggcggcatca ccgaggacgc gatgaaggag ctgaacaagc gcaagtgcgg cgtgctgatc   1440
ggctcgggcc tgggcggcat gaaggtcttc tccgacagca tcgaggccct gcgcacctcg   1500
tataagaaga tctcccccttt ctgcgtgccc ttcagcacca ccaacatggg ctcggcgatc   1560
ctggcgatgg acctgggctg gatgggcccc aactattcca tcagcaccgc gtgcgccacc   1620
tcgaacttct gcatcctgaa cgcggccaac cacatcatca agggcgaggc ggacatgatg   1680
ctgtgcggcg gctccgacgc cgcggtgctg cccgtcggcc tgggcggctt cgtggcctgc   1740
cgcgcgctga gccagcgcaa caacgacccc accaaggcct cgcgcccctg ggactccaac   1800
cgcgacggct tcgtcatggg cgagggcgcg ggcgtgctgc tgctggagga gctggagcac   1860
gccaagaagc gcggcgcgac catctatgcc gagttcctgg gcggcagctt cacctgcgac   1920
gcgtatcaca tgaccgagcc ccaccccgag ggcgccggcg tcatcctgtg catcgagaag   1980
gcgctggccc agtcgggcgt gtcccgcgag gacgtgaact atatcaacgc gcacgccacc   2040
```

-continued

```
agcacccccg cgggcgacat caaggagtat caggccctgg cgcactgctt cggccagaac   2100
tcggagctgc gcgtcaactc caccaagagc atgatcggcc acctgctggg cggcgccggc   2160
ggcgtggagg cggtcgccgt ggtccaggcg atccgcaccg gctggatcca ccccaacatc   2220
aacctggagg accccgacga gggcgtggac gccaagctgc tggtcggccc caagaaggag   2280
aagctgaagg tgaaggtcgg cctgtcgaac tccttcggct tcggcggcca caacagctcg   2340
atcctgttcg cgccctgcaa ctgactcgag acagacgacc ttggcaggcg tcgggtaggg   2400
aggtggtggt gatggcgtct cgatgccatc gcacgcatcc aacgaccgta tacgcatcgt   2460
ccaatgaccg tcggtgtcct ctctgcctcc gttttgtgag atgtctcagg cttggtgcat   2520
cctcgggtgg ccagccacgt tgcgcgtcgt gctgcttgcc tctcttgcgc ctctgtggta   2580
ctggaaaata tcatcgaggc ccgttttttt gctcccattt cctttccgct acatcttgaa   2640
agcaaacgac aaacgaagca gcaagcaaag agcacgagga cggtgaacaa gtctgtcacc   2700
tgtatacatc tatttccccg cgggtgcacc tactctctct cctgccccgg cagagtcagc   2760
tgccttacgt gaccctaggt gcggtgagaa tcgaaaatgc atcgtttcta ggttcggaga   2820
cggtcaattc cctgctccgg cgaatctgtc ggtcaagctg gccagtggac aatgttgcta   2880
tggcagcccg cgcacatggg cctcccgacg cggccatcag gagcccaaac agcgtgtcag   2940
ggtatgtgaa actcaagagg tccctgctgg gcactccggc cccactccgg gggcgggacg   3000
ccaggcattc gcggtcggtc ccgcgcgacg agcgaaatga tgattcggtt acgagaccag   3060
gacgtcgtcg aggtcgagag gcagcctcgg acacgtctcg ctagggcaac gccccgagtc   3120
cccgcgaggg ccgtaaacat tgtttctggg tgtcggagtg ggcattttgg gcccgatcca   3180
atcgcctcat gccgctctcg tctggtcctc acgttcgcgt acggcctgga tcccggaaag   3240
ggcggatgca cgtggtgttg ccccgccatt ggcgcccacg tttcaaagtc cccggccaga   3300
aatgcacagg accggcccgg ctcgcacagg ccatgctgaa cgcccagatt tcgacagcaa   3360
caccatctag aataatcgca accatccgcg ttttgaacga aacgaaacgg cgctgtttag   3420
catgtttccg acatcgtggg ggccgaagca tgctccgggg ggaggaaagc gtggcacagc   3480
ggtagcccat tctgtgccac acgccgacga ggaccaatcc ccggcatcag ccttcatcga   3540
cggctgcgcc gcacatataa agccggacgc ctaaccggtt tcgtggttat gactagtatg   3600
ttcgcgttct acttcctgac ggcctgcatc tccctgaagg gcgtgttcgg cgtctccccc   3660
tcctacaacg gcctgggcct gacgccccag atgggctggg acaactggaa cacgttcgcc   3720
tgcgacgtct ccgagcagct gctgctggac acggccgacc gcatctccga cctgggcctg   3780
aaggacatgg gctacaagta catcatcctg gacgactgct ggtcctccgg ccgcgactcc   3840
gacggcttcc tggtcgccga cgagcagaag ttccccaacg gcatgggcca cgtcgccgac   3900
cacctgcaca acaactcctt cctgttcggc atgtactcct ccgcgggcga gtacacgtgc   3960
gccggctacc ccggctccct gggccgcgag gaggaggacg cccagttctt cgcgaacaac   4020
cgcgtggact acctgaagta cgacaactgc tacaacaagg gccagttcgg cacgcccgag   4080
atctcctacc accgctacaa ggccatgtcc gacgccctga acaagacggg ccgccccatc   4140
ttctactccc tgtgcaactg gggccaggac ctgaccttct actggggctc cggcatcgcg   4200
aactcctggc gcatgtccgg cgacgtcacg gcggagttca cgcgccccga ctcccgctgc   4260
ccctgcgacg gcgacgagta cgactgcaag tacgccggct tccactgctc catcatgaac   4320
atcctgaaca aggccgcccc catgggccag aacgcgggcg tcggcggctg gaacgacctg   4380
gacaacctgg aggtcggcgt cggcaacctg acggacgacg aggagaaggc gcacttctcc   4440
```

```
atgtgggcca tggtgaagtc ccccctgatc atcggcgcga acgtgaacaa cctgaaggcc   4500

tcctcctact ccatctactc ccaggcgtcc gtcatcgcca tcaaccagga ctccaacggc   4560

atccccgcca cgcgcgtctg gcgctactac gtgtccgaca cggacgagta cggccagggc   4620

gagatccaga tgtggtccgg cccccctggac aacggcgacc aggtcgtggc gctgctgaac   4680

ggcggctccg tgtcccgccc catgaacacg accctggagg agatcttctt cgactccaac   4740

ctgggctcca agaagctgac ctccacctgg gacatctacg acctgtgggc gaaccgcgtc   4800

gacaactcca cggcgtccgc catcctgggc cgcaacaaga ccgccaccgg catcctgtac   4860

aacgccaccg agcagtccta caaggacggc ctgtccaaga acgacacccg cctgttcggc   4920

cagaagatcg gctccctgtc ccccaacgcg atcctgaaca cgaccgtccc cgcccacggc   4980

atcgcgttct accgcctgcg cccctcctcc tgatacaact tattacgtat tctgaccggc   5040

gctgatgtgg cgcggacgcc gtcgtactct ttcagacttt actcttgagg aattgaacct   5100

ttctcgcttg ctggcatgta aacattggcg caattaattg tgtgatgaag aaagggtggc   5160

acaagatgga tcgcgaatgt acgagatcga caacgatggt gattgttatg aggggccaaa   5220

cctggctcaa tcttgtcgca tgtccggcgc aatgtgatcc agcggcgtga ctctcgcaac   5280

ctggtagtgt gtgcgcaccg ggtcgctttg attaaaactg atcgcattgc catcccgtca   5340

actcacaagc ctactctagc tcccattgcg cactcgggcg cccggctcga tcaatgttct   5400

gagcggaggg cgaagcgtca ggaaatcgtc tcggcagctg gaagcgcatg gaatgcggag   5460

cggagatcga atcagatatc aagctccatc gagctccagc cacggcaaca ccgcgcgcct   5520

tgcggccgag cacggcgaca agaacctgag caagatctgc gggctgatcg ccagcgacga   5580

gggccggcac gagatcgcct acacgcgcat cgtggacgag ttcttccgcc tcgaccccga   5640

gggcgccgtc gccgcctacg ccaacatgat gcgcaagcag atcaccatgc ccgcgcacct   5700

catggacgac atgggccacg gcgaggccaa cccgggccgc aacctcttcg ccgacttctc   5760

cgcggtcgcc gagaagatcg acgtctacga cgccgaggac tactgccgca tcctggagca   5820

cctcaacgcg cgctggaagg tggacgagcg ccaggtcagc ggccaggccg ccgcggacca   5880

ggagtacgtc ctgggcctgc cccagcgctt ccggaaactc gccgagaaga ccgccgccaa   5940

gcgcaagcgc gtcgcgcgca ggcccgtcgc cttctcctgg atctccgggc gcgagatcat   6000

ggtctaggga gcgacgagtg tgcgtgcggg gctggcggga gtgggacgcc ctcctcgctc   6060

ctctctgttc tgaacggaac aatcggccac cccgcgctac gcgccacgca tcgagcaacg   6120

aagaaaaccc cccgatgata ggttgcggtg gctgccggga tatagatccg gccgcacatc   6180

aaagggcccc tccgccagag aagaagctcc tttcccagca gactcct                 6227
```

```
<210> SEQ ID NO 61
<211> LENGTH: 1545
<212> TYPE: DNA
<213> ORGANISM: Artificial Sequence
<220> FEATURE:
<223> OTHER INFORMATION: C. hookeriana KASIV CDS codon optimized for P.
      moriformis

<400> SEQUENCE: 61

atggcttccg cggcattcac catgtcggcg tgccccgcga tgactggcag ggcccctggg     60

gcacgtcgct ccggacggcc agtcgccacc cgcctgaggg gcagcacctt ccagtgcctg    120

gacccctgca accagcagcg cttcctgggc gacaacggct tcgcgtcgct gttcggctcc    180

aagcccctgc gcagcaaccg cggccacctg cgcctgggcc gcacctcgca ctccggcgag    240
```

```
gtgatggccg tcgcgatgca gcccgcccag gaggtgagca ccaacaagaa gcccgcgacc    300

aagcagcgcc gcgtggtcgt gaccggcatg ggcgtcgtga ccccccctggg ccacgacccc    360

gacgtgtatt ataacaacct gctggacggc atctcgggca tctccgagat cgagaacttc    420

gactgcagcc agttccccac ccgcatcgcc ggcgagatca agtcgttctc caccgacggc    480

tgggtcgcgc ccaagttcag cgagcgcatg gacaagttca tgctgtatat gctgaccgcc    540

ggcaagaagg cgctggccga cggcggcatc accgaggacg cgatgaagga gctgaacaag    600

cgcaagtgcg gcgtgctgat cggctcgggc ctgggcggca tgaaggtctt ctccgacagc    660

atcgaggccc tgcgcacctc gtataagaag atctcccccct tctgcgtgcc cttcagcacc    720

accaacatgg gctcggcgat cctggcgatg gacctgggct ggatgggccc caactattcc    780

atcagcaccg cgtgcgccac ctcgaacttc tgcatcctga acgcggccaa ccacatcatc    840

aagggcgagg cggacatgat gctgtgcggc ggctccgacg ccgcggtgct gcccgtcggc    900

ctgggcggct tcgtggcctg ccgcgcgctg agccagcgca acaacgaccc caccaaggcc    960

tcgcgcccct gggactccaa ccgcgacggc ttcgtcatgg gcgagggcgc gggcgtgctg   1020

ctgctggagg agctggagca cgccaagaag cgcggcgcga ccatctatgc cgagttcctg   1080

ggcggcagct tcacctgcga cgcgtatcac atgaccgagc cccaccccga gggcgccggc   1140

gtcatcctgt gcatcgagaa ggcgctggcc cagtcgggcg tgtcccgcga ggacgtgaac   1200

tatatcaacg cgcacgccac cagcaccccc gcgggcgaca tcaaggagta tcaggccctg   1260

gcgcactgct tcggccagaa ctcggagctg cgcgtcaact ccaccaagag catgatcggc   1320

cacctgctgg gcggcgccgg cggcgtggag gcggtcgccg tggtccaggc gatccgcacc   1380

ggctggatcc accccaacat caacctggag gaccccgacg agggcgtgga cgccaagctg   1440

ctggtcggcc ccaagaagga gaagctgaag gtgaaggtcg gcctgtcgaa ctccttcggc   1500

ttcggcggcc acaacagctc gatcctgttc gcgccctgca actga                  1545
```

<210> SEQ ID NO 62
<211> LENGTH: 542
<212> TYPE: PRT
<213> ORGANISM: Cuphea aequipetala
<220> FEATURE:
<221> NAME/KEY: MISC_FEATURE
<223> OTHER INFORMATION: KASIV

<400> SEQUENCE: 62

```
Met Ala Ala Ala Ala Ser Met Val Ala Ser Pro Leu Cys Thr Trp Leu
1               5                   10                  15

Val Ala Ala Cys Met Ser Thr Ser Phe Asp Asn Asp Pro Arg Ser Pro
            20                  25                  30

Ser Ile Lys Arg Ile Pro Arg Arg Arg Arg Ile Leu Ser Gln Ser Ser
        35                  40                  45

Leu Arg Gly Ser Thr Phe Gln Cys Leu Val Thr Ser Tyr Ile Asp Pro
    50                  55                  60

Cys Asn Gln Phe Ser Ser Ser Ala Ser Leu Ser Phe Leu Gly Asp Asn
65                  70                  75                  80

Gly Phe Ala Ser Leu Phe Gly Ser Lys Pro Phe Arg Ser Ile Arg Gly
                85                  90                  95

His Arg Arg Leu Gly Arg Ala Ser His Ser Gly Glu Ala Met Ala Val
            100                 105                 110

Ala Leu Glu Pro Ala Gln Glu Val Ala Thr Lys Lys Lys Pro Val Val
        115                 120                 125
```

-continued

Lys Gln Arg Arg Val Val Val Thr Gly Met Gly Val Val Thr Pro Leu
    130                 135                 140

Gly His Glu Pro Asp Val Tyr Tyr Asn Asn Leu Leu Asp Gly Val Ser
145                 150                 155                 160

Gly Ile Ser Glu Ile Glu Thr Phe Asp Cys Asn Gln Phe Pro Thr Arg
                165                 170                 175

Ile Ala Gly Glu Ile Lys Ser Phe Ser Thr Asp Gly Trp Val Ala Pro
            180                 185                 190

Lys Leu Ser Lys Arg Met Asp Lys Phe Met Leu Tyr Leu Leu Thr Ala
        195                 200                 205

Gly Lys Lys Ala Leu Ala Asp Gly Gly Ile Thr Asp Asp Val Met Lys
    210                 215                 220

Glu Leu Asp Lys Arg Lys Cys Gly Val Leu Ile Gly Ser Gly Leu Gly
225                 230                 235                 240

Gly Met Lys Leu Phe Ser Asp Ser Ile Glu Ala Leu Arg Ile Ser Tyr
                245                 250                 255

Lys Lys Met Asn Pro Phe Cys Val Pro Phe Ala Thr Thr Asn Met Gly
            260                 265                 270

Ser Ala Met Leu Ala Met Asp Leu Gly Trp Met Gly Pro Asn Tyr Ser
        275                 280                 285

Ile Ser Thr Ala Cys Ala Thr Ser Asn Phe Cys Ile Leu Asn Ser Ala
    290                 295                 300

Asn His Ile Val Arg Gly Glu Ala Asp Met Met Leu Cys Gly Gly Ser
305                 310                 315                 320

Asp Ala Val Ile Ile Pro Ile Gly Leu Gly Gly Phe Val Ala Cys Arg
                325                 330                 335

Ala Leu Ser Gln Arg Asn Asn Asp Pro Thr Lys Ala Ser Arg Pro Trp
            340                 345                 350

Asp Ser Asn Arg Asp Gly Phe Val Met Gly Glu Gly Ala Gly Val Leu
        355                 360                 365

Leu Leu Glu Glu Leu Glu His Ala Lys Lys Arg Gly Ala Thr Ile Tyr
    370                 375                 380

Ala Glu Phe Leu Gly Gly Ser Phe Thr Cys Asp Ala Tyr His Met Thr
385                 390                 395                 400

Glu Pro His Pro Glu Gly Ala Gly Val Ile Leu Cys Ile Glu Lys Ala
                405                 410                 415

Leu Ala Gln Ala Gly Val Ser Arg Glu Asp Val Asn Tyr Ile Asn Ala
            420                 425                 430

His Ala Thr Ser Thr Pro Ala Gly Asp Ile Lys Glu Tyr Gln Ala Leu
        435                 440                 445

Ala His Cys Phe Gly His Asn Ser Glu Leu Arg Val Asn Ser Thr Lys
    450                 455                 460

Ser Met Ile Gly His Leu Ile Gly Ala Ala Gly Gly Val Glu Ala Val
465                 470                 475                 480

Thr Val Val Gln Ala Ile Arg Thr Gly Trp Ile His Pro Asn Leu Asn
                485                 490                 495

Leu Glu Asp Pro Asp Lys Ala Val Asp Ala Lys Leu Leu Val Gly Pro
            500                 505                 510

Lys Lys Glu Arg Leu Asn Val Lys Val Gly Leu Ser Asn Ser Phe Gly
        515                 520                 525

Phe Gly Gly His Asn Ser Ser Ile Leu Phe Ala Pro Tyr Asn
    530                 535                 540

<210> SEQ ID NO 63
<211> LENGTH: 539
<212> TYPE: PRT
<213> ORGANISM: Cuphea glassostoma
<220> FEATURE:
<221> NAME/KEY: MISC_FEATURE
<223> OTHER INFORMATION: C. glassostoma KASIV S07 Cg Locus 4548
Transcript 4/9 translation

<400> SEQUENCE: 63

```
Met Ala Ala Ala Ala Ser Ser Gln Leu Cys Thr Trp Leu Val Ala Ala
1               5                   10                  15

Cys Met Ser Thr Ser Phe Asp Asn Asn Pro Arg Ser Pro Ser Ile Lys
            20                  25                  30

Arg Leu Pro Arg Arg Arg Arg Val Leu Ser His Cys Ser Leu Arg Gly
        35                  40                  45

Ser Thr Phe Gln Cys Leu Val Thr Ser Tyr Ile Asp Pro Cys Asn Gln
    50                  55                  60

Tyr Cys Ser Ser Ala Ser Leu Ser Phe Leu Gly Asp Asn Gly Phe Thr
65                  70                  75                  80

Pro Leu Ile Gly Ser Lys Pro Phe Arg Ser Asn Arg Gly His Pro Arg
                85                  90                  95

Leu Gly Arg Ala Ser His Ser Gly Glu Ala Met Ala Val Ala Leu Gln
            100                 105                 110

Pro Ala Gln Glu Val Ala Thr Lys Lys Lys Pro Ala Met Lys Gln Arg
        115                 120                 125

Arg Val Val Val Thr Gly Met Gly Val Val Thr Pro Leu Gly His Glu
    130                 135                 140

Pro Asp Val Tyr Tyr Asn Asn Leu Leu Asp Gly Val Ser Gly Ile Ser
145                 150                 155                 160

Glu Ile Glu Thr Phe Asp Cys Thr Gln Phe Pro Thr Arg Ile Ala Gly
                165                 170                 175

Glu Ile Lys Ser Phe Ser Thr Asp Gly Trp Val Ala Pro Lys Leu Ser
            180                 185                 190

Lys Arg Met Asp Lys Phe Met Leu Tyr Leu Leu Thr Ala Gly Lys Lys
        195                 200                 205

Ala Leu Ala Asp Gly Gly Ile Thr Asp Asp Val Met Lys Glu Leu Asp
    210                 215                 220

Lys Arg Lys Cys Gly Val Leu Ile Gly Ser Gly Met Gly Gly Met Lys
225                 230                 235                 240

Leu Phe Asn Asp Ser Ile Glu Ala Leu Arg Val Ser Tyr Lys Lys Met
                245                 250                 255

Asn Pro Phe Cys Val Pro Phe Ala Thr Thr Asn Met Gly Ser Ala Met
            260                 265                 270

Leu Ala Met Asp Leu Gly Trp Met Gly Pro Asn Tyr Ser Ile Ser Thr
        275                 280                 285

Ala Cys Ala Thr Ser Asn Phe Cys Ile Leu Asn Ala Ala Asn His Ile
    290                 295                 300

Val Arg Gly Glu Ala Asp Met Met Leu Cys Gly Gly Ser Asp Ala Val
305                 310                 315                 320

Ile Ile Pro Ile Gly Leu Gly Gly Phe Val Ala Cys Arg Ala Leu Ser
                325                 330                 335

Gln Arg Asn Asn Asp Pro Thr Lys Ala Ser Arg Pro Trp Asp Ser Asn
            340                 345                 350

Arg Asp Gly Phe Val Met Gly Glu Gly Ala Gly Val Leu Leu Leu Glu
```

355 360 365

Glu Leu Glu His Ala Lys Lys Arg Gly Ala Thr Ile Tyr Ala Glu Phe
370 375 380

Leu Gly Gly Ser Phe Thr Cys Asp Ala Tyr His Met Thr Glu Pro His
385 390 395 400

Pro Glu Gly Ala Gly Val Ile Leu Cys Ile Glu Lys Ala Leu Ala Gln
405 410 415

Ala Gly Val Ser Arg Glu Asp Val Asn Tyr Ile Asn Ala His Ala Thr
420 425 430

Ser Thr Pro Ala Gly Asp Ile Lys Glu Tyr Gln Ala Leu Ala His Cys
435 440 445

Phe Gly Gln Asn Ser Glu Leu Arg Val Asn Ser Thr Lys Ser Met Ile
450 455 460

Gly His Leu Leu Gly Ala Ala Gly Gly Val Glu Ala Val Thr Val Ile
465 470 475 480

Gln Ala Ile Arg Thr Gly Trp Ile His Pro Asn Leu Asn Leu Asp Asp
485 490 495

Pro Asp Lys Ala Val Asp Ala Lys Phe Leu Val Gly Pro Lys Lys Glu
500 505 510

Arg Leu Asn Val Lys Val Gly Leu Ser Asn Ser Phe Gly Phe Gly Gly
515 520 525

His Asn Ser Ser Ile Leu Phe Ala Pro Tyr Asn
530 535

<210> SEQ ID NO 64
<211> LENGTH: 530
<212> TYPE: PRT
<213> ORGANISM: Cuphea hookeriana
<220> FEATURE:
<221> NAME/KEY: MISC_FEATURE
<223> OTHER INFORMATION: KASIV

<400> SEQUENCE: 64

Met Ala Ala Ser Ser Cys Met Val Gly Ser Pro Phe Cys Thr Trp Leu
1 5 10 15

Val Ser Ala Cys Met Ser Thr Ser Phe Asp Asn Asp Pro Arg Ser Leu
20 25 30

Ser His Lys Arg Leu Arg Leu Ser Arg Arg Arg Arg Thr Leu Ser Ser
35 40 45

His Cys Ser Leu Arg Gly Ser Thr Pro Gln Cys Leu Asp Pro Cys Asn
50 55 60

Gln His Cys Phe Leu Gly Asp Asn Gly Phe Ala Ser Leu Phe Gly Ser
65 70 75 80

Lys Pro Pro Arg Ser Asp Leu Gly His Leu Arg Leu Gly Arg Thr Ser
85 90 95

His Ser Gly Glu Val Met Ala Val Ala Gln Glu Val Ser Thr Asn Lys
100 105 110

Lys Pro Ala Thr Lys Gln Arg Arg Val Val Val Thr Gly Met Gly Val
115 120 125

Val Thr Pro Leu Gly His Asp Pro Asp Val Tyr Tyr Asn Asn Leu Leu
130 135 140

Asp Gly Val Ser Gly Ile Ser Glu Ile Glu Thr Phe Asp Cys Thr Gln
145 150 155 160

Phe Pro Thr Arg Ile Ala Gly Glu Ile Lys Ser Phe Ser Thr Asp Gly
165 170 175

```
Leu Val Ala Pro Lys Leu Ser Lys Arg Met Asp Lys Phe Met Leu Tyr
            180                 185                 190

Ile Leu Thr Ala Gly Lys Lys Ala Leu Ala Asp Gly Gly Ile Thr Glu
        195                 200                 205

Asp Val Met Lys Glu Leu Asp Lys Arg Lys Cys Gly Val Leu Ile Gly
    210                 215                 220

Ser Gly Leu Gly Gly Met Lys Val Phe Ser Asp Ser Val Glu Ala Leu
225                 230                 235                 240

Arg Ile Ser Tyr Lys Lys Ile Ser Pro Phe Cys Val Pro Phe Ser Thr
                245                 250                 255

Thr Asn Met Gly Ser Ala Ile Leu Ala Met Asp Leu Gly Trp Met Gly
            260                 265                 270

Pro Asn Tyr Ser Ile Ser Thr Ala Cys Ala Thr Ser Asn Phe Cys Ile
        275                 280                 285

Leu Asn Ala Ala Asn His Ile Thr Lys Gly Glu Ala Asp Met Met Leu
    290                 295                 300

Cys Gly Gly Ser Asp Ala Ala Ile Leu Pro Ile Gly Met Gly Gly Phe
305                 310                 315                 320

Val Ala Cys Arg Ala Leu Ser Gln Arg Asn Asn Asp Pro Thr Lys Ala
                325                 330                 335

Ser Arg Pro Trp Asp Ser Asn Arg Asp Gly Phe Val Met Gly Glu Gly
            340                 345                 350

Ala Gly Val Leu Leu Leu Glu Glu Leu Glu His Ala Lys Lys Arg Gly
        355                 360                 365

Ala Thr Ile Tyr Ala Glu Phe Leu Gly Gly Ser Phe Thr Cys Asp Ala
    370                 375                 380

Tyr His Met Thr Glu Pro His Pro Glu Gly Ala Gly Val Ile Leu Cys
385                 390                 395                 400

Ile Glu Lys Ala Leu Ala Gln Ala Gly Val Ser Arg Glu Asp Val Asn
                405                 410                 415

Tyr Ile Asn Ala His Ala Thr Ser Thr Pro Ala Gly Asp Ile Lys Glu
            420                 425                 430

Tyr Gln Ala Leu Ala His Cys Phe Gly Gln Asn Ser Glu Leu Arg Val
        435                 440                 445

Asn Ser Thr Lys Ser Met Ile Gly His Leu Ile Gly Ala Ala Gly Gly
    450                 455                 460

Val Glu Ala Val Thr Val Ile Gln Ala Ile Arg Thr Gly Trp Ile His
465                 470                 475                 480

Pro Asn Leu Asn Leu Glu Asn Pro Asp Lys Ala Val Asp Ala Lys Leu
                485                 490                 495

Leu Val Gly Pro Lys Lys Glu Arg Leu Asp Val Lys Val Gly Leu Ser
            500                 505                 510

Asn Ser Phe Gly Phe Gly Gly His Asn Ser Ser Ile Leu Phe Ala Pro
        515                 520                 525

Tyr Asn
    530
```

<210> SEQ ID NO 65
<211> LENGTH: 515
<212> TYPE: PRT
<213> ORGANISM: Cuphea glassostoma
<220> FEATURE:
<221> NAME/KEY: MISC_FEATURE
<223> OTHER INFORMATION: C. glassostoma KASIV S07 Cg Locus 3059
Transcript 2/2 translation

<400> SEQUENCE: 65

Met Ala Ala Ala Ser Ser Met Val Ala Ser Ser Phe Ser Thr Ser Leu
1               5                   10                  15

Val Ala Ala Cys Met Ser Thr Ser Phe Asp Asn Asp Pro Arg Phe Leu
            20                  25                  30

Ser His Lys Arg Ile Arg Leu Ser Leu Arg Arg Gly Ser Thr Phe Gln
        35                  40                  45

Cys Leu Gly Asp Asn Gly Phe Ala Ser Leu Ile Gly Ser Lys Pro Pro
    50                  55                  60

Arg Ser Asn His Gly His Arg Arg Leu Gly Arg Thr Ser His Ser Gly
65                  70                  75                  80

Glu Ala Met Ala Val Ala Met Gln Pro Ala Gln Glu Ala Ser Thr Lys
                85                  90                  95

Asn Lys His Val Thr Lys Gln Arg Arg Val Val Val Thr Gly Met Gly
            100                 105                 110

Val Val Thr Pro Leu Gly His Asp Pro Asp Val Tyr Tyr Asn Asn Leu
        115                 120                 125

Leu Asp Gly Val Ser Gly Ile Ser Glu Ile Glu Asn Phe Asp Cys Ser
    130                 135                 140

Gln Phe Pro Thr Arg Ile Ala Gly Glu Ile Lys Ser Phe Ser Thr Glu
145                 150                 155                 160

Gly Tyr Val Ile Pro Lys Phe Ala Lys Arg Met Asp Lys Phe Met Leu
                165                 170                 175

Tyr Leu Leu Thr Ala Gly Lys Lys Ala Leu Glu Asp Gly Gly Ile Thr
            180                 185                 190

Glu Asp Val Met Lys Glu Leu Asp Lys Arg Lys Cys Gly Val Leu Ile
        195                 200                 205

Gly Ser Gly Met Gly Gly Met Lys Ile Ile Asn Asp Ser Ile Ala Ala
    210                 215                 220

Leu Asn Val Ser Tyr Lys Lys Met Thr Pro Phe Cys Val Pro Phe Ser
225                 230                 235                 240

Thr Thr Asn Met Gly Ser Ala Met Leu Ala Ile Asp Leu Gly Trp Met
                245                 250                 255

Gly Pro Asn Tyr Ser Ile Ser Thr Ala Cys Ala Thr Ser Asn Tyr Cys
            260                 265                 270

Ile Leu Asn Ala Ala Asn His Ile Ile Arg Gly Glu Ala Asn Met Met
        275                 280                 285

Leu Cys Gly Gly Ser Asp Ala Val Val Ile Pro Val Gly Leu Gly Gly
    290                 295                 300

Phe Val Ala Cys Arg Ala Leu Ser Gln Arg Asn Asn Asp Pro Thr Lys
305                 310                 315                 320

Ala Ser Arg Pro Trp Asp Ser Asn Arg Asp Gly Phe Val Met Gly Glu
                325                 330                 335

Gly Ala Gly Val Leu Leu Leu Glu Glu Leu Glu His Ala Lys Lys Arg
            340                 345                 350

Gly Ala Thr Ile Tyr Ala Glu Phe Leu Gly Gly Ser Phe Thr Cys Asp
        355                 360                 365

Ala Tyr His Met Thr Glu Pro His Pro Asp Gly Ala Gly Val Ile Leu
    370                 375                 380

Cys Ile Glu Lys Ala Leu Ala Gln Ser Gly Val Ser Arg Glu Asp Val
385                 390                 395                 400

Asn Tyr Ile Asn Ala His Ala Thr Ser Thr Pro Ala Gly Asp Ile Lys
                405                 410                 415

```
Glu Tyr Gln Ala Leu Ala His Cys Phe Gly Gln Asn Ser Glu Leu Arg
            420                 425                 430

Val Asn Ser Thr Lys Ser Met Ile Gly His Leu Leu Gly Ala Ala Gly
        435                 440                 445

Gly Val Glu Ala Val Ser Val Val Gln Ala Ile Arg Thr Gly Trp Ile
    450                 455                 460

His Pro Asn Ile Asn Leu Glu Asp Pro Asp Glu Ala Val Asp Ala Lys
465                 470                 475                 480

Leu Leu Val Gly Pro Lys Lys Glu Lys Leu Lys Val Lys Val Gly Leu
                485                 490                 495

Ser Asn Ser Phe Gly Phe Gly Gly His Asn Ser Ser Ile Leu Phe Ala
            500                 505                 510

Pro Cys Asn
        515


<210> SEQ ID NO 66
<211> LENGTH: 545
<212> TYPE: PRT
<213> ORGANISM: Cuphea carthagenesis
<220> FEATURE:
<221> NAME/KEY: MISC_FEATURE
<223> OTHER INFORMATION: C. carthagenesis KASIV S05 CcrKASIV 17190 Seq
      7/7 translation

<400> SEQUENCE: 66

Met Ala Ala Ala Ala Ala Phe Ala Ser Pro Phe Cys Thr Trp Leu Val
1               5                   10                  15

Ala Ala Cys Met Ser Ser Ala Ser Arg His Asp Pro Leu Pro Ser Pro
            20                  25                  30

Ser Ser Lys Pro Arg Leu Arg Arg Lys Ile Leu Phe Gln Cys Ala Gly
        35                  40                  45

Arg Gly Ser Ser Ala Gly Ser Gly Ser Ser Phe His Ser Leu Val Thr
    50                  55                  60

Ser Tyr Leu Gly Cys Leu Glu Pro Cys His Glu Tyr Tyr Thr Ser Ser
65                  70                  75                  80

Ser Ser Leu Gly Phe Ser Ser Leu Phe Gly Ser Thr Pro Gly Arg Thr
                85                  90                  95

Ser Arg Arg Gln Arg Arg Leu His Arg Ala Ser His Ser Gly Glu Ala
            100                 105                 110

Met Ala Val Ala Leu Gln Pro Ala Gln Glu Val Thr Thr Lys Lys Lys
        115                 120                 125

Pro Ser Ile Lys Gln Arg Arg Val Val Val Thr Gly Met Gly Val Val
    130                 135                 140

Thr Pro Leu Gly His Asp Pro Asp Val Phe Tyr Asn Asn Leu Leu Asp
145                 150                 155                 160

Gly Ala Ser Gly Ile Ser Glu Ile Glu Thr Phe Asp Cys Ala Gln Phe
                165                 170                 175

Pro Thr Arg Ile Ala Gly Glu Ile Lys Ser Phe Ser Thr Asp Gly Trp
            180                 185                 190

Val Ala Pro Lys Leu Ser Lys Arg Met Asp Lys Phe Met Leu Tyr Met
        195                 200                 205

Leu Thr Ala Gly Lys Lys Ala Leu Ala Asp Gly Gly Ile Ser Glu Asp
    210                 215                 220

Val Met Lys Glu Leu Asp Lys Arg Lys Cys Gly Val Leu Ile Gly Ser
225                 230                 235                 240
```

```
Ala Met Gly Gly Met Lys Val Phe Asn Asp Ala Ile Glu Ala Leu Arg
                245                 250                 255

Ile Ser Tyr Lys Lys Met Asn Pro Phe Cys Val Pro Phe Ala Thr Thr
            260                 265                 270

Asn Met Gly Ser Ala Met Leu Ala Met Asp Leu Gly Trp Met Gly Pro
        275                 280                 285

Asn Tyr Ser Ile Ser Thr Ala Cys Ala Thr Ser Asn Phe Cys Ile Leu
    290                 295                 300

Asn Ala Ala Asn His Ile Thr Arg Gly Glu Ala Asp Met Met Leu Cys
305                 310                 315                 320

Gly Gly Ser Asp Ala Val Ile Ile Pro Ile Gly Leu Gly Gly Phe Val
                325                 330                 335

Ala Cys Arg Ala Leu Ser Gln Arg Asn Asn Asp Pro Thr Lys Ala Ser
            340                 345                 350

Arg Pro Trp Asp Ser Asn Arg Asp Gly Phe Val Met Gly Glu Gly Ala
        355                 360                 365

Gly Val Leu Leu Leu Glu Glu Leu Glu His Ala Lys Lys Arg Gly Ala
    370                 375                 380

Thr Ile Tyr Ala Glu Phe Leu Gly Gly Ser Phe Thr Cys Asp Ala Tyr
385                 390                 395                 400

His Met Thr Glu Pro His Pro Lys Gly Ala Gly Val Ile Leu Cys Ile
                405                 410                 415

Glu Arg Ala Leu Ala Gln Ser Gly Val Ser Arg Glu Asp Val Asn Tyr
            420                 425                 430

Ile Asn Ala His Ala Thr Ser Thr Pro Ala Gly Asp Ile Lys Glu Tyr
        435                 440                 445

Gln Ala Leu Ala His Cys Phe Gly Gln Asn Ser Glu Leu Arg Val Asn
    450                 455                 460

Ser Thr Lys Ser Met Ile Gly His Leu Leu Gly Ala Ala Gly Gly Val
465                 470                 475                 480

Glu Ala Val Thr Val Val Gln Ala Ile Arg Thr Gly Trp Val His Pro
                485                 490                 495

Asn Ile Asn Leu Glu Asn Pro Asp Glu Gly Val Asp Ala Lys Leu Leu
            500                 505                 510

Val Gly Pro Lys Lys Glu Lys Leu Lys Val Lys Val Gly Leu Ser Asn
        515                 520                 525

Ser Phe Gly Phe Gly Gly His Asn Ser Ser Ile Leu Phe Ala Pro Tyr
    530                 535                 540

Asn
545
```

<210> SEQ ID NO 67
<211> LENGTH: 516
<212> TYPE: PRT
<213> ORGANISM: Cuphea carthagenesis
<220> FEATURE:
<221> NAME/KEY: MISC_FEATURE
<223> OTHER INFORMATION: C. carthagenesis KASIV S05 CcrKASIV 17190 Seq 6/7 translation

<400> SEQUENCE: 67

```
Met Ala Ala Ala Ala Ser Val Val Ala Ser Pro Phe Cys Thr Trp Leu
1               5                   10                  15

Val Ala Ala Cys Met Ser Ala Ser Phe Asp Asn Glu Pro Arg Ser Leu
            20                  25                  30

Ser Pro Lys Arg Arg Arg Ser Leu Ser Arg Ser Ser Ser Ala Ser Leu
```

-continued

```
        35                  40                  45

Arg Phe Leu Gly Gly Asn Gly Phe Ala Ser Leu Phe Gly Ser Asp Pro
    50                  55                  60

Leu Arg Pro Asn Arg Gly His Arg Arg Leu Arg His Ala Ser His Ser
65                  70                  75                  80

Gly Glu Ala Met Ala Val Ala Leu Gln Pro Ala Gln Glu Val Ser Thr
                85                  90                  95

Lys Lys Lys Pro Val Thr Lys Gln Arg Arg Val Val Val Thr Gly Met
            100                 105                 110

Gly Val Val Thr Pro Leu Gly His Asp Pro Asp Val Tyr Tyr Asn Asn
        115                 120                 125

Leu Leu Asp Gly Val Ser Gly Ile Ser Glu Ile Glu Thr Phe Asp Cys
    130                 135                 140

Thr Gln Phe Pro Thr Arg Ile Ala Gly Glu Ile Lys Ser Phe Ser Thr
145                 150                 155                 160

Asp Gly Trp Val Ala Pro Lys Leu Ser Lys Arg Met Asp Lys Phe Met
                165                 170                 175

Leu Tyr Met Leu Thr Ala Gly Lys Lys Ala Leu Ala Asp Gly Gly Ile
            180                 185                 190

Thr Glu Glu Val Met Lys Glu Leu Asp Lys Arg Lys Cys Gly Val Leu
        195                 200                 205

Ile Gly Ser Gly Met Gly Gly Met Lys Leu Phe Asn Asp Ser Ile Glu
    210                 215                 220

Ala Leu Arg Ile Ser Tyr Lys Lys Met Asn Pro Phe Cys Val Pro Phe
225                 230                 235                 240

Ala Thr Thr Asn Met Gly Ser Ala Met Leu Ala Met Asp Leu Gly Trp
                245                 250                 255

Met Gly Pro Asn Tyr Ser Ile Ser Thr Ala Cys Ala Thr Ser Asn Phe
            260                 265                 270

Cys Ile Leu Asn Ala Ala Asn His Ile Thr Arg Gly Glu Ala Asp Met
        275                 280                 285

Met Leu Cys Gly Gly Ser Asp Ala Val Ile Ile Pro Ile Gly Leu Gly
    290                 295                 300

Gly Phe Val Ala Cys Arg Ala Leu Ser Gln Arg Asn Asn Asp Pro Thr
305                 310                 315                 320

Lys Ala Ser Arg Pro Trp Asp Ser Asn Arg Asp Gly Phe Val Met Gly
                325                 330                 335

Glu Gly Ala Gly Val Leu Leu Leu Glu Glu Leu Glu His Ala Lys Lys
            340                 345                 350

Arg Gly Ala Thr Ile Tyr Ala Glu Phe Leu Gly Gly Ser Phe Thr Cys
        355                 360                 365

Asp Ala Tyr His Met Thr Glu Pro His Pro Lys Gly Ala Gly Val Ile
    370                 375                 380

Leu Cys Ile Glu Arg Ala Leu Ala Gln Ser Gly Val Ser Arg Glu Asp
385                 390                 395                 400

Val Asn Tyr Ile Asn Ala His Ala Thr Ser Thr Pro Ala Gly Asp Ile
                405                 410                 415

Lys Glu Tyr Gln Ala Leu Ala His Cys Phe Gly Gln Asn Ser Glu Leu
            420                 425                 430

Arg Val Asn Ser Thr Lys Ser Met Ile Gly His Leu Leu Gly Ala Ala
        435                 440                 445

Gly Gly Val Glu Ala Val Thr Val Val Gln Ala Ile Arg Thr Gly Trp
    450                 455                 460
```

```
Val His Pro Asn Ile Asn Leu Glu Asn Pro Asp Glu Gly Val Asp Ala
465                 470                 475                 480

Lys Leu Leu Val Gly Pro Lys Lys Glu Lys Leu Lys Val Lys Val Gly
                485                 490                 495

Leu Ser Asn Ser Phe Gly Phe Gly Gly His Asn Ser Ser Ile Leu Phe
            500                 505                 510

Ala Pro Tyr Asn
        515


<210> SEQ ID NO 68
<211> LENGTH: 546
<212> TYPE: PRT
<213> ORGANISM: Cuphea pulcherrima
<220> FEATURE:
<221> NAME/KEY: MISC_FEATURE
<223> OTHER INFORMATION: KASIV

<400> SEQUENCE: 68

Met Pro Ala Ala Ser Ser Leu Leu Ala Ser Pro Leu Cys Thr Trp Leu
1               5                   10                  15

Leu Ala Ala Cys Met Ser Thr Ser Phe His Pro Ser Asp Pro Leu Pro
            20                  25                  30

Pro Ser Ile Ser Ser Pro Arg Arg Arg Leu Ser Arg Arg Ile Leu
        35                  40                  45

Ser Gln Cys Ala Pro Leu Pro Ser Ala Ser Ser Ala Leu Arg Gly Ser
    50                  55                  60

Ser Phe His Thr Leu Val Thr Ser Tyr Leu Ala Cys Phe Glu Pro Cys
65                  70                  75                  80

His Asp Tyr Tyr Thr Ser Ala Ser Leu Phe Gly Ser Arg Pro Ile Arg
                85                  90                  95

Thr Thr Arg Arg His Arg Arg Leu Asn Arg Ala Ser Pro Ser Arg Glu
            100                 105                 110

Ala Met Ala Val Ala Leu Gln Pro Glu Gln Glu Val Thr Thr Lys Lys
        115                 120                 125

Lys Pro Ser Ile Lys Gln Arg Arg Val Val Val Thr Gly Met Gly Val
    130                 135                 140

Val Thr Pro Leu Gly His Asp Pro Asp Val Phe Tyr Asn Asn Leu Leu
145                 150                 155                 160

Asp Gly Thr Ser Gly Ile Ser Glu Ile Glu Thr Phe Asp Cys Ala Gln
                165                 170                 175

Phe Pro Thr Arg Ile Ala Gly Glu Ile Lys Ser Phe Ser Thr Asp Gly
            180                 185                 190

Trp Val Ala Pro Lys Leu Ser Lys Arg Met Asp Lys Phe Met Leu Tyr
        195                 200                 205

Met Leu Thr Ala Gly Lys Lys Ala Leu Thr Asp Gly Gly Ile Thr Glu
    210                 215                 220

Asp Val Met Lys Glu Leu Asp Lys Arg Lys Cys Gly Val Leu Ile Gly
225                 230                 235                 240

Ser Ala Met Gly Gly Met Lys Val Phe Asn Asp Ala Ile Glu Ala Leu
                245                 250                 255

Arg Ile Ser Tyr Lys Lys Met Asn Pro Phe Cys Val Pro Phe Ala Thr
            260                 265                 270

Thr Asn Met Gly Ser Ala Met Leu Ala Met Asp Leu Gly Trp Met Gly
        275                 280                 285

Pro Asn Tyr Ser Ile Ser Thr Ala Cys Ala Thr Ser Asn Phe Cys Ile
```

```
    290                 295                 300

Met Asn Ala Ala Asn His Ile Ile Arg Gly Glu Ala Asp Val Met Leu
305                 310                 315                 320

Cys Gly Gly Ser Asp Ala Val Ile Ile Pro Ile Gly Met Gly Gly Phe
                325                 330                 335

Val Ala Cys Arg Ala Leu Ser Gln Arg Asn Ser Asp Pro Thr Lys Ala
            340                 345                 350

Ser Arg Pro Trp Asp Ser Asn Arg Asp Gly Phe Val Met Gly Glu Gly
        355                 360                 365

Ala Gly Val Leu Leu Leu Glu Glu Leu Glu His Ala Lys Lys Arg Gly
    370                 375                 380

Ala Thr Ile Tyr Ala Glu Phe Leu Gly Gly Ser Phe Thr Cys Asp Ala
385                 390                 395                 400

Tyr His Met Thr Glu Pro His Pro Asp Gly Ala Gly Val Ile Leu Cys
                405                 410                 415

Ile Glu Lys Ala Leu Ala Gln Ser Gly Val Ser Arg Glu Asp Val Asn
            420                 425                 430

Tyr Ile Asn Ala His Ala Thr Ser Thr Pro Ala Gly Asp Ile Lys Glu
        435                 440                 445

Tyr Gln Ala Leu Ile His Cys Phe Gly Gln Asn Arg Glu Leu Lys Val
    450                 455                 460

Asn Ser Thr Lys Ser Met Ile Gly His Leu Leu Gly Ala Ala Gly Gly
465                 470                 475                 480

Val Glu Ala Val Ser Val Val Gln Ala Ile Arg Thr Gly Trp Ile His
                485                 490                 495

Pro Asn Ile Asn Leu Glu Asn Pro Asp Glu Gly Val Asp Thr Lys Leu
            500                 505                 510

Leu Val Gly Pro Lys Lys Glu Arg Leu Asn Val Lys Val Gly Leu Ser
        515                 520                 525

Asn Ser Phe Gly Phe Gly Gly His Asn Ser Ser Ile Leu Phe Ala Pro
    530                 535                 540

Tyr Ile
545


<210> SEQ ID NO 69
<211> LENGTH: 534
<212> TYPE: PRT
<213> ORGANISM: Artificial Sequence
<220> FEATURE:
<223> OTHER INFORMATION: Clade 1 KASIV consensus C8 and C10
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (108)..(108)
<223> OTHER INFORMATION: Xaa can be any naturally occurring amino acid

<400> SEQUENCE: 69

Met Ala Ala Ala Ser Cys Met Val Ala Ser Pro Phe Cys Thr Trp Leu
1               5                   10                  15

Val Ala Ala Cys Met Ser Thr Ser Xaa Asp Asn Asp Pro Arg Ser Leu
            20                  25                  30

Ser His Lys Arg Leu Arg Leu Ser Arg Arg Arg Arg Thr Leu Ser Ser
```

-continued

```
        35                  40                  45

His Cys Ser Leu Arg Gly Ser Thr Phe Gln Cys Leu Asp Pro Cys Asn
    50                  55                  60

Gln His Cys Phe Leu Gly Asp Asn Gly Phe Ala Ser Leu Phe Gly Ser
65                  70                  75                  80

Lys Pro Pro Arg Ser Asn Arg Gly His Leu Arg Leu Gly Arg Thr Ser
                85                  90                  95

His Ser Gly Glu Val Met Ala Val Ala Xaa Gln Xaa Ala Gln Glu Val
            100                 105                 110

Ser Thr Asn Lys Lys Pro Ala Thr Lys Gln Arg Arg Val Val Val Thr
        115                 120                 125

Gly Met Gly Val Val Thr Pro Leu Gly His Asp Pro Asp Val Tyr Tyr
    130                 135                 140

Asn Asn Leu Leu Asp Gly Val Ser Gly Ile Ser Glu Ile Glu Asn Phe
145                 150                 155                 160

Asp Cys Ser Gln Phe Pro Thr Arg Ile Ala Gly Glu Ile Lys Ser Phe
                165                 170                 175

Ser Thr Asp Gly Trp Val Ala Pro Lys Leu Ser Lys Arg Met Asp Lys
            180                 185                 190

Phe Met Leu Tyr Ile Leu Thr Ala Gly Lys Lys Ala Leu Ala Asp Gly
        195                 200                 205

Gly Ile Thr Glu Asp Val Met Lys Glu Leu Asp Lys Arg Lys Cys Gly
    210                 215                 220

Val Leu Ile Gly Ser Gly Leu Gly Gly Met Lys Val Phe Ser Asp Ser
225                 230                 235                 240

Ile Glu Ala Leu Arg Thr Ser Tyr Lys Lys Ile Ser Pro Phe Cys Val
                245                 250                 255

Pro Phe Ser Thr Thr Asn Met Gly Ser Ala Ile Leu Ala Met Asp Leu
            260                 265                 270

Gly Trp Met Gly Pro Asn Tyr Ser Ile Ser Thr Ala Cys Ala Thr Ser
        275                 280                 285

Asn Phe Cys Ile Leu Asn Ala Ala Asn His Ile Thr Lys Gly Glu Ala
    290                 295                 300

Asp Met Met Leu Cys Gly Gly Ser Asp Ala Ala Ile Leu Pro Ile Gly
305                 310                 315                 320

Met Gly Gly Phe Val Ala Cys Arg Ala Leu Ser Gln Arg Asn Asn Asp
                325                 330                 335

Pro Thr Lys Ala Ser Arg Pro Trp Asp Ser Asn Arg Asp Gly Phe Val
            340                 345                 350

Met Gly Glu Gly Ala Gly Val Leu Leu Leu Glu Glu Leu Glu His Ala
        355                 360                 365

Lys Lys Arg Gly Ala Thr Ile Tyr Ala Glu Phe Leu Gly Gly Ser Phe
    370                 375                 380

Thr Cys Asp Ala Tyr His Met Thr Glu Pro His Pro Glu Gly Ala Gly
385                 390                 395                 400

Val Ile Leu Cys Ile Glu Lys Ala Leu Ala Gln Ser Gly Val Ser Arg
                405                 410                 415

Glu Asp Val Asn Tyr Ile Asn Ala His Ala Thr Ser Thr Pro Ala Gly
            420                 425                 430

Asp Ile Lys Glu Tyr Gln Ala Leu Ala His Cys Phe Gly Gln Asn Ser
        435                 440                 445

Glu Leu Arg Val Asn Ser Thr Lys Ser Met Ile Gly His Leu Leu Gly
    450                 455                 460
```

```
Gly Ala Gly Gly Val Glu Ala Val Thr Val Val Gln Ala Ile Arg Thr
465                 470                 475                 480

Gly Trp Ile His Pro Asn Ile Asn Leu Glu Asp Pro Asp Glu Gly Val
                485                 490                 495

Asp Ala Lys Leu Leu Val Gly Pro Lys Lys Glu Lys Leu Lys Val Lys
            500                 505                 510

Val Gly Leu Ser Asn Ser Phe Gly Phe Gly Gly His Asn Ser Ser Ile
        515                 520                 525

Leu Phe Ala Pro Cys Asn
    530


<210> SEQ ID NO 70
<211> LENGTH: 543
<212> TYPE: PRT
<213> ORGANISM: Artificial Sequence
<220> FEATURE:
<223> OTHER INFORMATION: Clade 2 KASIV consensus C10 only
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (254)..(254)
<223> OTHER INFORMATION: Xaa can be any naturally occurring amino acid
<220> FEATURE:
<221> NAME/KEY: misc_feature
<222> LOCATION: (483)..(483)
<223> OTHER INFORMATION: Xaa can be any naturally occurring amino acid

<400> SEQUENCE: 70

Met Ala Ala Ala Ala Ser Met Xaa Xaa Ser Pro Leu Cys Thr Trp Leu
1               5                   10                  15

Val Ala Ala Cys Met Ser Thr Ser Phe Asp Asn Asp Pro Arg Ser Pro
            20                  25                  30

Ser Ile Lys Arg Leu Pro Arg Arg Arg Arg Val Leu Ser Gln Cys Ser
        35                  40                  45

Leu Arg Gly Ser Thr Phe Gln Cys Leu Val Thr Ser Tyr Ile Asp Pro
    50                  55                  60

Cys Asn Gln Tyr Cys Ser Ser Ala Ser Leu Ser Phe Leu Gly Asp Asn
65                  70                  75                  80

Gly Phe Ala Ser Leu Phe Gly Ser Lys Pro Phe Arg Ser Asn Arg Gly
                85                  90                  95

His Arg Arg Leu Gly Arg Ala Ser His Ser Gly Glu Ala Met Ala Val
            100                 105                 110

Ala Leu Gln Pro Ala Gln Glu Val Ala Thr Lys Lys Lys Pro Val Ile
        115                 120                 125

Lys Gln Arg Arg Val Val Val Thr Gly Met Gly Val Val Thr Pro Leu
    130                 135                 140

Gly His Glu Pro Asp Val Tyr Tyr Asn Asn Leu Leu Asp Gly Val Ser
145                 150                 155                 160

Gly Ile Ser Glu Ile Glu Thr Phe Asp Cys Thr Gln Phe Pro Thr Arg
                165                 170                 175

Ile Ala Gly Glu Ile Lys Ser Phe Ser Thr Asp Gly Trp Val Ala Pro
            180                 185                 190

Lys Leu Ser Lys Arg Met Asp Lys Phe Met Leu Tyr Leu Leu Thr Ala
        195                 200                 205

Gly Lys Lys Ala Leu Ala Asp Gly Gly Ile Thr Asp Asp Val Met Lys
    210                 215                 220
```

Glu Leu Asp Lys Arg Lys Cys Gly Val Leu Ile Gly Ser Gly Met Gly
225 230 235 240

Gly Met Lys Leu Phe Asn Asp Ser Ile Glu Ala Leu Arg Xaa Ser Tyr
245 250 255

Lys Lys Met Asn Pro Phe Cys Val Pro Phe Ala Thr Thr Asn Met Gly
260 265 270

Ser Ala Met Leu Ala Met Asp Leu Gly Trp Met Gly Pro Asn Tyr Ser
275 280 285

Ile Ser Thr Ala Cys Ala Thr Ser Asn Phe Cys Ile Leu Asn Ala Ala
290 295 300

Asn His Ile Val Arg Gly Glu Ala Asp Met Met Leu Cys Gly Gly Ser
305 310 315 320

Asp Ala Val Ile Ile Pro Ile Gly Leu Gly Gly Phe Val Ala Cys Arg
325 330 335

Ala Leu Ser Gln Arg Asn Asn Asp Pro Thr Lys Ala Ser Arg Pro Trp
340 345 350

Asp Ser Asn Arg Asp Gly Phe Val Met Gly Glu Gly Ala Gly Val Leu
355 360 365

Leu Leu Glu Glu Leu Glu His Ala Lys Lys Arg Gly Ala Thr Ile Tyr
370 375 380

Ala Glu Phe Leu Gly Gly Ser Phe Thr Cys Asp Ala Tyr His Met Thr
385 390 395 400

Glu Pro His Pro Glu Gly Ala Gly Val Ile Leu Cys Ile Glu Lys Ala
405 410 415

Leu Ala Gln Ala Gly Val Ser Arg Glu Asp Val Asn Tyr Ile Asn Ala
420 425 430

His Ala Thr Ser Thr Pro Ala Gly Asp Ile Lys Glu Tyr Gln Ala Leu
435 440 445

Ala His Cys Phe Gly Gln Asn Ser Glu Leu Arg Val Asn Ser Thr Lys
450 455 460

Ser Met Ile Gly His Leu Leu Gly Ala Ala Gly Gly Val Glu Ala Val
465 470 475 480

Thr Val Xaa Gln Ala Ile Arg Thr Gly Trp Ile His Pro Asn Leu Asn
485 490 495

Leu Glu Asp Pro Asp Lys Ala Val Asp Ala Lys Leu Leu Val Gly Pro
500 505 510

Lys Lys Glu Arg Leu Asn Val Lys Val Gly Leu Ser Asn Ser Phe Gly
515 520 525

Phe Gly Gly His Asn Ser Ser Ile Leu Phe Ala Pro Tyr Asn Val
530 535 540

<210> SEQ ID NO 71
<211> LENGTH: 414
<212> TYPE: PRT
<213> ORGANISM: Artificial Sequence
<220> FEATURE:
<223> OTHER INFORMATION: Clade 1 KASIV consensus mature protein

<400> SEQUENCE: 71

Lys Gln Arg Arg Val Val Val Thr Gly Met Gly Val Val Thr Pro Leu
1 5 10 15

Gly His Asp Pro Asp Val Tyr Tyr Asn Asn Leu Leu Asp Gly Val Ser
20 25 30

Gly Ile Ser Glu Ile Glu Asn Phe Asp Cys Ser Gln Phe Pro Thr Arg
35 40 45

Ile Ala Gly Glu Ile Lys Ser Phe Ser Thr Asp Gly Trp Val Ala Pro
    50                  55                  60

Lys Leu Ser Lys Arg Met Asp Lys Phe Met Leu Tyr Ile Leu Thr Ala
65                  70                  75                  80

Gly Lys Lys Ala Leu Ala Asp Gly Gly Ile Thr Glu Asp Val Met Lys
                85                  90                  95

Glu Leu Asp Lys Arg Lys Cys Gly Val Leu Ile Gly Ser Gly Leu Gly
            100                 105                 110

Gly Met Lys Val Phe Ser Asp Ser Ile Glu Ala Leu Arg Thr Ser Tyr
        115                 120                 125

Lys Lys Ile Ser Pro Phe Cys Val Pro Phe Ser Thr Thr Asn Met Gly
    130                 135                 140

Ser Ala Ile Leu Ala Met Asp Leu Gly Trp Met Gly Pro Asn Tyr Ser
145                 150                 155                 160

Ile Ser Thr Ala Cys Ala Thr Ser Asn Phe Cys Ile Leu Asn Ala Ala
                165                 170                 175

Asn His Ile Thr Lys Gly Glu Ala Asp Met Met Leu Cys Gly Gly Ser
            180                 185                 190

Asp Ala Ala Ile Leu Pro Ile Gly Met Gly Gly Phe Val Ala Cys Arg
        195                 200                 205

Ala Leu Ser Gln Arg Asn Asn Asp Pro Thr Lys Ala Ser Arg Pro Trp
    210                 215                 220

Asp Ser Asn Arg Asp Gly Phe Val Met Gly Glu Gly Ala Gly Val Leu
225                 230                 235                 240

Leu Leu Glu Glu Leu Glu His Ala Lys Lys Arg Gly Ala Thr Ile Tyr
                245                 250                 255

Ala Glu Phe Leu Gly Gly Ser Phe Thr Cys Asp Ala Tyr His Met Thr
            260                 265                 270

Glu Pro His Pro Glu Gly Ala Gly Val Ile Leu Cys Ile Glu Lys Ala
        275                 280                 285

Leu Ala Gln Ser Gly Val Ser Arg Glu Asp Val Asn Tyr Ile Asn Ala
    290                 295                 300

His Ala Thr Ser Thr Pro Ala Gly Asp Ile Lys Glu Tyr Gln Ala Leu
305                 310                 315                 320

Ala His Cys Phe Gly Gln Asn Ser Glu Leu Arg Val Asn Ser Thr Lys
                325                 330                 335

Ser Met Ile Gly His Leu Leu Gly Gly Ala Gly Gly Val Glu Ala Val
            340                 345                 350

Thr Val Val Gln Ala Ile Arg Thr Gly Trp Ile His Pro Asn Ile Asn
        355                 360                 365

Leu Glu Asp Pro Asp Glu Gly Val Asp Ala Lys Leu Leu Val Gly Pro
    370                 375                 380

Lys Lys Glu Lys Leu Lys Val Lys Val Gly Leu Ser Asn Ser Phe Gly
385                 390                 395                 400

Phe Gly Gly His Asn Ser Ser Ile Leu Phe Ala Pro Cys Asn
                405                 410

<210> SEQ ID NO 72
<211> LENGTH: 415
<212> TYPE: PRT
<213> ORGANISM: Artificial Sequence
<220> FEATURE:
<223> OTHER INFORMATION: Clade 2 KASIV consensus mature protein
<220> FEATURE:
<221> NAME/KEY: misc_feature

```
<222> LOCATION: (126)..(126)
<223> OTHER INFORMATION: Xaa can be any naturally occurring amino acid
<220> FEATURE:
<221> NAME/KEY: misc_feature
<222> LOCATION: (355)..(355)
<223> OTHER INFORMATION: Xaa can be any naturally occurring amino acid

<400> SEQUENCE: 72

Lys Gln Arg Arg Val Val Val Thr Gly Met Gly Val Val Thr Pro Leu
1               5                   10                  15

Gly His Glu Pro Asp Val Tyr Tyr Asn Asn Leu Leu Asp Gly Val Ser
            20                  25                  30

Gly Ile Ser Glu Ile Glu Thr Phe Asp Cys Thr Gln Phe Pro Thr Arg
        35                  40                  45

Ile Ala Gly Glu Ile Lys Ser Phe Ser Thr Asp Gly Trp Val Ala Pro
    50                  55                  60

Lys Leu Ser Lys Arg Met Asp Lys Phe Met Leu Tyr Leu Leu Thr Ala
65                  70                  75                  80

Gly Lys Lys Ala Leu Ala Asp Gly Gly Ile Thr Asp Asp Val Met Lys
                85                  90                  95

Glu Leu Asp Lys Arg Lys Cys Gly Val Leu Ile Gly Ser Gly Met Gly
            100                 105                 110

Gly Met Lys Leu Phe Asn Asp Ser Ile Glu Ala Leu Arg Xaa Ser Tyr
        115                 120                 125

Lys Lys Met Asn Pro Phe Cys Val Pro Phe Ala Thr Thr Asn Met Gly
    130                 135                 140

Ser Ala Met Leu Ala Met Asp Leu Gly Trp Met Gly Pro Asn Tyr Ser
145                 150                 155                 160

Ile Ser Thr Ala Cys Ala Thr Ser Asn Phe Cys Ile Leu Asn Ala Ala
                165                 170                 175

Asn His Ile Val Arg Gly Glu Ala Asp Met Met Leu Cys Gly Gly Ser
            180                 185                 190

Asp Ala Val Ile Ile Pro Ile Gly Leu Gly Gly Phe Val Ala Cys Arg
        195                 200                 205

Ala Leu Ser Gln Arg Asn Asn Asp Pro Thr Lys Ala Ser Arg Pro Trp
    210                 215                 220

Asp Ser Asn Arg Asp Gly Phe Val Met Gly Glu Gly Ala Gly Val Leu
225                 230                 235                 240

Leu Leu Glu Glu Leu Glu His Ala Lys Lys Arg Gly Ala Thr Ile Tyr
                245                 250                 255

Ala Glu Phe Leu Gly Gly Ser Phe Thr Cys Asp Ala Tyr His Met Thr
            260                 265                 270

Glu Pro His Pro Glu Gly Ala Gly Val Ile Leu Cys Ile Glu Lys Ala
        275                 280                 285

Leu Ala Gln Ala Gly Val Ser Arg Glu Asp Val Asn Tyr Ile Asn Ala
    290                 295                 300

His Ala Thr Ser Thr Pro Ala Gly Asp Ile Lys Glu Tyr Gln Ala Leu
305                 310                 315                 320

Ala His Cys Phe Gly Gln Asn Ser Glu Leu Arg Val Asn Ser Thr Lys
                325                 330                 335

Ser Met Ile Gly His Leu Leu Gly Ala Ala Gly Gly Val Glu Ala Val
            340                 345                 350

Thr Val Xaa Gln Ala Ile Arg Thr Gly Trp Ile His Pro Asn Leu Asn
        355                 360                 365

Leu Glu Asp Pro Asp Lys Ala Val Asp Ala Lys Leu Leu Val Gly Pro
```

-continued

```
    370                 375                 380

Lys Lys Glu Arg Leu Asn Val Lys Val Gly Leu Ser Asn Ser Phe Gly
385                 390                 395                 400

Phe Gly Gly His Asn Ser Ser Ile Leu Phe Ala Pro Tyr Asn Val
                405                 410                 415
```

KETOACYL ACP SYNTHASE GENES AND USES THEREOF

CROSS REFERENCE TO RELATED APPLICATIONS

This application claims the benefit under 35 U.S.C. 119(e) of U.S. Provisional Patent Application No. 62/023,112, filed Jul. 10, 2014, and US Provisional Patent Application No. 62/081,143, filed Nov. 18, 2014, each of which is incorporated herein by reference in its entirety. This application includes subject matter related to that disclosed in US provisional patent application No. 62/023,109, entitled "Tailored Oils," filed Jul. 10, 2014, which is hereby incorporated by reference in its entirety for all purposes.

REFERENCE TO A SEQUENCE LISTING

This application includes an electronic sequence listing in a file named "465964-Sequence.txt", created on Sep. 28, 2015, and containing 235,869 bytes, which is hereby incorporated by reference in its entirety for all purposes.

TECHNICAL FIELD

The present invention relates to novel β-ketoacyl ACP synthase genes and methods for using the genes including expressing the genes in oleaginous host cells to produce triglycerides with altered fatty acid profiles.

BACKGROUND

Certain organisms including plants and some microalgae use a type II fatty acid biosynthetic pathway, characterized by the use of discrete enzymes in a multimeric complex for fatty acid synthesis. In contrast, mammals and fungi use a single, large, multifunctional protein.

In organisms that use a type II fatty acid biosynthetic pathway, β-ketoacyl-ACP synthase I (KAS I, EC 2.3.1.41) is one of the enzymes responsible for elongation of growing medium-chain fatty acyl-ACP from 4 to 16 carbon atoms in length. KAS I uses C2-C14 acyl-ACPs as substrates for condensation with a C2 unit derived from malonyl-ACP. KASIV is a related enzyme that serves a similar elongation function. Thus, KASI and KASIV can both be considered KASI-like enzymes.

Such genes have been introduced to plants using recombinant DNA technology. See for example U.S. Pat. No. 7,301,070, U.S. Pat. No. 6,348,642, U.S. Pat. No. 6,660,849, U.S. Pat. No. 6,770,465 and US2006/0094088 (of which ¶¶ 194-200 and the entirety of the document are hereby incorporated herein by reference). In plastidic cells such as those from plants, macroalgae and microalgae, KAS I-like enzymes are located in the chloroplasts or other plastids together with other enzyme of the fatty acid synthesis (FAS) pathway.

PCT publications WO2010/063032, WO2011/150411, WO2012/106560, and WO2013/158938 disclose genetic engineering of oleaginous microalgae including targeting of exogenous FAS gene products to the microalgal plastid.

SUMMARY

In one aspect, embodiments of the invention include a non-natural, isolated polynucleotide having at least 80, 85, 90, 91, 92, 93, 94, 95, 96, 97, 98, or 99% sequence identity or equivalent sequence by virtue of the degeneracy of the genetic code to any one of SEQ ID NOs: 21-37, or 39-55, or encoding a KASI-like protein having at least 80, 85, 85.5, 86, 86.5, 87, 87.5, 88, 88.5, 89, 89.5, 90, 90.5, 91, 91.5, 92, 92.5, 93, 93.5, 94, 94.5, 95, 95.5, 96, 96.5, 97, 97.5, 98, 98.5, 99 or 99.5% amino acid sequence identity to any one of SEQ ID NOs: 2-18, 62-72, or a mature protein produced therefrom, or the complement of the polynucleotide.

In another aspect, embodiments of the invention include a transformation vector comprising a cDNA molecule comprising a polynucleotide as discussed above. In some cases, the vector comprises promoter and 3'UTR sequences in operable linkage to the cDNA, and optionally a flanking sequence for homologous recombination. The promoter or the 3'UTR sequences are heterologous nucleotide sequences. The heterologous promoter or the heterologous 3'UTR sequences can be from a different organism than the organism from which the nucleotide sequences encoding KAS was first obtained.

In one aspect, the transformation vector comprises a heterologous promoter or a heterologous 3'UTR sequence obtained from the same organism from which the KAS gene was first isolated. When the promoter sequence, the 3'UTR sequence and the KAS nucleotide sequences are from the same organism, the heterologous promoter does not naturally drive the expression of KAS, and the 3'UTR does not naturally occur downstream from the KAS nucleotide sequences in the source organism.

In yet another aspect, the transformation vector is used to express the KAS gene in the organism from which the KAS gene was first isolated. When the KAS gene is recombinantly expressed in the organism from which the KAS gene was first isolated, the gene is expressed in a different chromosomal locus than the natural chromosomal locus of the KAS gene. Alternatively, the KAS gene is expressed in the cytoplasm.

In another aspect, embodiments of the invention include a host cell comprising the polynucleotide and/or the vector discussed above, and expressing a functional KAS protein encoded by the cDNA. In some cases, the host cell further comprises an exogenous gene encoding a functional FATA acyl-ACP thioesterase or FATB acyl-ACP thioesterase. In one aspect, the FATB acyl-ACP thioesterase has at least 80, 85, 90, 91, 92, 93, 94, 95, 96, 97, 98, or 99% amino acid sequence identity to any one of SEQ ID NOs: 1 or SEQ ID NO: 57. In some cases, the host cell produces a cell oil characterized by a fatty acid profile with (i) at least 30, 40, 50, or 55% C14:0, (ii) at least 7, 8, 9, 10, 11, 12, 13, or 14% C8:0, (iii) at least 10, 15, 20, 25, 30, or 35 area % for the sum of C8:0 and C10:0, or (iv) a C8/C10 ratio in the range of 2.2-2.5, 2.5-3.0, or 3.0-3.4. In some cases, the host cell is a plastidic oleaginous cell having a type II fatty acid biosynthesis pathway. In some cases, the host cell is a microalga. In some cases, the host cell is of Trebouxiophyceae, and optionally of the genus *Chlorella* or *Prototheca*. In some cases, the microalga is of the species *Prototheca moriformis*.

In another aspect, embodiments of the invention include a method for making a cell-oil, the method comprising cultivating a host cell as discussed above so as produce the cell-oil, wherein the oil comprises triglcyerides and microalgal sterols. In some cases, the cell oil comprises sterols characterized by a sterol profile and the sterol profile has an excess of ergosterol over β-sitosterol and/or the presence of 22, 23-dihydrobrassicasterol, poriferasterol or clionasterol.

BRIEF DESCRIPTION OF THE DRAWINGS

FIG. 1 shows a phylogenetic tree for KASI-like genes in connection with Example 3.

DETAILED DESCRIPTION OF EMBODIMENTS OF THE INVENTION

As used with respect to nucleic acids, the term "isolated" refers to a nucleic acid that is free of at least one other component that is typically present with the naturally occurring nucleic acid. Thus, a naturally occurring nucleic acid is isolated if it has been purified away from at least one other component that occurs naturally with the nucleic acid.

A "cell oil" or "cell fat" shall mean a predominantly triglyceride oil obtained from an organism, where the oil has not undergone blending with another natural or synthetic oil, or fractionation so as to substantially alter the fatty acid profile of the triglyceride. In connection with an oil comprising triglycerides of a particular regiospecificity, the cell oil or cell fat has not been subjected to interesterification or other synthetic process to obtain that regiospecific triglyceride profile, rather the regiospecificity is produced naturally, by a cell or population of cells. For a cell oil or cell fat produced by a cell, the sterol profile of oil is generally determined by the sterols produced by the cell, not by artificial reconstitution of the oil by adding sterols in order to mimic the cell oil. In connection with a cell oil or cell fat, and as used generally throughout the present disclosure, the terms oil and fat are used interchangeably, except where otherwise noted. Thus, an "oil" or a "fat" can be liquid, solid, or partially solid at room temperature, depending on the makeup of the substance and other conditions. Here, the term "fractionation" means removing material from the oil in a way that changes its fatty acid profile relative to the profile produced by the organism, however accomplished. The terms "cell oil" and "cell fat" encompass such oils obtained from an organism, where the oil has undergone minimal processing, including refining, bleaching and/or degumming, which does not substantially change its triglyceride profile. A cell oil can also be a "noninteresterified cell oil", which means that the cell oil has not undergone a process in which fatty acids have been redistributed in their acyl linkages to glycerol and remain essentially in the same configuration as when recovered from the organism.

"Exogenous gene" shall mean a nucleic acid that codes for the expression of an RNA and/or protein that has been introduced into a cell (e.g. by transformation/transfection), and is also referred to as a "transgene". A cell comprising an exogenous gene may be referred to as a recombinant cell, into which additional exogenous gene(s) may be introduced. The exogenous gene may be from a different species (and so heterologous), or from the same species (and so homologous), relative to the cell being transformed. Thus, an exogenous gene can include a homologous gene that occupies a different location in the genome of the cell or is under different control, relative to the endogenous copy of the gene. An exogenous gene may be present in more than one copy in the cell. An exogenous gene may be maintained in a cell, for example, as an insertion into the genome (nuclear or plastid) or as an episomal molecule.

"Fatty acids" shall mean free fatty acids, fatty acid salts, or fatty acyl moieties in a glycerolipid. It will be understood that fatty acyl groups of glycerolipids can be described in terms of the carboxylic acid or anion of a carboxylic acid that is produced when the triglyceride is hydrolyzed or saponified.

"Microalgae" are microbial organisms that contain a chloroplast or other plastid, and optionally that are capable of performing photosynthesis, or a prokaryotic microbial organism capable of performing photosynthesis. Microalgae include obligate photoautotrophs, which cannot metabolize a fixed carbon source as energy, as well as heterotrophs, which can live solely off of a fixed carbon source. Microalgae include unicellular organisms that separate from sister cells shortly after cell division, such as *Chlamydomonas*, as well as microbes such as, for example, Volvox, which is a simple multicellular photosynthetic microbe of two distinct cell types. Microalgae include cells such as *Chlorella, Dunaliella*, and *Prototheca*. Microalgae also include other microbial photosynthetic organisms that exhibit cell-cell adhesion, such as *Agmenellum, Anabaena*, and *Pyrobotrys*. Microalgae also include obligate heterotrophic microorganisms that have lost the ability to perform photosynthesis, such as certain dinoflagellate algae species and species of the genus *Prototheca*.

An "oleaginous" cell is a cell capable of producing at least 20% lipid by dry cell weight, naturally or through recombinant or classical strain improvement. An "oleaginous microbe" or "oleaginous microorganism" is a microbe, including a microalga that is oleaginous.

The term "percent sequence identity," in the context of two or more amino acid or nucleic acid sequences, refers to two or more sequences or subsequences that are the same or have a specified percentage of amino acid residues or nucleotides that are the same, when compared and aligned for maximum correspondence, as measured using a sequence comparison algorithm or by visual inspection. For sequence comparison to determine percent nucleotide or amino acid identity, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted using the NCBI BLAST software (ncbi.nlm.nih.gov/BLAST/) set to default parameters. For example, to compare two nucleic acid sequences, one may use blastn with the "BLAST 2 Sequences" tool Version 2.0.12 (Apr. 21, 2000) set at the following default parameters: Matrix: BLOSUM62; Reward for match: 1; Penalty for mismatch: −2; Open Gap: 5 and Extension Gap: 2 penalties; Gap x drop-off: 50; Expect: 10; Word Size: 11; Filter: on. For a pairwise comparison of two amino acid sequences, one may use the "BLAST 2 Sequences" tool Version 2.0.12 (Apr. 21, 2000) with blastp set, for example, at the following default parameters: Matrix: BLOSUM62; Open Gap: 11 and Extension Gap: 1 penalties; Gap x drop-off 50; Expect: 10; Word Size: 3; Filter: on.

Where multiple sequence identities are given for a strain having a pair of exogenous genes, this encompasses all combinations of sequence identities. For example, coexpression of a first gene encoding a first protein having at least 85, 90, 91, 92, 93, 94, 95, 96, 97, 98, or 99% with gene A and a second gene encoding a second protein having at least 85, 90, 91, 92, 93, 94, 95, 96, 97, 98, or 99% with gene A shall be understood to encompass (i) at least 85% identity with gene A and least 85% identity with gene B, (ii)) at least 85% identity with gene A and least 99% identity with gene B, (iii)

at least 92% identity with gene A and least 95% identity with gene B, and all other combinations.

In connection with a cell oil, a "profile" is the distribution of particular species of triglycerides or fatty acyl groups within the oil. A "fatty acid profile" is the distribution of fatty acyl groups in the triglycerides of the oil without reference to attachment to a glycerol backbone. Fatty acid profiles are typically determined by conversion to a fatty acid methyl ester (FAME), followed by gas chromatography (GC) analysis with flame ionization detection (FID). The fatty acid profile can be expressed as one or more percent of a fatty acid in the total fatty acid signal determined from the area under the curve for that fatty acid. FAME-GC-FID measurement approximate weight percentages of the fatty acids.

As used herein, an oil is said to be "enriched" in one or more particular fatty acids if there is at least a 10% increase in the mass of that fatty acid in the oil relative to the non-enriched oil. For example, in the case of a cell expressing a heterologous FatB gene described herein, the oil produced by the cell is said to be enriched in, e.g., C8 and C16 fatty acids if the mass of these fatty acids in the oil is at least 10% greater than in oil produced by a cell of the same type that does not express the heterologous FatB gene (e.g., wild type oil).

"Recombinant" is a cell, nucleic acid, protein or vector that has been modified due to the introduction of an exogenous nucleic acid or the alteration of a native nucleic acid. Thus, e.g., recombinant (host) cells can express genes that are not found within the native (non-recombinant) form of the cell or express native genes differently than those genes are expressed by a non-recombinant cell. Recombinant cells can, without limitation, include recombinant nucleic acids that encode a gene product or suppression elements such as mutations, knockouts, antisense, interfering RNA (RNAi) or dsRNA that reduce the levels of active gene product in a cell. A "recombinant nucleic acid" is a nucleic acid originally formed in vitro, in general, by the manipulation of nucleic acid, e.g., using polymerases, ligases, exonucleases, and endonucleases, using chemical synthesis, or otherwise is in a form not normally found in nature. Recombinant nucleic acids may be produced, for example, to place two or more nucleic acids in operable linkage. Thus, an isolated nucleic acid or an expression vector formed in vitro by nucleic by ligating DNA molecules that are not normally joined in nature, are both considered recombinant for the purposes of this invention. Recombinant nucleic acids can also be produced in other ways; e.g., using chemical DNA synthesis. Once a recombinant nucleic acid is made and introduced into a host cell or organism, it may replicate using the in vivo cellular machinery of the host cell; however, such nucleic acids, once produced recombinantly, although subsequently replicated intracellularly, are still considered recombinant for purposes of this invention. Similarly, a "recombinant protein" is a protein made using recombinant techniques, i.e., through the expression of a recombinant nucleic acid.

A "KAS I-like" gene or enzyme shall mean either a KAS I or KAS IV gene or enzyme.

Embodiments of the present invention relate to the use of KASI-like genes isolated from plants or other organisms, which can be expressed in a transgenic host cell in order to alter the fatty acid profile of a cell-oil produced by the host cell. Although the microalga *Prototheca moriformis* was used to screen the genes for ability to the alter fatty acid profile, the genes discovered are useful in a wide variety of host cells for which genetic transformation techniques are known. For example, the genes can be expressed in bacteria, cyanobacteria, other eukaryotic microalgae, or higher plants. The genes can be expressed in higher plants according to the methods disclosed in U.S. Pat. No. 7,301,070, U.S. Pat. No. 6,348,642, U.S. Pat. No. 6,660,849, and U.S. Pat. No. 6,770,465. We have found that KASI-like transgenes can be used alone or in combination with a FatB transgene (encoding an active acyl-ACP thioesterase) can boost the levels of mid-chain fatty acids (e.g., capric, caprylic, lauric, myristic or palmitic acids) in the fatty acid profile of the cell oil. Combining an exogenous KASI-like gene with an exogenous FATA or FATB gene in a host cell can give levels of mid-chain fatty acids and/or long-chain fatty acids (e.g., stearic or oleic) greater than either exogenous gene alone. The fatty acids of the cell oil can be further converted to triglycerides, fatty aldehydes, fatty alcohols and other oleochemicals either synthetically or biosynthetically.

In specific embodiments, triglycerides are produced by a host cell expressing a novel KASI-like gene (from a novel cDNA and/or under control of a heterologous promoter). A cell oil can be recovered from the host cell. Typically, the cell oil comprises mainly triglycerides and sterols. The cell oil can be refined, degummed, bleached and/or deodorized. The oil, in its unprocessed or processed form, can be used for foods, chemicals, fuels, cosmetics, plastics, and other uses. In other embodiments, the KASI-like gene may not be novel, but the expression of the gene in a microalga is novel.

The KAS genes can be used in a variety of genetic constructs including plasmids or other vectors for expression or recombination in a host cell. The genes can be codon optimized for expression in a target host cell. The genes can be included in an expression cassette that includes a promoter (e.g., a heterologous promoter) and downstream regulatory element. The vector can include flanking sequences for homologous recombination. For example, the vector can cause insertion into a chromosome of the host cell, where it can be stably expressed. The proteins produced by the genes can be used in vivo or in purified form. In an embodiment, an expression cassette comprises a homologous promoter, a CDS operable to express a KASI-like enzyme of Table 1 and a 3'UTR. The 3'UTR can comprise a polyadenylation site.

As described in the examples below, novel KAS genes are were discovered from cDNA produced from plant seed mRNA transcripts. Accordingly the gene sequences are non-natural because they lack introns that are present in the plant genes and mRNA transcripts of the genes prior to mRNA splicing. Accordingly, the invention comprises an isolated non-natural KASI-like gene of Table 1. Further departure from the natural gene is in the use of heterologous regulatory elements and expression in host cells for which such genes do not occur in nature.

For example, the gene can be prepared in an expression vector comprising an operably linked promoter and 5'UTR. Where a plastidic cell is used as the host, a suitably active plastid targeting peptide (also referred to below as a "transit peptide") can be fused to the KASI-like gene, as in the examples below. The disclosed genes comprise a hydrophobic N-terminal plastid targeting sequence, which can be replaced with alternative targeting sequence and varied in length. Varying the plastid targeting peptide can improve cellular localization and enzyme activity for a given host-cell type. Thus, the invention contemplates deletions and fusion proteins in order to optimize enzyme activity in a given host cell. For example, a transit peptide from the host or related species may be used instead of that of the newly discovered plant genes described here. Additional terminal or internal deletions may be made so-long as the enzymatic activity is retained. The targeting peptide can be cleaved by the host cell to produce a mature KASI-like protein that lacks the targeting peptide.

A selectable marker gene may be included in the vector to assist in isolating a transformed cell. Examples of selectable markers useful in microalgae include sucrose invertase, alpha galactosidase (for selection on melibiose) and antibiotic resistance genes.

The gene sequences disclosed can also be used to prepare antisense, or inhibitory RNA (e.g., RNAi or hairpin RNA) to inhibit complementary genes in a plant or other organism. For example, armed with the knowledge of a gene sequence of Table 1, one can engineer a plant with the same or similar KASI-like gene to express an RNAi construct, gene knockout, point mutation, or the like, and thereby reduce the KASI or KASIV activity of the plant's seed. As a result, the plant can produce an oil with an altered fatty acid profile in which the mean chain length is decreased or increased, depending on the presence of other fatty acid synthesis genes.

KASI-like genes/proteins found to be useful in producing desired fatty acid profiles in a cell are summarized below in Table 1, and related proteins discovered from transcript sequencing (as in Examples 1-2) are shown in Table 1a. Nucleic acids or proteins having the sequence of SEQ ID NOS: 2-18, 59, 62-72, 21-37 or 39-55 can be used to alter the fatty acid profile of a recombinant cell. Variant nucleic acids can also be used; e.g., variants having at least 70, 80, 85, 90, 95, 96, 97, 98, or 99% sequence identity to SEQ ID NOS: 21-37 or 39-55. Codon optimization of the genes for a variety of host organisms is contemplated, as is the use of gene fragments. Preferred codons for *Prototheca* strains and for *Chlorella* protothecoides are shown below in Tables 2 and 3, respectively. Codon usage for *Cuphea wrightii* is shown in Table 4. Codon usage for *Arabidopsis* is shown in Table 5; for example, the most preferred codon for each amino acid can be selected. Codon tables for other organisms including microalgae and higher plants are known in the art. In some embodiments, the first and/or second most preferred *Prototheca* codons are employed for codon optimization. In specific embodiments, the novel amino acid sequences contained in the sequence listings below are converted into nucleic acid sequences according to the most preferred codon usage in *Prototheca, Chlorella, Cuphea wrightii*, or *Arabidopsis* as set forth in tables 2 through 3b or nucleic acid sequences having at least 70, 80, 85, 90, 95, 96, 97, 98, or 99% sequence identity to these derived nucleic acid sequences. For example, the KASI-like gene can be codon optimized for *Prototheca moriformis* by substituting most preferred codons according to Table 2 for at least 10, 20, 30, 40, 50, 60, 70, 80, or 90% of all codons. Likewise, the KASI-like gene can be codon optimized for *Chlorella protothecoides* by substituting most-preferred codons according to Table 3 for at least 10, 20, 30, 40, 50, 60, 70, 80, or 90% of all codons. Alternately, the KASI-like gene can be codon optimized for *Chlorella protothecoides* or *Prototheca moriformis* by substituting first or second most-preferred codons according to Table 2 or 3 for at least 10, 20, 30, 40, 50, 60, 70, 80, or 90% of all codons. Codon-optimized genes are non-naturally occurring because they are optimized for expression in a host organism.

In certain embodiments, percent sequence identity for variants of the nucleic acids or proteins discussed above can be calculated by using the full-length nucleic acid sequence (e.g., one of SEQ ID NOS: 21-37 or 39-55 or full-length amino acid sequence (e.g., one of SEQ ID NOS: 2-18) as the reference sequence and comparing the full-length test sequence to this reference sequence. For fragments, percent sequence identity for variants of nucleic acid or protein fragments can be calculated over the entire length of the fragment. In certain embodiments, there is a nucleic acid or protein fragment have at least 70, 80, 85, 90, 95, 96, 97, 98, or 99% sequence identity to one of SEQ ID NOS: 21-37, 39-55 or 2-18.

Optionally, the plastidic targeting peptide can be swapped with another peptide that functions to traffic the KASI-like enzyme to a fatty acid synthesizing plastid of a plastidic host cell. Accordingly, in various embodiments of the invention, a transgene or transgenic host cell comprises a nucleotide or corresponding peptidic fusion of a plastic targeting sequence and an enzyme-domain sequence (the sequence remaining after deletion of the transit peptide), where the mature protein has at least 70, 80, 85, 90, 95, 96, 97, 98, or 99% sequence identity to an mature protein sequence listed in Table 1 or Table 1a. Plastid transit/targeting peptides are underlined in the accompanying informal sequence listing. Examples of targeting peptides include those of Table 1 and others known in the art, especially in connection with the targeting of KAS I, KAS II, KAS III, FATA, FATB and SAD (stearoyl-ACP desaturase) gene products to chloroplasts or other plastids of plants and microalgae. See examples of *Chorophyta* given in PCT publications WO2010/063032, WO2011/150411, WO2012/106560, and WO2013/158938. Optionally, the KASI-like genes encode 450, 475 or 500 amino acids or more (with or without the transit peptide), or about 555 residues (with the transit peptide,) in contrast to known truncated sequences.

TABLE 1

KASI-like genes: The expression cassette used to test the genes in combination with a FATB transgene is given in SEQ ID NO: 38 (i.e., substituting the Cpal KASIV coding sequence of SEQ ID NO: 38 with various other coding sequences of Table 1), except that the *Cuphea hookeriana* KASIV was tested using the expression cassette of SEQ ID NO: 61. See Examples 1-4.

| Species | Gene Name | Amino Acid Sequence | nucleotide coding sequence (from cDNA produced from seed mRNA, not codon-optimized) | *Prototheca moriformis* codon-optimized nucleotide sequence |
|---|---|---|---|---|
| *Cuphea palustris* | KASIV | 2 | 21 | 39 |
| *Cinnamonum camphora* | KASIV | 3 | 22 | 40 |
| *Cinnamonum camphora* | KASI | 4 | 23 | 41 |
| *Umbellularia californica* | KASI | 5 | 24 | 42 |
| *U. californica* | KASIV | 6 | 25 | 43 |
| *Cuphea. wrightii* | KASAI | 7 | 26 | 44 |
| *Cuphea avigera* | KASIVb | 8 | 27 | 45 |
| *Cuphea paucipetala* | KASIVb | 9 | 28 | 46 |
| *C. ignea* | KASIVb | 10 | 29 | 47 |
| *Cuphea procumbens* | KASIV | 11 | 30 | 48 |
| *C. paucipetala* | KASIVa | 12 | 31 | 49 |
| *Cuphea painteri* | KASIV | 13 | 32 | 50 |
| *C. avigera* | KASIVa | 14 | 33 | 51 |
| *C. ignea* | KASIVa | 15 | 34 | 52 |

TABLE 1-continued

KASI-like genes: The expression cassette used to test the genes in combination with a FATB transgene is given in SEQ ID NO: 38 (i.e., substituting the Cpal KASIV coding sequence of SEQ ID NO: 38 with various other coding sequences of Table 1), except that the *Cuphea hookeriana* KASIV was tested using the expression cassette of SEQ ID NO: 61. See Examples 1-4.

| Species | Gene Name | Amino Acid Sequence | nucleotide coding sequence (from cDNA produced from seed mRNA, not codon-optimized) | *Prototheca moriformis* codon-optimized nucleotide sequence |
|---|---|---|---|---|
| *C. avigera* | KASIa | 16 | 35 | 53 |
| *C. pulcherrima* | KASI | 17 | 36 | 54 |
| *C. avigera* | mito-chondrial KAS | 18 | 37 | 55 |
| *Cuphea hookeriana* | KASIV | 59 | | 60, 61 |

TABLE 1a

Additional proteins encoded by cDNA discovered from transcript profiling of seeds. Coding sequences can be derived from codon tables for various host cells.

| Species | Gene Name | Amino Acid Sequence |
|---|---|---|
| Various (Clade 1) | KASIV consensus sequence | 69, 71 |
| Various (Clade 2) | KASIV consensus sequence | 70, 72 |
| *Cuphea aequipetala* | KASIV | 62 |
| *Cuphea glassostoma* | KASIV | 63 |
| *Cuphea hookeriana* | KASIV | 64 |
| *Cuphea glassostoma* | KASIV | 65 |
| *Cuphea carthagenesis* | KASIV | 66, 67 |
| *C. pulcherrima* | KASIV | 68 |

TABLE 2

Codon usage in *Prototheca* strains.

| | | |
|---|---|---|
| Ala | GCG | 345 (0.36) |
| | GCA | 66 (0.07) |
| | GCT | 101 (0.11) |
| | GCC | 442 (0.46) |
| Cys | TGT | 12 (0.10) |
| | TGC | 105 (0.90) |
| Asp | GAT | 43 (0.12) |
| | GAC | 316 (0.88) |
| Glu | GAG | 377 (0.96) |
| | GAA | 14 (0.04) |
| Phe | TTT | 89 (0.29) |
| | TTC | 216 (0.71) |
| Gly | GGG | 92 (0.12) |
| | GGA | 56 (0.07) |
| | GGT | 76 (0.10) |
| | GGC | 559 (0.71) |
| His | CAT | 42 (0.21) |
| | CAC | 154 (0.79) |
| Ile | ATA | 4 (0.01) |
| | ATT | 30 (0.08) |
| | ATC | 338 (0.91) |
| Lys | AAG | 284 (0.98) |
| | AAA | 7 (0.02) |
| Leu | TTG | 26 (0.04) |
| | TTA | 3 (0.00) |
| | CTG | 447 (0.61) |
| | CTA | 20 (0.03) |
| | CTT | 45 (0.06) |
| | CTC | 190 (0.26) |
| Met | ATG | 191 (1.00) |
| Asn | AAT | 8 (0.04) |
| | AAC | 201 (0.96) |
| Pro | CCG | 161 (0.29) |
| | CCA | 49 (0.09) |
| | CCT | 71 (0.13) |
| | CCC | 267 (0.49) |
| Gln | CAG | 226 (0.82) |
| | CAA | 48 (0.18) |
| Arg | AGG | 33 (0.06) |
| | AGA | 14 (0.02) |
| | CGG | 102 (0.18) |
| | CGA | 49 (0.08) |
| | CGT | 51 (0.09) |
| | CGC | 331 (0.57) |
| Ser | AGT | 16 (0.03) |
| | AGC | 123 (0.22) |
| | TCG | 152 (0.28) |
| | TCA | 31 (0.06) |
| | TCT | 55 (0.10) |
| | TCC | 173 (0.31) |
| Thr | ACG | 184 (0.38) |
| | ACA | 24 (0.05) |
| | ACT | 21 (0.05) |
| | ACC | 249 (0.52) |
| Val | GTG | 308 (0.50) |
| | GTA | 9 (0.01) |
| | GTT | 35 (0.06) |
| | GTC | 262 (0.43) |
| Trp | TGG | 107 (1.00) |
| Tyr | TAT | 10 (0.05) |
| | TAC | 180 (0.95) |
| Stop | TGA/TAG/TAA | |

TABLE 3

Preferred codon usage in *Chlorella protothecoides*.

| |
|---|
| TTC (Phe) |
| TGG (Trp) |
| CTG (Leu) |
| GAC (Asp) |

TABLE 3-continued

| Preferred codon usage in *Chlorella protothecoides*. |
|---|
| GCC (Ala) |
| GAG (Glu) |
| TAC (Tyr) |
| CCC (Pro) |
| CAG (Gln) |
| TCC (Ser) |
| AAC (Asn) |
| TGC (Cys) |
| CAC (His) |
| ATC (Ile) |
| ATG (Met) |
| GGC (Gly) |
| TGA (Stop) |
| CGC (Arg) |
| ACC (Thr) |
| AAG (Lys) |
| GTG (Val) |

TABLE 4

| Codon usage for *Cuphea wrightii* (codon, amino acid, frequency, per thousand, number) | | | |
|---|---|---|---|
| UUU F 0.48 19.5 (52) | UCU S 0.21 19.5 (52) | UAU Y 0.45 6.4 (17) | UGU C 0.41 10.5 (28) |
| UUC F 0.52 21.3 (57) | UCC S 0.26 23.6 (63) | UAC Y 0.55 7.9 (21) | UGC C 0.59 15.0 (40) |
| UUA L 0.07 5.2 (14) | UCA S 0.18 16.8 (45) | UAA * 0.33 0.7 (2) | UGA * 0.33 0.7 (2) |
| UUG L 0.19 14.6 (39) | UCG S 0.11 9.7 (26) | UAG * 0.33 0.7 (2) | UGG W 1.00 15.4 (41) |
| CUU L 0.27 21.0 (56) | CCU P 0.48 21.7 (58) | CAU H 0.60 11.2 (30) | CGU R 0.09 5.6 (15) |
| CUC L 0.22 17.2 (46) | CCC P 0.16 7.1 (19) | CAC H 0.40 7.5 (20) | CGC R 0.13 7.9 (21) |
| CUA L 0.13 10.1 (27) | CCA P 0.21 9.7 (26) | CAA Q 0.31 8.6 (23) | CGA R 0.11 6.7 (18) |
| CUG L 0.12 9.7 (26) | CCG P 0.16 7.1 (19) | CAG Q 0.69 19.5 (52) | CGG R 0.16 9.4 (25) |
| AUU I 0.44 22.8 (61) | ACU T 0.33 16.8 (45) | AAU N 0.66 31.4 (84) | AGU S 0.18 16.1 (43) |
| AUC I 0.29 15.4 (41) | ACC T 0.27 13.9 (37) | AAC N 0.34 16.5 (44) | AGC S 0.07 6.0 (16) |
| AUA I 0.27 13.9 (37) | ACA T 0.26 13.5 (36) | AAA K 0.42 21.0 (56) | AGA R 0.24 14.2 (38) |
| AUG M 1.00 28.1 (75) | ACG T 0.14 7.1 (19) | AAG K 0.58 29.2 (78) | AGG R 0.27 16.1 (43) |
| GUU V 0.28 19.8 (53) | GCU A 0.35 31.4 (84) | GAU D 0.63 35.9 (96) | GGU G 0.29 26.6 (71) |
| GUC V 0.21 15.0 (40) | GCC A 0.20 18.0 (48) | GAC D 0.37 21.0 (56) | GGC G 0.20 18.0 (48) |
| GUA V 0.14 10.1 (27) | GCA A 0.33 29.6 (79) | GAA E 0.41 18.3 (49) | GGA G 0.35 31.4 (84) |
| GUG V 0.36 25.1 (67) | GCG A 0.11 9.7 (26) | GAG E 0.59 26.2 (70) | GGG G 0.16 14.2 (38) |

TABLE 5

| Codon usage for *Arabidopsis* (codon, amino acid, frequency, per thousand) | | | | | | | | | | | | | | | |
|---|---|---|---|---|---|---|---|---|---|---|---|---|---|---|---|
| UUU | F | 0.51 | 21.8 | UCU | S | 0.28 | 25.2 | UAU | Y | 0.52 | 14.6 | UGU | C | 0.60 | 10.5 |
| UUC | F | 0.49 | 20.7 | UCC | S | 0.13 | 11.2 | UAC | Y | 0.48 | 13.7 | UGC | C | 0.40 | 7.2 |
| UUA | L | 0.14 | 12.7 | UCA | S | 0.20 | 18.3 | UAA | * | 0.36 | 0.9 | UGA | * | 0.44 | 1.2 |
| UUG | L | 0.22 | 20.9 | UCG | S | 0.10 | 9.3 | UAG | * | 0.20 | 0.5 | UGG | W | 1.00 | 12.5 |
| CUU | L | 0.26 | 24.1 | CCU | P | 0.38 | 18.7 | CAU | H | 0.61 | 13.8 | CGU | R | 0.17 | 9.0 |
| CUC | L | 0.17 | 16.1 | CCC | P | 0.11 | 5.3 | CAC | H | 0.39 | 8.7 | CGC | R | 0.07 | 3.8 |

TABLE 5-continued

| Codon usage for *Arabidopsis* (codon, amino acid, frequency, per thousand) | | | | | | | | | | | | | | | |
|---|---|---|---|---|---|---|---|---|---|---|---|---|---|---|---|
| CUA | L | 0.11 | 9.9 | CCA | P | 0.33 | 16.1 | CAA | Q | 0.56 | 19.4 | CGA | R | 0.12 | 6.3 |
| CUG | L | 0.11 | 9.8 | CCG | P | 0.18 | 8.6 | CAG | Q | 0.44 | 15.2 | CGG | R | 0.09 | 4.9 |
| AUU | I | 0.41 | 21.5 | ACU | T | 0.34 | 17.5 | AAU | N | 0.52 | 22.3 | AGU | S | 0.16 | 14.0 |
| AUC | I | 0.35 | 18.5 | ACC | T | 0.20 | 10.3 | AAC | N | 0.48 | 20.9 | AGC | S | 0.13 | 11.3 |
| AUA | I | 0.24 | 12.6 | ACA | T | 0.31 | 15.7 | AAA | K | 0.49 | 30.8 | AGA | R | 0.35 | 19.0 |
| AUG | M | 1.00 | 24.5 | ACG | T | 0.15 | 7.7 | AAG | K | 0.51 | 32.7 | AGG | R | 0.20 | 11.0 |
| GUU | V | 0.40 | 27.2 | GCU | A | 0.43 | 28.3 | GAU | D | 0.68 | 36.6 | GGU | G | 0.34 | 22.2 |
| GUC | V | 0.19 | 12.8 | GCC | A | 0.16 | 10.3 | GAC | D | 0.32 | 17.2 | GGC | G | 0.14 | 9.2 |
| GUA | V | 0.15 | 9.9 | GCA | A | 0.27 | 17.5 | GAA | E | 0.52 | 34.3 | GGA | G | 0.37 | 24.2 |
| GUG | V | 0.26 | 17.4 | GCG | A | 0.14 | 9.0 | GAG | E | 0.48 | 32.2 | GGG | G | 0.16 | 10.2 |

Gene Combinations

In an embodiment, a gene/gene-product of Table 1 is co-expressed in a host cell with an exogenous FATA or FATB acyl-ACP thioesterase gene. In a specific embodiment, the FATB gene product has at least 85, 90, 91, 92, 93, 94, 95, 95.5, 96, 96.5 97, 97.5, 98, 98.5 or 99% amino acid sequence identity to the *Cuphea palustris* FATB2 ("Cpal FATB2", accession AAC49180, SEQ ID NO: 1) or *C. hookeriana* FATB2 ("Ch FATB2", accession U39834, SEQ ID NO: 57) or fragment thereof. Optionally the FATB gene product has at least 85, 90, 91, 92, 93, 94, 95, 95.5, 96, 96.5 97, 97.5, 98, 98.5 or 99% amino acid sequence identity to the non-transit-peptide domain of *Cuphea palustris* FATB2 ("Cpal FATB2", accession AAC49180, SEQ ID NO: 1) or *C. hookeriana* FATB2 ("Ch FATB2", accession U39834 SEQ ID NO: 57)).

FATA genes encode enzymes that preferentially, but not exclusively, hydrolyze long-chain fatty acids with highest activity towards C18:1. FATB genes encode a group of enzymes with more heterogeneous substrate specificities but generally show higher activity toward saturated fatty acids. The substrate specificities of FATB enzymes are quite heterogenous; there are a number of FATB enzymes that show high activity towards C18:0 and C18:1. FATA and FATB enzymes terminate the synthesis of fatty acids by hydrolyzing the thioester bond between the acyl moiety and the acyl carrier protein (ACP).

In an embodiment, a host cell is transformed to express both a FATA or FATB and KASI-like transgene. The host-cell produces a cell oil. Together, the FATA or FATB and KASI-like genes are expressed to produce their respective gene products and thereby alter the fatty acid profile of the cell oil. The two genes function either additively or synergistically with respect to control strains lacking one of the two genes. Optionally, the host cell is oleaginous and can be an oleaginous eukaryotic microalgae such as those described above or below. The fatty acid profile of the cell oil can be enriched (relative to an appropriate control) in C14:0 (myristic), C8:0, C10:0 or a combination of C8/C10.

In an embodiment, the fatty acid profile of the cell is enriched in C14:0 fatty acids. In this embodiment, the FATB gene expresses an acyl-ACP thioesterase enzyme having at least 85, 90, 91, 92, 93, 94, 95, 95.5, 96, 96.5 97, 97.5, 98, 98.5 or 99% amino acid sequence identity percent amino acid identity to the enzyme of SEQ ID NO: 1. The co-expressed KASI-like gene encodes a beta-ketoacyl ACP synthase having at least 85, 90, 91, 92, 93, 94, 95, 95.5, 96, 96.5 97, 97.5, 98, 98.5 or 99% amino acid sequence identity percent amino acid identity to the enzyme of SEQ ID NO: 2. Alternately The co-expressed KASI-like gene encodes a beta-ketoacyl ACP synthase having at least 85, 90, 91, 92, 93, 94, 95, 95.5, 96, 96.5 97, 97.5, 98, 98.5 or 99% amino acid sequence identity percent amino acid identity to the enzyme of SEQ ID NO: 7. Optionally, the cell oil has a fatty acid profile characterized by at least 10%, 20%, 30%, 40%, 50% or at least 55% C14:0 (area % by FAME-GC-FID).

In another embodiment, the fatty acid profile of the cell is enriched in C8:0 and/or C10:0 fatty acids. In this embodiment, the FATB gene expresses an acyl-ACP thioesterase enzyme having at least 85, 90, 91, 92, 93, 94, 95, 95.5, 96, 96.5 97, 97.5, 98, 98.5 or 99% amino acid sequence identity percent amino acid identity to the enzyme of SEQ ID NO: 57. The co-expressed KASI-like gene encodes a beta-ketoacyl ACP synthase having at least 85, 90, 91, 92, 93, 94, 9595.5, 96, 96.5 97, 97.5, 98, 98.5 or 99% amino acid sequence identity percent amino acid identity to an enzyme of one of SEQ ID NOs: 2, 8, 9, 10, 11, 12, 13, 14, 15, 16, 17, 19, 37. In a related embodiment, the co-expressed KASI-like gene encodes a beta-ketoacyl ACP synthase having at least 85, 90, 91, 92, 93, 94, 95, 95.5, 96, 96.5 97, 97.5, 98, 98.5 or 99% amino acid sequence identity percent amino acid identity to enzyme of one of SEQ ID NO: 2, 8, 11, 12, 13, 14, or 15. Optionally, the cell oil has a fatty acid profile characterized by at least 7, 8, 9, 10, 11, 12, 13, or 14 area % C8:0 (by FAME-GC-FID). Optionally, the cell oil has a fatty acid profile characterized by at least 10, 15, 20, 25, 30, or 35 area % for the sum of C8:0 and C10:0 fatty acids (by FAME-GC-FID). Optionally, the C8/C10 ratio of the cell oil is in the range of 2.2-2.5, 2.5-3.0, or 3.0-3.4.

Optionally, the oils produced by these methods can have a sterol profile in accord with those described below.

Host Cells

The host cell can be a single cell (e.g., microalga, bacteria, yeast) or part of a multicellular organism such as a plant or fungus. Methods for expressing KASI-like genes in a plant are given in U.S. Pat. No. 7,301,070, U.S. Pat. No. 6,348,642, U.S. Pat. No. 6,660,849, and U.S. Pat. No. 6,770,465, or can be accomplished using other techniques generally known in plant biotechnology. Engineering of eukaryotic oleaginous microbes including eukaryotic microalgae (e.g., of Chlorophyta) is disclosed in WO2010/063032, WO2011/150411, and WO2012/106560 and in the examples below.

Examples of oleaginous host cells include plant cells and microbial cells having a type II fatty acid biosynthetic pathway, including plastidic oleaginous cells such as those of oleaginous algae. Specific examples of microalgal cells include heterotrophic or obligate heterotrophic eukaryotic microalgae of the phylum Chlorophtya, the class Trebouxiophytae, the order Chlorellales, or the family Chlorellacae. Examples of eukaryotic oleaginous microalgae host cells are provided in Published PCT Patent Applications WO2008/151149, WO2010/06032, WO2011/150410, and WO2011/150411, including species of *Chlorella* and *Prototheca*, a genus comprising obligate heterotrophs. The oleaginous cells can be, for example, capable of producing 25, 30, 40, 50, 60, 70, 80, 85, or about 90% oil by cell weight, ±5%. Optionally, the oils produced can be low in DHA or EPA fatty acids. For example, the oils can comprise less than 5%, 2%, or 1% DHA and/or EPA. The above-mentioned publications also disclose methods for cultivating such cells and extracting oil, especially from microalgal cells; such methods are applicable to the cells disclosed herein and incorporated by reference for these teachings. When microalgal cells are used they can be cultivated autotrophically (unless an obligate heterotroph) or in the dark using a sugar (e.g., glucose, fructose and/or sucrose). When cultivated heterotrophically, the cells and cell oil can comprise less than 200 ppm, 20 ppm, or 2 ppm of color-generating impurities or of chlorophyll. In any of the embodiments described herein, the cells can be heterotrophic cells comprising an exogenous invertase gene so as to allow the cells to produce oil from a sucrose feedstock. Alternately, or in addition, the cells can metabolize xylose from cellulosic feedstocks. For example, the cells can be genetically engineered to express one or more xylose metabolism genes such as those encoding an active xylose transporter, a xylulose-5-phosphate transporter, a xylose isomerase, a xylulokinase, a xylitol dehydrogenase and a xylose reductase. See WO2012/154626, “GENETICALLY ENGINEERED MICROORGANISMS THAT METABOLIZE XYLOSE”, published Nov. 15, 2012. The cells can be cultivated on a depolymerized cellulosic feedstock such as acid or enzyme hydrolyzed bagasse, sugar beet pulp, corn stover, wood chips, sawdust or switchgrass. Optionally, the cells can be cultivated on a depolymerized cellulosic feedstock comprising glucose and at least 5, 10, 20, 30 or 40% xylose, while producing at least 20% lipid by dry weight. Optionally, the lipid comprises triglycerides having a fatty acid profile characterized by at least 10, 15 or 20% C12:0

Optionally, the host cell comprises 23S rRNA having at least 65, 70, 75, 80, 85, 90 or 95% nucleotide sequence identity to SEQ ID NO: 58.

Oils and Related Products

The oleaginous cells express one or more exogenous genes encoding fatty acid biosynthesis enzymes. As a result, some embodiments feature cell oils that were not obtainable from a non-plant or non-seed oil, or not obtainable at all.

The oleaginous cells produce a storage oil, which is primarily triacylglyceride and may be stored in storage bodies of the cell. A raw oil may be obtained from the cells by disrupting the cells and isolating the oil. WO2008/151149, WO2010/06032, WO2011/150410, and WO2011/1504 disclose heterotrophic cultivation and oil isolation techniques. For example, oil may be obtained by cultivating, drying and pressing the cells. The cell oils produced may be refined, bleached and deodorized (RBD) as known in the seed-oil art or as described in WO2010/120939. The refining step may comprise degumming. The raw, refined, or RBD oils may be used in a variety of food, chemical, and industrial products or processes. After recovery of the oil, a valuable residual biomass remains. Uses for the residual biomass include the production of paper, plastics, absorbents, adsorbents, as animal feed, for human nutrition, or for fertilizer.

Where a fatty acid profile of a triglyceride (also referred to as a “triacylglyceride” or “TAG”) cell oil is given here, it will be understood that this refers to a nonfractionated sample of the storage oil extracted from the cell analyzed under conditions in which phospholipids have been removed or with an analysis method that is substantially insensitive to the fatty acids of the phospholipids (e.g. using chromatography and mass spectrometry). The oil may be subjected to an RBD process to remove phospholipids, free fatty acids and odors yet have only minor or negligible changes to the fatty acid profile of the triglycerides in the oil. Because the cells are oleaginous, in some cases the storage oil will constitute the bulk of all the TAGs in the cell.

The stable carbon isotope value δ13C is an expression of the ratio of 13C/12C relative to a standard (e.g. PDB, carbonite of fossil skeleton of *Belemnite americana* from Peedee formation of South Carolina). The stable carbon isotope value δ13C (0/00) of the oils can be related to the δ13C value of the feedstock used. In some embodiments, the oils are derived from oleaginous organisms heterotrophically grown on sugar derived from a C4 plant such as corn or sugarcane. In some embodiments the δ13C (0/00) of the oil is from −10 to −17 0/00 or from −13 to −16 0/00.

The oils produced according to the above methods in some cases are made using a microalgal host cell. As described above, the microalga can be, without limitation, be a eukaryotic microalga falling in the classification of Chlorophyta, Trebouxiophyceae, Chlorellales, Chlorellaceae, or Chlorophyceae. It has been found that microalgae of Trebouxiophyceae can be distinguished from vegetable oils based on their sterol profiles. Oil produced by *Chlorella protothecoides* (a close relative of *Prototheca moriformis*) was found to produce sterols that appeared to be brassicasterol, ergosterol, campesterol, stigmasterol, and beta-sitosterol, when detected by GC-MS. However, it is believed that all sterols produced by *Chlorella* have C24β stereochemistry. Thus, it is believed that the molecules detected as campesterol, stigmasterol, and beta-sitosterol, are actually 22,23-dihydrobrassicasterol, proferasterol and clionasterol, respectively. Thus, the oils produced by the microalgae described above can be distinguished from plant oils by the presence of sterols with C24α stereochemistry and the absence of C24α stereochemistry in the sterols present. For example, the oils produced may contain 22, 23-dihydrobrassicasterol while lacking campesterol; contain clionasterol, while lacking in beta-sitosterol, and/or contain poriferasterol while lacking stigmasterol. Alternately, or in addition, the oils may contain significant amounts of $\Delta^7$-poriferasterol.

In one embodiment, the oils provided herein are not vegetable oils. Vegetable oils are oils extracted from plants and plant seeds. Vegetable oils can be distinguished from the non-plant oils provided herein on the basis of their oil content. A variety of methods for analyzing the oil content can be employed to determine the source of the oil or whether adulteration of an oil provided herein with an oil of a different (e.g. plant) origin has occurred. The determination can be made on the basis of one or a combination of the analytical methods. These tests include but are not limited to analysis of one or more of free fatty acids, fatty acid profile, total triacylglycerol content, diacylglycerol content, peroxide values, spectroscopic properties (e.g. UV absorption), sterol profile, sterol degradation products, antioxidants (e.g.

tocopherols), pigments (e.g. chlorophyll), d13C values and sensory analysis (e.g. taste, odor, and mouth feel). Many such tests have been standardized for commercial oils such as the Codex Alimentarius standards for edible fats and oils.

Sterol profile analysis is a particularly well-known method for determining the biological source of organic matter. Campesterol, β-sitosterol, and stigmasterol are common plant sterols, with β-sitosterol being a principle plant sterol. For example, β-sitosterol was found to be in greatest abundance in an analysis of certain seed oils, approximately 64% in corn, 29% in rapeseed, 64% in sunflower, 74% in cottonseed, 26% in soybean, and 79% in olive oil (Gul et al. J. Cell and Molecular Biology 5:71-79, 2006).

Oil isolated from *Prototheca moriformis* strain UTEX1435 were separately clarified (CL), refined and bleached (RB), or refined, bleached and deodorized (RBD) and were tested for sterol content according to the procedure described in JAOCS vol. 60, no. 8, August 1983. Results of the analysis are shown below (units in mg/100 g) in Table 6.

TABLE 6

Sterols in microalgal oil.

| | Sterol | Crude | Clarified | Refined & bleached | Refined, bleached, & deodorized |
|---|---|---|---|---|---|
| 1 | Ergosterol | 384 (56%) | 398 (55%) | 293 (50%) | 302 (50%) |
| 2 | 5,22-cholestadien-24-methyl-3-ol (Brassicasterol) | 14.6 (2.1%) | 18.8 (2.6%) | 14 (2.4%) | 15.2 (2.5%) |
| 3 | 24-methylcholest-5-en-3-ol (Campesterol or 22,23-dihydrobrassicasterol) | 10.7 (1.6%) | 11.9 (1.6%) | 10.9 (1.8%) | 10.8 (1.8%) |
| 4 | 5,22-cholestadien-24-ethyl-3-ol (Stigmasterol or poriferasterol) | 57.7 (8.4%) | 59.2 (8.2%) | 46.8 (7.9%) | 49.9 (8.3%) |
| 5 | 24-ethylcholest-5-en-3-ol (β-Sitosterol or clionasterol) | 9.64 (1.4%) | 9.92 (1.4%) | 9.26 (1.6%) | 10.2 (1.7%) |
| 6 | Other sterols | 209 | 221 | 216 | 213 |
| | Total sterols | 685.64 | 718.82 | 589.96 | 601.1 |

These results show three striking features. First, ergosterol was found to be the most abundant of all the sterols, accounting for about 50% or more of the total sterols. The amount of ergosterol is greater than that of campesterol, beta-sitosterol, and stigmasterol combined. Ergosterol is steroid commonly found in fungus and not commonly found in plants, and its presence particularly in significant amounts serves as a useful marker for non-plant oils. Secondly, the oil was found to contain brassicasterol. With the exception of rapeseed oil, brassicasterol is not commonly found in plant based oils. Thirdly, less than 2% beta-sitosterol was found to be present. Beta-sitosterol is a prominent plant sterol not commonly found in microalgae, and its presence particularly in significant amounts serves as a useful marker for oils of plant origin. In summary, *Prototheca moriformis* strain UTEX1435 has been found to contain both significant amounts of ergosterol and only trace amounts of beta-sitosterol as a percentage of total sterol content. Accordingly, the ratio of ergosterol:beta-sitosterol or in combination with the presence of brassicasterol can be used to distinguish this oil from plant oils.

In some embodiments, the oil content of an oil provided herein contains, as a percentage of total sterols, less than 20%, 15%, 10%, 5%, 4%, 3%, 2%, or 1% beta-sitosterol. In other embodiments the oil is free from beta-sitosterol.

In some embodiments, the oil is free from one or more of beta-sitosterol, campesterol, or stigmasterol. In some embodiments the oil is free from beta-sitosterol, campesterol, and stigmasterol. In some embodiments the oil is free from campesterol. In some embodiments the oil is free from stigmasterol.

In some embodiments, the oil content of an oil provided herein comprises, as a percentage of total sterols, less than 20%, 15%, 10%, 5%, 4%, 3%, 2%, or 1% 24-ethylcholest-5-en-3-ol. In some embodiments, the 24-ethylcholest-5-en-3-ol is clionasterol. In some embodiments, the oil content of an oil provided herein comprises, as a percentage of total sterols, at least 1%, 2%, 3%, 4%, 5%, 6%, 7%, 8%, 9%, or 10% clionasterol.

In some embodiments, the oil content of an oil provided herein contains, as a percentage of total sterols, less than 20%, 15%, 10%, 5%, 4%, 3%, 2%, or 1% 24-methylcholest-5-en-3-ol. In some embodiments, the 24-methylcholest-5-en-3-ol is 22, 23-dihydrobrassicasterol. In some embodiments, the oil content of an oil provided herein comprises, as a percentage of total sterols, at least 1%, 2%, 3%, 4%, 5%, 6%, 7%, 8%, 9%, or 10% 22,23-dihydrobrassicasterol.

In some embodiments, the oil content of an oil provided herein contains, as a percentage of total sterols, less than 20%, 15%, 10%, 5%, 4%, 3%, 2%, or 1% 5,22-cholestadien-24-ethyl-3-ol. In some embodiments, the 5, 22-cholestadien-24-ethyl-3-ol is poriferasterol. In some embodiments, the oil content of an oil provided herein comprises, as a percentage of total sterols, at least 1%, 2%, 3%, 4%, 5%, 6%, 7%, 8%, 9%, or 10% poriferasterol.

In some embodiments, the oil content of an oil provided herein contains ergosterol or brassicasterol or a combination of the two. In some embodiments, the oil content contains, as a percentage of total sterols, at least 5%, 10%, 20%, 25%, 35%, 40%, 45%, 50%, 55%, 60%, or 65% ergosterol. In some embodiments, the oil content contains, as a percentage of total sterols, at least 25% ergosterol. In some embodiments, the oil content contains, as a percentage of total sterols, at least 40% ergosterol. In some embodiments, the oil content contains, as a percentage of total sterols, at least 5%, 10%, 20%, 25%, 35%, 40%, 45%, 50%, 55%, 60%, or 65% of a combination of ergosterol and brassicasterol.

In some embodiments, the oil content contains, as a percentage of total sterols, at least 1%, 2%, 3%, 4% or 5% brassicasterol. In some embodiments, the oil content contains, as a percentage of total sterols less than 10%, 9%, 8%, 7%, 6%, or 5% brassicasterol.

In some embodiments the ratio of ergosterol to brassicasterol is at least 5:1, 10:1, 15:1, or 20:1.

In some embodiments, the oil content contains, as a percentage of total sterols, at least 5%, 10%, 20%, 25%, 35%, 40%, 45%, 50%, 55%, 60%, or 65% ergosterol and less than 20%, 15%, 10%, 5%, 4%, 3%, 2%, or 1% beta-sitosterol. In some embodiments, the oil content contains, as a percentage of total sterols, at least 25% ergosterol and less than 5% beta-sitosterol. In some embodiments, the oil content further comprises brassicasterol. For any of the oils or cell-oils disclosed in this application, the oil can have the sterol profile of any column of Table 6, above, with a sterol-by-sterol variation of 30%, 20%, 10% or less.

Sterols contain from 27 to 29 carbon atoms (C27 to C29) and are found in all eukaryotes. Animals exclusively make C27 sterols as they lack the ability to further modify the C27 sterols to produce C28 and C29 sterols. Plants however are able to synthesize C28 and C29 sterols, and C28/C29 plant sterols are often referred to as phytosterols. The sterol profile of a given plant is high in C29 sterols, and the primary sterols in plants are typically the C29 sterols beta-sitosterol and stigmasterol. In contrast, the sterol profile of non-plant organisms contain greater percentages of C27 and C28 sterols. For example the sterols in fungi and in many microalgae are principally C28 sterols. The sterol profile and particularly the striking predominance of C29 sterols over C28 sterols in plants has been exploited for determining the proportion of plant and marine matter in soil samples (Huang, Wen-Yen, Meinschein W. G., "Sterols as ecological indicators"; Geochimica et Cosmochimia Acta. Vol 43. pp 739-745).

In some embodiments the primary sterols in the microalgal oils provided herein are sterols other than beta-sitosterol and stigmasterol. In some embodiments of the microalgal oils, C29 sterols make up less than 50%, 40%, 30%, 20%, 10%, or 5% by weight of the total sterol content.

In some embodiments the microalgal oils provided herein contain C28 sterols in excess of C29 sterols. In some embodiments of the microalgal oils, C28 sterols make up greater than 50%, 60%, 70%, 80%, 90%, or 95% by weight of the total sterol content. In some embodiments the C28 sterol is ergosterol. In some embodiments the C28 sterol is brassicasterol.

In embodiments of the present invention, oleaginous cells expressing one or more of the genes of Table 1 can produce an oil with at least 20, 40, 60 or 70% of C8, C10, C12, C14 or C16 fatty acids. In a specific embodiment, the level of myristate (C14:0) in the oil is greater than 30%.

Thus, in embodiments of the invention, there is a process for producing an oil, triglyceride, fatty acid, or derivative of any of these, comprising transforming a cell with any of the nucleic acids discussed herein. In another embodiment, the transformed cell is cultivated to produce an oil and, optionally, the oil is extracted. Oil extracted in this way can be used to produce food, oleochemicals or other products.

The oils discussed above alone or in combination are useful in the production of foods, fuels and chemicals (including plastics, foams, films, detergents, soaps, etc). The oils, triglycerides, fatty acids from the oils may be subjected to C—H activation, hydroamino methylation, methoxy-carbonation, ozonolysis, enzymatic transformations, epoxidation, methylation, dimerization, thiolation, metathesis, hydro-alkylation, lactonization, or other chemical processes.

After extracting the oil, a residual biomass may be left, which may have use as a fuel, as an animal feed, or as an ingredient in paper, plastic, or other product. For example, residual biomass from heterotrophic algae can be used in such products.

described in WO2013/158938, example 53 (p. 231). The amino acid sequence of the Cpal FATB2 gene is given in SEQ ID NO: 1. This strain (S6336) produced a cell oil characterized by a fatty acid profile having about 38% myristic acid (C14:0).

Six KASI-like genes were cloned from seed oil genomes. Total RNA was extracted from dried mature seeds using a liquid-nitrogen-chilled mortar and pestle to break open the seed walls. RNA was then precipitated with an 8M urea, 3M LiCl solution followed by a phenol-chloroform extraction. A cDNA library was generated with oligo dT primers using the purified RNA and subjected to Next Generation sequencing. The novel KAS genes were identified from the assembled transcriptome using BLAST with known KAS genes as bait. The identified KAS gene sequences were codon optimized for expression in *Prototheca* and synthesized for incorporation into an expression cassette.

To test the impact on myristate accumulation, S6336 was transformed with a linearized plasmid designed for homologous recombination at the pLOOP locus and to express the KASI-like genes with coexpression of a selection marker (see WO2013/1589380). The vector is described in SEQ ID NO 38, the remaining codon optimized KAS genes were substituted into the KAS CDS segment of this vector prior to transformation. As shown in Table 7, increases in C14:0 levels in extracted cell oil were observed with the expression of the *C. camphora* KASIV (D3147), *C. camphora* KASI (D3148), *U. californica* KASI (D3150) or *U. californica* KASVI (D3152) genes in S6336. Even greater increases in C14:0 levels resulted from expression the KASI gene from *C. palustris* KASIV (D3145) or *C. wrightii* KASAI (D3153), with some individual lines producing >50% or >55% C14:0. The C14 production far exceeded the negligible amount found in the wild-type oil (see Table 7a).

TABLE 7

KAS genes that effect an increase in C14 fatty acids in eukaryotic microalgal oil.

| Gene (transformant ID) | SEQ ID NOs: | C14:0 (area %. mean of 4 transformants) | Highest C14:0 observed |
|---|---|---|---|
| *C. camphora* KASIV | 3, 22, 40 | 38.0 | 40.3 |
| *C. camphora* KASI | 4, 23, 41 | 33.8 | 39.3 |
| *U. californica* KASI | 5, 24, 42 | 37.4 | 42.3 |
| *U. californica* KASVI | 6, 25, 43 | 38.4 | 41.6 |
| *C. palustris* KASIV | 2, 21, 39 | 45.4 | 58.4 |
| *C. wrightii* KASAI | 7, 26, 44 | 43.2 | 53.6 |

TABLE 7a

Fatty acid profile of wild-type *Prototheca moriformis* oil (area %).

| C8:0 | C10:0 | C12:0 | C14:0 | C16:0 | C18:0 | C18:1 | C18:2 | C18:3 |
|---|---|---|---|---|---|---|---|---|
| 0 | 0 | 0 | 2 | 38 | 4 | 48 | 5 | 1 |

EXAMPLES

Example 1: Screening KAS Genes in Combination with *Cuphea palustris* FATB2 Acyl-ACP Thioesterase A *Prototheca moriformis* strain expressing codon optimized *Cuphea palustris* (Cpal) FATB2 was constructed as

Example 2: Screening KAS Genes in Combination with *Cuphea hookeriana* FATB Acyl-ACP Thioesterase

*P. moriformis* strains were constructed that express ChFATB2 acyl-ACP thioesterase together with a KAS gene selected from ten KASI, one KASIII and one mitochondrial KAS were cloned from seed oil genomes, codon optimized and introduced into *Prototheca* as described in Example 1. The KAS genes were fused to an HA epitope TAG at the c-terminus of each KAS to allow confirmation of protein expression.

TABLE 8

Mean C8:0-C10:0 fatty acid profiles derived from transformation of FATB2-expressing microalgal strain with KASI-like genes isolated from seed oil genomes.

| KAS Gene | SEQ ID NOS: (amino acid, CDS, codon optimized CDS) | C8:0 (mean area %) | C10:0 (mean area %) | Sum C8:0 + C10:0 | C10/C8 ratio |
|---|---|---|---|---|---|
| *C. avigera* KASIa | 16, 35, 53 | 8.0 | 21.4 | 29.3 | 2.7 |
| *C. pulcherrima* KASI | 17, 36, 54 | 7.7 | 20.3 | 28.0 | 2.6 |
| *C. avigera* Mitochondrial KAS | NL, 37, 55 | 7.8 | 20.4 | 28.2 | 2.6 |
| *C. avigera* KAS III | 19, NL, 56 | 9.5 | 22.8 | 32.3 | 2.4 |
| *C. paucipetala* KASIVb | 9, 28, 46 | 7.9 | 22.5 | 30.3 | 2.9 |
| *C. ignea* KASIVb | 10, 29, 47 | 6.6 | 18.7 | 25.4 | 2.8 |
| *C. painteri* KASIV | 13, 32, 50 | 9.0 | 22.4 | 31.4 | 2.5 |
| *C. palustris* KASIVa | 2, 21, 38 | 8.6 | 21.6 | 30.4 | 2.5 |
| *C. avigera* KASIVb | 8, 27, 45 | 11.0 | 23.8 | 34.8 | 2.2 |
| *C. procumbens* KASIV | 11, 30, 48 | 8.2 | 25.8 | 34.0 | 3.2 |
| *C. paucipetala* KASIVa | 12, 31, 49 | 8.8 | 29.9 | 39.4 | 3.4 |
| *C. ignea* KASIVa | 15, 34, 52 | 8.6 | 25.8 | 34.4 | 3.0 |
| *C avigera* KASIVa | 14, 33, 51 | 10.0 | 23.0 | 32.9 | 2.3 |
| *C. hookeriana* KASIV | 59, NL, 61 | 14.5 | 27.81 | 42.6 | 3.0 |

The parental strain is a stable microalgal strain expressing the *C. hookeriana* FATB2 under the control of the pH5-compatible PmUAPA1 promoter. The parental strain accumulates 27.8% C8:0-C10:0 with a C10/C8 ratio of 2.6. All transformants are derived from integrations of the KASI transgenes at the pLOOP locus of the parental strain. Means are calculated from at least 19 individual transformants for each KAS transgene (NL=not listed).

As can be seen from Table 8, expression of the following KAS genes significantly increased C8:0-C10:0 levels: *C. avigera* KASIVb (D3287), *C. procumbens* KASIV (D3290), *C. paucipetala* KASIVa (D3291), *C. avigera* KASIVa (D3293), and *C. ignea* KASIVa (D3294). Importantly, expression of the *C. avigera* KASIVb (D3287) augmented the accumulation of both C8:0 and C10:0 fatty acids, while only C10:0 levels were increased upon expression of D3290, D3291, D3293 and D3294. In some cases the sum of C8:0 and C10:0 fatty acids in the fatty acid profile was at least 30%, or at least 35% (area % by FAME-GC-FID). The midchain production far exceeded the negligible amount found in the wild-type oil (see Table 7a).

The mean C8/C10 ratios of Table 8 ranged from 2.2 to 3.4. The sum of mean C8 and C10 ranged from 25.4 to 39.4.

The highest C8:0 producing strain found was D3287, which combined *C. avigera* KASIV with *C. hookeriana* FATB2. The mean was 11.0% C8:0 with a range of 12.4 to 14.8. Thus, a cell oil with a fatty acid profile of greater than 14% C8 was produced. Furthermore, the C10/C8 ratio was less than 2.5.

Example 3: Identification of KAS Clades and Consensus Sequences

The newly identified sequences of KASI-like genes were compared to those in the ThYme database of thioester-active enzymes maintained by Iowa State University (enzyme.cbirc.iastate.edu) using the blast algorithm and the top hits were extracted. The top 50 BLAST hits were downloaded and a multiple alignment was created using ClustalW alignment algorithm and a phylogenetic tree (FIG. 1) was created using that alignment with the Jukes-Cantor Neighbor-Joining method. The new KASIV genes grouped together with only 4 ThYme KAS genes internal to that group out of the 50 possible. The total ThYme KAS sequences were reduced to 12 because nearly all ThYme KAS grouped away from the new KAS sequences. The ThYme sequences are only 222 residues while the new KASIV are approximately 555 residues in length including the targeting peptide.

Two new clades were identified Clade 1 and Clade 2, characterized by consensus SEQ ID NO: 69 and SEQ ID NO:70, which include transit peptides. The clades can also be characterized by the sequences of the mature consensus proteins SEQ ID NO: 71 and SEQ ID NO: 72, respectively. The KAS genes of Clade 1 are associated with production of elevated C8 and C10 fatty acids based on based on transformations in *P. moriformis* in combination with a FATB acyl-ACP thioesterase as in Example 2. The KAS genes of Clade 2 are associated with production of elevated C10 fatty acids based on transformations in *P. moriformis* in combination with a FATB acyl-ACP thioesterase as in Example 2.

Although the above discussion discloses various exemplary embodiments of the invention, it should be apparent that those skilled in the art can make various modifications that will achieve some of the advantages of the invention without departing from the true scope of the invention.

SEQUENCE LISTING

SEQ ID NO: 1

*Cuphea palustris* FATB2 amino acid sequence (Genbank Accession No. AAC49180.1)

```
MVAAAASAAFFSVATPRTNISPSSLSVPFKPKSNHNGGFQVKANASAHPKANGSAVS
LKSGSLETQEDKTSSSSPPPRTFINQLPVWSMLLSAVTTVFGVAEKQWPMLDRKSKR
PDMLVEPLGVDRIVYDGVSFRQSFSIRSYEIGADRTASIETLMNMFQETSLNHCKIIGL
LNDGFGRTPEMCKRDLIWVVTKMQIEVNRYPTWGDTIEVNTWVSASGKHGMGRD
WLISDCHTGEILIRATSVWAMMNQKTRRLSKIPYEVRQEIEPQFVDSAPVIVDDRKFH
KLDLKTGDSICNGLTPRWTDLDVNQHVNNVKYIGWILQSVPTEVFETQELCGLTLEY
RRECGRDSVLESVTAMDPSKEGDRSLYQHLLRLEDGADIVKGRTEWRPKNAGAKG
AILTGKTSNGNSIS
```

-continued

SEQUENCE LISTING

SEQ ID NO: 2
Amino acid sequence of the *C. palustris* KASIV (D3145 and D3295, pSZ4312). The algal transit peptide is underlined.
MASAAFTMSACPAMTGRAPGARRSGRPVATRLRGSTFQCLVTSYIDPCNQFSSSASL
SFLGDNGFASLFGSKPERSNRGHRRLGRASHSGEAMAVALEPAQEVATKKKPLVKQ
RRVVVTGMGVVTPLGHEPDVYYNNLLDGVSGISEIEAFDCTQFPTRIAGEIKSFSTDG
WVAPKLSKRMDKFMLYLLTAGKKALADGGITDDVMKELDKRKCGVLIGSGLGGM
KLFSDSIEALRISYKKMNPFCVPFATTNMGSAMLAMDLGWMGPNYSISTACATSNFC
ILNSANHIVRGEADMMLCGGSDAVIIPIGLGGFVACRALSQRNNDPTKASRPWDSNR
DGFVMGEGAGVLLLEELEHAKKRGATIYAEFLGGSFTCDAYHMTEPHPEGAGVILCI
EKALAQAGVSREDVNYINAHATSTPAGDIKEYQALAHCFGQNSELRVNSTKSMIGHL
IGAAGGVEAVTVVQAIRTGWIHPNLNLEDPDKAVDAKVLVGPKKERLNVKVGLSNS
FGFGGHNSSILFAPYN SEQ ID NO: 3
Amino acid sequence of the *C. camphora* KASIV (D3147, pSZ4338).
MAMMAGSCSNLVIGNRELGGNGPSLLHYNGLRPLENIQTASAVKKPNGLFASSTAR
KSKAVRAMVLPTVTAPKREKDPKKRIVITGMGLVSVFGNDIDTFYSKLLEGESGIGPI
DRFDASSFSVRFAGQIHNFSSKGYIDGKNDRRLDDCWRYCLVAGRRALEDANLGPE
VLEKMDRSRIGVLIGTGMGGLSAFSNGVESLIQKGYKKITPFFIPYSITNMGSALLAID
TGVMGPNYSISTACATANYCFHAAANHIRRGEAEIMVTGGTEAAVSATGVGGFIACR
ALSHRNDEPQTASRPWDKDRDGFVMGEGAGVLVMESLHHARKRGANIIAEYLGGA
VTCDAHHMTDPRADGLGVSSCITKSLEDAGVSPEEVNYVNAHATSTLAGDLAEVNA
IKKVFKDTSEMKMNGTKSMIGHCLGAAGGLEAIATIKAINTGWLHPTINQFNIEPAVT
IDTVPNVKKKHDIHVGISNSFGFGGHNSVVVFAPFMP SEQ ID NO: 4 Amino acid sequence of the *C. camphora* KASI (D3148, pSZ4339).
MQILQTPSSSSSSLRMSSMESLSLTPKSLPLKTLLPLRPRPKNLSRRKSQNPRPISSSSSP
ERETDPKKRVVITGMGLVSVFGNDVDAYYDRLLSGESGIAPIDRFDASKFPTRFAGQI
RGFTSDGYIDGKNDRRLDDCLRYCIVSGKKALENAGLGPHLMDGKIDKERAGVLVG
TGMGGLTVFSNGVQTLHEKGYRKMTPFFIPYAITNMGSALLAIELGEMGPNYSISTAC
ATSNYCFYAAANHIRRGEADLMLAGGTEAAIIPIGLGGFVACRALSQRNDDPQTASR
PWDKDRDGFVMGEGAGVLVMESLEHAMKRDAPIIAEYLGGAVNCDAYHMTDPRA
DGLGVSTCIERSLEDAGVAPEEVNYINAHATSTLAGDLAEVNAIKKVFTNTSEIKINA
TKSMIGHCLGAAGGLEAIATIKAINTGWLHPSINQFNPEPSVEFDTVANKKQQHEVN
VAISNSFGFGGHNSVVVFSAFKP SEQ ID NO: 5
Amino acid sequence of the *U. californica* KASI (D3150, pSZ4341).
MESLSLTPKSLPLKTLLPFRPRPKNLSRRKSQNPKPISSSSSPERETDPKKRVVITGMGL
VSVFGNDVDAYYDRLLSGESGIAPIDRFDASKFPTRFAGQIRGFTSDGYIDGKNDRRL
DDCLRYCIVSGKKALENAGLGPDLMDGKIDKERAGVLVGTGMGGLTVFSNGVQTL
HEKGYRKMTPFFIPYAITNMGSALLAIDLGFMGPNYSISTACATSNYCFYAAANHIRR
GEADVMLAGGTEAAIIPIGLGGFVACRALSQRNDDPQTASRPWDKDRDGFVMGEGA
GVLVMESLEHAMKRDAPIIAEYLGGAVNCDAYHMTDPRADGLGVSTCIERSLEDAG
VAPEEVNYINAHATSTLAGDLAEVNAIKKVFTNTSEIKINATKSMIGHCLGAAGGLE
AIATIKAINTGWLHPSINQFNPEPSVEFDTVANKKQQHEVNVAISNSFGFGGHNSVVV
FSAFKP SEQ ID NO: 6
Amino acid sequence of the *U. californica* KASIV (D3152, pSZ4343).
MTQTLICPSSMETLSLTKQSHFRLRLPTPPHIRRGGGHRHPPPFISASAAPRRETDPKK
RVVITGMGLVSVFGTNVDVYYDRLLAGESGVGTIDRFDASMFPTRFGGQIRRFTSEG
YIDGKNDRRLDDYLRYCLVSGKKAIESAGFDLHNITNKIDKERAGILVGSGMGGLKV
FSDGVESLIEKGYRKISPFFIPYMIPNMGSALLGIDLGFMGPNYSISTACATSNYCIYAA
ANHIRQGDADLMVAGGTEAPIIPIGLGGFVACRALSTRNDDPQTASRPWDIDRDGFV
MGEGAGILVLESLEHAMKRDAPILAEYLGGAVNCDAHHMTDPRADGLGVSTCIESS
LEDAGVAAEEVNYINAHATSTPTGDLAEMKAIKNVFRNTSEIKINATKSMIGHCLGA
SGGLEAIATLKAITTGWLHPTINQFNPEPSVDFDTVAKKKKQHEVNVAISNSFGFGGH
NSVLVFSAFKP SEQ ID NO: 7
Amino acid sequence of the *C. wrightii* KASAI (D3153, pSZ4379). The algal transit peptide is underlined.
MASAAFTMSACPAMTGRAPGARRSGRPVATRLRYVFQCLVASCIDPCDQYRSSASL
SFLGDNGFASLFGSKPFMSNRGHRRLRRASHSGEAMAVALQPAQEAGTKKKPVIKQ
RRVVVTGMGVVTPLGHEPDVFYNNLLDGVSGISEIETFDCTQFPTRIAGEIKSFSTDG
WVAPKLSKRMDKFMLYLLTAGKKALADGGITDEVMKELDKRKCGVLIGSGMGGM
KVFNDAIEALRVSYKKMNPFCVPFATTNMGSAMLAMDLGWMGPNYSISTACATSN
FCILNAANHIIRGEADMMLCGGSDAVIIPIGLGGFVACRALSQRNSDPTKASRPWDSN
RDGFVMGEGAGVLLLEELEHAKKRGATIYAEFLGGSFTCDAYHMTEPHPEGAGVIL
CIEKALAQAGVSKEDVNYINAHATSTSAGDIKEYQALARCFGQNSELRVNSTKSMIG
HLLGAAGGVEAVTVVQAIRTGWIHPNLNLEDPDKAVDAKLLVGPKKERLNVKVGL
SNSFGFGGHNSSILFAPCNV -continued

SEQUENCE LISTING

SEQ ID NO: 8
Amino acid sequence of the *C. avigera* KASIVb (D3287, pSZ4453).
MASAAFTMSACPAMTGRAPGARRSGRPVATRLRGSTFQCYIGDNGFGSKPPRSNRG
HLRLGRTSHSGEVMAVAMQSAQEVSTKEKPATKQRRVVVTGMGVVTALGHDPDV
YYNNLLDGVSGISEIENFDCSQLPTRIAGEIKSFSADGWVAPKFSRRMDKFMLYILTA
GKKALVDGGITEDVMKELDKRKCGVLIGSGLGGMKVFSESIEALRTSYKKISPECVPF
STTNMGSAILAMDLGWMGPNYSISTACATSNFCILNAANHITKGEADMMLCGGSDS
VILPIGMGGFVACRALSQRNNDPTKASRPWDSNRDGFVMGEGAGVLLLEELEHAKK
RGATIYAEFLGGSFTCDAYHMTEPHPEGAGVILCIEKALAQSGVSREDVNYINAHATS
TPAGDIKEYQALAHCFGQNSELRVNSTKSMIGHLLGGAGGVEAVTVVQAIRTGWIHP
NINLDDPDEGVDAKLLVGPKKEKLKVKVGLSNSFGFGGHNSSILFAPCN SEQ ID NO: 9
Amino acid sequence of the *C. paucipetala* KASIVb (D3288, pSZ4454).
MASAAFTMSACPAMTGRAPGARRSGRPVATRLRGSTFQCLGDIGFASLIGSKPPRSN
RNHRRLGRTSHSGEVMAVAMQPAHEASTKNKPVTKQRRVVVTGMGVATPLGHDP
DVYYNNLLDGVSGISQIENFDCTQFPTRIAGEIKSFSTEGYVIPKFAKRMDKFMLYLL
TAGKKALEDGGITEDVMKELDKRKCGVLIGSGMGGMKIINDSIAALNVSYKKMTPF
CVPFSTTNMGSAMLAIDLGWMGPNYSISTACATSNYCILNAANHIVRGEADMMLCG
GSDAVIIPVGLGGFVACRALSQRNNDPTKASRPWDSNRDGFVMGEGAGVLLLEELE
HAKKRGATIYAEFLGGSFTCDAYHMTEPHPDGAGVILCIEKALAQSGVSREDVNYIN
AHATSTPAGDIKEYQALAHCFGQNSELRVNSTKSMIGHLLGAAGGVEAVTVVQAIR
TGWIHPNINLENPDEAVDAKLLVGPKKEKLKVKVGLSNSFGFGGHNSSILFAPYN SEQ ID NO: 10
Amino acid sequence of the *C. ignea* KASIVb (D3289, pSZ4455). The algal transit peptide is underlined.
MASAAFTMSACPAMTGRAPGARRSGRPVATRLRGSTSQCLVTSYIDPCNKYCSSASL
SFLGDNGFASLFGSKPERSNRGHRRLGRASHSGEAMAVALQPAQEVTTKKKPVIKQR
RVVVTGMGVVTPLGHEPDVYYNNLLDGVSGISEIETFDCTQFPTRIAGEIKSFSTDGW
VAPKLSKRMDKFMLYLLTAGKKALADGGITDDVMKELDKRKCGVLIGSGMGGMK
LENDSIEALRISYKKMNPFCVPFATTNMGSAMLAMDLGWMGPNYSISTACATSNFCI
LNASNHIVRGEADMMLCGGSDSVTVPLGVGGFVACRALSQRNNDPTKASRPWDSN
RDGFVMGEGAGVLLLEELEHAKKRGATIYAEFLGGSFTSDAYHMTEPHPEGAGVILC
IEKALAQSGVSREDVNYINAHATSTPAGDIKEYQALARCFGQNSELRVNSTKSMIGH
LLGAAGGVEAVAVIQAIRTGWIHPNINLEDPDEAVDPKLLVGPKKEKLKVKVALSNS
FGFGGHNSSILFAPCN SEQ ID NO: 11
Amino acid sequence of the *C. procumbens* KASIV (D3290, pSZ4456). The algal transit peptide is underlined.
MASAAFTMSACPAMTGRAPGARRSGRPVATRLRGSTFQCLVTSHNDPCNQYCSSAS
LSFLGDNGFGSKPFRSNRGHRRLGRASHSGEAMAVALQPAQEVATKKKPAMKQRR
VVVTGMGVVTPLGHEPDVYYNNLLDGVSGISEIETFDCTQFPTRIAGEIKSFSTDGWV
APKLSKRMDKFMLYLLTAGKKALADGGITDDVMKELDKRKCGVLIGSGMGGMKLF
NDSIEALRVSYKKMNPFCVPFATTNMGSAMLAMDLGWMGPNYSISTACATSNFCIL
NAANHIVRGEADMMLCGGSDAVIIPIGLGGFVACRALSQRNNDPTKASRPWDSNRD
GFVMGEGAGVLLLEELEHAKKRGATIYAEFLGGSFTCDAYHMTEPHPEGAGVILCIE
KALAQSGVSREDVNYINAHATSTPAGDIKEYQALAHCFGQNSELRVNSTKSMIGHLL
GAAGGVEAVTVIQAIRTGWIHPNLNLEDPDKAVDAKFLVGPKKERLNVKVGLSNSF
GFGGHNSSILFAPCN SEQ ID NO: 12
Amino acid sequence of the *C. paucipetala* KASIVa (D3291, pSZ4457). The algal transit peptide is underlined.
MASAAFTMSACPAMTGRAPGARRSGRPVATRLRGSTFQCLVNSHIDPCNQNVSSAS
LSFLGDNGFGSNPFRSNRGHRRLGRASHSGEAMAVALQPAQEVATKKKPAIKQRRV
VVTGMGVVTPLGHEPDVFYNNLLDGVSGISEIETFDCTQFPTRIAGEIKSFSTDGWVA
PKLSKRMDKFMLYLLTAGKKALADAGITEDVMKELDKRKCGVLIGSGMGGMKLFN
DSIEALRVSYKKMNPFCVPFATTNMGSAMLAMDLGWMGPNYSISTACATSNFCILN
AANHIIRGEADMMLCGGSDAVIIPIGLGGFVACRALSQRNSDPTKASRPWDSNRDGF
VMGEGAGVLLLEELEHAKKRGATIYAEFLGGSFTCDAYHMTEPHPDGAGVILCIEKA
LAQSGVSREDVNYINAHATSTPAGDIKEYQALAHCFGQNSELRVNSTKSMIGHLLGA
AGGVEAVTVIQAIRTGWIHPNLNLEDPDEAVDAKFLVGPKKERLNVKVGLSNSFGFG
GHNSSILFAPYN SEQ ID NO: 13
Amino acid sequence of the *C. painteri* KASIV (D3292, pSZ4458). The algal transit peptide is underlined.
MASAAFTMSACPAMTGRAPGARRSGRPVATRLRGSTPQCLDPCNQHCFLGDNGFAS
LIGSKPPRSNLGHLRLGRTSHSGEVMAVAQEVSTNKKHATKQRRVVVTGMGVVTPL
GHDPDVYYNNLLEGVSGISEIENFDCSQLPTRIAGEIKSFSTDGLVAPKLSKRMDKFM
LYILTAGKKALADGGITEDVMKELDKRKCGVLIGSGLGGMKVFSDSVEALRISYKKI
SPFCVPFSTTNMGSAMLAMDLGWMGPNYSISTACATSNFCILNAANHITKGEADMM
LCGGSDAAILPIGMGGFVACRALSQRNNDPTKASRPWDSNRDGFVMGEGAGVLLLE
ELEHAKKRGATIYAEFLGGSFTCDAYHMTEPHPDGAGVILCIEKALAQSGVSREEVN -continued

SEQUENCE LISTING

YINAHATSTPAGDIKEYQALAHCFGQNSELRVNSTKSMIGHLLGGAGGVEAVTVVQ
AIRTGWIHPNINLEDPDKGVDAKLLVGPKKEKLKVKVGLSNSFGFGGHNSSILFAPCN

SEQ ID NO: 14
Amino acid sequence of the *C. avigera* KASIVa (D3293, pSZ4459). The algal transit peptide is underlined.
MASAAFTMSACPAMTGRAPGARRSGRPVATRLRGSTFQCLVTSYNDPCEQYRSSAS
LSFLGDNGFASLFGSKPFRSNRGHRRLGRASHSGEAMAVALQPAQEVGTKKKPVIKQ
RRVVVTGMGVVTPLGHEPDVYYNNLLDGVSGISEIETFDCTQFPTRIAGEIKSFSTDG
WVAPKLSKRMDKFMLYLLTAGKKALADGGITDDVMKELDKRKCGVLIGSGLGGM
KVFSESIEALRTSYKKISPFCVPFSTTNMGSAILAMDLGWMGPNYSISTACATSNFCIL
NAANHITKGEADMMLCGGSDSVILPIGMGGFVACRALSQRNNDPTKASRPWDSNRD
GFVMGEGAGVLLLEELEHAKKRGATIYAEFLGGSFTCDAYHMTEPHPEGAGVILCIE
KALAQSGVSREDVNYINAHATSTPAGDIKEYQALAHCFGQNSELRVNSTKSMIGHLL
GGAGGVEAVTVVQAIRTGWIHPNINLDDPDEGVDAKLLVGPKKE KLKVKVGLSNSF
GFGGHNSSILFAPCN SEQ ID NO: 15
Amino acid sequence of the *C. ignea* KASIVa (D3294, pSZ4460). The algal transit peptide is underlined.
MASAAFTMSACPAMTGRAPGARRSGRPVATRLRGSTSQCLVTSYIDPCNKYCSSASL
SFLGDNGFASLFGSKPFRSNRGHRRLGRASHSGEAMAVALQPAQEVTTKKKPVIKQR
RVVVTGMGVVTPLGHEPDVYYNNLLDGVSGISEIETFDCTQFPTRIAGEIKSFSTDGW
VAPKLSKRMDKFMLYLLTAGKKALADGGITDDVMKELDKRKCGVLIGSGMGGMK
LFNDSIEALRISYKKMNPFCVPFATTNMGSAMLAMDLGWMGPNYSISTACATSNFCI
LNASNHIVRGEADMMLCGGSDAVIIPIGLGGFVACRALSQRNNDPTKASRPWDSNRD
GFVMGEGAGVLLLEELEHAKKRGATIYAEFLGGSFTCDAYHMTEPHPEGAGVILCIE
KALAQAGVSKEDVNYINAHATSTPAGDIKEYQALAQCFGQNSELRVNSTKSMIGHL
LGAAGGVEAVTVVQAIRTGWIHPNLNLEDPDKAVDAKLLVGPKKERLNVKVGLSNS
FGFGGHNSSILFAPYN SEQ ID NO: 16
Amino acid sequence of the *C. avigera* KASIa (D3342, pSZ4511).
MQSLHSPALRASPLDPLRLKSSANGPSSTAAFRPLRRATLPNIRAASPTVSAPKRETDP
KKRVVITGMGLVSVFGSDVDAYYEKLLSGESGISLIDRFDASKFPTRFGGQIRGFNAT
GYIDGKNDRRLDDCLRYCIVAGKKALENSDLGGDSLSKIDKERAGVLVGTGMGGLT
VFSDGVQNLIEKGHRKISPFFIPYAITNMGSALLAIDLGLMGPNYSISTACATSNYCFY
AAANHIRRGEADLMIAGGTEAAIIPIGLGGFVACRALSQRNDDPQTASRPWDKDRDG
FVMGEGAGVLVMESLEHAMKRGAPIIAEYLGGAVNCDAYHMTDPRADGLGVSSCIE
SSLEDAGVSPEEVNYINAHATSTLAGDLAEINAIKKVFKNTKDIKINATKSMIGHCLG
ASGGLEAIATIKGITTGWLHPSINQFNPEPSVEFDTVANKKQQHEVNVAISNSFGFGG
HNSVVAFSAFKP SEQ ID NO: 17
Amino acid sequence of the *C. pulcherima* KASI (D3343, pSZ4512).
MHSLQSPSLRASPLDPFRPKSSTVRPLHRASIPNVRAASPTVSAPKRETDPKKRVVITG
MGLVSVFGSDVDAYYDKLLSGESGIGPIDRFDASKFPTRFGGQIRGFNSMGYIDGKN
DRRLDDCLRYCIVAGKKSLEDADLGADRLSKIDKERAGVLVGTGMGGLTVFSDGVQ
SLIEKGHRKITPFFIPYAITNMGSALLAIELGLMGPNYSISTACATSNYCFHAAANHIRR
GEADLMIAGGTEAAIIPIGLGGFVACRALSQRNDDPQTASRPWDKDRDGFVMGEGA
GVLVLESLEHAMKRGAPIIAEYLGGAINCDAYHMTDPRADGLGVSSCIESSLEDAGV
SPEEVNYINAHATSTLAGDLAEINAIKKVFKNTKDIKINATKSMIGHCLGASGGLEAI
ATIKGINTGWLHPSINQFNPEPSVEFDTVANKKQQHEVNVAISNSFGFGGHNSVVAFS
AFKP SEQ ID NO: 18
Amino acid sequence of the *C. avigera* mitochondrial KAS (D3344, pSZ4513).
MVFLPWRKMLCPSQYRFLRPLSSSTTFDPRRVVVTGLGMVTPLGCGVNTTWKQLIE
GKCGIRAISLEDLKMDAFDIDTQAYVFDQLTSKVAATVPTGVNPGEFNEDLWFNQKE
HRAIARFIAYALCAADEALKDANWEPTEPEEREMTGVSIGGGTGSISDVLDAGRMIC
EKKLRRLSPFFIPRILINMASGHVSMKYGFQGPNHAAVTACATGAHSIGDAARMIQF
GDADVMVAGGTESSIDALSIAGFCRSRALTTKYNSCPQEASRPFDTDRDGFVIGEGSG
VLVLEELDHARKRGAKMYAEFCGYGMSGDAHHITQPHSDGRGAILAMTRALKQSN
LHPDQVDYVNAHATSTSLGDAIEAKAIKTVFSDHAMSGSLALSSTKGAIGHLLGAAG
AVEAIFSILAIKNGLAPLTLNVARPDPVFTERFVPLTASKEMHVRAALSNSFGFGGTN
TTLLFTSPPQN SEQ ID NO: 19
Amino acid sequence of the *C. avigera* KASIII (D3345, pSZ4514).
MANAYGFVGSSVPTVGRAAQFQQMGSGFCSVDFISKRVFCCSAVQGADKPASGDSR
AEYRTPRLVSRGCKLIGSGSAIPTLQVSNDDLAKIVDTNDEWISVRTGIRNRRVLTGK
DSLTNLATEAARKALEMAQVDAEDVDMVLMCTSTPEDLFGSAPQIQKALGCKKNPL
SYDITAACSGFVLGLVSAACHIRGGGFNNVLVIGADSLSRYVDWTDRGTCILFGDAA
GAVLVQSCDAEEDGLFAFDLHSDGDGQRHLRAVITENETDHAVGTNGSVSDFPPRRS
SYSCIQMNGKEVFRFACRSVPQSIELALGKAGLNGSNIDWLLLHQANQRIIDAVATRL
EVPQERVISNLANYGNTSAASIPLALDEAVRGGKVKPGHLIATAGFGAGLTWGSAIV
RWG -continued

SEQUENCE LISTING

SEQ ID NO: 20
HA Epitope TAG amino acid sequence
TMYPYDVPDYA

SEQ ID NO: 21
*C. palustris* KASIV CDS
ATGGCGGCCGCCGCTTCCATGGTTGCGTCCCCACTCTGTACGTGGCTCGTAGCCG
CTTGCATGTCCACTTCCTTCGACAACGACCCACGTTCCCCGTCCATCAAGCGTCTC
CCCCGCCGGAGGAGGACTCTCTCCCAATCCTCCCTCCGCGGCGGATCCACCTTCC
AATGCCTCGTCACCTCATACATCGACCCTTGCAATCAGTTCTCCTCCTCCGCCTCC
CTTAGCTTCCTCGGGGATAACGGATTCGCATCCCTTTTCGGATCCAAGCCTTTCCG
GTCCAATCGCGGCCACCGGAGGCTCGGCCGTGCTTCCCATTCCGGGGAGGCCATG
GCCGTGGCTTTGGAACCTGCACAGGAAGTCGCCACGAAGAAGAAACCTCTTGTC
AAGCAAAGGCGAGTAGTTGTTACAGGAATGGGCGTGGTGACTCCTCTAGGCCAT
GAACCTGATGTTTACTACAACAATCTCCTAGATGGAGTAAGCGGCATAAGTGAG
ATAGAGGCCTTCGACTGCACTCAGTTTCCCACGAGAATTGCCGGAGAGATCAAGT
CTTTTTCCACAGATGGATGGGTGGCCCCAAAGCTCTCCAAGAGGATGGACAAGTT
CATGCTTTACTTGTTGACTGCTGGCAAGAAAGCATTAGCGGATGGTGGAATCACC
GATGATGTGATGAAAGAGCTTGATAAAAGAAAGTGTGGAGTTCTCATTGGCTCC
GGATTGGGCGGCATGAAGCTGTTCAGTGATTCCATTGAAGCTCTGAGGATTTCAT
ATAAGAAGATGAATCCCTTTTGTGTACCTTTTGCTACTACAAATATGGGATCAGC
TATGCTTGCAATGGACTTGGGATGGATGGGTCCTAACTACTCGATATCAACTGCC
TGTGCTACAAGTAATTTCTGTATACTGAATTCTGCAAATCACATAGTCAGAGGCG
AAGCTGACATGATGCTTTGTGGTGGCTCGGATGCGGTCATTATACCTATTGGTTT
GGGAGGTTTTGTGGCGTGCCGAGCTTTGTCACAGAGGAATAATGACCCTACCAA
AGCTTCGAGACCATGGGACAGTAATCGTGATGGATTTGTAATGGGCGAAGGAGC
TGGAGTGTTACTTCTCGAGGAGTTAGAGCATGCAAAGAAAAGAGGTGCCACCAT
TTATGCGGAATTTTTAGGGGGCAGTTTCACTTGCGATGCCTACCATATGACCGAG
CCTCACCCTGAAGGTGCTGGAGTGATCCTCTGCATAGAGAAGGCCTTGGCTCAGG
CCGGAGTCTCTAGAGAAGACGTAAATTACATAAATGCGCATGCAACTTCCACTCC
TGCTGGAGATATCAAGGAATACCAAGCTCTCGCACACTGCTTCGGCCAAAACAG
TGAGCTGAGAGTGAATTCCACTAAATCGATGATCGGTCATCTTATTGGAGCAGCT
GGTGGTGTAGAAGCAGTTACCGTAGTTCAGGCGATAAGGACTGGGTGGATCCAT
CCAAATCTTAATTTGGAGGACCCGGACAAAGCCGTGGATGCAAAAGTGCTCGTA
GGACCTAAGAAGGAGAGACTAAATGTCAAGGTCGGTTTGTCCAATTCATTTGGGT
TCGGTGGTCATAACTCGTCCATACTCTTCGCCCCTTACAATTAG SEQ ID NO: 22
*C. camphora* KASIV CDS
ATGGCAATGATGGCAGGTTCTTGTTCCAATTTGGTGATTGGAAACAGAGAATTGG
GTGGGAATGGGCCTTCTTTGCTTCACTACAATGGCCTCAGACCATTGGAAAATAT
TCAAACAGCCTCAGCTGTGAAAAAGCCAAATGGGTTATTTGCATCTTCTACAGCT
CGAAAATCCAAAGCTGTCAGAGCCATGGTATTGCCCACTGTAACAGCTCCAAAA
CGCGAAAAAGATCCCAAGAAGCGGATTGTAATAACAGGAATGGGCCTGGTTTCC
GTCTTTGGAAATGACATTGATACATTTTATAGTAAACTACTGGAAGGAGAGAGCG
GGATTGGCCCAATCGACAGATTTGATGCTTCTTCCTTCTCAGTGAGATTTGCTGGT
CAGATTCACAATTTCTCATCCAAAGGATACATTGATGGGAAGAATGATCGTCGGC
TAGATGACTGCTGGAGGTATTGCCTTGTGGCTGGAAGAAGAGCCCTTGAAGATG
CCAATCTTGGACCAGAGGTATTGGAAAAAATGGACCGATCTCGAATAGGGGTGC
TGATAGGGACAGGAATGGGTGGGTTGTCAGCCTTTAGCAATGGAGTTGAGTCTCT
GATCCAGAAGGGCTACAAGAAAATCACTCCATTTTTTATTCCTTACTCCATCACC
AATATGGGCTCTGCTCTTTTAGCAATCGACACGGGCGTAATGGGACCAAACTACT
CCATTTCAACAGCATGTGCAACCGCAAACTATTGCTTCCATGCTGCTGCAAATCA
TATAAGAAGGGGTGAAGCTGAAATCATGGTGACTGGAGGGACAGAGGCAGCAG
TCTCAGCTACTGGAGTTGGCGGATTCATAGCATGTAGAGCCTTATCGCACAGGAA
TGATGAGCCCCAGACGGCCTCGAGACCATGGGATAAAGATCGGGATGGTTTCGT
CATGGGCGAAGGCGCTGGTGTGCTGGTGATGGAGAGCTTGCATCATGCAAGAAA
GAGAGGAGCAAACATAATTGCAGAGTATTTAGGAGGAGCAGTAACATGTGATGC
ACATCACATGACAGATCCTCGAGCTGATGGTCTCGGGGTTTCTTCTTGCATAACC
AAGAGCTTAGAAGATGCAGGAGTCTCCCCAGAAGAGGTGAACTATGTGAATGCT
CATGCAACATCAACACTTGCAGGAGATTTAGCAGAGGTTAATGCCATAAAGAAG
GTCTTCAAGGACACATCTGAAATGAAAATGAATGGAACTAAGTCAATGATTGGA
CACTGTCTTGGAGCAGCTGGTGGATTAGAAGCCATTGCGACCATCAAAGCTATCA
ATACTGGCTGGCTACATCCAACCATCAATCAATTTAACATAGAACCAGCGGTAAC
TATCGACACGGTCCCAAATGTGAAGAAAAAGCATGATATCCATGTTGGCATCTCT
AACTCATTTGGCTTTGGTGGGCACAACTCGGTGGTCGTTTTTGCTCCCTTCATGCC
ATGA SEQ ID NO: 23
*C. camphora* KASI CDS
ATGCAAATCCTCCAAACCCCATCATCATCATCGTCTTCTCTCCGCATGTCGTCCAT
GGAATCTCTCTCTCTCACCCCTAAATCTCTCCCTCTCAAAACCCTTCTTCCCCTTC
GTCCTCGCCCTAAAAACCTCTCCAGACGCAAATCCCAAAACCCTAGACCCATCTC
CTCCTCTTCCTCCCCCGAGAGAGAGACGGATCCCAAGAAGCGAGTCGTCATCACC
GGGATGGGCCTCGTCTCCGTCTTCGGCAACGATGTCGATGCCTACTACGACCGCC
TCCTCTCGGGAGAGAGCGGCATCGCCCCCATCGATCGCTTCGACGCCTCCAAGTT -continued

SEQUENCE LISTING

CCCCACCAGATTCGCCGGTCAGATCCGAGGGTTCACCTCCGACGGCTACATTGAC
GGGAAGAACGACCGCCGGTTAGACGATTGTCTCAGATACTGTATTGTTAGTGGG
AAGAAGGCGCTCGAGAATGCCGGCCTCGGACCCCATCTCATGGACGGAAAGATT
GACAAGGAGAGAGCTGGTGTGCTTGTCGGGACAGGCATGGGTGGTCTTACAGTT
TTCTCTAATGGGGTCCAGACTCTACATGAGAAAGGTTACAGGAAAATGACTCCGT
TTTTCATCCCTTATGCCATAACAAACATGGGTTCTGCCTTGCTTGCAATTGAACTT
GGTTTTATGGGCCCAAACTATTCTATCTCAACTGCATGTGCTACCTCCAATTATTG
CTTTTATGCTGCTGCTAACCATATACGGAGAGGTGAGGCTGATCTGATGCTTGCT
GGTGGAACTGAAGCTGCAATTATTCCTATTGGATTAGGAGGCTTTGTTGCATGTA
GAGCTTTATCACAGAGAAATGATGACCCCCAGACAGCTTCAAGACCATGGGACA
AAGATCGAGACGGTTTTGTTATGGGTGAAGGTGCTGGAGTATTGGTAATGGAGA
GCTTGGAGCATGCTATGAAACGTGATGCACCAATTATTGCTGAGTATTTAGGAGG
TGCAGTGAACTGTGATGCGTATCATATGACGGATCCTAGAGCTGATGGGCTCGGG
GTTTCAACATGCATAGAAAGAAGTCTTGAAGATGCTGGTGTGGCACCTGAAGAG
GTTAACTACATAAATGCACATGCAACTTCCACTCTTGCAGGAGACCTGGCTGAGG
TGAATGCGATCAAAAAGGTTTTTACAAACACTTCAGAGATCAAAATCAATGCAA
CCAAGTCTATGATAGGGCACTGCCTTGGAGCGGCCGGGGGGTTAGAAGCCATTG
CCACAATCAAAGCAATAAATACTGGTTGGCTGCACCCTTCTATAAACCAATTTAA
TCCAGAGCCCTCTGTTGAGTTTGACACTGTAGCAAATAAAAAGCAGCAGCATGA
AGTGAATGTTGCCATTTCCAACTCTTTCGGGTTTGGCGGACACAACTCAGTCGTG
GTGTTTTCGGCATTCAAGCCTTGA

SEQ ID NO: 24
*Umbellularia californica* KASI CDS
ATGGAATCTCTCTCTCTCACCCCTAAATCTCTCCCTCTCAAAACCCTTCTTCCCTTT
CGTCCTCGCCCTAAAAACCTCTCCAGACGCAAATCCCAAAACCCTAAACCCATCT
CCTCCTCTTCCTCCCCGGAGAGAGAGACGGATCCCAAGAAGCGAGTCGTCATCAC
CGGGATGGGCCTCGTCTCCGTCTTCGGCAACGACGTCGATGCCTACTACGACCGC
CTCCTCTCCGGAGAGAGCGGCATCGCCCCCATCGATCGCTTCGACGCCTCCAAGT
TCCCCACCAGATTCGCCGGTCAGATCCGAGGGTTCACCTCCGACGGCTACATTGA
CGGGAAGAACGACCGCCGGTTAGACGATTGTCTCAGATACTGTATCGTTAGTGG
GAAGAAGGCGCTCGAGAATGCCGGCCTCGGACCCGATCTCATGGACGGAAAGAT
TGACAAGGAGCGAGCTGGTGTGCTTGTCGGGACAGGCATGGGTGGTCTTACAGT
TTTCTCTAATGGGGTTCAGACTCTCCATGAGAAAGGTTACAGGAAAATGACTCCG
TTTTTCATCCCTTATGCCATAACAAACATGGGTTCTGCCTTGCTTGCAATTGACCT
TGGTTTTATGGGCCCAAACTATTCTATCTCAACTGCATGTGCTACCTCCAATTATT
GCTTTTATGCTGCTGCTAACCATATACGGAGAGGTGAGGCTGATGTGATGCTTGC
TGGTGGAACTGAAGCTGCAATTATTCCTATTGGCTTAGGAGGCTTTGTTGCATGT
AGAGCTTTATCACAGCGAAATGATGACCCCCAGACAGCTTCAAGACCATGGGAC
AAAGATCGAGACGGTTTTGTTATGGGTGAAGGTGCTGGAGTATTGGTAATGGAG
AGCTTGGAGCATGCTATGAAACGTGATGCACCAATTATTGCTGAGTATTTAGGAG
GTGCAGTGAACTGTGATGCGTATCATATGACGGATCCTAGAGCTGATGGGCTCGG
GGTTTCAACATGCATAGAAAGAAGTCTTGAAGATGCTGGTGTGGCACCTGAAGA
GGTTAACTACATAAATGCACATGCAACTTCCACACTTGCAGGTGACCTGGCCGAG
GTGAATGCCATCAAAAAGGTTTTTACAAACACTTCAGAGATCAAAATCAATGCA
ACCAAGTCTATGATAGGGCACTGCCTTGGAGCGGCCGGGGGTTTAGAAGCCATT
GCCACAATCAAAGCAATAAATACTGGTTGGCTGCACCCTTCTATAAACCAATTTA
ATCCAGAGCCCTCTGTTGAGTTTGACACTGTAGCAAATAAAAAGCAGCAGCATG
AAGTGAATGTTGCCATTTCCAACTCTTTCGGGTTTGGTGGACACAACTCGGTCGT
GGTGTTTTCGGCATTCAAGCCTTGA SEQ ID NO: 25
*Umbellularia californica* KASIV CDS
ATGACGCAAACCCTCATCTGCCCATCCTCCATGGAAACCCTCTCTCTTACCAAAC
AATCCCATTTCAGACTCAGGCTACCCACTCCTCCTCACATCAGACGCGGCGGCGG
CCATCGCCATCCTCCTCCCTTCATCTCCGCCTCCGCCGCCCCTAGGAGAGAGACC
GATCCGAAGAAGAGAGTCGTCATCACGGGAATGGGCCTCGTCTCCGTCTTCGGC
ACCAACGTCGATGTCTACTACGATCGCCTCCTCGCCGGCGAGAGCGGCGTTGGCA
CTATCGATCGCTTCGACGCGTCGATGTTCCCGACGAGATTCGGCGGCCAGATCCG
GAGGTTCACGTCGGAGGGGTACATCGACGGGAAGAACGACCGGCGGCTGGATGA
CTACCTCCGGTACTGCCTCGTCAGCGGGAAGAAGGCGATCGAGAGTGCTGGCTTC
GATCTCCATAACATCACCAACAAGATTGACAAGGAGCGAGCTGGGATACTTGTT
GGGTCAGGCATGGGCGGTCTTAAAGTTTTCTCTGATGGTGTTGAGTCTCTTATCG
AGAAAGGTTACAGGAAAATAAGTCCATTTTTCATCCCTTATATGATACCAAACAT
GGGTTCTGCTTTGCTTGGAATTGACCTTGGTTTCATGGGACCAAACTACTCAATTT
CAACTGCTTGTGCTACGTCAAATTATTGCATTTATGCTGCTGCAAATCATATCCGA
CAAGGTGATGCCGACCTAATGGTTGCTGGTGGAACTGAGGCTCCAATTATTCCAA
TTGGCTTAGGGGGCTTTGTAGCATGTAGAGCTTTGTCAACAAGAAATGATGATCC
CCAGACAGCTTCAAGGCCATGGGACATAGACCGAGATGGTTTTGTTATGGGCGA
AGGAGCTGGAATATTGGTATTGGAGAGCTTGGAACATGCAATGAAACGTGATGC
ACCAATTCTTGCTGAGTATTTAGGAGGTGCAGTTAACTGTGATGCTCATCATATG
ACAGATCCTCGAGCTGATGGGCTTGGGGTTTCAACATGCATTGAAAGCAGTCTTG
AAGATGCCGGCGTGGCAGCAGAAGAGGTTAACTATATAAATGCACACGCGACTT
CAACACCTACAGGTGACCTGGCTGAGATGAAGGCTATAAAAAATGTATTTAGGA
ACACTTCTGAGATCAAAATCAATGCAACCAAGTCTATGATTGGGCATTGCCTTGG
AGCGTCTGGGGGGCTAGAAGCCATTGCCACATTGAAAGCGATTACAACTGGTTG
GCTTCATCCAACTATAAACCAATTTAATCCAGAGCCTTCTGTTGACTTTGATACG -continued

SEQUENCE LISTING

GTGGCAAAGAAAAAGAAGCAGCATGAAGTTAATGTTGCCATTTCAAACTCTTTTG
GATTCGGAGGACACAACTCAGTGTTGGTGTTTTCGGCATTCAAGCCTTGA

SEQ ID NO: 26
*C. wrightii* KASAI CDS (D3153, pSZ4379)
atggcttccgcggcattcaccatgtcggcgtgccccgcgatgactggcagggcccctggggcacgtcgctccggacggccagtcgc
cacccgcctgaggtacgtattccagtgcctggtggccagctgcatcgacccctgcgaccagtaccgcagcagcgccagcctgagctt
cctgggcgacaacggcttcgccagcctgttcggcagcaagcccttcatgagcaaccgcggccaccgccgcctgcgccgcgccagc
cacagcggcgaggccatggccgtggccctgcagcccgcccaggaggccggcaccaagaagaagcccgtgatcaagcagcgcc
gcgtggtggtgaccggcatgggcgtggtgacccccctgggccacgagcccgacgtgttctacaacaacctgctggacggcgtgag
cggcatcagcgagatcgagaccttcgactgcacccagttccccacccgcatcgccggcgagatcaagagcttcagcaccgacggct
gggtggcccccaagctgagcaagcgcatggacaagttcatgctgtacctgctgaccgccggcaagaaggccctggccgacggcgg
catcaccgacgaggtgatgaaggagctggacaagcgcaagtgcggcgtgctgatcggcagcggcatgggcggcatgaaggtgttc
aacgacgccatcgaggccctgcgcgtgagctacaagaagatgaaccccttctgcgtgcccttcgccaccaccaacatgggcagcgc
catgctggccatggacctgggctggatgggccccaactacagcatcagcaccgcctgcgccaccagcaacttctgcatcctgaacgc
cgccaaccacatcatccgcggcgaggccgacatgatgctgtgcggcggcagcgacgccgtgatcatccccatcggcctgggcggc
ttcgtggcctgccgcgccctgagccagcgcaacagcgaccccaccaaggccagccgcccctgggacagcaaccgcgacggcttc
gtgatgggcgagggcgccggcgtgctgctgctggaggagctggagcacgccaagaagcgcggcgccaccatctacgccgagttc
ctgggcggcagcttcacctgcgacgcctaccacatgaccgagccccaccccgagggcgccggcgtgatcctgtgcatcgagaagg
ccctggcccaggccggcgtgagcaaggaggacgtgaactacatcaacgcccacgccaccagcaccagcgccggcgacatcaag
gagtaccaggccctggcccgctgcttcggccagaacagcgagctgcgcgtgaacagcaccaagagcatgatcggccacctgctgg
gcgccgccggcggcgtggaggccgtgaccgtggtgcaggccatccgcaccggctggattcaccccaacctgaacctggaggacc
ccgacaaggccgtggacgccaagctgctggtgggccccaagaaggagcgcctgaacgtgaaggtgggcctgagcaacagcttcg
gcttcggcggccacaacagcagcatcctgttcgcccccctgcaacgtgtga SEQ ID NO: 27
*C. avigera* KASIVb CDS
ATGGCGGCCGCTTCTTGCATGGCTGCGTCCCCTTTCTGTACGTCGCTCGTGGCTGC
ATGCATGTCGACTTCATCCGACAACGACCCATGTCCCCTTTCCCGCCGCGGATCC
ACCTTCCAATGCTACATCGGGGATAACGGATTCGGATCGAAGCCTCCCCGTTCAA
ATCGTGGCCACCTGAGGCTCGGCCGCACTTCACATTCCGGAGAGGTGATGGCTGT
GGCTATGCAATCTGCACAAGAAGTCTCCACAAAGGAGAAACCTGCTACCAAGCA
AAGGCGAGTTGTTGTCACGGGTATGGGTGTGGTGACTGCTCTAGGCCATGACCCC
GATGTTTACTACAACAATCTCCTAGACGGAGTAAGCGGCATAAGCGAGATAGAA
AACTTTGACTGTTCTCAGCTTCCCACGAGAATTGCCGGAGAGATCAAGTCTTTTT
CTGCAGATGGGTGGGTGGCCCCGAAGTTCTCCAGGAGGATGGACAAGTTTATGC
TTTACATTCTGACTGCAGGCAAGAAAGCATTAGTAGATGGTGGAATCACTGAAG
ATGTGATGAAAGAGCTCGATAAAAGAAAGTGTGGAGTTCTCATTGGCTCCGGAT
TGGGCGGTATGAAGGTATTTAGCGAGTCCATTGAAGCTCTGAGGACTTCATATAA
GAAGATCAGTCCCTTTTGTGTACCTTTTTCTACCACGAATATGGGATCCGCTATTC
TTGCAATGGACTTGGGATGGATGGGCCCTAACTATTCGATATCGACTGCCTGTGC
AACAAGTAACTTCTGTATACTGAATGCTGCGAACCACATAACCAAAGGCGAAGC
AGACATGATGCTTTGTGGTGGCTCGGATTCGGTCATTTTACCTATTGGTATGGGA
GGTTTCGTAGCATGCCGAGCTTTGTCACAGAGGAATAATGACCCTACCAAAGCTT
CGAGACCATGGGACAGTAATCGTGATGGATTTGTGATGGGAGAAGGTGCTGGAG
TTTTACTTCTCGAGGAGTTAGAGCATGCAAAGAAAAGAGGCGCAACCATTTATGC
GGAATTTCTTGGTGGGAGTTTCACTTGCGATGCCTACCACATGACCGAGCCTCAC
CCTGAAGGAGCTGGAGTGATCCTCTGCATAGAGAAGGCCTTGGCTCAGTCCGGA
GTCTCGAGGGAAGACGTAAATTACATAAATGCGCATGCAACTTCCACTCCCGCTG
GAGATATCAAAGAATACCAAGCTCTCGCCCACTGTTTCGGCCAAAACAGTGAGTT
AAGAGTGAATTCCACCAAGTCGATGATCGGTCACCTTCTTGGAGGAGCCGGTGG
CGTAGAAGCAGTTACAGTCGTTCAGGCAATAAGGACTGGATGGATCCATCCAAA
TATTAATTTGGACGACCCGGACGAAGGCGTGGATGCAAAACTGCTCGTCGGCCCT
AAGAAGGAGAAACTGAAGGTCAAGGTCGGTTTGTCCAATTCATTCGGGTTCGGC
GGCCATAACTCATCCATACTCTTTGCCCCATGCAATTAG SEQ ID NO: 28
*C. paucipetala* KASIVb CDS
ATGGCGGCCGCTTCATCAATGGTTGCCTCCCCATTCTCTACGTCCCTCGTAGCCGC
CTGCATGTCCACTTCATTCGACAACGACCCACGTTCCCTTTCCCACAACCGCATCC
GCCTCCGCGGATCCACCTTCCAATGCCTCGGGGATATCGGATTCGCTTCCCTCAT
CGGATCCAAGCCTCCGCGTTCAAATCGCAACCACCGGAGGCTCGGCCGCACTTCC
CATTCCGGGGAGGTCATGGCTGTGGCTATGCAACCTGCACATGAAGCTTCCACAA
AGAATAAACCTGTTACCAAGCAAAGGCGAGTAGTTGTGACAGGTATGGGCGTGG
CGACTCCTCTAGGCCATGACCCCGATGTTTACTACAACAATCTCCTAGACGGAGT
AAGTGGCATAAGTCAGATAGAGAACTTCGACTGCACTCAGTTTCCCACGAGAATT
GCCGGAGAGATCAAGTCTTTCTCCACAGAAGGGTATGTGATCCCGAAGTTCGCCA
AGAGGATGGACAAGTTCATGCTTTACTTGCTGACTGCAGGCAAGAAAGCATTAG
AAGATGGTGGAATCACTGAAGATGTGATGAAAGAGCTCGATAAAAGAAAGTGTG
GAGTTCTCATTGGCTCCGGAATGGGCGGTATGAAGATAATCAACGATTCCATTGC
AGCTCTGAATGTTTCATATAAGAAGATGACTCCCTTTTGTGTACCCTTTTCCACCA
CAAATATGGGATCCGCTATGCTTGCGATAGACTTGGGATGGATGGGCCCGAACT
ATTCGATATCAACTGCCTGTGCAACAAGTAACTACTGTATACTGAATGCTGCGAA
CCACATAGTCAGAGGCGAAGCAGATATGATGCTTTGTGGTGGCTCGGATGCGGT
CATTATACCTGTTGGTTTGGGAGGTTTCGTAGCATGCCGAGCTTTGTCACAGAGG
AACAATGACCCTACCAAAGCTTCGAGACCTTGGGACAGTAACCGTGATGGATTT
GTGATGGGAGAAGGAGCCGGAGTGTTACTTCTCGAGGAGTTAGAGCATGCAAAG -continued

SEQUENCE LISTING

AAAAGAGGTGCAACCATTTATGCGGAATTTCTAGGTGGGAGTTTCACTTGCGATG
CCTACCACATGACCGAGCCTCACCCTGATGGAGCTGGAGTGATCCTCTGCATAGA
GAAGGCTTTGGCACAGTCCGGAGTCTCGAGGGAAGACGTCAATTACATAAATGC
GCATGCAACTTCTACTCCTGCTGGAGATATCAAGGAATACCAAGCTCTCGCCCAC
TGTTTCGGCCAAAACAGTGAGTTAAGAGTGAATTCCACCAAATCGATGATCGGTC
ACCTTCTTGGAGCTGCTGGTGGCGTAGAAGCAGTTACAGTAGTTCAGGCAATAAG
GACTGGGTGGATCCATCCAAATATTAATTTGGAAAACCCGGACGAAGCTGTGGA
TGCAAAATTGCTCGTCGGCCCTAAGAAGGAGAAACTGAAGGTCAAGGTCGGTTT
GTCCAATTCATTTGGGTTCGGTGGGCATAACTCATCCATACTCTTCGCCCCTTACA
ATTAG

SEQ ID NO: 29
*C. ignea* KASIVb CDS
ATGGCGGCGGCCGCTTCCATGTTTACGTCCCCACTCTGTACGTGGCTCGTAGCCT
CTTGCATGTCGACTTCCTTCGACAACGACCCACGTTCGCCGTCCGTCAAGCGTCT
CCCCCGCCGGAGGAGGATTCTCTCCCAATGCTCCCTCCGCGGATCCACCTCCCAA
TGCCTCGTCACCTCATACATCGACCCTTGCAATAAGTACTGCTCCTCCGCCTCCCT
TAGCTTCCTCGGGGATAACGGATTCGCATCCCTTTTCGGATCTAAGCCATTCCGG
TCCAATCGCGGCCACCGGAGGCTCGGCCGTGCTTCCCATTCCGGGGAGGCCATGG
CTGTGGCTCTGCAACCTGCACAGGAAGTCACCACGAAGAAGAAACCTGTGATCA
AGCAAAGGCGAGTAGTTGTTACAGGAATGGGCGTGGTGACTCCTCTAGGCCATG
AACCTGATGTTTACTACAACAATCTCCTAGATGGAGTAAGCGGCATAAGTGAGAT
AGAGACCTTCGACTGCACTCAGTTTCCCACGAGAATCGCCGGAGAGATCAAGTCT
TTTTCCACAGATGGGTGGGTGGCCCCAAAGCTCTCCAAGAGGATGGACAAGTTC
ATGCTTTACTTGTTGACTGCTGGCAAGAAAGCATTAGCAGATGGTGGAATCACCG
ATGATGTGATGAAAGAGCTTGATAAAAGAAAGTGTGGGGTTCTCATTGGCTCTG
GAATGGGCGGCATGAAGTTGTTCAACGATTCCATTGAAGCTCTGAGGATTTCATA
TAAAAAGATGAATCCCTTTTGTGTACCTTTTGCTACCACAAATATGGGATCAGCT
ATGCTTGCAATGGACTTGGGATGGATGGGTCCTAACTACTCGATATCAACTGCCT
GTGCAACAAGTAATTTCTGTATACTGAATGCTTCAAACCACATAGTCAGAGGCGA
AGCTGACATGATGCTTTGTGGTGGCTCGGATTCTGTCACTGTACCTTTAGGTGTG
GGAGGTTTCGTAGCATGCCGAGCTTTGTCACAGAGGAATAATGACCCTACCAAA
GCTTCGAGACCTTGGGACAGTAATCGGGATGGATTTGTGATGGGAGAAGGAGCT
GGAGTGTTACTTCTTGAGGAGTTAGAGCATGCAAAGAAAAGAGGTGCAACCATT
TATGCGGAATTTCTCGGTGGGAGCTTTACTTCTGATGCCTACCACATGACCGAGC
CTCACCCCGAAGGAGCTGGAGTGATTCTCTGCATTGAGAAGGCCTTGGCTCAGTC
CGGAGTCTCGAGGGAAGACGTGAATTATATAAATGCGCATGCAACTTCCACTCCT
GCTGGTGATATAAAGGAATACCAAGCTCTCGCCCGCTGTTTCGGCCAAAACAGTG
AGTTAAGAGTGAATTCCACCAAATCGATGATCGGTCACCTTCTTGGAGCAGCTGG
TGGCGTAGAAGCAGTTGCAGTAATTCAGGCAATAAGGACTGGATGGATCCATCC
AAATATTAATTTGGAAGACCCCGACGAAGCCGTGGATCCAAAATTGCTCGTCGG
CCCTAAGAAGGAGAAACTGAAGGTCAAGGTAGCTTTGTCCAATTCATTCGGGTTC
GGCGGGCATAACTCATCCATACTCTTTGCCCCTTGCAATTAG SEQ ID NO: 30
*C. procumbens* KASIV CDS
ATGGCGGCGGCGCCCTCTTCCCCACTCTGTACGTGGCTCGTAGCCGCTTGCATGT
CCACTTCCTTCGACAACAACCCACGTTCGCCCTCCATCAAGCGTCTCCCCCGCCG
GAGGAGGGTTCTCTCCCAATGCTCCCTCCGTGGATCCACCTTCCAATGCCTCGTC
ACCTCACACAACGACCCTTGCAATCAGTACTGCTCCTCCGCCTCCCTTAGCTTCCT
CGGGGATAACGGATTCGGATCCAAGCCATTCCGGTCCAATCGCGGCCACCGGAG
GCTCGGCCGTGCTTCGCATTCCGGGGAGGCCATGGCTGTGGCCTTGCAACCTGCA
CAGGAAGTCGCCACGAAGAAGAAACCTGCTATGAAGCAAAGGCGAGTAGTTGTT
ACAGGAATGGGCGTGGTGACTCCTCTGGGCCATGAACCTGATGTTTACTACAACA
ATCTCCTAGATGGAGTAAGCGGCATAAGTGAGATAGAGACCTTCGACTGCACTC
AGTTTCCCACGAGAATCGCCGGAGAGATCAAGTCTTTTTCCACAGATGGATGGGT
GGCCCCAAAGCTCTCCAAGAGGATGGACAAGTTCATGCTTTACTTGTTGACTGCT
GGCAAGAAAGCATTAGCAGATGGTGGAATCACTGATGATGTGATGAAAGAGCTT
GATAAAAGAAAGTGTGGAGTTCTCATTGGCTCTGGAATGGGCGGCATGAAGTTG
TTCAACGATTCCATTGAAGCTCTGAGAGTTTCATATAAGAAGATGAATCCCTTTT
GTGTACCTTTTGCTACCACAAATATGGGATCAGCTATGCTTGCAATGGACTTGGG
ATGGATGGGTCCTAACTACTCGATATCAACTGCCTGTGCAACAAGTAATTTCTGT
ATACTGAATGCTGCAAACCACATAGTCAGAGGCGAAGCTGACATGATGCTTTGT
GGTGGCTCGGATGCGGTCATTATACCTATTGGTTTGGGAGGTTTTGTGGCGTGCC
GAGCTTTGTCACAGAGGAATAATGACCCTACCAAGGCTTCGAGACCATGGGATA
GTAATCGTGATGGATTTGTAATGGGCGAAGGAGCTGGAGTGTTACTTCTCGAGGA
GTTAGAGCATGCAAAGAAAAGAGGTGCAACCATTTATGCGGAATTTTTAGGGGG
CAGTTTCACTTGCGATGCCTACCATATGACCGAGCCTCACCCTGAAGGAGCTGGA
GTGATCCTCTGCATAGAGAAGGCCTTGGCTCAGTCCGGAGTCTCTAGAGAAGAC
GTAAATTACATAAATGCGCATGCAACTTCCACTCCTGCTGGAGATATCAAAGAAT
ACCAAGCTCTCGCCCACTGTTTCGGCCAAAACAGTGAGCTGAGAGTGAATTCCAC
TAAATCGATGATCGGTCATCTTCTTGGAGCAGCTGGTGGTGTAGAAGCAGTTACC
GTAATTCAGGCGATAAGGACTGGGTGGATCCATCCAAATCTTAATTTGGAAGACC
CGGACAAAGCCGTGGATGCAAAATTTCTCGTGGGACCTAAGAAGGAGAGACTGA
ATGTCAAGGTCGGTTTGTCCAATTCATTTGGGTTCGGGGGGCATAACTCATCCAT
ACTCTTTGCCCCTTGCAATTAG -continued

SEQUENCE LISTING

SEQ ID NO: 31
*C. paucipetala* KASIVa CDS
ATGGCGGCGGCGGCCTCTTCCCCACTCTGCACATGGCTCGTAGCCGCTTGCATGT
CCACTTCATTCGACAACAACCCACGTTCGCCCTCCATCAAGCGTCTCCCCCGCCG
GAGGAGGGTTCTCTCCCAATGCTCCCTCCGCGGATCCACCTTCCAATGCCTCGTC
AACTCACACATCGACCCTTGCAATCAGAACGTCTCCTCCGCCTCCCTTAGCTTCCT
CGGGGATAACGGATTCGGATCCAATCCATTCCGGTCCAATCGCGGCCACCGGAG
GCTCGGCCGGGCTTCCCATTCCGGGGAGGCCATGGCTGTTGCTCTGCAACCTGCA
CAGGAAGTCGCCACGAAGAAGAAACCTGCTATCAAGCAAAGGCGAGTAGTTGTT
ACAGGAATGGGCGTGGTGACTCCTCTAGGCCATGAGCCTGATGTTTTCTACAACA
ATCTCCTAGATGGAGTAAGCGGCATAAGTGAGATAGAGACCTTCGACTGCACTC
AGTTTCCCACGAGAATTGCCGGAGAGATCAAGTCTTTTTCCACAGATGGGTGGGT
GGCCCCAAAGCTCTCCAAGAGGATGGACAAGTTCATGCTTTACTTGTTGACTGCT
GGCAAGAAAGCATTAGCAGATGCTGGAATTACCGAGGATGTGATGAAAGAGCTT
GATAAAAGAAAGTGTGGAGTTCTCATTGGCTCCGGAATGGGCGGCATGAAGTTG
TTCAACGATTCCATTGAAGCTCTGAGGGTTTCATATAAGAAGATGAATCCCTTTT
GTGTACCTTTTGCTACCACAAATATGGGATCAGCTATGCTTGCAATGGACTTGGG
ATGGATGGGTCCTAACTACTCGATATCGACTGCCTGTGCAACAAGTAATTTCTGT
ATACTGAATGCTGCAAACCACATAATCAGAGGCGAAGCTGACATGATGCTTTGT
GGTGGTTCGGATGCGGTCATTATACCTATTGGTTTGGGAGGTTTTGTGGCGTGCC
GAGCTTTGTCACAGAGGAATAGTGACCCTACCAAAGCTTCGAGACCATGGGATA
GTAATCGTGATGGATTTGTAATGGGCGAAGGAGCTGGAGTGTTACTTCTCGAGGA
GTTAGAGCATGCAAAGAAAAGAGGTGCAACCATTTATGCGGAATTTTTAGGGGG
CAGCTTCACTTGCGATGCCTACCACATGACCGAGCCTCACCCTGATGGAGCTGGA
GTGATCCTCTGCATAGAGAAGGCTTTGGCACAGTCCGGAGTCTCGAGGGAAGAC
GTCAATTACATAAATGCGCATGCAACTTCTACTCCTGCTGGAGATATCAAGGAAT
ACCAAGCTCTCGCCCACTGTTTCGGCCAAAACAGTGAGCTGAGAGTGAATTCCAC
TAAATCGATGATCGGTCATCTTCTTGGTGCAGCTGGTGGTGTAGAAGCTGTTACT
GTAATTCAGGCGATAAGGACTGGGTGGATTCATCCAAATCTTAATTTGGAAGACC
CGGACGAAGCCGTGGATGCAAAATTTCTCGTGGGACCTAAGAAGGAGAGATTGA
ATGTCAAGGTCGGTTTGTCCAATTCATTTGGGTTCGGTGGGCATAACTCATCCAT
ACTCTTCGCCCCTTACAATTAG SEQ ID NO: 32
*C. painteri* KASIV CDS
ATGGCGGCCTCCTCTTGCATGGTTGCGTCCCCGTTCTGTACGTGGCTCGTATCCGC
ATGCATGTCTACTTCATTCGACAACGACCCACGTTCCCTTTCCCACAAGCGGCTC
CGCCTCTCCCGTCGCCGGAGGCCTCTCTCCTCTCATTGCTCCCTCCGCGGATCCAC
TCCCCAATGCCTCGACCCTTGCAATCAGCACTGCTTCCTCGGGGATAACGGATTC
GCTTCCCTCATCGGATCCAAGCCTCCCCGTTCCAATCTCGGCCACCTGAGGCTCG
GCCGCACTTCCCATTCCGGGGAGGTCATGGCTGTGGCACAGGAAGTCTCCACAA
ATAAGAAACATGCTACCAAGCAAAGGCGAGTAGTTGTGACAGGTATGGGCGTGG
TGACTCCTCTAGGCCATGACCCCGATGTTTACTACAACAATCTCCTAGAAGGAGT
AAGTGGCATCAGTGAGATAGAGAACTTCGACTGCTCTCAGCTTCCCACGAGAATT
GCCGGAGAGATCAAGTCTTTTTCCACAGATGGTTGGTGGCCCCGAAGCTCTCCA
AGAGGATGGACAAGTTCATGCTTTACATCCTGACTGCAGGCAAGAAAGCATTAG
CAGATGGTGGAATCACTGAAGATGTGATGAAAGAGCTCGATAAAAGAAAGTGTG
GAGTTCTCATTGGCTCCGGATTGGGCGGTATGAAGGTATTCAGCGACTCCGTTGA
AGCTCTGAGGATTTCATATAAGAAGATCAGTCCCTTTTGTGTACCTTTTTCTACCA
CAAATATGGGATCCGCTATGCTTGCAATGGACTTGGGATGGATGGGCCCTAACTA
TTCGATATCAACTGCCTGTGCAACAAGTAACTTCTGTATACTGAATGCTGCGAAC
CACATAACCAAAGGCGAAGCTGACATGATGCTTTGTGGTGGCTCGGATGCGGCC
ATTTTACCTATTGGTATGGGAGGTTTCGTGGCATGCCGAGCTTTGTCACAGAGGA
ATAATGACCCTACCAAAGCTTCGAGACCATGGGACAGTAATCGTGATGGATTTGT
GATGGGAGAAGGAGCTGGAGTGTTACTTCTCGAGGAGTTAGAGCATGCAAAGAA
AAGAGGTGCAACCATTTATGCGGAATTTCTAGGTGGGAGTTTCACTTGCGATGCC
TACCACATGACCGAGCCTCACCCTGATGGAGCTGGAGTGATCCTCTGCATAGAGA
AGGCCTTGGCTCAGTCCGGAGTCTCGAGGGAAGAAGTAAATTACATAAATGCGC
ATGCAACTTCCACTCCTGCTGGAGATATCAAGGAATACCAAGCTCTCGCCCATTG
TTTCGGCCAAAACAGTGAGTTAAGAGTGAATTCCACCAAATCGATGATCGGTCAC
CTTCTTGGAGGAGCTGGTGGCGTAGAAGCAGTTACAGTAGTTCAGGCAATAAGG
ACTGGATGGATCCATCCAAATATTAATTTGGAAGACCCGGACAAAGGCGTGGAT
GCAAAACTGCTCGTCGGCCCTAAGAAGGAGAAACTGAAGGTCAAGGTCGGTTTG
TCCAATTCATTTGGGTTCGGCGGCCATAACTCATCCATACTCTTTGCCCCATGCAA
TTAG SEQ ID NO: 33
*C. avigera* KASIVa CDS
ATGGCGGCCGCCGCTTCCATGGTTGCGTCCCCATTCTGTACGTGGCTCGTAGCCG
CTTGCATGTCCACTTCCGTCGACAAAGACCCACGTTCGCCGTCTATCAAGCGTCT
CCCCCGCCGGAAGAGGATTCATTCCCAATGCTCCCTCCGCGGATCCACCTTCCAA
TGCCTCGTCACCTCATACAACGACCCTTGCGAACAATACCGCTCATCCGCCTCCC
TTAGCTTCCTCGGGGATAACGGATTCGCATCCCTTTTCGGATCCAAGCCATTCCG
GTCCAATCGCGGCCACCGGAGGCTCGGCCGTGCTTCCCATTCCGGGGAGGCCATG
GCCGTGGCACTGCAACCTGCACAGGAAGTTGGCACGAAGAAGAAACCTGTTATC
AAGCAAAGGCGAGTAGTTGTTACAGGAATGGGCGTGGTGACTCCTCTAGGCCAT
GAACCTGATGTTTACTACAACAATCTCCTAGACGGAGTAAGCGGCATAAGTGAG -continued

SEQUENCE LISTING

ATAGAGACCTTCGACTGCACTCAGTTTCCCACGAGAATTGCCGGAGAGATCAAGT
CTTTTTCCACAGATGGGTGGGTGGCTCCAAAGCTCTCTAAGAGGATGGACAAGTT
CATGCTTTACTTGTTGACTGCTGGCAAGAAAGCATTGGCAGATGGTGGAATCACC
GATGATGTGATGAAAGAGCTTGATAAAAGAAAGTGTGGAGTTCTCATTGGCTCC
GGATTGGGCGGTATGAAGGTATTTAGCGAGTCCATTGAAGCTCTGAGGACTTCAT
ATAAGAAGATCAGTCCCTTTTGTGTACCTTTTTCTACCACGAATATGGGATCCGCT
ATTCTTGCAATGGACTTGGGATGGATGGGCCCTAACTATTCGATATCGACTGCCT
GTGCAACAAGTAACTTCTGTATACTGAATGCTGCGAACCACATAACCAAAGGCG
AAGCAGACATGATGCTTTGTGGTGGCTCGGATTCGGTCATTTTACCTATTGGTAT
GGGAGGTTTCGTAGCATGCCGAGCTTTGTCACAGAGGAATAATGACCCTACCAA
AGCTTCGAGACCATGGGACAGTAATCGTGATGGATTTGTGATGGGAGAAGGTGC
TGGAGTTTTACTTCTCGAGGAGTTAGAGCATGCAAAGAAAAGAGGCGCAACCAT
TTATGCGGAATTTCTTGGTGGGAGTTTCACTTGCGATGCCTACCACATGACCGAG
CCTCACCCTGAAGGAGCTGGAGTGATCCTCTGCATAGAGAAGGCCTTGGCTCAGT
CCGGAGTCTCGAGGGAAGACGTAAATTACATAAATGCGCATGCAACTTCCACTC
CCGCTGGAGATATCAAAGAATACCAAGCTCTCGCCCACTGTTTCGGCCAAAACA
GTGAGTTAAGAGTGAATTCCACCAAGTCGATGATCGGTCACCTTCTTGGAGGAGC
CGGTGGCGTAGAAGCAGTTACAGTCGTTCAGGCAATAAGGACTGGATGGATCCA
TCCAAATATTAATTTGGACGACCCGGACGAAGGCGTGGATGCAAAACTGCTCGT
CGGCCCTAAGAAGGAGAAACTGAAGGTCAAGGTCGGTTTGTCCAATTCATTCGG
GTTCGGCGGCCATAACTCATCCATACTCTTTGCCCCATGCAATTAG

SEQ ID NO: 34
*C. ignea* KASIVa CDS
ATGGCGGCGGCCGCTTCCATGTTTACGTCCCCACTCTGTACGTGGCTCGTAGCCT
CTTGCATGTCGACTTCCTTCGACAACGACCCACGTTCGCCGTCCGTCAAGCGTCT
CCCCCGCCGGAGGAGGATTCTCTCCCAATGCTCCCTCCGCGGATCCACCTCCCAA
TGCCTCGTCACCTCATACATCGACCCTTGCAATAAGTACTGCTCCTCCGCCTCCCT
TAGCTTCCTCGGGGATAACGGATTCGCATCCCTTTTCGGATCTAAGCCATTCCGG
TCCAATCGCGGCCACCGGAGGCTCGGCCGTGCTTCCCATTCCGGGGAGGCCATGG
CTGTGGCTCTGCAACCTGCACAGGAAGTCACCACGAAGAAGAAACCTGTGATCA
AGCAAAGGCGAGTAGTTGTTACAGGAATGGGCGTGGTGACTCCTCTAGGCCATG
AACCTGATGTTTACTACAACAATCTCCTAGATGGAGTAAGCGGCATAAGTGAGAT
AGAGACCTTCGACTGCACTCAGTTTCCCACGAGAATCGCCGGAGAGATCAAGTCT
TTTTCCACAGATGGGTGGGTGGCCCCAAAGCTCTCCAAGAGGATGGACAAGTTC
ATGCTTTACTTGTTGACTGCTGGCAAGAAAGCATTAGCAGATGGTGGAATCACCG
ATGATGTGATGAAAGAGCTTGATAAAAGAAAGTGTGGGGTTCTCATTGGCTCTG
GAATGGGCGGCATGAAGTTGTTCAACGATTCCATTGAAGCTCTGAGGATTTCATA
TAAAAAGATGAATCCCTTTTGTGTACCTTTTGCTACCACAAATATGGGATCAGCT
ATGCTTGCAATGGACTTGGGATGGATGGGTCCTAACTACTCGATATCAACTGCCT
GTGCAACAAGTAATTTCTGTATACTGAATGCTTCAAACCACATAGTCAGAGGCGA
AGCTGACATGATGCTTTGTGGTGGCTCGGATGCGGTTATTATACCTATTGGTTTG
GGAGGTTTTGTGGCGTGCCGAGCTTTGTCACAGAGGAATAATGACCCTACCAAA
GCTTCGAGGCCATGGGATAGTAATCGTGATGGATTTGTAATGGGCGAAGGAGCT
GGAGTGTTACTTCTCGAGGAGTTAGAGCATGCAAAGAAAAGAGGTGCAACCATT
TATGCGGAATTTTTAGGGGGCAGTTTCACTTGCGATGCCTACCACATGACCGAGC
CTCACCCTGAAGGAGCTGGAGTGATCCTCTGCATAGAGAAGGCCTTGGCTCAGG
CCGGAGTCTCTAAAGAAGATGTAAATTACATAAATGCGCATGCAACTTCTACTCC
TGCTGGAGATATCAAGGAATACCAAGCTCTCGCCCAATGTTTCGGCCAAAACAGT
GAGCTGAGAGTGAATTCCACTAAATCGATGATCGGTCATCTTCTTGGAGCAGCTG
GTGGTGTAGAAGCAGTTACTGTGGTTCAGGCGATAAGGACTGGGTGGATCCATC
CAAATCTTAATTTGGAAGACCCGGACAAAGCCGTGGATGCAAAGTTGCTCGTGG
GACCTAAGAAGGAGAGACTGAATGTCAAGGTCGGTTTGTCCAATTCATTTGGGTT
CGGTGGGCATAATTCGTCCATACTCTTCGCCCCTTACAATTAG SEQ ID NO: 35
*C. avigera* KASIa CDS
ATGCAATCCCTCCATTCCCCTGCCCTCCGGGCCTCCCCTCTCGACCCTCTCCGACT
CAAATCCTCCGCCAATGGCCCCTCTTCCACCGCCGCTTTCCGTCCCCTCCGCCGCG
CCACCCTCCCCAACATTCGGGCCGCCTCCCCCACCGTCTCCGCCCCCAAGCGCGA
GACCGACCCCAAGAAGCGTGTCGTCATCACCGGCATGGGCCTCGTCTCCGTCTTC
GGCTCCGATGTCGACGCTTATTACGAAAAGCTCCTCTCCGGCGAGAGCGGGATCA
GCTTAATCGACCGCTTCGACGCTTCCAAGTTCCCCACGAGGTTCGGCGGCCAGAT
CCGGGGATTCAACGCCACGGGATACATCGACGGCAAAAACGACAGGAGGCTCGA
CGATTGCCTCCGCTACTGCATTGTCGCCGGGAAGAAGGCTCTCGAAAATTCCGAT
CTCGGCGGCGATAGTCTCTCAAAGATTGATAAGGAGAGAGCTGGAGTGCTAGTT
GGAACTGGCATGGGTGGCCTAACCGTCTTCTCTGACGGGGTTCAGAATCTAATCG
AGAAAGGTCACCGGAAGATCTCCCCGTTTTTCATTCCATATGCCATTACAAACAT
GGGGTCTGCCCTGCTTGCCATCGATTTGGGTCTGATGGGCCCAAATTATTCGATTT
CAACTGCATGTGCTACTTCCAACTACTGCTTTTATGCTGCTGCTAATCATATCCGC
CGAGGCGAGGCTGACCTCATGATTGCTGGAGGAACTGAGGCTGCAATCATTCCA
ATTGGGTTAGGAGGATTCGTTGCTTGCAGGGCTTTATCTCAAAGGAATGATGACC
CTCAGACTGCCTCAAGGCCGTGGGATAAGGACCGTGATGGTTTTGTGATGGGTGA
AGGGGCTGGAGTATTGGTTATGGAGAGCTTAGAACATGCAATGAAACGAGGAGC
GCCGATTATTGCAGAATATTTGGGAGGTGCAGTCAACTGTGATGCTTATCATATG
ACTGATCCAAGGGCTGATGGGCTTGGTGTCTCCTCGTGCATTGAGAGCAGTCTCG
AAGATGCCGGGGTCTCACCTGAAGAGGTCAATTACATAAATGCTCATGCGACTTC -continued

SEQUENCE LISTING

TACTCTTGCTGGGGATCTTGCCGAGATAAATGCCATCAAGAAGGTTTTCAAGAAC
ACCAAGGATATCAAAATCAATGCAACTAAGTCGATGATTGGACACTGTCTTGGA
GCATCAGGGGGTCTTGAAGCCATTGCGACAATTAAGGGAATAACCACTGGCTGG
CTTCATCCCAGCATAAACCAATTCAATCCCGAGCCATCAGTGGAATTTGACACTG
TTGCCAACAAGAAGCAGCAACATGAAGTCAATGTTGCTATCTCAAATTCATTCGG
ATTCGGAGGCCACAACTCAGTTGTAGCTTTCTCAGCTTTCAAGCCATGA

SEQ ID NO: 36
*C. pulcherrima* KASI CDS
ATGCATTCCCTCCAGTCACCCTCCCTTCGGGCCTCCCCGCTCGACCCCTTCCGCCC
CAAATCATCCACCGTCCGCCCCCTCCACCGAGCATCAATTCCCAACGTCCGGGCC
GCTTCCCCCACCGTCTCCGCTCCCAAGCGCGAGACCGACCCCAAGAAGCGCGTCG
TGATCACCGGAATGGGCCTTGTCTCCGTTTTCGGCTCCGACGTCGATGCGTACTA
CGACAAGCTCCTGTCAGGCGAGAGCGGGATCGGCCCAATCGACCGCTTCGACGC
CTCCAAGTTCCCCACCAGGTTCGGCGGCCAGATTCGTGGCTTCAACTCCATGGGA
TACATTGACGGCAAAAACGACAGGCGGCTTGATGATTGCCTTCGCTACTGCATTG
TCGCCGGGAAGAAGTCTCTTGAGGACGCCGATCTCGGTGCCGACCGCCTCTCCAA
GATCGACAAGGAGAGAGCCGGAGTGCTGGTTGGGACAGGAATGGGTGGTCTGAC
TGTCTTCTCTGACGGGGTTCAATCTCTTATCGAGAAGGGTCACCGGAAAATCACC
CCTTTCTTCATCCCCTATGCCATTACAAACATGGGGTCTGCCCTGCTCGCTATTGA
ACTCGGTCTGATGGGCCCAAACTATTCAATTTCCACTGCATGTGCCACTTCCAAC
TACTGCTTCCATGCTGCTGCTAATCATATCCGCCGTGGTGAGGCTGATCTTATGAT
TGCTGGAGGCACTGAGGCCGCAATCATTCCAATTGGGTTGGGAGGCTTTGTGGCT
TGCAGGGCTCTGTCTCAAAGGAACGATGACCCTCAGACTGCCTCTAGGCCCTGGG
ATAAAGACCGTGATGGTTTTGTGATGGGTGAAGGTGCTGGAGTGTTGGTGCTGGA
GAGCTTGGAACATGCAATGAAACGAGGAGCACCTATTATTGCAGAGTATTTGGG
AGGTGCAATCAACTGTGATGCTTATCACATGACTGACCCAAGGGCTGATGGTCTC
GGTGTCTCCTCTTGCATTGAGAGTAGCCTTGAAGATGCTGGCGTCTCACCTGAAG
AGGTCAATTACATAAATGCTCATGCGACTTCTACTCTAGCTGGGGATCTCGCCGA
GATAAATGCCATCAAGAAGGTTTTCAAGAACACAAAGGATATCAAAATTAATGC
AACTAAGTCAATGATCGGACACTGTCTTGGAGCCTCTGGAGGTCTTGAAGCTATA
GCGACTATTAAGGGAATAAACACCGGCTGGCTTCATCCCAGCATTAATCAATTCA
ATCCTGAGCCATCCGTGGAGTTCGACACTGTTGCCAACAAGAAGCAGCAACACG
AAGTTAATGTTGCGATCTCGAATTCATTTGGATTCGGAGGCCACAACTCAGTCGT
GGCTTTCTCGGCTTTCAAGCCATGA SEQ ID NO: 37
*C. aviga* mitochondrial KAS CDS
ATGGTGTTTCTTCCTTGGCGAAAAATGCTCTGTCCATCTCAATACCGTTTTTTGCG
GCCCTTATCTTCATCTACAACTTTTGATCCTCGTAGGGTTGTTGTTACAGGCCTGG
GTATGGTGACTCCATTAGGATGCGGGGTGAACACCACATGGAAACAACTCATAG
AGGGGAAATGTGGGATAAGAGCAATATCCCTTGAAGACCTAAAGATGGATGCTT
TTGATATTGATACTCAGGCCTATGTATTTGATCAGCTGACCTCGAAGGTCGCTGC
CACCGTGCCCACCGGAGTGAATCCCGGAGAATTTAATGAAGATTTATGGTTCAAT
CAGAAGGAGCACCGTGCTATTGCAAGGTTCATAGCTTATGCACTCTGTGCAGCTG
ATGAAGCTCTTAAAGATGCAAATTGGGAACCTACTGAACCTGAAGAGAGAGAAA
TGACGGGTGTCTCCATTGGTGGAGGGACTGGAAGCATTAGCGATGTATTAGATGC
TGGTCGGATGATTTGTGAGAAGAAATTGCGTCGCCTAAGTCCATTCTTCATTCCA
CGCATATTGATAAATATGGCCTCTGGTCATGTGAGCATGAAATATGGTTTCCAGG
GACCCAACCATGCTGCTGTGACAGCTTGTGCAACAGGGGCTCATTCGATAGGTGA
TGCTGCAAGGATGATACAGTTTGGAGATGCAGATGTCATGGTCGCTGGAGGCAC
AGAATCTAGCATAGACGCCTTATCCATTGCAGGATTTTGCAGGTCAAGGGCTCTT
ACAACAAAGTATAATTCTTGCCCACAAGAAGCTTCACGACCCTTTGATACCGATA
GAGATGGGTTTGTAATAGGTGAAGGGTCTGGCGTCTTGGTATTGGAGGAACTAG
ATCATGCAAGAAAACGTGGTGCAAAGATGTATGCCGAGTTCTGTGGATATGGAA
TGTCTGGTGATGCGCATCATATAACCCAACCTCATAGCGATGGAAGAGGTGCCAT
TTTAGCAATGACCCGTGCATTGAAGCAGTCAAATCTACATCCGGATCAGGTGGAT
TATGTAAATGCTCACGCTACGTCTACTTCTTTAGGTGATGCAATTGAAGCTAAGG
CGATTAAAACAGTTTTCTCGGATCATGCGATGTCAGGTTCGCTCGCCCTTTCCTCC
ACCAAGGGAGCTATTGGGCATCTCCTCGGAGCAGCGGGTGCTGTGGAAGCCATT
TTCTCCATTCTGGCTATAAAAAACGGACTTGCGCCTTTGACGCTAAATGTCGCAA
GACCAGACCCTGTGTTTACCGAGCGGTTTGTGCCTTTGACTGCTTCAAAAGAGAT
GCATGTAAGGGCGGCGTTGTCAAACTCTTTTGGCTTTGGAGGTACAAATACTACA
CTTCTTTTCACTTCACCTCCTCAAAACTAA

SEQUENCE LISTING

SEQ ID NO: 38
*Cuphea palustris* KASIV codon optimized for Prototheca with cloning sequence and tags.
Nucleotide sequence of the *C. palustris* KASIV *expression vector (D3145 and D3295, pSZ4312)*. The 5' and 3' homology arms enabling targeted integration into the pLOOP locus are noted with lowercase; the PmHXT1-2 promoter is noted in uppercase italic which drives expression of the ScMelibiase selection marker noted with lowercase italic followed by the PmPGK 3'UTR terminator highlighted in uppercase. The PmACP promoter (noted in bold text) drives the expression of the codon optimized CpaI KASIV (noted with lowercase bold text) and is terminated with the CvNR 3'UTR noted in underlined, lower case bold. Restriction cloning sites and spacer DNA fragments are noted as underlined, uppercase plain lettering.

aacggaggtctgtcaccaaatggaccccgtctattgcgggaaaccacggcgatggcacgtttcaaaacttgatgaaatacaatattcag
tatgtcgcgggcggcgacggcggggagctgatgtcgcgctgggtattgcttaatcgccagcttcgcccccgtcttggcgcgaggcgt
gaacaagccgaccgatgtgcacgagcaaatcctgacactagaagggctgactcgcccggcacggctgaattacacaggcttgcaaa
aataccagaatttgcacgcaccgtattcgcggtattttgttggacagtgaatagcgatgcggcaatggcttgtggcgttagaaggtgcga
cgaaggtggtgccaccactgtgccagccagtcctggcggctcccagggccccgatcaagagccaggacatccaaactacccacag
catcaacgccccggcctatactcgaaccccacttgcactctgcaatggtatgggaaccacggggcagtcttgtgtgggtcgcgcctat
cgcggtcggcgaagaccgggaaGGTACC*CCGCTCCCGTCTGGTCCTCACGTTCGTGTACGGCCT*
*GGATCCCGGAAAGGGCGGATGCACGTGGTGTTGCCCCGCCATTGGCGCCCACGTTTC*
*AAAGTCCCCGGCCAGAAATGCACAGGACCGGCCCGGCTCGCACAGGCCATGACGAAT*
*GCCCAGATTTCGACAGCAAAACAATCTGGAATAATCGCAACCATTCGCGTTTTGAACGA*
*AACGAAAAGACGCTGTTTAGCACGTTTCCGATATCGTGGGGGCCGAAGCATGATTGGG*
*GGGAGGAAAGCGTGGCCCCAAGGTAGCCCATTCTGTGCCACACGCCGACGAGGACCA*
*ATCCCCGGCATCAGCCTTCATCGACGGCTGCGCCGCACATATAAAGCCGGACGCCTTC*
*CCGACACGTTCAAACAGTTTTATTTCCTCCACTTCCTGAATCAAACAAATCTTCAAGGAA*
*GATCCTGCTCTTGAGCA*ACTAGT*atgttcgcgttctacttcctgacggcctgcatctccctgaagggcgtgttcggc*
*gtctccccctcctacaacggcctgggcctgacgccccagatgggctgggacaactggaacacgttcgcctgcgacgtaccgagc*
*agctgctgctggacacggccgaccgcatctccgacctgggcctgaaggacatgggctacaagtacatcatcctggacgactgct*
*ggtcctccggccgcgactccgacggcttcctggtcgccgacgagcagaagttccccaacggcatgggccacgtcgccgaccacc*
*tgcacaacaactccucctgttcggcatgtactcctccgcgggcgagtacacgtgcgccggctaccccggctccctgggccgcgag*
*gaggaggacgcccagacttcgcgaacaaccgcgtggactacctgaagtacgacaactgctacaacaagggccagacggcac*
*gcccgagatctcctaccaccgctacaaggccatgtccgacgccctgaacaagacgggccgccccatcactactccctgtgcaac*
*tggggccaggacctgaccactactggggctccggcatcgcgaactcctggcgcatgtccggcgacgtcacggcggagacacgc*
*gccccgactcccgctgcccctgcgacggcgacgagtacgactgcaagtacgccggcaccactgctccatcatgaacatcctgaa*
*caaggccgcccccatgggccagaacgcgggcgtcggcggctggaacgacctggacaacctggaggtcggcgtcggcaacct*
*gacggacgacgaggagaaggcgcacactccatgtgggccatggtgaagtccccctgatcatcggcgcgaacgtgaacaacc*
*tgaaggcctcctcctactccatctactcccaggcgtccgtcatcgccatcaaccaggactccaacggcatccccgccacgcgcgtc*
*tggcgctactacgtgtccgacacggacgagtacggccagggcgagatccagatgtggtccggccccctggacaacggcgacca*
*ggtcgtggcgctgctgaacggcggctccgtgtcccgccccatgaacacgaccctggaggagatcacttcgactccaacctgggct*
*ccaagaagctgacctccacctgggacatctacgacctgtgggcgaaccgcgtcgacaactccacggcgtccgccatcctgggcc*
*gcaacaagaccgccaccggcatcctgtacaacgccaccgagcagtcctacaaggacggcctgtccaagaacgacacccgcct*
*gttcggccagaagatcggctccctgtcccccaacgcgatcctgaacacgaccgtccccgcccacggcatcgcgactaccgcctg*
*cgcccctcctcctga*TACAACTTATTACGTATTCTGACCGGCGCTGATGTGGCGCGGACGC
CGTCGTACTCTTTCAGACTTTACTCTTGAGGAATTGAACCTTTCTCGCTTGCTGGC
ATGTAAACATTGGCGCAATTAATTGTGTGATGAAGAAAGGGTGGCACAAGATGG
ATCGCGAATGTACGAGATCGACAACGATGGTGATTGTTATGAGGGGCCAAACCT
GGCTCAATCTTGTCGCATGTCCGGCGCAATGTGATCCAGCGGCGTGACTCTCGCA
ACCTGGTAGTGTGTGCGCACCGGGTCGCTTTGATTAAAACTGATCGCATTGCCAT
CCCGTCAACTCACAAGCCTACTCTAGCTCCCATTGCGCACTCGGGCGCCCGGCTC
GATCAATGTTCTGAGCGGAGGGCGAAGCGTCAGGAAATCGTCTCGGCAGCTGGA
AGCGCATGGAATGCGGAGCGGAGATCGAATCAGGATCCCGCGTCTCGAACAGAG
CGCGCAGAGGAACGCTGAAGGTCTCGCCTCTGTCGCACCTCAGCGCGGCATACA
CCACAATAACCACCTGACGAATGCGCTTGGTTCTTCGTCCATTAGCGAAGCGTCC
GGTTCACACACGTGCCACGTTGGCGAGGTGGCAGGTGACAATGATCGGTGGAGC
TGATGGTCGAAACGTTCACAGCCTAGGGATATCGCCTGCTCAAGCGGGCGCTC
AACATGCAGAGCGTCAGCGAGACGGGCTGTGGCGATCGCGAGACGGACGA
GGCCGCCTCTGCCCTGTTTGAACTGAGCGTCAGCGCTGGCTAAGGGGAGGG
AGACTCATCCCCAGGCTCGCGCCAGGGCTCTGATCCCGTCTCGGGCGGTGA
TCGGCGCGCATGACTACGACCCAACGACGTACGAGACTGATGTCGGTCCCG
ACGAGGAGCGCCGCGAGGCACTCCCGGGCCACCGACCATGTTTACACCGAC
CGAAAGCACTCGCTCGTATCCATTCCGTGCGCCCGCACATGCATCATCTTTT
GGTACCGACTTCGGTCTTGTTTTACCCCTACGACCTGCCTTCCAAGGTGTGA
GCAACTCGCCCGGACATGACCGAGGGTGATCATCCGGATCCCCAGGCCCCA
GCAGCCCCTGCCAGAATGGCTCGCGCTTTCCAGCCTGCAGGCCCGTCTCCC
AGGTCGACGCAACCTACATGACCACCCCAATCTGTCCCAGACCCCAAACACC
CTCCTTCCCTGCTTCTCTGTGATCGCTGATCAGCAACACATatggcttccgcggcattca
ccatgtcggcgtgccccgcgatgactggcagggcccctggggcacgtcgctccggacggccagtcgccacccgcctgagggg
ctccaccttccagtgcctggtgacctcctacatcgaccccctgcaaccagttctcctcctccgcctccctgtccttcctgggcgaca
acggcttcgcctccctgttcggctccaagcccttccgctccaaccgcggccaccgccgcctgggccgcgcctcccactccggcg
aggccatggccgtggccctggagcccgcccaggaggtggccaccaagaagaagcccctggtgaagcagcgccgcgtggtg
gtgaccggcatgggcgtggtgacccccctgggccacgagcccgacgtgtactacaacaacctgctggacggcgtgtccggca
tctccgagatcgaggccttcgactgcacccagttccccacccgcatcgccggcgagatcaagtccttctccaccgacggctggg
tggcccccaagctgtccaagcgcatggacaagttcatgctgtacctgctgaccgccggcaagaaggccctggccgacggcgg
catcaccgacgacgtgatgaaggagctggacaagcgcaagtgcggcgtgctgatcggctccggcctgggcggcatgaagct
gttctccgactccatcgaggccctgcgcatctcctacaagaagatgaaccccttctgcgtgcccttcgccaccaccaacatggg
ctccgccatgctggccatggacctgggctggatgggccccaactactccatctccaccgcctgcgccacctccaacttctgcatc -continued

SEQUENCE LISTING ctgaactcgccaaccacatcgtgcgccggcgaggccgacatgatgctgtgcggcggtccgacgccgtgatcatccccatcgg
cctgggcggcttcgtggcctgccgcgccctgtcccagcgcaacaacgaccccaccaaggcctcccgcccctgggactccaacc
gcgacggcttcgtgatgggcgagggcgccggcgtgctgctgctggaggagctggagcacgccaagaagcgcggcgccacc
atctacgccgagttcctgggcggctccttcacctgcgacgcctaccacatgaccgagccccaccccgagggcgccggcgtgat
cctgtgcatcgagaaggccctggcccaggccggcgtgtcccgcgaggacgtgaactacatcaacgcccacgccacctccacc
cccgccggcgacatcaaggagtaccaggccctggcccactgcttcggccagaactccgagctgcgcgtgaactccaccaaagt
ccatgatcggccacctgatcggcgccgccggcggcgtggaggccgtgaccgtggtgcaggccatccgcaccggctggatcca
ccccaacctgaacctggaggaccccgacaaggccgtggacgccaaggtgctggtgggccccaagaaggagcgcctgaacg
tgaaggtgggcctgtccaactccttcggcttcggcggccacaactcctccatcctgttcgcccccctacaacaccatgtacccta
cgacgtgcccgactacgcctgaTATCGAGgcagcagcagctcggatagtatcgacacactctggacgctggtcgtgtga
tggactgttgccgccacacttgctgccttgacctgtgaatatccctgccgcttttatcaaacagcctcagtgtgtttgatcttgtgt
gtacgcgcttttgcgagttgctagctgcttgtgctatttgcgaataccacccccagcatccccttccctcgtttcatatcgcttgcat
cccaaccgcaacttatctacgctgtcctgctatccctcagcgctgctcctgctcctgctcactgcccctcgcacagccttggtttgg
gctccgcctgtattctcctggtactgcaacctgtaaaccagcactgcaatgctgatgcacgggaagtagtgggatgggaacac
aaatggaAAGCTTGAGCTCagcggcgacggtcctgctaccgtacgacgttgggcacgcccatgaaagtttgtataccga
gcttgttgagcgaactgcaagcgcggctcaaggatacttgaactcctggattgatatcggtccaataatggatggaaaatccgaacctc
gtgcaagaactgagcaaacctcgttacatggatgcacagtcgccagtccaatgaacattgaagtgagcgaactgttcgcttcggtggc
agtactactcaaagaatgagctgctgttaaaaatgcactctcgttctctcaagtgagtggcagatgagtgctcacgccttgcacttcgctg
cccgtgtcatgccctgcgccccaaaatttgaaaaaagggatgagattattgggcaatggacgacgtcgtcgctccgggagtcaggac
cggcggaaaataagaggcaacacactccgcttctta SEQ ID NO: 39
*Cuphea palustris* KAS IV codon optimized for Prototheca
atggcttccgcggcattcaccatgtcggcgtgccccgcgatgactggcagggcccctggggcacgtcgctccggacggccagtcgc
cacccgcctgaggggctccaccttccagtgcctggtgacctcctacatcgaccccctgcaaccagttctcctcctccgcctccctgtcctt
cctgggcgacaacggcttcgcctccctgttcggctccaagcccttccgctccaaccgcggccaccgccgcctgggccgcgcctccc
actccggcgaggccatggccgtggccctggagcccgcccaggaggtggccaccaagaagaagcccctggtgaagcagcgccgc
gtggtggtgaccggcatgggcgtggtgacccccctgggccacgagcccgacgtgtactacaacaacctgctggacggcgtgtccg
gcatctccgagatcgaggccttcgactgcacccagttccccacccgcatcgccggcgagatcaagtccttctccaccgacggctggg
tggcccccaagctgtccaagcgcatggacaagttcatgctggtacctgctgaccgccggcaagaaggccctggccgacggcggcatc
accgacgacgtgatgaaggagctggacaagcgcaagtgcggcgtgctgatcggctccggcctgggcggcatgaagctgttctccg
actccatcgaggccctgcgcatctcctacaagaagatgaaccccttctgcgtgcccttcgccaccaccaacatgggctccgccatgct
ggccatggacctgggctggatgggcccaactactccatctccaccgcctgcgccacctccaacttctgcatcctgaactccgccaac
cacatcgtgcgcggcgaggccgacatgatgctgtgcggcggctccgacgccgtgatcatccccatcggcctgggcggcttcgtggc
ctgccgcgccctgtcccagcgcaacaacgaccccaccaaggcctcccgcccctgggactccaaccgcgacggcttcgtgatgggc
gagggcgccggcgtgctgctgctggaggagctggagcacgccaagaagcgcggcgccaccatctacgccgagttcctgggcggc
tccttcacctgcgacgcctaccacatgaccgagccccaccccgagggcgccggcgtgatcctgtgcatcgagaaggccctggccca
ggccggcgtgtcccgcgaggacgtgaactacatcaacgcccacgccacctccacccccgccggcgacatcaaggagtaccaggc
cctggcccactgcttcggccagaactccgagctgcgcgtgaactccaccaagtccatgatcggccacctgatcggcgccgccggcg
gcgtggaggccgtgaccgtggtgcaggccatccgcaccggctggatccaccccaacctgaacctggaggaccccgacaaggccg
tggacgccaaggtgctggtgggccccaagaaggagcgcctgaacgtgaaggtgggcctgtccaactccttcggcttcggcggccac
aactcctccatcctgttcgcccccctacaacaccatgtacccctacgacgtgcccgactacgcctga SEQ ID NO: 40
*C. camphora* KASIV codon optimized for Prototheca. Nucleotide sequence from the *C. camphora* KASIV (D3147, pSZ4338) expression vector. Only the codon optimized *C. camphora* KASIV sequence is shown, the promoter, 3'UTR, selection makrer and targeting arms are the same as in SEQ ID NO: 38.
atggccatgatggccggctcctgctccaacctggtgatcggcaaccgcgagctgggcggcaacggcccctccctgctgcactacaa
cggcctgcgccccctggagaacatccagaccgcctccgccgtgaagaagcccaacggcctgttcgcctcctccaccgcccgcaagt
ccaaggccgtgcgcgccatggtgctgcccaccgtgaccgcccccaagcgcgagaaggaccccaagaagcgcatcgtgatcaccg
gcatgggcctggtgtccgtgttcggcaacgacatcgacaccttctactccaagctgctggagggcgagtccggcatcggccccatcg
accgcttcgacgcctcctccttctccgtgcgcttcgccggccagatccacaacttctcctccaagggctacatcgacggcaagaacga
ccgccgcctggacgactgctggcgctactgcctggtggccggccgccgcgccctggaggacgccaacctgggccccgaggtgct
ggagaagatggaccgctcccgcatcggcgtgctgatcggcaccggcatgggcggcctgtccgccttctccaacggcgtggagtccc
tgatccagaagggctacaagaagatcacccccttcttcatcccctactccatcaccaacatgggctccgccctgctggccatcgacacc
ggcgtgatgggccccaactactccatctccaccgcctgcgccaccgccaactactgcttccacgccgccgccaaccacatccgccgc
ggcgaggccgagatcatggtgaccggcggcaccgaggccgccgtgtccgccaccggcgtgggcggcttcatcgcctgccgcgcc
ctgtcccaccgcaacgacgagcccagaccgcctcccgcccctgggacaaggaccgcgacggcttcgtgatgggcgagggcgcc
ggcgtgctggtgatggagtccctgcaccacgcccgcaagcgcggcgccaacatcatcgccgagtacctgggcggcgccgtgacct
gcgacgcccaccacatgaccgaccccgcgccgacggcctgggcgtgtcctcctgcatcaccaagtccctggaggacgccggcgt
gtcccccgaggaggtgaactacgtgaacgcccacgccacctccaccctggccggcgacctggccgaggtgaacgccatcaagaa
ggtgttcaaggacacctccgagatgaagatgaacggcaccaagtccatgatcggccactgcctgggcgccgccggcggcctggag
gccatcgccaccatcaaggccatcaacaccggctggctgcaccccaccatcaaccagttcaacatcgagcccgccgtgaccatcga
caccgtgcccaacgtgaagaagaagcacgacatccacgtgggcatctccaactccttcggcttcggcggccacaactccgtggtggt
gttcgccccttcatgcccaccatgtacccctacgacgtgcccgactacgcctga SEQ ID NO: 41
*C. camphora*KASI (D3148, pSZ4339) codon optimized for Prototheca
atgcagatcctgcagacccctcctcctcctcctcctccctgcgcatgtcctccatggagtccctgtccctgaccccccaagtccctgccc
ctgaagaccctgctgcccctgcgcccccgccccaagaacctgtcccgccgcaagtcccagaaccccgccccatctcctcctcctcc
tcccccgagcgcgagaccgaccccaagaagcgcgtggtgatcaccggcatgggcctggtgtccgtgttcggcaacgacgtggacg
cctactacgaccgcctgctgtccggcgagtccggcatcgcccccatcgaccgcttcgacgcctccaagttccccacccgcttcgccg
gccagatccgcggcttcacctccgacggctacatcgacggcaagaacgaccgccgcctggacgactgcctgcgctactgcatcgtg
tccggcaagaaggccctggagaacgccggcctgggccccacctgatggacggcaagatcgacaaggagcgcgccggcgtgct
ggtgggcaccggcatgggcggcctgaccgtgttctccaacggcgtgcagaccctgcacgagaagggctaccgcaagatgacccc
ttcttcatcccctacgccatcaccaacatgggctccgccctgctggccatcgagctgggcttcatgggccccaactactccatctccacc -continued

SEQUENCE LISTING gcctgcgccacctccaactactgcttctacgccgccgccaaccacatccgccgcggcgaggccgacctgatgctggccggcggca
ccgaggccgccatcatccccatcggcctgggcggcttcgtggcctgccgcgccctgtcccagcgcaacgacgaccccccagaccgc
ctcccgcccctgggacaaggaccgcgacggcttcgtgatgggcgagggcgccggcgtgctggtgatggagtccctggagcacgc
catgaagcgcgacgcccccatcatcgccgagtacctgggcggcgccgtgaactgcgacgcctaccacatgaccgacccccgcgcc
gacggcctgggcgtgtccacctgcatcgagcgctccctggaggacgccggcgtggcccccgaggaggtgaactacatcaacgccc
acgccacctccaccctggccggcgacctggccgaggtgaacgccatcaagaaggtgttcaccaacacctccgagatcaagatcaac
gccaccaagtccatgatcggccactgcctgggcgccgccggcggcctggaggccatcgccaccatcaaggccatcaacaccggct
ggctgcacccctccatcaaccagttcaaccccgagccctccgtggagttcgacaccgtggccaacaagaagcagcagcacgaggtg
aacgtggccatctccaactccttcggcttcggcggccacaactccgtggtggtgttctccgccttcaagcccaccatgtacccctacga
cgtgcccgactacgcctga SEQ ID NO: 42
*U. californica* KASI
*U. californica* KASI (D3150, pSZ4341) codon optimized for Prototheca
atggagtccctgtccctgacccccaagtccctgcccctgaagaccctgctgcccttccgcccccgccccaagaacctgtcccgccgc
aagtcccagaaccccaagcccatctcctcctcctcctcccccgagcgcgagaccgaccccaagaagcgcgtggtgatcaccggcat
gggcctggtgtccgtgttcggcaacgacgtggacgcctactacgaccgcctgctgtccggcgagtccggcatcgcccccatcgacc
gcttcgacgcctccaagttccccacccgcttcgccggccagatccgcggcttcacctccgacggctacatcgacggcaagaacgacc
gccgcctggacgactgcctgcgctactgcatcgtgtccggcaagaaggccctggagaacgccggcctgggccccgacctgatgga
cggcaagatcgacaaggagcgcgccggcgtgctggtgggcaccggcatgggcggcctgaccgtgttctccaacggcgtgcagac
cctgcacgagaagggctaccgcaagatgaccccttcttcatcccctacgccatcaccaacatgggctccgccctgctggccatcgac
ctgggcttcatgggccccaactactccatctccaccgcctgcgccacctccaactactgcttctacgccgccgccaaccacatccgcc
gcggcgaggccgacgtgatgctggccggcggcaccgaggccgccatcatccccatcggcctgggcggcttcgtggcctgccgcg
ccctgtcccagcgcaacgacgaccccagaccgcctcccgcccctgggacaaggaccgcgacggcttcgtgatgggcgagggcg
ccggcgtgctggtgatggagtccctggagcacgccatgaagcgcgacgcccccatcatcgccgagtacctgggcggcgccgtgaa
ctgcgacgcctaccacatgaccgacccccgcgccgacggcctgggcgtgtccacctgcatcgagcgctccctggaggacgccggc
gtggcccccgaggaggtgaactacatcaacgcccacgccacctccaccctggccggcgacctggccgaggtgaacgccatcaaga
aggtgttcaccaacacctccgagatcaagatcaacgccaccaagtccatgatcggccactgcctgggcgccgccggcggcctggag
gccatcgccaccatcaaggccatcaacaccggctggctgcacccctccatcaaccagttcaaccccgagccctccgtggagttcgac
accgtggccaacaagaagcagcagcacgaggtgaacgtggccatctccaactccttcggcttcggcggccacaactccgtggtggt
gttctccgccttcaagcccaccatgtacccctacgacgtgcccgactacgcctga SEQ ID NO: 43
*U. californica* KASIV (D3152, pSZ4343) codon optimized for Prototheca
atgacccagaccctgatctgcccctcctccatggagaccctgtccctgaccaagcagtcccacttccgcctgcgcctgcccaccccc
cccacatccgccgcggcggcggccaccgccaccccccccccttcatctccgcctccgccgcccccgccgcgagaccgacccca
agaagcgcgtggtgatcaccggcatgggcctggtgtccgtgttcggcaccaacgtggacgtgtactacgaccgcctgctggccggc
gagtccggcgtgggcaccatcgaccgcttcgacgcctccatgttccccacccgcttcggcggccagatccgccgcttcacctccgag
ggctacatcgacggcaagaacgaccgccgcctggacgactacctgcgctactgcctggtgtccggcaagaaggccatcgagtccg
ccggcttcgacctgcacaacatcaccaacaagatcgacaaggagcgcgccggcatcctggtgggctccggcatgggcggcctgaa
ggtgttctccgacggcgtggagtccctgatcgagaagggctaccgcaagatctccccttcttcatcccctacatgatccccaacatgg
gctccgccctgctgggcatcgacctgggcttcatgggccccaactactccatctccaccgcctgcgccacctccaactactgcatctac
gccgccgccaaccacatccgccagggcgacgccgacctgatggtggccggcggcaccgaggcccccatcatccccatcggcctg
ggcggcttcgtggcctgccgcgccctgtccacccgcaacgacgaccccagaccgcctcccgcccctgggacatcgaccgcgacg
gcttcgtgatgggcgagggcgccggcatcctggtgctggagtccctggagcacgccatgaggcgcgacgcccccatcctggccga
gtacctgggcggcgccgtgaactgcgacgcccaccacatgaccgacccccgcgccgacggcctgggcgtgtccacctgcatcgag
tcctccctggaggacgccggcgtggccgccgaggaggtgaactacatcaacgcccacgccacctccacccccaccggcgacctgg
ccgagatgaaggccatcaagaacgtgttccgcaacacctccgagatcaagatcaacgccaccaagtccatgatcggccactgcctgg
gcgcctccggcggcctggaggccatcgccaccctgaaggccatcaccaccggctggctgcaccccaccatcaaccagttcaaccc
cgagccctccgtggacttcgacaccgtggccaagaagaagaagcagcacgaggtgaacgtggccatctccaactccttcggcttcg
gcggccacaactccgtgctggtgttctccgccttcaagcccaccatgtacccctacgacgtgcccgactacgcctga SEQ ID NO: 44
*C. wrightii* KASAI (D3153, pSZ4379) codon optimized for Prototheca
atggcttccgcggcattcaccatgtcggcgtgccccgcgatgactggcagggcccctggggcacgtcgctccggacggccagtcgc
cacccgcctgaggtacgtattccagtgcctggtggccagctgcatcgacccctgcgaccagtaccgcagcagcgccagcctgagctt
cctgggcgacaacggcttcgccagcctgttcggcagcaagcccttcatgagcaaccgcggccaccgccgcctgcgccgcgccagc
cacagcggcgaggccatggccgtggccctgcagcccgcccaggaggccggaccaagaagaagcccgtgatcaagcagcgcc
gcgtggtggtgaccggcatgggcgtggtgacccccctgggccacgagcccgacgtgttctacaacaacctgctggacggcgtgag
cggcatcagcgagatcgagaccttcgactgcacccagttccccacccgcatcgccggcgagatcaagagcttcagcaccgacggct
gggtggcccccaagctgagcaagcgcatggacaagttcatgctgtacctgctgaccgccggcaagaaggccctggccgacggcgg
catcaccgacgaggtgatgaaggagctggacaagcgcaagtgcggcgtgctgatcggcagcggcatgggcggcatgaaggtgttc
aacgacgccatcgaggccctgcgcgtgagctacaagaagatgaaccccttctgcgtgcccttcgccaccaccaacatgggcagcgc
catgctggccatggacctgggctggatgggccccaactacagcatcagcaccgcctgcgccaccagcaacttctgcatcctgaacgc
cgccaaccacatcatccgcggcgaggccgacatgatgctgtgcggcggcagcgacgccgtgatcatccccatcggcctgggcggc
ttcgtggcctgccgcgccctgagccagcgcaacagcgaccccaccaaggccagccgcccctgggacagcaaccgcgacggcttc
gtgatgggcgagggcgccggcgtgctgctgctggaggagctggagcacgccaagaagcgcggcgccaccatctacgccgagttc
ctgggcggcagcttcacctgcgacgcctaccacatgaccgagccccaccccgagggcgccggcgtgatcctgtgcatcgagaagg
ccctggcccaggccggcgtgagcaaggaggacgtgaactacatcaacgcccacgccaccagcaccagcgccggcgacatcaag
gagtaccaggccctggcccgctgcttcggccagaacagcgagctgcgcgtgaacagcaccaagagcatgatcggccacctgctgg
gcgccgccggcggcgtggaggccgtgaccgtggtgcaggccatccgcaccggctggattcaccccaacctgaacctggaggacc
ccgacaaggccgtggacgccaagctgctggtgggccccaagaaggagcgcctgaacgtgaaggtgggcctgagcaacagcttcg
gcttcggcggccacaacagcagcatcctgttcgcccctgcaacgtgtga -continued

SEQUENCE LISTING

SEQ ID NO: 45
*C. avigera* KASIVb (D3287, pSZ4453) codon optimized for Prototheca
atggcttccgcggcattcaccatgtcggcgtgccccgcgatgactggcagggcccctggggcacgtcgctccggacggccagtcgc
cacccgcctgaggggctccaccttccagtgctacatcggcgacaacggcttcggctccaagcccccccgctccaaccgcggccacc
tgcgcctgggccgcacctcccactccggcgaggtgatggccgtggccatgcagtccgcccaggaggtgtccaccaaggagaagcc
cgccaccaagcagcgccgcgtggtggtgaccggcatgggcgtggtgaccgccctgggccacgaccccgacgtgtactacaacaa
cctgctggacggcgtgtccggcatctccgagatcgagaacttcgactgctcccagctgcccacccgcatcgccggcgagatcaagtc
cttctccgccgacggctgggtggcccccaagttctcccgccgcatggacaagttcatgctgtacatcctgaccgccggcaagaaggc
cctggtggacggcggcatcaccgaggacgtgatgaaggagctggacaagcgcaagtgcggcgtgctgatcggctccggcctggg
cggcatgaaggtgttctccgagtccatcgaggccctgcgcacctcctacaagaagatctccccctctgcgtgcccttctccaccacca
acatgggctccgccatcctggccatggacctgggctggatgggccccaactactccatctccaccgcctgcgccacctccaacttctg
catcctgaacgccgccaaccacatcaccaagggcgaggccgacatgatgctgtgcggcggctccgactccgtgatcctgcccatcg
gcatgggcggcttcgtggcctgccgcgccctgtcccagcgcaacaacgaccccaccaaggcctcccgcccctgggactccaaccg
cgacggcttcgtgatgggcgagggcgccggcgtgctgctgctggaggagctggagcacgccaagaagcgcggcgccaccatcta
cgccgagttcctgggcggctccttcacctgcgacgcctaccacatgaccgagccccaccccgagggcgccggcgtgatcctgtgca
tcgagaaggccctggcccagtccggcgtgtcccgcgaggacgtgaactacatcaacgcccacgccacctccacccccgccggcga
catcaaggagtaccaggccctggcccactgcttcggccagaactccgagctgcgcgtgaactccaccaagtccatgatcggccacct
gctgggcggcgccggcggcgtggaggccgtgaccgtggtgcaggccatccgcaccggctggatccaccccaacatcaacctgga
cgaccccgacgagggcgtggacgccaagctgctggtgggccccaagaaggagaagctgaaggtgaaggtgggcctgtccaactc
cttcggcttcggcggccacaactcctccatcctgttcgcccccctgcaacaccatgtacccctacgacgtgcccgactacgcctga SEQ ID NO: 46
*C. paucipetala* KASIVb codon optimized for Prototheca
atggcttccgcggcattcaccatgtcggcgtgccccgcgatgactggcagggcccctggggcacgtcgctccggacggccagtcgc
cacccgcctgaggggctccaccttccagtgcctgggcgacatcggcttcgcctccctgatcggctccaagcccccccgctccaaccg
caaccaccgccgcctgggccgcacctcccactccggcgaggtgatggccgtggccatgcagcccgcccacgaggcctccaccaa
gaacaagcccgtgaccaagcagcgccgcgtggtggtgaccggcatgggcgtggccacccccctgggccacgaccccgacgtgta
ctacaacaacctgctggacggcgtgtccggcatctcccagatcgagaacttcgactgcacccagttccccacccgcatcgccggcga
gatcaagtccttctccaccgagggctacgtgatccccaagttcgccaagcgcatggacaagttcatgctgtacctgctgaccgccggc
aagaaggccctggaggacggcggcatcaccgaggacgtgatgaaggagctggacaagcgcaagtgcggcgtgctgatcggctcc
ggcatgggcggcatgaagatcatcaacgactccatcgccgccctgaacgtgtcctacaagaagatgacccccttctgcgtgcccttct
ccaccaccaacatgggctccgccatgctggccatcgacctgggctggatgggccccaactactccatctccaccgcctgcgccacct
ccaactactgcatcctgaacgccgccaaccacatcgtgcgcggcgaggccgacatgatgctgtgcggcggctccgacgccgtgatc
atccccgtgggcctgggcggcttcgtggcctgccgcgccctgtcccagcgcaacaacgaccccaccaaggcctcccgcccctggg
actccaaccgcgacggcttcgtgatgggcgagggcgccggcgtgctgctgctggaggagctggagcacgccaagaagcgcggcg
ccaccatctacgccgagttcctgggcggctccttcacctgcgacgcctaccacatgaccgagccccaccccgacggcgccggcgtg
atcctgtgcatcgagaaggccctggcccagtccggcgtgtcccgcgaggacgtgaactacatcaacgcccacgccacctccacccc
cgccggcgacatcaaggagtaccaggccctggcccactgcttcggccagaactccgagctgcgcgtgaactccaccaagtccatga
tcggccacctgctgggcgccgccggcggcgtggaggccgtgaccgtggtgcaggccatccgcaccggctggatccaccccaacat
caacctggagaaccccgacgaggccgtggacgccaagctgctggtgggccccaagaaggagaagctgaaggtgaaggtgggcct
gtccaactccttcggcttcggcggccacaactcctccatcctgttcgcccccctacaacaccatgtacccctacgacgtgcccgactacg
cctga SEQ ID NO: 47
*C. ignea* KASIVb (D3289, pSZ4455) codon optimized for Prototheca
atggcttccgcggcattcaccatgtcggcgtgccccgcgatgactggcagggcccctggggcacgtcgctccggacggccagtcgc
cacccgcctgaggggctccacctcccagtgcctggtgacctcctacatcgacccctgcaacaagtactgctcctccgcctccctgtcct
tcctgggcgacaacggcttcgcctccctgttcggctccaagcccttccgctccaaccgcggccaccgccgcctgggccgcgcctccc
actccggcgaggccatggccgtggccctgcagcccgcccaggaggtgaccaccaagaagaagcccgtgatcaagcagcgccgc
gtggtggtgaccggcatgggcgtggtgacccccctgggccacgagcccgacgtgtactacaacaacctgctggacggcgtgtccg
gcatctccgagatcgagaccttcgactgcacccagttccccacccgcatcgccggcgagatcaagtccttctccaccgacggctgggt
ggcccccaagctgtccaagcgcatggacaagttcatgctgtacctgctgaccgccggcaagaaggccctggccgacggcggcatc
accgacgacgtgatgaaggagctggacaagcgcaagtgcggcgtgctgatcggctccggcatgggcggcatgaagctgttcaacg
actccatcgaggccctgcgcatctcctacaagaagatgaaccccttctgcgtgcccttcgccaccaccaacatgggctccgccatgct
ggccatggacctgggctggatgggccccaactactccatctccaccgcctgcgccacctccaacttctgcatcctgaacgcctccaac
cacatcgtgcgcggcgaggccgacatgatgctgtgcggcggctccgactccgtgaccgtgcccctgggcgtgggcggcttcgtggc
ctgccgcgccctgtcccagcgcaacaacgaccccaccaaggcctcccgcccctgggactccaaccgcgacggcttcgtgatgggc
gagggcgccggcgtgctgctgctggaggagctggagcacgccaagaagcgcggcgccaccatctacgccgagttcctgggcggc
tccttcacctccgacgcctaccacatgaccgagccccaccccgagggcgccggcgtgatcctgtgcatcgagaaggccctggccca
gtccggcgtgtcccgcgaggacgtgaactacatcaacgcccacgccacctccacccccgccggcgacatcaaggagtaccaggcc
ctggcccgctgcttcggccagaactccgagctgcgcgtgaactccaccaagtccatgatcggccacctgctgggcgccgccggcgg
cgtggaggccgtggccgtgatccaggccatccgcaccggctggatccaccccaacatcaacctggaggaccccgacgaggccgtg
gaccccaagctgctggtgggccccaagaaggagaagctgaaggtgaaggtggccctgtccaactccttcggcttcggcggccacaa
ctcctccatcctgttcgcccccctgcaacaccatgtacccctacgacgtgcccgactacgcctga SEQ ID NO: 48
*Cuphea procumbens* KASIV (D3290, pSZ4456) codon optimized for Prototheca
atggcttccgcggcattcaccatgtcggcgtgccccgcgatgactggcagggcccctggggcacgtcgctccggacggccagtcgc
cacccgcctgaggggctccaccttccagtgcctggtgacctcccacaacgacccctgcaaccagtactgctcctccgcctccctgtcc
ttcctgggcgacaacggcttcggctccaagcccttccgctccaaccgcggccaccgccgcctgggccgcgcctcccactccggcga
ggccatggccgtggccctgcagcccgcccaggaggtggccaccaagaagaagcccgccatgaagcagcgccgcgtggtggtga
ccggcatgggcgtggtgacccccctgggccacgagcccgacgtgtactacaacaacctgctggacggcgtgtccggcatctccgag
atcgagaccttcgactgcacccagttccccacccgcatcgccggcgagatcaagtccttctccaccgacggctgggtggcccccaag
ctgtccaagcgcatggacaagttcatgctgtacctgctgaccgccggcaagaaggccctggccgacggcggcatcaccgacgacgt
gatgaaggagctggacaagcgcaagtgcggcgtgctgatcggctccggcatgggcggcatgaagctgttcaacgactccatcgag
gccctgcgcgtgtcctacaagaagatgaaccccttctgcgtgcccttcgccaccaccaacatgggctccgccatgctggccatggacc -continued

SEQUENCE LISTING tgggctggatgggccccaactactccatctccaccgcctgcgccacctccaacttctgcatcctgaacgccgccaaccacatcgtgcg
cggcgaggccgacatgatgctgtgcggcggctccgacgccgtgatcatccccatcggcctgggcggcttcgtggcctgccgcgccc
tgtcccagcgcaacaacgaccccaccaaggcctcccgcccctgggactccaaccgcgacggcttcgtgatgggcgagggcgccg
gcgtgctgctgctggaggagctggagcacgccaagaagcgcggcgccaccatctacgccgagttcctgggcggctccttcacctgc
gacgcctaccacatgaccgagccccaccccgagggcgccggcgtgatcctgtgcatcgagaaggccctggcccagtccggcgtgt
cccgcgaggacgtgaactacatcaacgcccacgccacctccacccccgccggcgacatcaaggagtaccaggccctggcccactg
cttcggccagaactccgagctgcgcgtgaactccaccaagtccatgatcggccacctgctgggcgccgccggcggcgtggaggcc
gtgaccgtgatccaggccatccgcaccggctggatccaccccaacctgaacctggaggaccccgacaaggccgtggacgccaagt
tcctggtgggccccaagaaggagcgcctgaacgtgaaggtgggcctgtccaactccttcggcttcggcggccacaactcctccatcc
tgttcgcccccctgcaacaccatgtacccctacgacgtgcccgactacgcctga SEQ ID NO: 49
*C paucipetala* KASIVa (D3291, pSZ4457) codon optimized for Prototheca
atggcttccgcggcattcaccatgtcggcgtgccccgcgatgactggcagggcccctggggcacgtcgctccggacggccagtcgc
cacccgcctgaggggctccaccttccagtgcctggtgaactcccacatcgaccccctgcaaccagaacgtgtcctccgcctccctgtcc
ttcctgggcgacaacggcttcggctccaaccccttccgctccaaccgcggccaccgccgcctgggccgcgcctcccactccggcga
ggccatggccgtggccctgcagcccgcccaggaggtggccaccaagaagaagcccgccatcaagcagcgccgcgtggtggtga
ccggcatgggcgtggtgacccccctgggccacgagcccgacgtgttctacaacaacctgctggacggcgtgtccggcatctccgag
atcgagaccttcgactgcacccagttccccacccgcatcgccggcgagatcaagtccttctccaccgacggctgggtggcccccaag
ctgtccaagcgcatggacaagttcatgctgtacctgctgaccgccggcaagaaggccctggccgacgccggcatcaccgaggacgt
gatgaaggagctggacaagcgcaagtgcggcgtgctgatcggctccggcatgggcggcatgaagctgttcaacgactccatcgag
gccctgcgcgtgtcctacaagaagatgaaccccttctgcgtgcccttcgccaccaccaacatgggctccgccatgctggccatggacc
tgggctggatgggccccaactactccatctccaccgcctgcgccacctccaacttctgcatcctgaacgccgccaaccacatcatccg
cggcgaggccgacatgatgctgtgcggcggctccgacgccgtgatcatccccatcggcctgggcggcttcgtggcctgccgcgccc
tgtcccagcgcaactccgaccccaccaaggcctcccgcccctgggactccaaccgcgacggcttcgtgatgggcgagggcgccgg
cgtgctgctgctggaggagctggagcacgccaagaagcgcggcgccaccatctacgccgagttcctgggcggctccttcacctgcg
acgcctaccacatgaccgagccccaccccgacggcgccggcgtgatcctgtgcatcgagaaggcccttggcccagtccggcgtgtc
ccgcgaggacgtgaactacatcaacgcccacgccacctccacccccgccggcgacatcaaggagtaccaggccctggcccactgc
ttcggccagaactccgagctgcgcgtgaactccaccaagtccatgatcggccacctgctgggcgccgccggcggcgtggaggccg
tgaccgtgatccaggccatccgcaccggctggatccaccccaacctgaacctggaggaccccgacgaggccgtggacgccaagtt
cctggtgggccccaagaaggagcgcctgaacgtgaaggtgggcctgtccaactccttcggcttcggcggccacaactcctccatcct
gttcgcccccctacaacaccatgtacccctacgacgtgcccgactacgcctga SEQ ID NO: 50
*Cuphea painteri* KASIV (D3292, pSZ4458) codon optimized for Prototheca
atggcttccgcggcattcaccatgtcggcgtgccccgcgatgactggcagggcccctggggcacgtcgctccggacggccagtcgc
cacccgcctgaggggctccacccccccagtgcctggacccctgcaaccagcactgcttcctgggcgacaacggcttcgcctccctgat
cggctccaagcccccccgctccaacctgggccacctgcgcctgggccgcacctcccactccggcgaggtgatggccgtggcccag
gaggtgtccaccaacaagaagcacgccaccaagcagcgccgcgtggtggtgaccggcatgggcgtggtgacccccctgggccac
gaccccgacgtgtactacaacaacctgctggagggcgtgtccggcatctccgagatcgagaacttcgactgctcccagctgcccacc
cgcatcgccggcgagatcaagtccttctccaccgacggcctggtggcccccaagctgtccaagcgcatggacaagttcatgctgtac
atcctgaccgccggcaagaaggccctggccgacggcggcatcaccgaggacgtgatgaaggagctggacaagcgcaagtgcgg
cgtgctgatcggctccggcctgggcggcatgaaggtgttctccgactccgtggaggccctgcgcatctcctacaagaagatctccccc
ttctgcgtgcccttctccaccaccaacatgggctccgccatgctggccatggacctgggctggatgggccccaactactccatctccac
cgcctgcgccacctccaacttctgcatcctgaacgccgccaaccacatcaccaagggcgaggccgacatgatgctgtgcggcggct
ccgacgccgccatcctgcccatcggcatgggcggcttcgtggcctgccgcgccctgtcccagcgaacaacgaccccaccaaggc
ctcccgcccctgggactccaaccgcgacggcttcgtgatgggcgagggcgccggcgtgctgctgctggaggagctggagcacgcc
aagaagcgcggcgccaccatctacgccgagttcctgggcggctccttcacctgcgacgcctaccacatgaccgagccccaccccga
cggcgccggcgtgatcctgtgcatcgagaaggccctggcccagtccggcgtgtcccgcgaggaggtgaactacatcaagcccac
gccacctccacccccgccggcgacatcaaggagtaccaggccctggcccactgcttcggccagaactccgagctgcgcgtgaactc
caccaagtccatgatcggccacctgctgggcggcgccggcggcgtggaggccgtgaccgtggtgcaggccatccgcaccggctg
gatccaccccaacatcaacctggaggaccccgacaagggcgtggacgccaagctgctggtgggccccaagaaggagaagctgaa
ggtgaaggtgggcctgtccaactccttcggcttcggcggccacaactcctccatcctgttcgcccccctgcaacaccatgtacccctacg
acgtgcccgactacgcctga SEQ ID NO: 51
*C. avigera* KASIVa (D3293, pSZ4459) codon optimized for Prototheca
atggcttccgcggcattcaccatgtcggcgtgccccgcgatgactggcagggcccctggggcacgtcgctccggacggccagtcgc
cacccgcctgaggggctccaccttccagtgcctggtgacctcctacaacgaccccctgcgagcagtaccgctcctccgcctccctgtcc
ttcctgggcgacaacggcttcgcctccctgttcggctccaagcccttccgctccaaccgcggccaccgccgcctgggccgcgcctcc
cactccggcgaggccatggccgtggccctgcagcccgcccaggaggtgggcaccaagaagaagcccgtgatcaagcagcgccg
cgtggtggtgaccggcatgggcgtggtgacccccctgggccacgagcccgacgtgtactacaacaacctgctggacggcgtgtccg
gcatctccgagatcgagaccttcgactgcacccagttccccacccgcatcgccggcgagatcaagtccttctccaccgacggctgggt
ggcccccaagctgtccaagcgcatggacaagttcatgctgtacctgctgaccgccggcaagaaggccctggccgacggcggcatc
accgacgacgtgatgaaggagctggacaagcgcaagtgcggcgtgctgatcggctccggcctgggcggcatgaaggtgttctccg
agtccatcgaggccctgcgcacctcctacaagaagatctccccctctgcgtgcccttctccaccaccaacatgggctccgccatcctg
gccatggacctgggctggatgggccccaactactccatctccaccgcctgcgccacctccaacttctgcatcctgaacgccgccaacc
acatcaccaagggcgaggccgacatgatgctgtgcggcggctccgactccgtgatcctgcccatcggcatgggcggcttcgtggcct
gccgcgccctgtcccagcgcaacaacgaccccaccaaggcctcccgcccctgggactccaaccgcgacggcttcgtgatgggcga
gggcgccggcgtgctgctgctggaggagctggagcacgccaagaagcgcggcgccaccatctacgccgagttcctgggcggctc
cttcacctgcgacgcctaccacatgaccgagccccaccccgagggcgccggcgtgatcctgtgcatcgagaaggccctggcccagt
ccggcgtgtcccgcgaggacgtgaactacatcaacgcccacgccacctccacccccgccggcgac atcaaggagtaccaggccct
ggcccactgcttcggccagaactccgagctgcgcgtgaactccaccaagtccatgatcggccacctgctgggcggcgccggcggc
gtggaggccgtgaccgtggtgcaggccatccgcaccggctggatccaccccaacatcaacctggacgaccccgacgagggcgtg
gacgccaagctgctggtgggccccaagaaggagaagctgaaggtgaaggtgggcctgtccaactccttcggcttcggcggccaca
actcctccatcctgttcgcccccctgcaacaccatgtacccctacgacgtgcccgactacgcctga -continued

SEQUENCE LISTING

SEQ ID NO: 52
*C ignea* KASIVa (D3294, pSZ4460) codon optimized for Prototheca
atggcttccgcggcattcaccatgtcggcgtgccccgcgatgactggcagggcccctggggcacgtcgctccggacggccagtcgc
cacccgcctgaggggctccacctcccagtgcctggtgacctcctacatcgacccctgcaacaagtactgctcctccgcctccctgtcct
tcctgggcgacaacggcttcgcctccctgttcggctccaagcccttccgctccaaccgcggccaccgccgcctgggccgcgcctccc
actccggcgaggccatggccgtggccctgcagcccgcccaggaggtgaccaccaagaagaagcccgtgatcaagcagcgccgc
gtggtggtgaccggcatgggcgtggtgacccccctgggccacgagcccgacgtgtactacaacaacctgctggacggcgtgtccg
gcatctccgagatcgagaccttcgactgcacccagttccccacccgcatcgccggcgagatcaagtccttctccaccgacggctgggt
ggcccccaagctgtccaagcgcatggacaagttcatgctgtaccgctgaccgccggcaagaaggccctggccgacggcggcatc
accgacgacgtgatgaaggagctggacaagcgcaagtgcggcgtgctgatcggctccggcatgggcggcatgaagctgttcaacg
actccatcgaggccctgcgcatctcctacaagaagatgaaccccttctgcgtgcccttcgccaccaccaacatgggctccgccatgct
ggccatggacctgggctggatgggccccaactactccatctccaccgcctgcgccacctccaacttctgcatcctgaacgcctccaac
cacatcgtgcgcggcgaggccgacatgatgctgtgcggcggctccgacgccgtgatcatccccatcggcctgggcggcttcgtggc
ctgccgcgccctgtcccagcgcaacaacgaccccaccaaggcctcccgcccctgggactccaaccgcgacggcttcgtgatgggc
gagggcgccggcgtgctgctgctggaggagctggagcacgccaagaagcgcggcgccaccatctacgccgagttcctgggcggc
tccttcacctgcgacgcctaccacatgaccgagccccaccccgagggcgccggcgtgatcctgtgcatcgagaaggccctggccca
ggccggcgtgtccaaggaggacgtgaactacatcaacgcccacgccacctccacccccgccggcgacatcaaggagtaccaggc
cctggcccagtgcttcggccagaactccgagctgcgcgtgaactccaccaagtccatgatcggccacctgctgggcgccgccggcg
gcgtggaggccgtgaccgtggtgcaggccatccgcaccggctggatccaccccaacctgaacctggaggaccccgacaaggccg
tggacgccaagctgctggtgggccccaagaaggagcgcctgaacgtgaaggtgggcctgtccaactccttcggcttcggcggccac
aactcctccatcctgttcgcccccctacaacaccatgtacccctacgacgtgcccgactacgcctga SEQ ID NO: 53
*C. avigera* KASIa (D3342, pSZ4511) codon optimized for Prototheca
atgcagtccctgcactcccccgccctgcgcgcctccccccctggacccccctgcgcctgaagtcctccgccaacggcccctcctccacc
gccgccttccgcccccctgcgccgcgccaccctgcccaacatccgcgccgcctcccccaccgtgtccgcccccaagcgcgagaccg
accccaagaagcgcgtggtgatcaccggcatgggcctggtgtccgtgttcggctccgacgtggacgcctactacgagaagctgctgt
ccggcgagtccggcatctccctgatcgaccgcttcgacgcctccaagttccccacccgcttcggcggccagatccgcggcttcaacg
ccaccggctacatcgacggcaagaacgaccgccgcctggacgactgcctgcgctactgcatcgtggccggcaagaaggccctgga
gaactccgacctgggcggcgactccctgtccaagatcgacaaggagcgcgccggcgtgctggtgggcaccggcatgggcggcct
gaccgtgttctccgacggcgtgcagaacctgatcgagaagggccaccgcaagatctccccctcttcatcccctacgccatcaccaac
atgggctccgccctgctggccatcgacctgggcctgatgggccccaactactccatctccaccgcctgcgccacctccaactactgctt
ctacgccgccgccaaccacatccgccgcggcgaggccgacctgatgatcgccggcggcaccgaggccgccatcatccccatcgg
cctgggcggcttcgtggcctgccgcgccctgtcccagcgcaacgacgaccccagaccgcctcccgcccctgggacaaggaccg
cgacggcttcgtgatgggcgaggcgccggcgtgctggtgatggagtccctggagcacgccatgaagcgcggcgcccccatcatc
gccgagtacctgggcggcgccgtgaactgcgacgcctaccacatgaccgacccccgcgccgacggcctgggcgtgtcctcctgca
tcgagtcctccctggaggacgccggcgtgtcccccgaggaggtgaactacatcaacgcccacgccacctccaccctggccggcga
cctggccgagatcaacgccatcaagaaggtgttcaagaacaccaaggacatcaagatcaacgccaccaagtccatgatcggccact
gcctgggcgcctccggcggcctggaggccatcgccaccatcaagggcatcaccaccggctggctgcacccctccatcaaccagttc
aaccccgagccctccgtggagttcgacaccgtggccaacaagaagcagcagcacgaggtgaacgtggccatctccaactccttcgg
cttcggcggccacaactccgtggtggccttctccgccttcaagcccaccatgtacccctacgacgtgcccgactacgcctga SEQ ID NO: 54
*C. pulcherrima* KASI (D3343, pSZ4512) codon optimized for Prototheca
atgcactccctgcagtcccccctccctgcgcgcctccccccctggaccccttccgccccaagtcctccaccgtgcgcccccctgcaccgc
gcctccatccccaacgtgcgcgccgcctcccccaccgtgtccgcccccaagcgcgagaccgaccccaagaagcgcgtggtgatca
ccggcatgggcctggtgtccgtgttcggctccgacgtggacgcctactacgacaagctgctgtccggcgagtccggcatcggcccca
tcgaccgcttcgacgcctccaagttccccacccgcttcggcggccagatccgcggcttcaactccatgggctacatcgacggcaaga
acgaccgccgcctggacgactgcctgcgctactgcatcgtggccggcaagaagtccctggaggacgccgacctgggcgccgacc
gcctgtccaagatcgacaaggagcgcgccggcgtgctggtgggcaccggcatgggcggcctgaccgtgttctccgacggcgtgca
gtccctgatcgagaagggccaccgcaagatcacccccttcttcatcccctacgccatcaccaacatgggctccgccctgctggccatc
gagctgggcctgatgggccccaactactccatctccaccgcctgcgccacctccaactactgcttccacgccgccgccaaccacatc
cgccgcggcgaggccgacctgatgatcgccggcggcaccgaggccgccatcatccccatcggcctgggcggcttcgtggcctgcc
gcgccctgtcccagcgcaacgacgacccccagaccgcctcccgcccctgggacaaggaccgcgacggcttcgtgatgggcgagg
gcgccggcgtgctggtgctggagtccctggagcacgccatgaagcgcggcgcccccatcatcgccgagtacctgggcggcgccat
caactgcgacgcctaccacatgaccgacccccgcgccgacggcctgggcgtgtcctcctgcatcgagtcctccctggaggacgccg
gcgtgtcccccgaggaggtgaactacatcaacgcccacgccacctccaccctggccggcgacctggccgagatcaacgccatcaa
gaaggtgttcaagaacaccaaggacatcaagatcaacgccaccaagtccatgatcggccactgcctgggcgcctccggcggcctgg
aggccatcgccaccatcaagggcatcaacaccggctggctgcacccctccatcaaccagttcaaccccgagccctccgtggagttcg
acaccgtggccaacaagaagcagcagcacgaggtgaacgtggccatctccaactccttcggcttcggcggccacaactccgtggtg
gccttctccgccttcaagcccaccatgtacccctacgacgtgcccgactacgcctga SEQ ID NO: 55
*C. avigera* mitochondrial KAS (D3344, pSZ4513) codon optimized for Prototheca
atggtgttcctgccctggcgcaagatgctgtgcccctcccagtaccgcttcctgcgcccccctgtcctcctccaccaccttcgacccccg
ccgcgtggtggtgaccggcctgggcatggtgacccccctgggctgcggcgtgaacaccacctggaagcagctgatcgagggcaag
tgcggcatccgcgccatctccctggaggacctgaagatggacgccttcgacatcgacacccaggcctacgtgttcgaccagctgacc
tccaaggtggccgccaccgtgcccaccggcgtgaaccccggcgagttcaacgaggacctgtggttcaaccagaaggagcaccgcg
ccatcgcccgcttcatcgcctacgccctgtgcgccgccgacgaggccctgaaggacgccaactgggagcccaccgagcccgagg
agcgcgagatgaccggcgtgtccatcggcggcggcaccggctccatctcccgacgtgctggacgccggccgcatgatctgcgagaa
gaagctgcgccgcctgtccccccttcttcatcccccgcatcctgatcaacatggcctccggccacgtgtccatgaagtacggcttccagg
gccccaaccacgccgccgtgaccgcctgcgccaccggcgcccactccatcggcgacgccgcccgcatgatccagttcggcgacg
ccgacgtgatggtggccggcggcaccgagtcctccatcgacgccctgtccatcgccggcttctgccgctcccgcgccctgaccacc
aagtacaactcctgcccccaggaggcctcccgccccttcgacaccgaccgcgacggcttcgtgatcggcgagggctccggcgtgct
ggtgctggaggagctggaccacgcccgcaagcgcggcgccaagatgtacgccgagttctgcggctacggcatgtccggcgacgc
ccaccacatcacccagccccactccgacggccgcggcgccatcctggccatgacccgcgccctgaagcagtccaacctgcacccc
gaccaggtggactacgtgaacgcccacgccacctccacctccctgggcgacgccatcgaggccaaggccatcaagaccgtgttctc -continued

SEQUENCE LISTING cgaccacgccatgtccggctccctggccctgtcctccaccaagggcgccatcggccacctgctgggcgccgccggcgccgtggag
gccatcttctccatcctggccatcaagaacggcctggccccctgaccctgaacgtggcccgccccgaccccgtgttcaccgagcgc
ttcgtgcccctgaccgcctccaaggagatgcacgtgcgcgccgccctgtccaactccttcggcttcggcggcaccaacaccaccctg
ctgttcacctcccccccccagaacaccatgtacccctacgacgtgcccgactacgcctga SEQ ID NO: 56
*C. avigera* KASIII (D3345, pSZ4514) Codon optimized for Prototheca.
atggccaacgcctacggcttcgtgggctcctccgtgcccaccgtgggccgcgccgcccagttccagcagatgggctccggcttctgc
tccgtggacttcatctccaagcgcgtgttctgctgctccgccgtgcagggcgccgacaagcccgcctccggcgactcccgcgccgag
taccgcacccccgcctggtgtcccgcggctgcaagctgatcggctccggctccgccatccccaccctgcaggtgtccaacgacga
cctggccaagatcgtggacaccaacgacgagtggatctccgtgcgcaccggcatccgcaaccgccgcgtgctgaccggcaaggac
tccctgaccaacctggccaccgaggccgcccgcaaggccctggagatggcccaggtggacgccgaggacgtggacatggtgctg
atgtgcacctccacccccgaggacctgttcggctccgcccccagatccagaaggccctgggctgcaagaagaacccctgtcctac
gacatcaccgccgcctgctccggcttcgtgctgggcctggtgtccgccgcctgccacatccgcggcggcggcttcaacaacgtgctg
gtgatcggcgccgactccctgtcccgctacgtggactggaccgaccgcggcacctgcatcctgttcggcgacgccgccggcgccgt
gctggtgcagtcctgcgacgccgaggaggacggcctgttcgccttcgacctgcactccgacggcgacggccagcgccacctgcgc
gccgtgatcaccgagaacgagaccgaccacgccgtgggcaccaacggctccgtgtccgacttcccccccgccgctcctcctactc
ctgcatccagatgaacggcaaggaggtgttccgcttcgcctgccgctccgtgccccagtccatcgagctggccctgggcaaggccg
gcctgaacggctccaacatcgactggctgctgctgcaccaggccaaccagcgcatcatcgacgccgtggccacccgcctggaggtg
ccccaggagcgcgtgatctccaacctggccaactacggcaacacctccgccgcctccatcccccctggccctggacgaggccgtgcg
cggcggcaaggtgaagcccggccacctgatcgccaccgccggcttcggcgccggcctgacctggggctccgccatcgtgcgctg
gggcaccatgtacccctacgacgtgcccgactacgcctga SEQ ID NO: 57
*C. hookeriana* FATB2 (“Ch FATB2”)
MVAAAASSAFFPVPAPGASPKPGKFGNWPSSLSPSFKPKSIPNGGFQVKANDSAHPK
ANGSAVSLKSGSLNTQEDTSSSPPPRTFLHQLPDWSRLLTAITTVFVKSKRPDMHDRK
SKRPDMLVDSFGLESTVQDGLVFRQSFSIRSYEIGTDRTASIETLMNHLQETSLNHCK
STGILLDGFGRTLEMCKRDLIWVVIKMQIKVNRYPAWGDTVEINTRFSRLGKIGMGR
DWLISDCNTGEILVRATSAYAMMNQKTRRLSKLPYEVHQEIVPLFVDSPVIEDSDLK
VHKFKVKTGDSIQKGLTPGWNDLDVNQHVSNVKYIGWILESMPTEVLETQELCSLA
LEYRRECGRDSVLESVTAMDPSKVGVRSQYQHLLRLEDGTAIVNGATEWRPKNAGA
NGAISTGKTSNGNSVS SEQ ID NO: 58
23S rRNA for UTEX 1439, UTEX 1441, UTEX 1435, UTEX 1437 *Prototheca moriformis*
TGTTGAAGAATGAGCCGGCGACTTAAAATAAATGGCAGGCTAAGAGAATTAATA
ACTCGAAACCTAAGCGAAAGCAAGTCTTAATAGGGCGCTAATTTAACAAAACAT
TAAATAAAATCTAAAGTCATTTATTTTAGACCCGAACCTGAGTGATCTAACCATG
GTCAGGATGAAACTTGGGTGACACCAAGTGGAAGTCCGAACCGACCGATGTTGA
AAAATCGGCGGATGAACTGTGGTTAGTGGTGAAATACCAGTCGAACTCAGAGCT
AGCTGGTTCTCCCCGAAATGCGTTGAGGCGCAGCAATATATCTCGTCTATCTAGG
GGTAAAGCACTGTTTCGGTGCGGGCTATGAAAATGGTACCAAATCGTGGCAAAC
TCTGAATACTAGAAATGACGATATATTAGTGAGACTATGGGGGATAAGCTCCAT
AGTCGAGAGGGAAACAGCCCAGACCACCAGTTAAGGCCCCAAAATGATAATGAA
GTGGTAAAGGAGGTGAAAATGCAAATACAACCAGGAGGTTGGCTTAGAAGCAGC
CATCCTTTAAAGAGTGCGTAATAGCTCACTG SEQ ID NO: 59
Amino acid sequence of the *C. hookeriana KASIV(D3668, pSZ4756). The algal transit* peptide is underlined.
MASAAFTMSACPAMTGRAPGARRSGRPVATRLRGSTFQCLDPCNQQRFLGDNGFAS
LFGSKPLRSNRGHLRLGRTSHSGEVMAVAMQPAQEVSTNKKPATKQRRVVVTGMG
VVTPLGHDPDVYYNNLLDGISGISEIENFDCSQFPTRIAGEIKSFSTDGWVAPKFSERM
DKFMLYMLTAGKKALADGGITEDAMKELNKRKCGVLIGSGLGGMKVFSDSIEALRT
SYKKISPFCVPFSTTNMGSAILAMDLGWMGPNYSISTACATSNFCILNAANHIIKGEA
DMMLCGGSDAAVLPVGLGGFVACRALSQRNNDPTKASRPWDSNRDGFVMGEGAG
VULEELEHAKKRGATIYAEFLGGSFTCDAYHMTEPHPEGAGVILCIEKALAQSGVSR
EDVNYINAHATSTPAGDIKEYQALAHCFGQNSELRVNSTKSMIGHLLGGAGGVEAV
AVVQAIRTGWIHPNINLEDPDEGVDAKLLVGPKKEKLKVKVGLSNSFGFGGHNSSIL
FAPCN SEQ ID NO: 60
Nucleotide sequence of the *C. hookeriana* KASIV (D3668, pSZ4756) expression vector. The 5' and 3' homology arms enabling targeted integration into the SAD2-1 locus are noted with lowercase. The endogenous SAD2-1 promoter (present within the 5' homology targeting arm) drives the expression of the codon optimized Ch KASIV (noted with lowercase bold text) and is terminated with the PmHSP90 3'UTR noted in underlined, lower case bold. The PmHXT1-2 promoter is noted in uppercase italic which drives expression of the ScMelibiase selection marker noted with lowercase italic followed by the PmPGK 3'UTR terminator highlighted in uppercase. Restriction cloning sites and spacer DNA fragments are noted as underlined, uppercase plain lettering.
gccggtcaccacccgcatgctcgtactacagcgcacgcaccgcttcgtgatccaccgggtgaacgtagtcctcgacggaaacatctg
gttcgggcctcctgcttgcactcccgcccatgccgacaacctttctgctgttaccacgacccacaatgcaacgcgacacgaccgtgtg
ggactgatcggttcactgcacctgcatgcaattgtcacaagcgcttactccaattgtat-
tcgtttgttttctgggagcagttgctcgaccgc
ccgcgtcccgcaggcagcgatgacgtgtgcgtggcctgggtgtttcgtcgaaaggccagcaaccctaaatcgcaggcgatccggag
attgggatctgatccgagtttggaccagatccgccccgatgcggcacgggaactgcatcgactcggcgcggaacccagctttcgtaa -continued

SEQUENCE LISTING atgccagattggtgtccgatacctggatttgccatcagcgaaacaagacttcagcagcgagcgtatttggcgggcgtgctaccagggtt
gcatacattgcccatttctgtctggaccgctttactggcgcagagggtgagttgatggggttggcaggcatcgaaacgcgcgtgcatgg
tgtgcgtgtctgttttcggctgcacgaattcaatagtcggatgggcgacggtagaattgggtgtggcgctcgcgtgcatgcctcgcccc
gtcgggtgtcatgaccgggactggaatccccccctcgcgaccatcttgctaacgctcccgactctcccgaccgcgcgcaggatagact
cttgttcaaccaatcgacaGGTACCatggcttccgcggcattcaccatgtcggcgtgccccgcgatgactggcagggcccct
ggggcacgtcgctccggacggccagtcgccacccgcctgaggggcagcaccttccagtgcctggaccccctgcaaccagcagc
gcttcctgggcgacaacggcttcgcgtcgctgttcggctccaagcccctgcgcagcaaccgcggccacctgcgcctgggccgc
acctcgcactccggcgaggtgatggccgtcgcgatgcagcccgcccaggaggtgagcaccaacaagaagcccgcgaccaa
gcagcgccgcgtggtcgtgaccggcatgggcgtcgtgacccccctgggccacgaccccgacgtgtattataacaacctgctgg
acggcatctcgggcatctccgagatcgagaacttcgactgcagccagttccccacccgcatcgccggcgagatcaagtcgttc
tccaccgacggctgggtcgcgcccaagttcagcgagcgcatggacaagttcatgctgtatatgctgaccgccggcaagaagg
cgctggccgacggcggcatcaccgaggacgcgatgaaggagctgaacaagcgcaagtgcggcgtgctgatcggctcgggc
ctgggcggcatgaaggtcttctccgacagcatcgaggccctgcgcacctcgtataagaagatctcccccttctgcgtgcccttc
agcaccaccaacatgggctcggcgatcctggcgatggacctgggctggatgggccccaactattccatcagcaccgcgtgcg
ccacctcgaacttctgcatcctgaacgcggccaaccacatcatcaagggcgaggcggacatgatgctgtgcggcggctccga
cgccgcggtgctgcccgtcggcctgggcggcttcgtggcctgccgcgcgctgagccagcgcaacaacgaccccaccaaggcc
tcgcgcccctgggactccaaccgcgacggcttcgtcatgggcgagggcgcgggcgtgctgctgctggaggagctggagcacg
ccaagaagcgcggcgcgaccatctatgccgagttcctgggcggcagcttcacctgcgacgcgtatcacatgaccgagcccca
ccccgagggcgccggcgtcatcctgtgcatcgagaaggcgctggcccagtcgggcgtgtcccgcgaggacgtgaactatatc
aacgcgcacgccaccagcacccccgcgggcgacatcaaggagtatcaggccctggcgcactgcttcggccagaactcggag
ctgcgcgtcaactccaccaagagcatgatcggccacctgctgggcggcgccggcggcgtggaggcggtcgccgtggtccagg
cgatccgcaccggctggatccaccccaacatcaacctggaggaccccgacgagggcgtggacgccaagctgctggtcggcc
ccaagaaggagaagctgaaggtgaaggtcggcctgtcgaactccttcggcttcggcggccacaacagctcgatcctgttcgc
gccctgcaactgaCTCGAGacagacgaccttggcaggcgtcgggtagggaggtggtggtgatggcgtctcgatgccatc
gcacgcatccaacgaccgtatacgcatcgtccaatgaccgtcggtgtcctctctgcctccgttttgtgagatgtctcaggcttggt
gcatcctcgggtggccagccacgttgcgcgtcgtgctgcttgcctctcttgcgcctctgtggtactggaaaatatcatcgaggcc
cgtttttttgctcccatttcctttccgctacatcttgaaagcaaacgacaaacgaagcagcaagcaaagagcacgaggacggtg
aacaagtctgtcacctgtatacatctatttccccgcgggtgcacctactctctctcctgccccggcagagtcagctgccttacgtg
acCCTAGGTGCGGTGAGAATCGAAAATGCATCGTTTCTAGGTTCGGAGACGGTCAATTC
CCTGCTCCGGCGAATCTGTCGGTCAAGCTGGCCAGTGGACAATGTTGCTATGGCAGC
CCGCGCACATGGGCCTCCCGACGCGGCCATCAGGAGCCCAAACAGCGTGTCAGGGT
ATGTGAAACTCAAGAGGTCCCTGCTGGGCACTCCGGCCCCACTCCGGGGGCGGGAC
GCCAGGCATTCGCGGTCGGTCCCGCGCGACGAGCGAAATGATGATTCGGTTACGAGA
CCAGGACGTCGTCGAGGTCGAGAGGCAGCCTCGGACACGTCTCGCTAGGGCAACGC
CCCGAGTCCCCGCGAGGGCCGTAAACATTGTTTCTGGGTGTCGGAGTGGGCATTTTG
GGCCCGATCCAATCGCCTCATGCCGCTCTCGTCTGGTCCTCACGTTCGCGTACGGCCT
GGATCCCGGAAAGGGCGGATGCACGTGGTGTTGCCCCGCCATTGGCGCCCACGTTTC
AAAGTCCCCGGCCAGAAATGCACAGGACCGGCCCGGCTCGCACAGGCCATGCTGAAC
GCCCAGATTTCGACAGCAACACCATCTAGAATAATCGCAACCATCCGCGTTTTGAACGA
AACGAAACGGCGCTGTTTAGCATGTTTCCGACATCGTGGGGGCCGAAGCATGCTCCG
GGGGGAGGAAAGCGTGGCACAGCGGTAGCCCATTCTGTGCCACACGCCGACGAGGA
CCAATCCCCGGCATCAGCCTTCATCGACGGCTGCGCCGCACATATAAAGCCGGACGC
CTAACCGGTTTCGTGGTTATGACTAGTatgttcgcgttctacttcctgacggcctgcatctccctgaagggcgtg
ttcggcgtctcccccctcctacaacggcctgggcctgacgccccagatgggctgggacaactggaacacgttcgcctgcgacgtctc
cgagcagctgctgctggacacggccgaccgcatctccgacctgggcctgaaggacatgggctacaagtacatcatcctggacga
ctgctggtcctccggccgcgactccgacggcacctggtcgccgacgagcagaagaccccaacggcatgggccacgtcgccga
ccacctgcacaacaactccacctgacggcatgtactcctccgcgggcgagtacacgtgcgccggctaccccggctccctgggcc
gcgaggaggaggacgcccagacttcgcgaacaaccgcgtggactacctgaagtacgacaactgctacaacaagggccagac
ggcacgcccgagatctcctaccaccgctacaaggccatgtccgacgccctgaacaagacgggccgccccatcactactccctgt
gcaactggggccaggacctgaccactactggggctccggcatcgcgaactcctggcgcatgtccggcgacgtcacggcggagtt
cacgcgccccgactcccgctgcccctgcgacggcgacgagtacgactgcaagtacgccggcaccactgctccatcatgaacatc
ctgaacaaggccgcccccatgggccagaacgcgggcgtcggcggctggaacgacctggacaacctggaggtcggcgtcggc
aacctgacggacgacgaggagaaggcgcacactccatgtgggccatggtgaagtccccccctgatcatcggcgcgaacgtgaa
caacctgaaggcctcctcctactccatctactcccaggcgtccgtcatcgccatcaaccaggactccaacggcatccccgccacg
cgcgtctggcgctactacgtgtccgacacggacgagtacggccagggcgagatccagatgtggtccggcccctggacaacgg
cgaccaggtcgtggcgctgctgaacggcggctccgtgtcccgccccatgaacacgaccctggaggagatcacttcgactccaac
ctgggctccaagaagctgacctccacctgggacatctacgacctgtgggcgaaccgcgtcgacaactccacggcgtccgccatc
ctgggccgcaacaagaccgccaccggcatcctgtacaacgccaccgagcagtcctacaaggacggcctgtccaagaacgaca
cccgcctgttcggccagaagatcggctccctgtcccccaacgcgatcctgaacacgaccgtcccgcccacggcatcgcgttcta
ccgcctgcgcccctcctcctgATACAACTTATTACGTATTCTGACCGGCGCTGATGTGGCGCG
GACGCCGTCGTACTCTTTCAGACTTTACTCTTGAGGAATTGAACCTTTCTCGCTTG
CTGGCATGTAAACATTGGCGCAATTAATTGTGTGATGAAGAAAGGGTGGCACAA
GATGGATCGCGAATGTACGAGATCGACAACGATGGTGATTGTTATGAGGGGCCA
AACCTGGCTCAATCTTGTCGCATGTCCGGCGCAATGTGATCCAGCGGCGTGACTC
TCGCAACCTGGTAGTGTGTGCGCACCGGGTCGCTTTGATTAAAACTGATCGCATT
GCCATCCCGTCAACTCACAAGCCTACTCTAGCTCCCATTGCGCACTCGGGCGCCC
GGCTCGATCAATGTTCTGAGCGGAGGGCGAAGCGTCAGGAAATCGTCTCGGCAG
CTGGAAGCGCATGGAATGCGGAGCGGAGATCGAATCAGATATCAAGCTCCATCG
AGCTCcagccacggcaacaccgcgcgccttgcggccgagcacggcgacaagaacctgagcaagatctgcgggctgatcgcc
agcgacgagggccggcacgagatcgcctacacgcgcatcgtggacgagttcttccgcctcgaccccgagggcgccgtcgccgcct
acgccaacatgatgcgcaagcagatcaccatgcccgcgcacctcatggacgacatgggccacggcgaggccaacccgggccgca
acctcttcgccgacttctccgcggtcgccgagaagatcgacgtctacgacgccgaggactactgccgcatcctggagcacctcaacg
cgcgctggaaggtggacgagcgccaggtcagcggccaggccgccgcggaccaggagtacgtcctgggcctgccccagcgcttcc
ggaaactcgccgagaagaccgccgccaagcgcaagcgcgtcgcgcgcaggcccgtcgccttctcctggatctccgggcgcgaga
tcatggtctagggagcgacgagtgtgcgtgcggggctggcgggagtgggacgccctcctcgctcctctctgttctgaacggaacaat
cggccaccccgcgctacgcgccacgcatcgagcaacgaagaaaacccccgatgataggttgcggtggctgccgggatatagatc
cggccgcacatcaaagggcccctccgccagagaagaagctcctttcccagcagactcct -continued

SEQUENCE LISTING

SEQ ID NO: 61
Nucleotide sequence of the *C. hookeriana* KASIV CDS codon optimized for *P. moriformis*.
atggcttccgcggcattcaccatgtcggcgtgccccgcgatgactggcagggcccctggggcacgtcgctccggacggccagtcgc
cacccgcctgaggggcagcaccttccagtgcctggacccctgcaaccagcagcgcttcctgggcgacaacggcttcgcgtcgctgtt
cggctccaagcccctgcgcagcaaccgcggccacctgcgcctgggccgcacctcgcactccggcgaggtgatggccgtcgcgat
gcagcccgcccaggaggtgagcaccaacaagaagcccgcgaccaagcagcgccgcgtggtcgtgaccggcatgggcgtcgtga
ccccccctgggccacgaccccgacgtgtattataacaacctgctggacggcatctcgggcatctccgagatcgagaacttcgactgca
gccagttccccacccgcatcgccggcgagatcaagtcgttctccaccgacggctgggtcgcgcccaagttcagcgagcgcatggac
aagttcatgctgtatatgctgaccgccggcaagaaggcgctggccgacggcggcatcaccgaggacgcgatgaaggagctgaaca
agcgcaagtgcggcgtgctgatcggctcgggcctgggcggcatgaaggtcttctccgacagcatcgaggccctgcgcacctcgtat
aagaagatctcccccttctgcgtgcccttcagcaccaccaacatgggctcggcgatcctggcgatggacctgggctggatgggcccc
aactattccatcagcaccgcgtgcgccacctcgaacttctgcatcctgaacgcggccaaccacatcatcaagggcgaggcggacatg
atgctgtgcggcggctccgacgccgcggtgctgcccgtcggcctgggcggcttcgtggcctgccgcgcgctgagccagcgcaaca
acgaccccaccaaggcctcgcgcccctgggactccaaccgcgacggcttcgtcatgggcgagggcgcgggcgtgctgctgctgga
ggagctggagcacgccaagaagcgcggcgcgaccatctatgccgagttcctgggcggcagcttcacctgcgacgcgtatcacatga
ccgagccccaccccgagggcgccggcgtcatcctgtgcatcgagaaggcgctggcccagtcgggcgtgtcccgcgaggacgtga
actatatcaacgcgcacgccaccagcacccccgcgggcgacatcaaggagtatcaggccctggcgcactgcttcggccagaactcg
gagctgcgcgtcaactccaccaagagcatgatcggccacctgctgggcggcgccggcggcgtggaggcggtcgccgtggtccag
gcgatccgcaccggctggatccaccccaacatcaacctggaggaccccgacgagggcgtggacgccaagctgctggtcggcccc
aagaaggagaagctgaaggtgaaggtcggcctgtcgaactccttcggcttcggcggccacaacagctcgatcctgttcgcgccctgc
aactga SEQ ID NO: 62
Amino acid sequence of the *C. aequipetala* KASIV. The alga1 transit peptide is underlined.
*C aeque* KASIV
MAAAASMVASPLCTWLVAACMSTSFDNDPRSPSIKRIPRRRRILSQSSLRGSTFQCLV
TSYIDPCNQFSSSASLSFLGDNGFASLFGSKPFRSIRGHRRLGRASHSGEAMAVALEPA
QEVATKKKPVVKQRRVVVTGMGVVTPLGHEPDVYYNNLLDGVSGISEIETFDCNQF
PTRIAGEIKSFSTDGWVAPKLSKRMDKFMLYLLTAGKKALADGGITDDVMKELDKR
KCGVLIGSGLGGMKLFSDSIEALRISYKKMNPFCVPFATTNMGSAMLAMDLGWMGP
NYSISTACATSNFCILNSANHIVRGEADMMLCGGSDAVIIPIGLGGfVACRALSQRNN
DPTKASRPWDSNRDGFVMGEGAGVLLLEELEHAKKRGATIYAEFLGGSFTCDAYHM
TEPHPEGAGVILCIEKALAQAGVSREDVNYINAHATSTPAGDIKEYQALAHCFGHNS
ELRVNSTKSMIGHLIGAAGGVEAVTVVQAIRTGWIHPNLNLEDPDKAVDAKLLVGP
KKERLNVKVGLSNSFGfGGHNSSILFAPYN SEQ ID NO: 63
Amino acid sequence of the *C. glassostoma* KASIV. The alga1 transit peptide is underlined.
S07_Cg_Locus_4548_Transcript_4/9_translation
MAAAASSQLCTWLVAACMSTSFDNNPRSPSIKRLPRRRRVLSHCSLRGSTFQCLVTS
YIDPCNQYCSSASLSFLGDNGFTPLIGSKPFRSNRGHPRLGRASHSGEAMAVALQPAQ
EVATKKKPAMKQRRVVVTGMGVVTPLGHEPDVYYNNLLDGVSGISEIETFDCTQFP
TRIAGEIKSFSTDGWVAPKLSKRMDKFMLYLLTAGKKALADGGITDDVMKELDKRK
CGVLIGSGMGGMKLFNDSIEALRVSYKKMNPFCVPFATTNMGSAMLAMDLGWMGP
NYSISTACATSNFCILNAANHIVRGEADMMLCGGSDAVIIPIGLGGFVACRALSQRNN
DPTKASRPWDSNRDGFVMGEGAGVLLLEELEHAKKRGATIYAEFLGGSFTCDAYHM
TEPHPEGAGVILCIEKALAQAGVSREDVNYINAHATSTPAGDIKEYQALAHCFGQNS
ELRVNSTKSMIGHLLGAAGGVEAVTVIQAIRTGWIHPNLNLDDPDKAVDAKFLVGP
KKERLNVKVGLSNSFGfGGHNSSILFAPYN SEQ ID NO: 64
Amino acid sequence of the *C. hookeriana* KASIV. The alga1 transit peptide is underlined.
S26_ChookKASIV_trinity_43853 - translation
MAASSCMVGSPFCTWLVSACMSTSFDNDPRSLSHKRLRLSRRRRTLSSHCSLRGSTP
QCLDPCNQHCFLGDNGFASLFGSKPPRSDLGHLRLGRTSHSGEVMAVAQEVSTNKK
PATKQRRVVVTGMGVVTPLGHDPDVYYNNLLDGVSGISEIETFDCTQFPTRIAGEIKS
FSTDGLVAPKLSKRMDKFMLYILTAGKKALADGGITEDVMKELDKRKCGVLIGSGL
GGMKVFSDSVEALRISYKKISPFCVPFSTTNMGSAILAMDLGWMGPNYSISTACATS
NFCILNAANHITKGEADMMLCGGSDAAILPIGMGGFVACRALSQRNNDPTKASRPW
DSNRDGFVMGEGAGVLLLEELEHAKKRGATIYAEFLGGSFTCDAYHMTEPHPEGAG
VILCIEKALAQAGVSREDVNYINAHATSTPAGDIKEYQALAHCFGQNSELRVNSTKS
MIGHLIGAAGGVEAVTVIQAIRTGWIHPNLNLENPDKAVDAKLLVGPKKERLDVKV
GLSNSFGFGGHNSSILFAPYN SEQ ID NO: 65
Amino acid sequence of the *C. glassostoma* KASIV. The alga1 transit peptide is underlined
S07_Cg_Locus_3059_Transcript_2/2_translation
MAAASSMVASSFSTSLVAACMSTSFDNDPRFLSHKRIRLSLRRGSTFQCLGDNGFAS
LIGSKPPRSNHGHRRLGRTSHSGEAMAVAMQPAQEASTKNKHVTKQRRVVVTGMG
VVTPLGHDPDVYYNNLLDGVSGISEIENFDCSQFPTRIAGEIKSFSTEGYVIPKFAKRM
DKFMLYLLTAGKKALEDGGITEDVMKELDKRKCGVLIGSGMGGMKIINDSIAALNV
SYKKMTPFCVPFSTTNMGSAMLAIDLGWMGPNYSISTACATSNYCILNAANHIIRGE -continued

SEQUENCE LISTING

ANMMLCGGSDAVVIPVGLGGFVACRALSQRNNDPTKASRPWDSNRDGFVMGEGA
GVLLLEELEHAKKRGATIYAEFLGGSFTCDAYHMTEPHPDGAGVILCIEKALAQSGV
SREDVNYINAHATSTPAGDIKEYQALAHCFGQNSELRVNSTKSMIGHLLGAAGGVEA
VSVVQAIRTGWIHPNINLEDPDEAVDAKLLVGPKKEKLKVKVGLSNSFGFGGHNSSI
LFAPCN

SEQ ID NO: 66
Amino acid sequence of the *C. carthagenesis* KASIV. The alga1 transit peptide is underlined
S05_CcrKASIV_17190_Seq_7/7_translation
MAAAAAFASPFCTWLVAACMSSASRHDPLPSPSSKPRLRRKILFQCAGRGSSAGSGS
SFHSLVTSYLGCLEPCHEYYTSSSSLGFSSLFGSTPGRTSRRQRRLHRASHSGEAMAV
ALQPAQEVTTKKKPSIKQRRVVVTGMGVVTPLGHDPDVFYNNLLDGASGISEIETFD
CAQFPTRIAGEIKSFSTDGWVAPKLSKRMDKFMLYMLTAGKKALADGGISEDVMKE
LDKRKCGVLIGSAMGGMKVFNDAIEALRISYKKMNPFCVPFATTNMGSAMLAMDL
GWMGPNYSISTACATSNFCILNAANHITRGEADMMLCGGSDAVIIPIGLGGFVACRA
LSQRNNDPTKASRPWDSNRDGFVMGEGAGVLLLEELEHAKKRGATIYAEFLGGSFT
CDAYHMTEPHPKGAGVILCIERALAQSGVSREDVNYINAHATSTPAGDIKEYQALAH
CFGQNSELRVNSTKSMIGHLLGAAGGVEAVTVVQAIRTGWVHPNINLENPDEGVDA
KLLVGPKKEKLKVKVGLSNSFGFGGHNSSILFAPYN SEQ ID NO: 67
Amino acid sequence of the *C. carthagenesis* KASIV. The alga1 transit peptide is underlined
S05_CcrKASIV_17190_Seq_6/7_translation
MAAAASVVASPFCTWLVAACMSASFDNEPRSLSPKRRRSLSRSSSASLRFLGGNGFA
SLFGSDPLRPNRGHRRLRHASHSGEAMAVALQPAQEVSTKKKPVTKQRRVVVTGM
GVVTPLGHDPDVYYNNLLDGVSGISEIETFDCTQFPTRIAGEIKSFSTDGWVAPKLSK
RMDKFMLYMLTAGKKALADGGITEEVMKELDKRKCGVLIGSGMGGMKLFNDSIEA
LRISYKKMNPFCVPFATTNMGSAMLAMDLGWMGPNYSISTACATSNFCILNAANHIT
RGEADMMLCGGSDAVIIPIGLGGFVACRALSQRNNDPTKASRPWDSNRDGFVMGEG
AGVLLLEELEHAKKRGATIYAEFLGGSFTCDAYHMTEPHPKGAGVILCIERALAQSG
VSREDVNYINAHATSTPAGDIKEYQALAHCFGQNSELRVNSTKSMIGHLLGAAGGVE
AVTVVQAIRTGWVHPNINLENPDEGVDAKLLVGPKKEKLKVKVGLSNSFGFGGHNS
SILFAPYN SEQ ID NO: 68
Amino acid sequence of the *C. pukherrima* KASIV. The alga1 transit peptide is underlined
pSZ2181 - Cpu1cKASIV
MPAASSLLASPLCTWLLAACMSTSFHPSDPLPPSISSPRRRLSRRRILSQCAPLPSASSA
LRGSSFHTLVTSYLACFEPCHDYYTSASLFGSRPIRTTRRHRRLNRASPSREAMAVAL
QPEQEVTTKKKPSIKQRRVVVTGMGVVTPLGHDPDVFYNNLLDGTSGISEIETFDCA
QFPTRIAGEIKSFSTDGWVAPKLSKRMDKFMLYMLTAGKKALTDGGITEDVMKELD
KRKCGVLIGSAMGGMKVFNDAIEALRISYKKMNPFCVPFATTNMGSAMLAMDLGW
MGPNYSISTACATSNFCIMNAANHIIRGEADVMLCGGSDAVIIPIGMGGFVACRALSQ
RNSDPTKASRPWDSNRDGFVMGEGAGVLLLEELEHAKKRGATIYAEFLGGSFTCDA
YHMTEPHPDGAGVILCIEKALAQSGVSREDVNYINAHATSTPAGDIKEYQALIHCFG
QNRELKVNSTKSMIGHLLGAAGGVEAVSVVQAIRTGWIHPNINLENPDEGVDTKLLV
GPKKERLNVKVGLSNSFGFGGHNSSILFAPYI SEQ ID NO: 69
Clade 1 KASIV consensus C8 and C10
MAAASCMVASPFCTWLVAACMSTSXDNDPRSLSHKRLRLSRRRRTLSSHCSLRGSTF
QCLDPCNQHCFLGDNGFASLFGSKPPRSNRGHLRLGRTSHSGEVMAVAXQXAQEVS
TNKKPATKQRRVVVTGMGVVTPLGHDPDVYYNNLLDGVSGISEIENFDCSQFPTRIA
GEIKSFSTDGWVAPKLSKRMDKFMLYILTAGKKALADGGITEDVMKELDKR KCGVL
IGSGLGGMKVFSDSIEALRTSYKKISPFCVPFSTTNMGSAILAMDLGWMGPNYSISTA
CATSNFCILNAANHITKGEADMMLCGGSDAAILPIGMGGFVACRALSQRNNDPTKAS
RPWDSNRDGFVMGEGAGVLLLEELEHAKKRGATIYAEFLGGSFTCDAYHMTEPHPE
GAGVILCIEKALAQSGVSREDVNYINAHATSTPAGDIKEYQALAHCFGQNSELRVNS
TKSMIGHLLGGAGGVEAVTVVQAIRTGWIHPNINLEDPDEGVDAKLLVGPKKEKLK
VKVGLSNSFGFGGHNSSILFAPCN SEQ ID NO: 70
Clade 2 KASIV consensus C10 only
MAAAASMXXSPLCTWLVAACMSTSFDNDPRSPSIKRLPRRRRVLSQCSLRGSTFQCL
VTSYIDPCNQYCSSASLSFLGDNGFASLFGSKPFRSNRGHRRLGRASHSGEAMAVAL
QPAQEVATKKKPVIKQRRVVVTGMGVVTPLGHEPDVYYNNLLDGVSGISEIETFDCT
QFPTRIAGEIKSFSTDGWVAPKLSKRMDKFMLYLLTAGKKALADGGITDDVMKELD
KRKCGVLIGSGMGGMKLFNDSIEALRXSYKKMNPFCVPFATTNMGSAMLAMDLGW
MGPNYSISTACATSNFCILNAANHIVRGEADMMLCGGSDAVIIPIGLGGFVACRALSQ
RNNDPTKASRPWDSNRDGFVMGEGAGVLLLEELEHAKKRGATIYAEFLGGSFTCDA
YHMTEPHPEGAGVILCIEKALAQAGVSREDVNYINAHATSTPAGDIKEYQALAHCFG
QNSELRVNSTKSMIGHLLGAAGGVEAVTVXQAIRTGWIHPNLNLEDPDKAVDAKLL
VGPKKERLNVKVGLSNSFGFGGHNSSILFAPYNV -continued

| SEQUENCE LISTING |
| --- |
| SEQ ID NO: 71<br>Clade 1 KASIV consensus mature protein<br>KQRRVVVTGMGVVTPLGHDPDVYYNNLLDGVSGISEIENFDCSQFPTRIAGEIKSFST<br>DGWVAPKLSKRMDKFMLYILTAGKKALADGGITEDVMKELDKRKCGVLIGSGLGG<br>MKVFSDSIEALRTSYKKISPFCVPFSTTNMGSAILAMDLGWMGPNYSISTACATSNFC<br>ILNAANHITKGEADMMLCGGSDAAILPIGMGGFVACRALSQRNNDPTKASRPWDSN<br>RDGFVMGEGAGVLLLEELEHAKKRGATIYAEFLGGSFTCDAYHMTEPHPEGAGVIL<br>CIEKALAQSGVSREDVNYINAHATSTPAGDIKEYQALAHCFGQNSELRVNSTKSMIG<br>HLLGGAGGVEAVTVVQAIRTGWIHPNINLEDPDEGVDAKLLVGPKKEKLKVKVGLS<br>NSFGFGGHNSSILFAPCN |
| SEQ ID NO: 72<br>Clade 2 KASIV consensus mature protein<br>KQRRVVVTGMGVVTPLGHEPDVYYNNLLDGVSGISEIETFDCTQFPTRIAGEIKSFST<br>DGWVAPKLSKRMDKFMLYLLTAGKKALADGGITDDVMKELDKRKCGVLIGSGMG<br>GMKLFNDSIEALRXSYKKMNPFCVPFATTNMGSAMLAMDLGWMGPNYSISTACAT<br>SNFCILNAANHIVRGEADMMLCGGSDAVIIPIGLGGFVACRALSQRNNDPTKASRPW<br>DSNRDGFVMGEGAGVLLLEELEHAKKRGATIYAEFLGGSFTCDAYHMTEPHPEGAG<br>VILCIEKALAQAGVSREDVNYINAHATSTPAGDIKEYQALAHCFGQNSELRVNSTKS<br>MIGHLLGAAGGVEAVTVXQAIRTGWIHPNLNLEDPDKAVDAKLLVGPKKERLNVK<br>VGLSNSFGFGGHNSSILFAPYNV |

What is claimed is:

1. A recombinant polynucleotide having at least 95% sequence identity or equivalent sequence by virtue of the degeneracy of the genetic code to SEQ ID NO: 31 encoding a β-keto-acyl ACP synthase IV (KASIV) protein, or the complement of the polynucleotide, wherein said protein has KASIV activity.

2. A transformation vector comprising the polynucleotide of claim 1.

3. The vector of claim 2, comprising promoter and 3'UTR sequences in operable linkage to the polynucleotide, and optionally a flanking sequence for homologous recombination.

4. A host cell comprising the vector of claim 2.

5. The host cell of claim 4, wherein the host cell is a plastidic oleaginous cell having a type II fatty acid biosynthesis pathway.

6. The host cell of claim 5, wherein the host cell is a microalga.

7. The host cell of claim 6, wherein the host cell is of Trebouxiophyceae, and optionally of the genus *Chlorella* or *Prototheca.*

8. The host cell of claim 7, wherein the microalga is of the species *Prototheca moriformis.*

9. A host cell comprising a recombinant polynucleotide having at least 95% sequence identity or equivalent sequence by virtue of the degeneracy of the genetic code to SEQ ID NO: 31, encoding a β-keto-acyl ACP synthase IV (KASIV) protein or the complement of the polynucleotide, wherein said protein has KASIV activity.

10. The host cell of claim 9 further comprising a polynucleotide encoding a fatty acyl-ACP thioesterase B (FATB) wherein the thioesterase has at least 90% amino acid sequence identity to SEQ ID NO: 1 or SEQ ID NO: 57.

11. The host cell of claim 9, wherein the host cell produces a cell oil characterized by a fatty acid profile with (i) at least 7, 8, 9, 10, 11, 12, 13, or 14 area % C8:0, (ii) at least 10, 15, 20, 25, 30, or 35 area % for the sum of C8:0 and C10:0, or (iii) a C8/C10 ratio in the range of 2.2-2.5, 2.5-3.0, or 3.0-3.4.

12. The host cell of claim 9, wherein the host cell is a plastidic oleaginous cell having a type II fatty acid biosynthesis pathway.

13. The host cell of claim 12, wherein the host cell is a microalga.

14. The host cell of claim 13, wherein the host cell is of Trebouxiophyceae, and optionally of the genus *Chlorella* or *Prototheca.*

15. The host cell of claim 14, wherein the microalga is of the species *Prototheca moriformis.*

16. The host cell of claim 9, wherein one or more of the polynucleotides is codon-optimized for expression in the host cell such that the polynucleotide's coding sequence contains the most or second most preferred codon for at least 60% of the codons of the coding sequence such that the codon-optimized sequence is more efficiently translated in the host cell relative to a non-optimized sequence.

17. The host cell of claim 16, wherein the coding sequence contains the most preferred codon for at least 80% of the codons of the coding sequence.

18. A recombinant polynucleotide having at least 85% sequence identity or equivalent sequence by virtue of the degeneracy of the genetic code to SEQ ID NO: 28 encoding a 3-keto-acyl ACP synthase IV (KASIV) protein, or the complement of the polynucleotide, wherein said protein has KASIV activity.

19. A transformation vector comprising the polynucleotide of claim 18.

20. The vector of claim 19, comprising promoter and 3'UTR sequences in operable linkage to the polynucleotide, and optionally a flanking sequence for homologous recombination.

21. A host cell comprising the vector of claim 19.

22. The host cell of claim 21, wherein the host cell is a plastidic oleaginous cell having a type II fatty acid biosynthesis pathway.

23. The host cell of claim 22, wherein the host cell is a microalga.

24. The host cell of claim 23, wherein the host cell is of Trebouxiophyceae, and optionally of the genus *Chlorella* or *Prototheca.*

25. The host cell of claim 24, wherein the microalga is of the species *Prototheca moriformis.*

26. A host cell comprising a recombinant polynucleotide having at least 85% sequence identity or equivalent sequence by virtue of the degeneracy of the genetic code to SEQ ID NO: 28, encoding a β-keto-acyl ACP synthase IV (KASIV) protein or the complement of the polynucleotide, wherein said protein has KASIV activity.

27. The host cell of claim 26 further comprising a polynucleotide encoding a fatty acyl-ACP thioesterase B (FATB), wherein the thioesterase has at least 90% amino acid sequence identity to SEQ ID NO: 1 or SEQ ID NO: 57.

28. The host cell of claim 26, wherein the host cell produces a cell oil characterized by a fatty acid profile with (i) at least 7, 8, 9, 10, 11, 12, 13, or 14 area % C8:0, (ii) at least 10, 15, 20, 25, 30, or 35 area % for the sum of C8:0 and C10:0, or (iii) a C8/C10 ratio in the range of 2.2-2.5, 2.5-3.0, or 3.0-3.4.

29. The host cell of claim 26, wherein the host cell is a plastidic oleaginous cell having a type II fatty acid biosynthesis pathway.

30. The host cell of claim 29, wherein the host cell is a microalga.

31. The host cell of claim 30, wherein the host cell is of Trebouxiophyceae, and optionally of the genus *Chlorella* or *Prototheca.*

32. The host cell of claim 31, wherein the microalga is of the species *Prototheca moriformis.*

33. The host cell of claim 26, wherein one or more of the polynucleotides is codon-optimized for expression in the host cell such that the polynucleotide's coding sequence contains the most or second most preferred codon for at least 60% of the codons of the coding sequence such that the codon-optimized sequence is more efficiently translated in the host cell relative to a non-optimized sequence.

34. The host cell of claim 33, wherein the coding sequence contains the most preferred codon for at least 80% of the codons of the coding sequence.

* * * * *

UNITED STATES PATENT AND TRADEMARK OFFICE
CERTIFICATE OF CORRECTION

PATENT NO. : 9,969,990 B2
APPLICATION NO. : 14/796406
DATED : May 15, 2018
INVENTOR(S) : David Davis et al.

It is certified that error appears in the above-identified patent and that said Letters Patent is hereby corrected as shown below:

In the Claims

In Column 220, Claim 18, Line 19, after the words "SEQ ID NO: 28 encoding", please delete "3" and insert --β--

Signed and Sealed this
Third Day of July, 2018

Andrei Iancu
*Director of the United States Patent and Trademark Office*